(12) United States Patent
McLaughlin et al.

(10) Patent No.: US 10,757,938 B2
(45) Date of Patent: *Sep. 1, 2020

(54) N-ACYLIMINO HETEROCYCLIC COMPOUNDS

(71) Applicant: BASF SE, Ludwigshafen am Rhein (DE)

(72) Inventors: Martin John McLaughlin, Bad Duerkheim (DE); Nina Gertrud Bandur, Ludwigshafen (DE); Matthias Pohlman, Freinsheim (DE); Jochen Dietz, Karlsruhe (DE); Wolfgang Von Deyn, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/245,471

(22) Filed: Jan. 11, 2019

(65) Prior Publication Data

US 2019/0142004 A1 May 16, 2019

Related U.S. Application Data

(63) Continuation of application No. 15/023,128, filed as application No. PCT/EP2014/069900 on Sep. 18, 2014, now Pat. No. 10,206,397.

(Continued)

(51) Int. Cl.
*A01N 43/40* (2006.01)
*C07D 405/14* (2006.01)
(Continued)

(52) U.S. Cl.
CPC ............. *A01N 43/40* (2013.01); *A01N 43/54* (2013.01); *A01N 43/78* (2013.01); *A01N 53/00* (2013.01);
(Continued)

(58) Field of Classification Search
CPC ............................... C07D 401/06; A01N 43/40
(Continued)

(56) References Cited

U.S. PATENT DOCUMENTS 4,803,277 A * 2/1989 Shiokawa ............... A01N 43/50
514/252.03
4,876,263 A 10/1989 Shiokawa et al.
(Continued)

FOREIGN PATENT DOCUMENTS

CA 1291992 C 11/1991
CA 2808414 A1 2/2012
(Continued)

OTHER PUBLICATIONS

Office Action, issued in co-pending U.S. Appl. No. 15/023,176, dated Jul. 25, 2018.
(Continued)

*Primary Examiner* — Rita J Desai
(74) *Attorney, Agent, or Firm* — Marshall, Gerstein & Borun LLP

(57) ABSTRACT

The present invention relates to N-acylimino compound of formula (I):

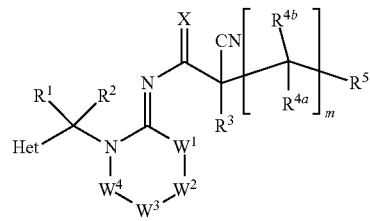

wherein X is O or S, in particular O;

m is an integer selected from 0, 1, 2, 3, 4, 5 or 6;

Het is a 5 or 6 membered carbon-bound or nitrogen-bound heterocyclic ring, $W^1$-$W^2$-$W^3$-$W^4$ represents a carbon chain group connected to N and C=N, and thus forming a saturated, unsaturated, or partially unsaturated 5 or 6 membered nitrogen containing heterocycle, wherein $W^1$, $W^2$, $W^3$ and $W^4$ each individually represent $CR'R^w$, $R^1$, $R^2$ may be hydrogen, halogen, etc.

$R^3$ may be hydrogen, halogen, CN, $C_1$-$C_6$-alkyl, etc.

$R^{4a}$, $R^{4b}$ if present, may be hydrogen, halogen, $C_1$-$C_6$-alkyl, etc.

$R^5$ may be hydrogen, halogen, $C_1$-$C_6$-alkyl, $C_1$-$C_6$-alkenyl, $C_1$-$C_6$-alkinyl, $C_3$-$C_8$-cycloalkyl, $S(O)_n NR^{9a}R^{9b}$, $NR^{9a}R^{9b}$, C(=O)$OR^8$, C(=O)$NR^{9a}R^{9b}$, C(=S)$NR^{9a}R^{9b}$, C(=O)$R^{7a}$, C(=S)$R^{7a}$, $NR^{9a}$—C(=O)$R^{7a}$, $NR^{9a}$—C(=S)$R^{7a}$, $NR^{9a}$—S(O)$_n R^{8a}$, a moitey Q-phenyl, where the phenyl ring is optionally substituted with one or more, e.g. 1, 2, 3, 4 or 5 identical or different substituents $R^{10}$, or a moiety Q-Het#, or $R^3$ and $R^5$ together may also form with the carbon atom they are bound to, a 3, 4, 5 or 6 membered saturated partially unsaturated carbocycle or heterocycle.

The invention also relates to the use of the N-acylimino heterocyclic compounds, their stereoisomers, their tautomers and their salts, for combating invertebrate pests. Furthermore the invention relates also to methods of combating invertebrate pests, which comprises applying such compounds.

22 Claims, No Drawings

Related U.S. Application Data

(60) Provisional application No. 61/879,691, filed on Sep. 19, 2013.

(51) Int. Cl.

| | |
|---|---|
| C07D 401/06 | (2006.01) |
| C07D 405/06 | (2006.01) |
| C07D 417/06 | (2006.01) |
| A01N 43/54 | (2006.01) |
| A01N 43/78 | (2006.01) |
| A01N 53/00 | (2006.01) |
| C07D 401/14 | (2006.01) |
| C07D 417/14 | (2006.01) |

(52) U.S. Cl.
CPC ......... *C07D 401/06* (2013.01); *C07D 401/14* (2013.01); *C07D 405/06* (2013.01); *C07D 405/14* (2013.01); *C07D 417/06* (2013.01); *C07D 417/14* (2013.01)

(58) Field of Classification Search
USPC .......................................................... 546/304
See application file for complete search history.

(56) References Cited

U.S. PATENT DOCUMENTS

| | | | |
|---|---|---|---|
| 4,988,712 | A | 1/1991 | Shiokawa et al. |
| 5,250,498 | A | 10/1993 | Andree et al. |
| 5,719,306 | A | 2/1998 | Chandrakumar et al. |
| 6,838,462 | B2 | 1/2005 | Jeschke et al. |
| 7,951,951 | B2 | 5/2011 | Jeschke et al. |
| 8,106,211 | B2 | 1/2012 | Jeschke et al. |
| 8,106,212 | B2 | 1/2012 | Jeschke et al. |
| 8,563,584 | B2 | 10/2013 | Velten et al. |
| 9,783,523 | B2 * | 10/2017 | Bandur ................ C07D 401/14 |
| 10,206,397 | B2 * | 2/2019 | McLaughlin ........ C07D 405/14 |
| 2004/0209896 | A1 | 10/2004 | Jeschke et al. |
| 2008/0312435 | A1 | 12/2008 | Saito et al. |
| 2009/0181947 | A1 | 7/2009 | Jeschke et al. |
| 2009/0247551 | A1 | 10/2009 | Jeschke et al. |
| 2011/0039894 | A1 | 2/2011 | Velten et al. |
| 2013/0129688 | A1 | 5/2013 | Brenner et al. |
| 2013/0150414 | A1 | 6/2013 | Kagabu et al. |
| 2014/0213791 | A1 | 7/2014 | Nakanishi et al. |

FOREIGN PATENT DOCUMENTS

| | | |
|---|---|---|
| CA | 2808144 | 2/2013 |
| CH | 461489 A | 8/1968 |
| CN | 101065125 A | 10/2007 |
| DE | 3639877 A1 | 5/1988 |
| DE | 19838138 A1 | 3/1999 |
| DE | 102006015467 A1 | 10/2007 |
| DE | 102006015470 A1 | 10/2007 |
| EP | 0268915 A2 | 6/1988 |
| EP | 259738 B1 | 4/1991 |
| EP | 0432600 A2 | 6/1991 |
| EP | 639569 A1 | 2/1995 |
| EP | 0296453 B1 | 8/1997 |
| EP | 2633756 B1 | 7/2016 |
| EP | 2634174 B1 | 5/2017 |
| WO | 9215564 A1 | 9/1992 |
| WO | 99027929 A1 | 6/1999 |
| WO | 02085915 A2 | 10/2002 |
| WO | 06051704 A1 | 5/2006 |
| WO | 07115643 A1 | 10/2007 |
| WO | 07115647 A1 | 10/2007 |
| WO | 07125984 A1 | 11/2007 |
| WO | 09048936 A1 | 4/2009 |
| WO | 09121507 A2 | 10/2009 |
| WO | 10005692 A2 | 1/2010 |
| WO | 12029672 A1 | 3/2012 |
| WO | 12136751 A1 | 10/2012 |
| WO | 13031671 A1 | 3/2013 |
| WO | 13129688 A1 | 9/2013 |
| WO | 13129692 A2 | 9/2013 |
| WO | WO-2013129692 A2 * | 9/2013 |
| WO | 13144088 A1 | 10/2013 |
| WO | 13144213 A1 | 10/2013 |
| WO | 13144223 A1 | 10/2013 |
| WO | 13149903 A1 | 10/2013 |
| WO | 14170300 A1 | 10/2014 |
| WO | 15028630 A1 | 3/2015 |
| WO | 15040162 A1 | 3/2015 |
| WO | 15075174 A1 | 5/2015 |
| WO | 15086790 A1 | 6/2015 |
| WO | 15091649 A1 | 6/2015 |
| WO | 15124606 A1 | 8/2015 |
| WO | 15144813 A1 | 10/2015 |
| WO | 15162244 A1 | 10/2015 |
| WO | 15165960 A1 | 11/2015 |

OTHER PUBLICATIONS

Office Action, issued in co-pending U.S. Appl. No. 14/784,126, dated Aug. 3, 2018.
Final Office Action, issued in co-pending U.S. Appl. No. 14/784,126, dated Mar. 15, 2018.
Office Action, issued in co-pending U.S. Appl. No. 15/023,176, dated Jun. 22, 2017.
Office Action, issued in co-pending U.S. Appl. No. 14/784,126, dated Nov. 23, 2016.
Final Office Action, issued in co-pending U.S. Appl. No. 14/784,126, dated Apr. 27, 2017.
Office Action, issued in co-pending U.S. Appl. No. 14/784,126, dated Sep. 18, 2017.
Dorwald, F. Saragoza, Preface, "Side reactions in organic synthesis a guide to successful synthesis design", weinheim, Wiley VCH Verlag GmbH KGaA, 2005.
Geffken et al., "Synthesis of 2-amino-imidazo[1,2-b][1,2,4]triazine-3,6,7(5H)-triones," Heterocyclic Communications, (2011), pp. 145-149.
Jeschke et al., "Review Neonicotinoids—from Zero to Hero in Insecticide Chemistry," Pest Management Science, vol. 64, (2008), pp. 1084-1098.
Jordan, V.C., "Tamoxifen: A most likely pioneering medicine", Nature Reviews Drug Discovery, vol. 2, Mar. 2003, p. 205-213.
Okazawa et al., "Three-Dimensional Quantitative Structure—Activity Relationship Analysis of Acyclic and Cyclic Chloronicotinyl Insecticides," Pest Management Science, vol. 56, (2000), pp. 509-515.
Reynolds et al., "The Structure of Certain Polyazaindenes. VII. 4-amino-6-methyl-1,3,3a,7-tetrazaindene and its Derivatives," J. Org. Chem., vol. 26, (1961), pp. 115-117.
Carey, F.A., et al. "Advanced Organic Chemistry Part B: Reactions and Synthesis" 5th Edition, Springer Sciences + Business Media, LLC, 2007 New York, NY, p. 216-288.
Smith, M.B. et al. "March's Advanced Organic Chemistry", 6th Edition, John Wiley and Sons Inc., 2007, Hoboken, NJ, p. 960-964.
March "Advanced Organic Chemistry," second edition, pp. 104-105 and 113 (1977).
Williams, et al. Foye's Principles of Medicinal Chemistry, 5th Edition, pp. 50 and 59-61, 2002.
Office Action, issued in co-pending U.S. Appl. No. 15/023,176, dated Dec. 14, 2018.
Final Office Action, issued in co-pending U.S. Appl. No. 14/784,126, dated Jan. 15, 2019.
Office Action, issued in co-pending U.S. Appl. No. 15/128,625, dated Oct. 15, 2018.

* cited by examiner

N-ACYLIMINO HETEROCYCLIC COMPOUNDS

CROSS REFERENCE TO RELATED APPLICATIONS

This application is a continuation of U.S. application Ser. No. 15/023,128, filed Mar. 18, 2016, the entire contents of which is hereby incorporated herein by reference. U.S. application Ser. No. 15/023,128 is a National Stage Application of International Application No. PCT/EP2014/069900, filed Sep. 18, 2014, which claims the benefit of U.S. Provisional Application No. 61/879,691, filed Sep. 19, 2013, the entire contents of each of which are hereby incorporated herein by reference.

The present invention relates to N-acylimino heterocyclic compounds, including their stereoisomers, tautomers and salts, and to compositions comprising such compounds. The invention also relates to the use of the N-acylimino heterocyclic compounds, their stereoisomers, their tautomers and their salts, for combating invertebrate pests. Furthermore the invention relates also to methods of combating invertebrate pests, which comprises applying such compounds.

BACKGROUND OF INVENTION

Invertebrate pests, such as insects, acaridae and nematode pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled.

EP 259738 discloses compounds of the formula A, which have insecticidal activity:

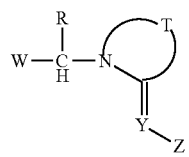

(A)

where W is a substituted pyridyl radical or a 5- or 6-membered heterocyclic radical, R is hydrogen or alkyl, T together with the atoms to which it is bound forms a 5- or 6-membered heterocyclic ring, Y is inter alia a nitrogen atom and Z is an electron withdrawing group selected from nitro and cyano.

Pesticidal compounds, which are similar to those of EP 259738, are known from EP 639569, where the moiety electron withdrawing moiety Z is an electron withdrawing group such as alkoxcarbonyl, arylcarbonyl, heterocyclic carbonyl, $C_1$-$C_4$-alkylsulfonyl, sulfamoyl or $C_1$-$C_4$-acyl.

US 2013/0150414 describe, inter alia, pesticidal compounds of the formula B

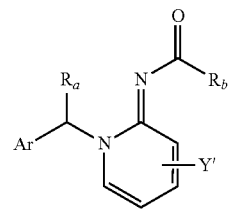

(B)

wherein Ar is an aryl or 5- or 6-membered heterocyclic group, $R^a$ is hydrogen or alkyl, Y' is hyddrogen, halogen, a hydroxyl group, an alkyl group or an alkoxy group and $R^b$ is an alkyl group substituted with halogen or an alkoxy group, optionally substituted with halogen.

Pesticidal compounds, which are similar to those of US 2013/0150414, are known from WO 2013/129688.

The pesticidal activity of the compounds is not satisfactory. It is therefore an object of the present invention to provide compounds having a good pesticidal activity, especially against difficult to control insects and acarid pests.

SUMMARY OF INVENTION

It has been found that these objects are solved by N-substituted acyl-imino compounds of the general formula (I) described below, by their stereoisomers, their tautomers and their salts. Therefore, the present invention relates to N-acylimino compound of formula (I):

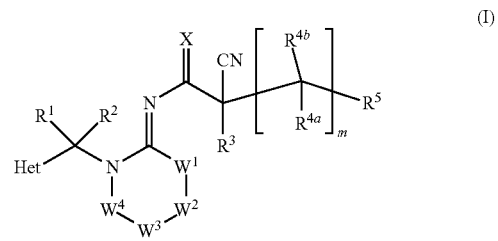

(I)

wherein
m is an integer selected from 0, 1, 2, 3, 4, 5 or 6, in particular 0 or 1;
X is O or S, in particular O;
Het is a 5 or 6 membered carbon-bound or nitrogen-bound heterocyclic or heteroaromatic ring, comprising 1, 2, 3, 4 or 5 carbon atoms and 1, 2 or 3 heteroatoms as ring members, which are independently selected from sulfur, oxygen or nitrogen, wherein the carbon, sulfur and nitrogen ring members can independently be partly or fully oxidized, and wherein each ring is optionally substituted by k identical or different substituents $R^6$, wherein k is an integer selected from 0, 1, 2, 3 or 4;
$W^1$-$W^2$-$W^3$-$W^4$ represents a carbon chain group connected to N and C=N, and thus forming a saturated, unsaturated, or partially unsaturated 5 or 6 membered nitrogen containing heterocycle, wherein
$W^1$, $W^2$, $W^3$ and $W^4$ each individually represent $CR'R^w$, wherein
each $R^w$ independently from each other, is selected from the group consisting hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, and wherein the carbon atoms of the aforementioned aliphatic and cycloaliphatic radicals may be unsubstituted or may be partly or fully halogenated and/or may optionally be substituted with 1, 2 or 3 identical or different radicals $R^7$, $OR^8$, $NR^{9a}R^{9b}$, $S(O)_nR^8$, $S(O)_nNR^{9a}R^{9b}$, $C(=O)R^{7a}$, $C(=O)NR^{9a}R^{9b}$, $C(=O)OR^8$, $C(=S)R^{7a}$, $C(=S)NR^{9a}R^{9b}$, $C(=S)OR^8$, $C(=S)SR^8$, $C(=NR^{17})R^{7a}$, $C(=NR^{17})NR^{9a}R^{9b}$ and $Si(R^{11})_2R^{12}$, each $R^v$ independently from each other, are selected from the group consisting of hydrogen, halogen, cyano, $C_1$-$C_{10}$-alkyl, $C_3$-$C_8$-cycloalkyl, $C_2$-$C_{10}$-alkenyl and $C_2$-$C_{10}$-alkynyl, wherein the carbon atoms of the aforementioned aliphatic and cycloaliphatic radicals may be unsubstituted or may be partly or fully halogenated or may optionally be further substituted with 1, 2 or 3 identical or different radicals $R^7$; or $R^v$ and $R^w$ present in one of the groups may together form =O, =$CR^{13}R^{14}$, =S, =$NR^{17}$, =$NOR^{16}$, =$NNR^{9a}R^{9b}$, or two $R^w$ of adjacent carbon atoms, may form both together and together with the existing bond a double bond between the adjacent carbon atoms;

and wherein one of $W^2$ or $W^3$ may optionally represent a single or a double bond between the adjacent carbon atoms;

$R^1$, $R^2$ are independently from each other selected from the group consisting of hydrogen, halogen, CN, SCN, nitro, $C_1$-$C_6$-alkyl, $C_3$-$C_6$-cycloalkyl, wherein each of the two aforementioned radicals are unsubstituted, partly or completely halogenated or may carry any combination of 1, 2 or 3 radicals $R^7$, $Si(R^{11})_2R^{12}$, $OR^8$, $OSO_2R^8$, $S(O)_nR^8$, $S(O)_nNR^{9a}R^{9b}$, $NR^{9a}R^{9b}$, $C(=O)NR^{9a}R^{9b}$, $C(=S)NR^{9a}R^{9b}$, $C(=O)OR^8$, $C(=O)R^{7a}$, $C(=S)R^{7a}$, phenyl, benzyl, where the phenyl ring in the last two radicals is unsubstituted or optionally substituted with 1, 2, 3, 4 or 5 identical or different substituents $R^{10}$, a 3-, 4-, 5-, 6- or 7-membered saturated, partly saturated or unsaturated aromatic heterocyclic ring comprising 1, 2 or 3 identical or different heteroatoms as ring members, which are selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, or $R^1$ and $R^2$ form, together with the carbon atom, which they attached to, a 3-, 4-, 5- or 6-membered saturated or partly unsaturated carbocyclic or heterocyclic ring, wherein each of the carbon atoms of said cycle are unsubstituted or may carry any combination of 1 or 2 identical or different radicals $R^7$, or $R^1$ and $R^2$ may together be =O, =$CR^{13}R^{14}$, =S, =$NR^{17}$, =$NOR^{16}$ or =$NNR^{9a}R^{9b}$;

$R^3$ is selected from the group consisting of hydrogen, halogen, CN, $C_1$-$C_6$-alkyl, $C_2$-$C_6$-alkenyl, $C_2$-$C_6$-alkynyl, $C_3$-$C_8$-cycloalkyl, wherein each of the 4 last mentioned radicals are unsubstituted, partly or completely halogenated or carries 1 or 2 radicals $R^7$, it being also possible for cycloalkyl to carry 1, 2, 3, 4, 5 or 6 $C_1$-$C_4$-alkyl groups, $S(O)_nNR^{9a}R^{9b}$, $NR^{9a}R^{9b}$, $C(=O)OR^8$, $C(=O)NR^{9a}R^{9b}$, $C(=S)NR^{9a}R^{9b}$, $C(=O)R^{7a}$, $C(=S)R^{7a}$, $NR^{9a}$—$C(=O)R^{7a}$, $NR^{9a}$—$C(=S)R^{7a}$, $NR^{9a}$—$S(O)_nR^{8a}$, phenyl, benzyl, where the phenyl ring in the last two mentioned radicals is unsubstituted or may be substituted with one or more, e.g. 1, 2, 3, 4 or 5 identical or different substituents $R^{10}$, and a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized;

$R^{4a}$, $R^{4b}$ are selected each independently from one another and independently from the integer of m from the group consisting of hydrogen, halogen, CN, $C_1$-$C_6$-alkyl, $C_1$-$C_6$-alkoxy, $C_1$-$C_6$-alkylthio, and $C_3$-$C_8$-cycloalkyl, wherein each of the 4 last mentioned radicals are unsubstituted, partly or completely halogenated, or $R^{4a}$ and $R^{4b}$ may form together with the carbon atom they are bound to, a 3, 4, 5 or 6 membered aliphatic ring, wherein each of the carbon atoms of the ring may be unsubstituted or may be partly or fully halogenated, and/or may carry 1, 2, 3, 4, 5 or 6 radicals selected from $C_1$-$C_4$-alkyl, $C_1$-$C_4$-haloalkyl, $C_1$-$C_4$-alkoxy and $C_1$-$C_4$-haloalkoxy;

or $R^{4a}$ and $R^{4b}$ may together form =O, =$CR^{13}R^{14}$, =S, =$NR^{17}$, =$NOR^{16}$, =$NNR^{9a}R^{9b}$, $R^5$ is selected from the group consisting of hydrogen, halogen, $C_1$-$C_6$-alkyl, $C_2$-$C_6$-alkenyl, $C_2$-$C_6$-alkynyl, $C_3$-$C_8$-cycloalkyl, wherein each of the 4 last mentioned radicals are unsubstituted, partly or completely halogenated or carries 1 or 2 radicals $R^7$, it being also possible for cycloalkyl radicals to carry 1, 2, 3, 4, 5 or 6 $C_1$-$C_4$-alkyl groups, $S(O)_nNR^{9a}R^{9b}$, $NR^{9a}R^{9b}$, $C(=O)OR^8$, $C(=O)NR^{9a}R^{9b}$, $C(=S)NR^{9a}R^{9b}$, $C(=O)R^{7a}$, $C(=S)R^{7a}$, $NR^{9a}$—$C(=O)R^{7a}$, $NR^{9a}$—$C(=S)R^{7a}$, $NR^{9a}$—$S(O)_nR^{8a}$, a moitey Q-phenyl, where the phenyl ring is optionally substituted with one or more, e.g. 1, 2, 3, 4 or 5 identical or different substituents $R^{10}$, and a moiety Q-Het#, where Het# represents a 3-, 4-, 5-, 6- or 7-membered saturated, partly saturated or unsaturated aromatic heterocyclic ring comprising 1, 2 or 3 heteroatoms as ring members, which are selected from oxygen, nitrogen and/or sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, and Q irrespectively of its occurrence, is a single bond, $NR^{9a}$, $NR^{9a}$—$C_1$-$C_4$-alkylene, —O—C(=O)—, —$NR^{9a}$—C(=O)—, —O—S(=O)$_2$—, —$NR^{9a}$—S(=O)$_2$—, —O—C(=O)—$C_1$-$C_4$-alkylene or —$NR^{9a}$—C(=O)—$C_1$-$C_4$-alkylene, where the heteroatom in the last 6 moieties is bound to the carbon atom of C(CN)$R^3$ or $CR^{4a}R^{4a}$, respectively;

or, if m=0,

R³ and R⁵ together may also form with the carbon atom they are bound to, a 3, 4, 5 or 6 membered saturated partially unsaturated carbocycle or heterocycle, wherein each of the carbon atoms of the carbocycle or heterocycle may be unsubstituted or may be partly or fully halogenated, and/or may carry 1, 2, 3, 4, 5 or 6 radicals $R^{7b}$, and where the heterocycle has 1 or 2 non-adjacent identical or different heteroatoms or heteroatom moieties as ring members, which are selected from O, S, N and N—$R^{17}$, or $R^3$ and $R^5$ may together form =O or =S;

where, independently of their occurrence, n is 0, 1 or 2;

$R^6$ is selected from the group consisting of halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, and wherein the carbon atoms of the aforementioned aliphatic and cyclo-aliphatic radicals may optionally be further substituted independently from one another with 1, 2 or 3 radicals $R^7$, $OR^8$, $NR^{17a}R^{17b}$, $S(O)_nR^8$, $S(O)_nNR^{17a}R^{17b}$, $C(=O)R^{7a}$, $C(=O)NR^{17a}R^{17b}$, $C(=O)OR^8$, $C(=S)R^{7a}$, $C(=S)NR^{17a}R^{17b}$, $C(=S)OR^8$, $C(=S)SR^8$, $C(=NR^{17})R^{7a}$, $C(=NR^{17})NR^{17a}R^{17b}$, $Si(R^{11})_2R^{12}$;

phenyl, optionally substituted with 1, 2, 3, 4 or 5 identical or different substituents $R^{10}$, a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, or two of $R^6$ present on one ring carbon may together form =O, =$CR^{13}R^{14}$, =S, =$NR^{17}$, =$NOR^{16}$, =$NNR^{9a}R^{9b}$, or two $R^6$ together form a linear $C_2$-$C_7$ alkylene chain, thus forming, together with the ring atom(s) to which they are bound, a 3-, 4-, 5-, 6-, 7- or 8-membered ring, where 1 or 2 $CH_2$ moieties of the alkylene chain may be replaced by 1 or 2 heteroatom moieties selected from O, S and $NR^{17c}$ and/or 1 or 2 of the $CH_2$ groups of the alkylene chain may be replaced by a group C=O, C=S and/or C=$NR^{17}$; and where the alkylene chain is unsubstituted or may be substituted with 1, 2, 3, 4, 5 or 6 radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted with 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted with 1, 2, 3, 4 or 5 radicals $R^{10}$;

$R^7$ independently of its occurrence, is selected from the group consisting of cyano, azido, nitro, —SCN, $SF_5$, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $Si(R^{11})_2R^{12}$, $OR^8$, $OSO_2R^8$, $S(O)_nR^8$, $S(O)_nNR^{17a}R^{17b}$, $NR^{17a}R^{17b}$, $C(=O)NR^{17a}R^{17b}$, $C(=S)NR^{17a}R^{17b}$, $C(=O)OR^8$, $C(=O)R^{15}$, $C(=S)R^{15}$, $C(=NR^{17})R^{15}$, phenyl, phenyl-$C_1$-$C_4$-alkyl, where the phenyl ring in the last two groups is optionally substituted with 1, 2, 3, 4 or 5 identical or different substituents $R^{10}$, and a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, or two $R^7$ present on one carbon atom may together form =O, =$CR^{13}R^{14}$, =S, =$NR^{17}$, =$NOR^{16}$, =$NNR^{9a}R^{9b}$, or two $R^7$ may form a 3-, 4-, 5-, 6-, 7- or 8-membered saturated or partly unsaturated carbocyclic or heterocyclic ring together with the carbon atoms to which the two $R^7$ are bonded, where the heterocyclic ring comprises 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$;

$R^{7a}$ independently of its occurrence, is selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, phenyl, optionally substituted with 1, 2, 3, 4 or 5 identical or different substituents $R^{10}$, and a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized;

$R^{7b}$ is selected from the group consisting of halogen, cyano, $C_1$-$C_{10}$-alkyl, $C_3$-$C_8$-cycloalkyl, $C_2$-$C_{10}$-alkenyl, $C_2$-$C_{10}$-alkynyl, $C_3$-$C_8$-cycloalkenyl, and wherein the carbon atoms of the aforementioned aliphatic and cycloaliphatic radicals may be partly or completely halogenated, and/or be substituted with 1, 2 or 3 identical or different radicals $R^7$, $OR^8$, $NR^{17a}R^{17b}$, $S(O)_nR^8$, $S(O)_nNR^{17a}R^{17b}$, $C(=O)R^{7a}$, $C(=O)NR^{17a}R^{17b}$, $C(=O)OR^8$, $C(=S)R^{7a}$, $C(=S)NR^{17a}R^{17b}$, $C(=S)OR^8$, $C(=NR^{17})R^{7a}$, $C(=NR^{17})NR^{17a}R^{17b}$, $Si(R^{11})_2R^{12}$;

phenyl, optionally substituted with 1, 2, 3, 4 or 5 identical or different substituents $R^{10}$, and a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, or two of $R^{7b}$ present on one ring carbon may together form =O, =S or =CR$^{13}$R$^{14}$, or two $R^{7b}$ together form a linear $C_2$-$C_7$ alkylene chain, thus forming, together with the ring atom(s) to which they are bound, a 3-, 4-, 5-, 6-, 7- or 8-membered ring, where 1 or 2 CH$_2$ moieties of the alkylene chain may be replaced by 1 or 2 heteroatom moieties selected from O, S and NR$^{17c}$ and/or 1 or 2 of the CH$_2$ groups of the alkylene chain may be replaced by a group C=O, C=S and/or C=NR$^{17}$; and where the alkylene chain is unsubstituted or may be substituted with 1, 2, 3, 4, 5 or 6 radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted with 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted with 1, 2, 3, 4 or 5 radicals $R^{10}$;

$R^8$ independently of its occurrence, is selected from the group consisting of hydrogen, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, C(=O)R$^{15}$, C(=O)NR$^{17a}$R$^{17b}$, C(=S)NR$^{17a}$R$^{17b}$, C(=O)OR$^{16}$, phenyl, phenyl-$C_1$-$C_4$-alkyl, where the phenyl ring in the last two mentioned radicals is unsubstituted or substituted with 1, 2, 3, 4 or 5 identical or different substituents $R^{10}$, and a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, $R^{8a}$ independently of its occurrence, is selected from the group consisting of $C_1$-$C_6$-alkyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl, wherein each of the five last mentioned radicals are unsubstituted, partly or completely halogenated, phenyl, benzyl, where the phenyl ring in the last two mentioned radicals is unsubstituted or may be substituted with one or more, e.g. 1, 2, 3, 4 or 5 identical or different substituents $R^{10}$, and a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, $R^9$ independently of its occurrence, is selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, phenyl, optionally substituted with 1, 2, 3, 4 or 5 identical or different substituents $R^{10}$;

a 3-, 4-, 5-, 6- or 7-membered saturated, partly saturated or unsaturated aromatic C-bound heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, $R^{9a}$, $R^{9b}$ are each independently from one another selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$ haloalkynyl, S(O)$_n$R$^{16}$, —S(O)$_n$NR$^{17a}$R$^{17b}$, C(=O)R$^{15}$, C(=O)OR$^{16}$, C(=O)NR$^{17a}$R$^{17b}$, C(=S)R$^{15}$, C(=S)SR$^{16}$, C(=S)NR$^{17a}$R$^{17b}$, C(=NR$^{17}$)R$^{15}$;

phenyl, benzyl, 1-phenethyl or 2-phenethyl, where the phenyl ring in the last four mentioned radicals is unsubstituted or may be substituted with 1, 2, 3, 4 or 5 identical or different substituents $R^{10}$; and a 3-, 4-, 5-, 6- or 7-membered saturated, partly saturated or unsaturated aromatic C-bound heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, or, $R^{9a}$ and $R^{9b}$ are together a $C_2$-$C_7$ alkylene chain and form a 3-, 4-, 5-, 6-, 7- or 8-membered saturated, partly saturated or unsaturated aromatic ring together with the nitrogen atom they are bonded to, wherein the alkylene chain may contain one or two heteroatoms, which are, independently of each other, selected from oxygen, sulfur or nitrogen, and where the alkylene chain may optionally be substituted with 1, 2, 3 or 4 radicals selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, phenyl, optionally substituted with 1, 2, 3, 4 or 5 identical or different substituents $R^{10}$, and a 3-, 4-, 5-, 6- or 7-membered saturated, partly saturated or unsaturated aromatic C-bound heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, or $R^{9a}$ and $R^{9b}$ together may form =CR$^{13}$R$^{14}$, =NR$^{17}$, =NOR$^{16}$, =NNR$^{17a}$R$^{17b}$ moiety;

$R^{9c}$, $R^{9d}$ are each independently from one another selected from the group consisting of hydrogen, $C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $S(O)_nR^{16}$, —$S(O)_nNR^{17a}R^{17b}$, $C(=O)R^{15}$, $C(=O)OR^{16}$, $C(=O)NR^{17a}R^{17b}$, $C(=S)R^{15}$, $C(=S)SR^{16}$, $C(=S)NR^{17a}R^{17b}$, $C(=NR^{17})R^{15}$;

phenyl, benzyl, where the phenyl ring in the last two mentioned radicals is unsubstituted or may be substituted with 1, 2, 3, 4 or 5 identical or different substituents $R^{10}$; and a 3-, 4-, 5-, 6- or 7-membered saturated, partly saturated or unsaturated aromatic C-bound heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized;

$R^{10}$ independently of its occurrence, is selected from the group consisting of halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cycloaliphatic radicals may optionally be substituted with 1, 2, 3, 4 or 5 identical or different radicals $R^{10a}$, $Si(R^{11})_2R^{12}$, $OR^{16}$, $OS(O)_nR^{16}$, —$S(O)_nR^{16}$, $S(O)_nNR^{17a}R^{17b}$, $NR^{17a}R^{17b}$, $C(=O)R^{15}$, $C(=S)R^{15}$, $C(=O)OR^{16}$, —$C(=NR^{17})R^{15}$, $C(=O)NR^{17a}R^{17b}$, $C(=S)NR^{17a}R^{17b}$, phenyl, optionally substituted with 1, 2, 3, 4 or 5 identical or different radicals selected from OH, halogen, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, where the heterocyclic ring is unsubstituted or may be substituted with 1, 2, 3, 4 or 5 substituents selected independently from one another from halogen, cyano, $NO_2$, $C_1$-$C_6$-alkyl, $C_1$-$C_6$-haloalkyl, $C_1$-$C_6$-alkoxy and $C_1$-$C_6$-haloalkoxy, and wherein the nitrogen and/or the sulfur atom(s) of the heterocyclic ring may optionally be oxidized;

or two $R^{10}$ present together on one carbon ring atom of a saturated or partly unsaturated heterocyclic radical may form =O, =$CR^{13}R^{14}$, =S, =$NR^{17}$, =$NOR^{16}$, =$NNR^{17a}R^{17b}$;

or, two $R^{10}$ on adjacent carbon ring atoms may also be a bivalent radical selected from $CH_2CH_2CH_2CH_2$, $CH=CH-CH=CH$, $N=CH-CH=CH$, $CH=N-CH=CH$, $N=CH-N=CH$, $OCH_2CH_2CH_2$, $OCH=CHCH_2$, $CH_2OCH_2CH_2$, $OCH_2CH_2O$, $OCH_2OCH_2$, $CH_2CH_2CH_2$, $CH=CHCH_2$, $CH_2CH_2O$, $CH=CHO$, $CH_2OCH_2$, $CH_2C(=O)O$, $C(=O)OCH_2$, $O(CH_2)O$, $SCH_2CH_2CH_2$, $SCH=CHCH_2$, $CH_2SCH_2CH_2$, $SCH_2CH_2S$, $SCH_2SCH_2$, $CH_2CH_2S$, $CH=CHS$, $CH_2SCH_2$, $CH_2C(=S)S$, $C(=S)SCH_2$, $S(CH_2)S$, $CH_2CH_2NR^{17}$, $CH_2CH=N$, $CH=CH-NR^{17}$, $OCH=N$, $SCH=N$ and form together with the carbon atoms to which the two $R^{10}$ are bonded to a 5-membered or 6-membered partly saturated or unsaturated, aromatic carbocyclic or heterocyclic ring, wherein the ring may optionally be substituted with one or two substituents selected from =O, OH, $CH_3$, $OCH_3$, halogen, cyano, halomethyl and halomethoxy;

$R^{10a}$ independently of its occurrence, is selected from the group consisting of halogen, cyano, $NO_2$, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, $Si(R^{11})_2R^{12}$, $OR^{16}$, $OS(O)_nR^{16}$, —$S(O)_nR^{16}$, $S(O)_nNR^{17a}R^{17b}$, $NR^{17a}R^{17b}$, $C(=O)R^{15}$, $C(=S)R^{15}$, $C(=O)OR^{16}$, —$C(=NR^{17})R^{15}$, $C(=O)NR^{17a}R^{17b}$, $C(=S)NR^{17a}R^{17b}$, phenyl, optionally substituted with 1, 2, 3, 4 or 5 identical or different radicals selected from OH, halogen, cyano, nitro, $C_1$-$C_6$-alkyl, $C_1$-$C_6$-haloalkyl, $C_1$-$C_6$-alkoxy and $C_1$-$C_6$-haloalkoxy;

$R^{11}$, $R^{12}$ independently of their occurrence, are selected from the group consisting of $C_1$-$C_6$-alkyl, $C_1$-$C_6$-haloalkyl, $C_1$-$C_6$-alkoxy, $C_1$-$C_6$-alkoxy-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, $C_1$-$C_6$-haloalkoxy-$C_1$-$C_4$-alkyl, phenyl and benzyl, where the phenyl ring in last two radicals are unsubstituted or substituted with 1, 2, 3, 4 or 5 identical or different radicals selected from halogen, OH, cyano, $NO_2$, $C_1$-$C_6$-alkyl, $C_1$-$C_6$-haloalkyl, $C_1$-$C_6$-alkoxy and $C_1$-$C_6$-haloalkoxy;

$R^{13}$, $R^{14}$ independently of their occurrence, are selected from the group consisting of hydrogen, halogen, CN, $C_1$-$C_6$-alkyl, $C_3$-$C_6$-cycloalkyl, $C_1$-$C_4$-alkoxy-$C_1$-$C_4$-alkyl, phenyl and benzyl;

$R^{15}$ independently of its occurrence, is selected from the group consisting of hydrogen, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cycloaliphatic radicals may be unsubstituted, partially or fully halogenated and/or oxygenated and/or may carry 1 or 2 radicals selected from $C_1$-$C_4$ alkoxy;

phenyl, benzyl and pyridyl, wherein the last three radicals may be unsubstituted, partially or fully halogenated and/or to carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino or di-($C_1$-$C_6$-alkyl)amino;

$R^{16}$ independently of its occurrence, is selected from the group consisting of hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, wherein the five last mentioned aliphatic and cycloaliphatic radicals may be unsubstituted, partially or fully halogenated and/or oxygenated and/or may carry 1 or 2 radicals selected from $C_1$-$C_4$ alkoxy, phenyl, benzyl and pyridyl, wherein the last three radicals may be unsubstituted, partially or fully halogenated and/or to carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino or di-($C_1$-$C_6$-alkyl)amino;

$R^{17}$ independently of its occurrence, is selected from the group consisting of hydrogen, $C_1$-$C_6$-alkoxy, $C_1$-$C_6$-haloalkoxy, $C_1$-$C_6$-alkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cycloaliphatic radicals may be unsubstituted, partially or fully halogenated and/or oxygenated and/or may carry 1 or 2 radicals selected from $C_1$-$C_4$-alkoxy, phenyl, benzyl, pyridyl, phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, $R^{17a}$, $R^{17b}$ are each independently from one another selected from the group consisting of hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy, phenyl, benzyl, pyridyl, phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, or, $R^{17a}$ and $R^{17b}$ may together be a $C_2$-$C_6$ alkylene chain forming a 3- to 7-membered saturated, partly saturated or unsaturated ring together with the nitrogen atom $R^{17a}$ and $R^{17b}$ are bonded to, wherein the alkylene chain may contain 1 or 2 heteroatoms selected, independently of each other, from oxygen, sulfur or nitrogen, and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

or $R^{17a}$ and $R^{17b}$ together may form $=CR^{13}R^{14}$, $=NR^{17}$ or $=NOR^{16}$ moiety;

$R^{17c}$ independently of its occurrence, is selected from the group consisting of hydrogen, CN, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, wherein the five last mentioned aliphatic and cycloaliphatic radicals may be unsubstituted, partially or fully halogenated and/or oxygenated and/or may carry 1 or 2 radicals selected from $C_1$-$C_4$ alkoxy, phenyl, benzyl and pyridyl, wherein the last three radicals may be unsubstituted, partially or fully halogenated and/or to carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino or di-($C_1$-$C_6$-alkyl)amino;

the stereoisomers, the tautomers and the salts thereof.

Moreover, the present invention relates to and includes the following embodiments:

agricultural and veterinary compositions comprising an amount of at least one compound of the formula (I) or a stereoisomer, tautomer or salt thereof;

the use of the compounds of formula (I), the stereoisomers, the tautomers or the salts thereof for combating invertebrate pests;

the use of the compounds of formula (I), the stereoisomers, the tautomers or the salts thereof for protecting growing plants from attack or infestation by invertebrate pests;

the use of the compounds of formula (I), the stereoisomers, the tautomers or the salts, thereof for protecting plant proparagation material, especially seeds, from soil insects;

the use of the compounds of formula (I), the stereoisomers, the tautomers or the salts thereof for protecting the seedlings roots and shoots of plants from soil and foliar insects;

a method for combating or controlling invertebrate pests, which method comprises contacting said pest or its food supply, habitat or breeding grounds with a pesticidally effective amount of at least one compound of the formula (I) or a stereoisomer, a tautomer or salt thereof;

a method for protecting growing plants from attack or infestation by invertebrate pests, which method comprises contacting a plant, or soil or water in which the plant is growing, with a pesticidally effective amount of at least one compound of the formula (I) or a stereoisomer, a tautomer or salt thereof, in particular a method protecting crop plants from attack or infestation by animal pests, which comprises contacting the crop plants with a pesticidally effective amount of at least one compound of the formula (I) or stereoisomer, a tautomer or salt thereof;

a method for the protection of plant propagation, especially seeds, from soil insects and of the seedlings' roots and shoots from soil and foliar insects comprising contacting the seeds before sowing and/or after pregermination with at least one compound of the formula (I) or stereoisomer, a tautomer or salt thereof;

seeds comprising a compound of the formula (I) or an enantiomer, diastereomer or salt thereof;

the use of compounds of formula (I), the stereoisomers, the tautomers or the salts, in particular the veterinary acceptable salts, thereof for combating parasites in and on animals, in particular for the use in the treatment of animals infested or infected by parasites, for preventing animals of getting infected or infested by parasites or for protecting animals against infestation or infection by parasites;

a method for treating animals infested or infected by parasites or preventing animals of getting infected or infested by parasites or protecting animals against infestation or infection by parasites which comprises administering or applying to the animals a parasiticidally effective amount of a compound of formula (I) or the stereoisomers and/or salts, in particular veterinary acceptable salts, thereof;

a process for the preparation of a veterinary composition for treating, controlling, preventing or protecting animals against infestation or infection by parasites which comprises formulating a compound of formula (I) or a stereoisomer, tautomer and/or veterinary acceptable salt thereof with a carrier composition suitable for veterinary use;

the use of a compound of formula (I) or the stereoisomers, tautomers and/or veterinary acceptable salt thereof for the preparation of a medicament for treating, controlling, preventing or protecting animals against infestation or infection by parasites.

The present invention also relates to plant propagation materials, in particular as mentioned above to seeds, containing at least one compound of formula (I), a stereoisomer, a tautomer and/or an agriculturally acceptable salt thereof.

DETAILED DESCRIPTION OF INVENTION

The present invention relates to every possible stereoisomer of the compounds of formula (I), i.e. to single enantiomers, diastereomers and E/Z-isomers as well as to mixtures thereof and also to the salts thereof. The present invention relates to each isomer alone, or mixtures or combinations of the isomers in any proportion to each other. Depending on the substitution pattern, the compounds of the formula (I) may have one or more centers of chirality, in which case they are present as mixtures of enantiomers or diastereomers. One center of chirality is the carbon ring atom carrying radical $R^1$. Another centre of chirality may be the carbon atom which carries $R^3$, in particular if $R^3$ is different from CN and the group $[CR^{4a}R^{4b}]_m R^5$. The invention provides both the pure enantiomers or diastereomers and their mixtures and the use according to the invention of the pure enantiomers or diastereomers of the compound I or its mixtures. Suitable compounds of the formula (I) also include all possible geometrical stereoisomers (cis/trans isomers) and mixtures thereof.

The present invention also relates to potential tautomers of the compounds of formula (I) and also to the salts of such tautomers. The present invention relates to the tautomer as such as well as to mixtures or combinations of the tautomers in any proportion to each other. The term "tautomers" encompasses isomers, which are derived from the compounds of formula (I) by the shift of an H-atom involving at least one H-atom located at a nitrogen, oxygen or sulphur atom. Examples of tautomeric forms are keto-enol forms, imine-enamine forms, urea-isourea forms, thiourea-isothiourea forms, (thio)amide-(thio)imidate forms etc.

The compounds of the present invention, i.e. the compounds of formula (I), their stereoisomers, their tautomers as well as their salts, in particular their agriculturally acceptable salts and their veterinarily acceptable salts, may be amorphous or may exist in one ore more different crystalline states (polymorphs) or modifications which may have a different macroscopic properties such as stability or show different biological properties such as activities. The present invention includes both amorphous and crystalline compounds of the formula (I), mixtures of different crystalline states or modifications of the respective stereoisomers or tautomers, as well as amorphous or crystalline salts thereof.

Salts of the compounds of the formula (I) are preferably agriculturally salts as well as veterinarily acceptable salts. They can be formed in a customary method, e.g. by reacting the compound with an acid of the anion in question if the compound of formula (I) has a basic functionality or by reacting an acidic compound of formula (I) with a suitable base.

Suitable agriculturally or veterinary useful salts are especially the salts of those cations or anions, in particular the acid addition salts of those acids, whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine. For example, partially or fully halogenated alkyl is also termed haloalkyl, partially or fully halogenated cycloalkyl is also termed halocycloalkyl, partially or fully halogenated alkylenyl is also termed haloalkenyl, partially or fully halogenated alkylynyl is also termed haloalkynyl, partially or fully halogenated alkoxy is also termed haloalkoxy, partially or fully halogenated alkylthio is also termed haloalkthio, partially or fully halogenated alkylsulfinyl is also termed haloalkylsulfinyl, partially or fully halogenated alkylsulfonyl is also termed haloalsulfonyl, partially or fully halogenated cycloalkylalkyl is also termed halocycloalkylalkyl.

The term "$C_1$-$C_m$-alkyl" as used herein, and also in $C_1$-$C_m$-alkylamino, di-$C_1$-$C_m$-alkylamino, $C_1$-$C_m$-alkylaminocarbonyl, di-($C_n$-$C_m$-alkylamino)carbonyl, $C_1$-$C_m$-alkylthio, $C_1$-$C_m$-alkylsulfinyl and $C_1$-$C_m$-alkylsulfonyl, refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_1$-$C_m$-haloalkyl" as used herein, and also in $C_1$-$C_m$-haloalkylthio (=$C_1$-$C_m$-haloalkylsulfenyl), $C_1$-$C_m$-haloalkylsulfinyl and $C_1$-$C_m$-haloalkylsulfonyl, refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl. "Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

Similarly, "$C_1$-$C_m$-alkoxy", "$C_1$-$C_m$-alkylthio", or "$C_1$-$C_m$-alkylsulfenyl", respectively, "$C_1$-$C_m$-alkylsulfinyl" or "$C_1$-$C_m$-alkylsulfonyl" refer to straight-chain or branched alkyl groups having n to m carbon atoms, e.g. 1 to 10, in particular 1 to 6 or 1 to 4 carbon atoms (as mentioned above) bonded through O, S, S(=O) or S(=O)$_2$ linkages, respectively, at any bond in the alkyl group. Accordingly, the terms "$C_1$-$C_m$-haloalkoxy", "$C_1$-$C_m$-haloalkylthio" or "$C_1$-$C_m$-alkylsulfenyl", respectively, "$C_1$-$C_m$-haloalkylsulfinyl" or "$C_1$-$C_m$-haloalkylsulfonyl", refer to straight-chain or branched alkyl groups having n to m carbon atoms, e.g. 1 to 10, in particular 1 to 6 or 1 to 4 carbon atoms (as mentioned above) bonded through O, S, S(=O) or S(=O)$_2$ linkages, respectively, at any bond in the haloalkyl group, where some or all of the hydrogen atoms in these groups may be replaced by halogen atoms as mentioned above.

The term "$C_1$-$C_m$-alkoxy" is a $C_1$-$C_m$-alkyl group, as defined above, attached via an oxygen atom. $C_1$-$C_2$-Alkoxy is methoxy or ethoxy. $C_1$-$C_4$-Alkoxy is, for example, methoxy, ethoxy, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-Alkoxy includes the meanings given for $C_1$-$C_4$-alkoxy and also includes, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy includes the meanings given for $C_1$-$C_6$-alkoxy and also includes, for example, heptyloxy, octyloxy, 2-ethylhexyloxy and positional isomers thereof. $C_1$-$C_{10}$-Alkoxy includes the meanings given for $C_1$-$C_8$-alkoxy and also includes, for example, nonyloxy, decyloxy and positional isomers thereof.

The term "$C_1$-$C_m$-alkylthio" is a $C_1$-$C_m$-alkyl group, as defined above, attached via an oxygen atom. $C_1$-$C_2$-Alkylthio is methylthio or ethylthio. $C_1$-$C_4$-Alkylthio is, for example, methylthio, ethylthio, n-propylthio, 1-methylethylthio (isopropylthio), butylthio, 1-methylpropylthio (sec-butylthio), 2-methylpropylthio (isobutylthio) or 1,1-dimethylethylthio (tert-butylthio). $C_1$-$C_6$-Alkylthio includes the meanings given for $C_1$-$C_4$-alkylthio and also includes, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio includes the meanings given for $C_1$-$C_6$-alkylthio and also includes, for example, heptylthio, octylthio, 2-ethylhexylthio and positional isomers thereof. $C_1$-$C_{10}$-Alkylthio includes the meanings given for $C_1$-$C_8$-alkylthio and also includes, for example, nonylthio, decylthio and positional isomers thereof.

The term "$C_1$-$C_m$-alkylsulfinyl" is a $C_1$-$C_m$-alkyl group, as defined above, attached via a S(=O) group. The term "$C_1$-$C_m$-alkylsulfonyl" is a $C_1$-$C_m$-alkyl group, as defined above, attached via a S(=O)$_2$ group.

The term "$C_1$-$C_m$-haloalkyloxy" is a $C_1$-$C_m$-haloalkyl group, as defined above, attached via an oxygen atom. Examples include $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy.

The term "$C_1$-$C_m$-haloalkylthio" is a $C_1$-$C_m$-haloalkyl group, as defined above, attached via a sulfur atom. Examples include $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like.

Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_1$-$C_m$-haloalkylsulfinyl" is a $C_1$-$C_m$-haloalkyl group, as defined above, attached via a S(=O) group. The term "$C_1$-$C_m$-haloalkylsulfonyl" is a $C_1$-$C_m$-haloalkyl group, as defined above, attached via a S(=O)$_2$ group.

The term "$C_2$-$C_m$-alkenyl" as used herein denotes a linear or branched ethylenically unsaturated hydrocarbon group having 2 to m, e.g. 2 to 10 or 2 to 6 carbon atoms and a C=C-double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl- 2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-haloalkenyl" as used herein, which is also expressed as "$C_2$-$C_m$-alkenyl which is partially or fully halogenated", refers to $C_2$-$C_m$-alkenyl, where some or all of the hydrogen atoms in these groups are replaced by halogen atoms as mentioned above, in particular fluorine, chlorine and bromine, for example 1-fluoroethenyl, 2-fluoroethenyl, 2,2-difluoroethenyl, 1,2,2-trifluoroethenyl, 1-fluoro-2-propenyl, 2-fluoro-2-propenyl, 3-fluoro-2-propenyl, 1-fluoro-1-propenyl, 1,2-difluoro-1-propenyl, 3,3-difluoropropen-2-yl, 1-chloroethenyl, 2-chloroethenyl, 2,2,-dichloroethenyl, 1-chloro-2-propenyl, and the like.

The term "$C_2$-$C_m$-alkynyl" as used herein refers to a linear or branched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_2$-$C_m$-haloalkynyl" as used herein, which is also expressed as "$C_2$-$C_m$-alkynyl which is partially or fully halogenated", refers to $C_2$-$C_m$-alkynyl, where some or all of the hydrogen atoms in these groups are replaced by halogen atoms as mentioned above, in particular fluorine, chlorine and bromine. Examples of $C_2$-$C_m$-haloalkynyl include 1-fluoro-2-propenyl, 2-fluoro-2-propenyl, 3-fluoro-2-propenyl, 1-fluoro-2-propynyl and 1,1-difluoro-2-propenyl, and the like.

The term "$C_3$-$C_m$-cycloalkyl" as used herein refers to a monocyclic and polycyclic 3- to m-membered saturated cycloaliphatic radicals, e.g. cyclopropyl, cyclobutyl, cyclopentyl, cyclohexyl, cycloheptyl, cyclooctyl, cyclodecyl, bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "$C_3$-$C_m$-halocycloalkyl" as used herein, which is also expressed as "cycloalkyl which is partially or fully halogenated", refers $C_3$-$C_m$-cycloalkyl as mentioned above, in which some or all of the hydrogen atoms are replaced by halogen atoms as mentioned above, in particular fluorine, chlorine and bromine. Examples of $C_3$-$C_m$-halocycloalkyl include 1-fluorocycloprpyl, 2-fluorocyclopropyl, 2,2-difluorocyclopropyl, 1-chlorocyclcopropyl, 2-chlorocyclopropyl, 2,2-dichlorocyclopropyl, 2,3-difluorocyclopropyl, 1-fluorocycobutyl etc.

The term "$C_3$-$C_m$-cycloalkyl-$C_1$-$C_4$-alkyl" refers to a $C_3$-$C_m$-cycloalkyl group as defined above, which is bound to the remainder of the molecule via a $C_1$-$C_4$-alkyl group, as defined above. Examples for $C_3$-$C_m$-cycloalkyl-$C_1$-$C_4$-alkyl are cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, cyclohexylmethyl, cyclohexylethyl and cyclohexylpropyl.

The term "$C_3$-$C_m$-halocycloalkyl-$C_1$-$C_4$-alkyl" refers to a $C_3$-$C_m$-halocycloalkyl group as defined above which is bound to the remainder of the molecule via a $C_1$-$C_4$-alkyl group, as defined above.

The term "$C_1$-$C_4$-alkoxy-$C_1$-$C_4$-alkyl" as used herein refers to alkyl having 1 to 4 carbon atoms, e.g. like specific examples mentioned above, wherein one hydrogen atom of the alkyl radical is replaced by an $C_1$-$C_4$-alkoxy group. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term $C_1$-$C_4$-haloalkoxy-$C_1$-$C_4$-alkyl is a straight-chain or branched alkyl group having from 1 to 4 carbon atoms, wherein one of the hydrogen atoms is replaced by a $C_1$-$C_4$-alkoxy group and wherein at least one, e.g. 1, 2, 3, 4 or all of the remaining hydrogen atoms, either in the alkoxy moiety or in the alkyl moiety or in both, are replaced by halogen atoms. Examples are difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoro-methoxymethyl ($CH_3OCF_2$), 1,1-difluoro-2-methoxyethyl, 2,2-difluoro-2-methoxyethyl and the like.

The term "$C_1$-$C_m$-alkoxycarbonyl" is a $C_1$-$C_m$-alkoxy group, as defined above, attached via an carbonyl group atom. $C_1$-$C_2$-Alkoxycarbonyl is methoxycarbonyl or ethoxycarbonyl. $C_1$-$C_4$-Alkoxy is, for example, methoxycarbonyl, ethoxycarbonyl, n-propoxycarbonyl, 1-methylethoxycarbonyl, butoxycarbonyl, 1-methylpropoxycarbonyl, 2-methylpropoxycarbonyl or 1,1-dimethylethoxycarbonyl. $C_1$-$C_6$-Alkoxycarbonyl includes the meanings given for $C_1$-$C_4$-alkoxycarbonyl and also includes, for example, pentoxycarbonyl, 1-methylbutoxycarbonyl, 2-methylbutoxycarbonyl, 3-methylbutoxycarbonyl, 1,1-dimethylpropoxycarbonyl, 1,2-dimethylpropoxycarbonyl, 2,2-dimethylpropoxycarbonyl, 1-ethylpropoxycarbonyl, hexoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxy, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl.

The term "cycloalkenyl" as used herein refers to monocyclic hydrocarbon radicals with at least one C=C double bond in the ring, which ring is however not aromatic, the hydrocarbon radicals having 3 to 8 ("$C_3$-$C_8$-cycloalkyl) carbon atoms. Examples are cyclopropenyl, such as cycloprop-1-enyl and cycloprop-2-yl, cyclobutenyl, such as cyclobut-1-enyl and cyclobut-2-enyl, cyclopentenyl, such as cyclopent-1-enyl, cyclopent-2-enyl and cyclopent-3-enyl, cyclopentadienyl, such as cyclopenta-1,3-dienyl, cyclpenta-1,4-dienyl and cyclpenta-2,4-dienyl, cyclohexenyl, such as cyclohex-1-enyl, cyclohex-2-enyl and cyclohex-3-enyl, cyclohexadienyl, such as cyclohexa-1,3-dienyl, cyclohexa-1,4-dienyl, cyclohexa-1,5-dienyl and cyclohexa-2,5-dienyl, cycloheptenyl, cycloheptadienyl, cycloheptatrienyl cyclooctenyl, cyclooctadieny, cyclooctatrienyl and cyclooctatetraenyl.

The term "aryl" as used herein refers to an aromatic hydrocarbon radical such as naphthyl or in particular phenyl.

The term "3- to 6-membered carbocyclic ring" as used herein refers to cyclopropane, cyclobutane, cyclopentane and cyclohexane rings. The term "3- to 7-membered carbocyclic ring" as used herein refers to cyclopropane, cyclobutane, cyclopentane, cyclohexane and cycloheptane rings.

The term "3-, 4-, 5-, 6- or 7-membered saturated, partially unsaturated or aromatic heterocyclic ring containing 1, 2 or 3 heteroatoms" or "containing heteroatom groups", wherein those heteroatom(s) (group(s)) are selected from N, O, S, NO, SO and $SO_2$ and are ring members, as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclic rings include: oxiranyl, aziridinyl, azetidinyl, 2 tetrahydrofuranyl, 3-tetrahydrofuranyl, 2 tetrahydrothienyl, 3 tetrahydrothienyl, 2-pyrrolidinyl, 3-pyrrolidinyl, 3 pyrazolidinyl, 4 pyrazolidinyl, 5-pyrazolidinyl, 2 imidazolidinyl, 4 imidazolidinyl, 2-oxazolidinyl, 4-oxazolidinyl, 5 oxazolidinyl, 3-isoxazolidinyl, 4 isoxazolidinyl, 5 isoxazolidinyl, 2 thiazolidinyl, 4-thiazolidinyl, 5-thiazolidinyl, 3 isothiazolidinyl, 4-isothiazolidinyl, 5 isothiazolidinyl, 1,2,4-oxadiazolidin-3-yl, 1,2,4 oxadiazolidin 5 yl, 1,2,4-thiadiazolidin-3-yl, 1,2,4 thiadiazolidin-5-yl, 1,2,4 triazolidin-3-yl, 1,3,4-oxadiazolidin-2-yl, 1,3,4 thiadiazolidin-2-yl, 1,3,4 triazolidin-2-yl, 2-tetrahydropyranyl, 4 tetrahydropyranyl, 1,3-dioxan-5-yl, 1,4-dioxan-2-yl, 2-piperidinyl, 3-piperidinyl, 4-piperidinyl, 3-hexahydropyridazinyl, 4 hexahydropyridazinyl, 2-hexahydropyrimidinyl, 4-hexahydropyrimidinyl, 5 hexahydropyrimidinyl, 2-piperazinyl, 1,3,5-hexahydrotriazin-2-yl and 1,2,4 hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like. Examples of 3-, 4-, 5-, 6- or 7-membered partially unsaturated heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3 dihydrothien-3-yl, 2,4 dihydrothien-2-yl, 2,4-dihydrothien-3-yl, 2-pyrrolin-2-yl, 2-pyrrolin-3-yl, 3 pyrrolin-2-yl, 3-pyrrolin-3-yl, 2-isoxazolin-3-yl, 3-isoxazolin-3-yl, 4 isoxazolin 3 yl, 2-isoxazolin-4-yl, 3-isoxazolin-4-yl, 4-isoxazolin-4-yl, 2 isoxazolin-5-yl, 3-isoxazolin-5-yl, 4-isoxazolin-5-yl, 2-isothiazolin-3-yl, 3 isothiazolin-3-yl, 4-isothiazolin-3-yl, 2-isothiazolin-4-yl, 3-isothiazolin-4-yl, 4 isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3 dihydropyrazol-4-yl, 2,3-dihydropyrazol-5-yl, 3,4-dihydropyrazol-1-yl, 3,4 dihydropyrazol-3-yl, 3,4-dihydropyrazol-4-yl, 3,4-dihydropyrazol-5-yl, 4,5 dihydropyrazol-1-yl, 4,5-dihydropyrazol-3-yl, 4,5-dihydropyrazol-4-yl, 4,5 dihydropyrazol-5-yl, 2,3-dihydrooxazol-2-yl, 2,3-dihydrooxazol-3-yl, 2,3 dihydrooxazol-4-yl, 2,3-dihydrooxazol-5-yl, 3,4-dihydrooxazol-2-yl, 3,4 dihydrooxazol-3-yl, 3,4-dihydrooxazol-4-yl, 3,4-dihydrooxazol-5-yl, 3,4 dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4 di- or tetrahydropyridazinyl, 2-di- or tetrahydropyrimidinyl, 4-di- or tetrahydropyrimidinyl, 5 di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7 tetrahydro[1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclic rings, also termed heteroaromatic rings or hetaryl, include: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4 thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

A "$C_2$-$C_m$-alkylene" is divalent branched or preferably non-branched or linear saturated aliphatic chain having 2 to m, e.g. 2 to 7 carbon atoms, for example $CH_2CH_2$, —CH($CH_3$)—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$.

Embodiments of the present invention as well preferred compounds of the present invention are outlined in the following paragraphs. The remarks made below concerning preferred embodiments of the variables of the compounds of formula (I), especially with respect to their substituents X, $W^1$, $W^2$, $W^3$, $W^4$, Het, $R^1$, $R^2$, $R^3$, $R^{4a}$, $R^{4b}$ and $R^5$ and their variable k and m are valid both on their own and, in particular, in every possible combination with each other.

When # appears in a formula showing a preferred substructure of a compound of the present invention, it denotes the attachment bond in the remainder molecule.

Preferred are compounds of formula (I), wherein Het is selected from the group consisting of radicals of formulae Het-1 to Het-24, with preference given to compounds of the formula (I), their stereoisomers, there tautomers and their salts, where Het is selected from the radicals of the formulae Het-1, Het-11 and Het-24:

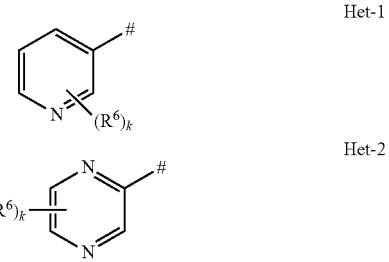

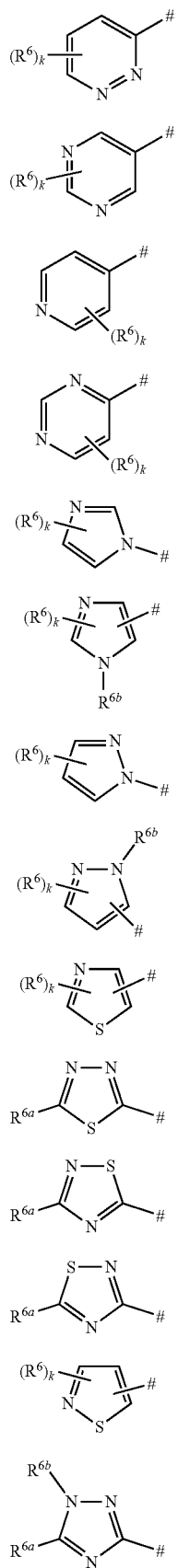

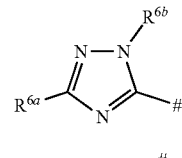
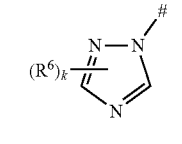
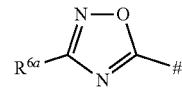
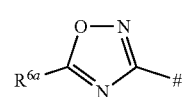
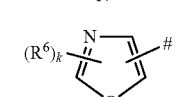
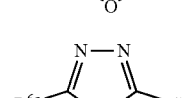
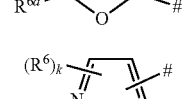
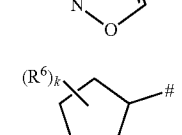

wherein # denotes the bond to the remainder of the molecule in formula (I), and wherein $R^6$ and k are as defined above and where $R^{6a}$ is hydrogen or has one of the meanings given for $R^6$ and where $R^{6b}$ is hydrogen or a C-bound radical mentioned as $R^6$ and where $R^{6b}$ is in particular hydrogen, $C_1$-$C_4$-alkyl or $C_1$-$C_4$-haloalkyl. In particular k is 0, 1 or 2, especially 0 or 1. In formulae Het-1, Het-2, Het-3, Het-4, Het-7, Het-8, Het-9, Het-10, Het-11, Het-18 and Het-21, k is especially 1. In particular $R^{6a}$ in formulae Het-12, Het-13, Het-14, Het-16, Het-17, Het-19, Het 20 and Het-22 is different from hydrogen.

Irrespectively of its occurrence, $R^6$ is preferably selected from the group consisting of halogen, cyano, $C_1$-$C_6$-alkyl, $C_3$-$C_8$-cycloalkyl, $C_2$-$C_6$-alkenyl, $C_2$-$C_6$-alkynyl, wherein the carbon atoms of the aforementioned aliphatic and cycloaliphatic radicals may optionally be partly or completely halogenated, in particular by fluorine or chlorine, or may further substituted independently from one another with one or more $R^7$, or $R^6$ may also be a radical selected from the group consisting of $OR^8$, $NR^{17a}R^{17b}$, $S(O)_nR^8$, $S(O)_nNR^{17a}R^{17b}$, $C(=O)R^{7a}$, $C(=O)NR^{17a}R^{17b}$, $C(=O)OR^8$, $C(=S)R^{7a}$, $C(=S)NR^{17a}R^{17b}$, $C(=NR^{17})R^{7a}$, $C(=NR^{17})NR^{17a}R^{17b}$. Irrespectively of its occurrence, $R^6$ is in particular selected from the group consisting of halogen, such as chlorine or fluorine, $C_1$-$C_4$-alkyl, such as methyl or ethyl, $C_1$-$C_4$-alkoxy, such as methoxy or ethoxy, $C_1$-$C_4$-haloalkoxy, such as difluoromethoxy or trifluoromethoxy, and $C_1$-$C_4$-haloalkyl, such as difluoromethyl, trifluoromethyl, 2,2-difluoroethyl, 2,2,2-trifluoroethyl or pentafluoroethyl, more preferably from halogen, $C_1$-$C_4$-alkyl and $C_1$-$C_4$-haloalkyl, even more preferably from fluorine, chlorine, $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl.

Irrespectively of its occurrence, $R^{6a}$ is preferably selected from the group consisting of hydrogen, halogen, cyano, $C_1$-$C_6$-alkyl, $C_3$-$C_8$-cycloalkyl, $C_2$-$C_6$-alkenyl and $C_2$-$C_6$-alkynyl, wherein the carbon atoms of the aforementioned aliphatic and cycloaliphatic radicals may optionally be partly or completely halogenated, in particular by fluorine or chlorine, or may further substituted independently from one another with one or more $R^7$, or $R^{6a}$ may also be a radical selected from the group consisting of $OR^8$, $NR^{17a}R^{17b}$, $S(O)_nR^8$, $S(O)_nNR^{17a}R^{17b}$, $C(=O)R^{7a}$, $C(=O)NR^{17a}R^{17b}$, $C(=O)OR^8$, $C(=S)R^{7a}$, $C(=S)NR^{17a}R^{17b}$, $C(=NR^{17})R^{7a}$, $C(=NR^{17})NR^{17a}R^{17b}$. Irrespectively of its occurrence, $R^{6a}$ is in particular selected from the group consisting of hydrogen, halogen, such as chlorine or fluorine, $C_1$-$C_4$-alkyl, such as methyl or ethyl, $C_1$-$C_4$-alkoxy, such as methoxy or ethoxy, $C_1$-$C_4$-haloalkoxy, such as difluoromethoxy or trifluoromethoxy, and $C_1$-$C_4$-haloalkyl, such as difluoromethyl, trifluoromethyl, 2,2-difluoroethyl, 2,2,2-trifluoroethyl or pentafluoroethyl, more preferably from halogen, $C_1$-$C_4$-alkyl and $C_1$-$C_4$-haloalkyl, even more preferably from fluorine, chlorine, $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl.

Irrespectively of its occurrence, $R^{6b}$ is in particular selected from the group consisting of hydrogen, $C_1$-$C_4$-alkyl, such as methyl or ethyl, and $C_1$-$C_4$-haloalkyl, such as difluoromethyl, trifluoromethyl, 2,2-difluoroethyl, 2,2,2-trifluoroethyl or pentafluoroethyl, more preferably $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl.

Particularly preferred are compounds of formula (I), wherein Het is selected from the group consisting of radicals of formulae Het-1, Het-11a and Het-24,

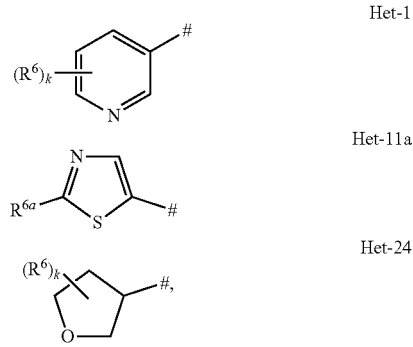

where
R$^6$ is selected from the group consisting of halogen, such as chlorine or fluorine, $C_1$-$C_4$-alkyl, such as methyl or ethyl, $C_1$-$C_4$-alkoxy, such as methoxy or ethoxy, $C_1$-$C_4$-haloalkoxy, such as difluoromethoxy or trifluoromethoxy, and $C_1$-$C_4$-haloalkyl, such as difluoromethyl, trifluoromethyl, 2,2-difluoroethyl, 2,2,2-trifluoroethyl or pentafluoroethyl, more preferably from halogen, $C_1$-$C_4$-alkyl and $C_1$-$C_4$-haloalkyl, even more preferably from fluorine, chlorine, $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl; and where $R^{6a}$ is selected from the group consisting of hydrogen, halogen, such as chlorine or fluorine, $C_1$-$C_4$-alkyl, such as methyl or ethyl, $C_1$-$C_4$-alkoxy, such as methoxy or ethoxy, $C_1$-$C_4$-haloalkoxy, such as difluoromethoxy or trifluoromethoxy, and $C_1$-$C_4$-haloalkyl, such as difluoromethyl, trifluoromethyl, 2,2-difluoroethyl, 2,2,2-trifluoroethyl or pentafluoroethyl, more preferably from halogen, $C_1$-$C_4$-alkyl and $C_1$-$C_4$-haloalkyl, even more preferably from fluorine, chlorine, $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl and k is 0, 1 or 2.

A particularly preferred group of embodiments relates to compounds of formula (I) to the stereoisomers, the tautomers and to the salts thereof, wherein Het is a radical of formula Het-1, where k is 0, 1 or 2, in particular 1 or 2 and especially 1 and where $R^6$ is as defined above and in particular selected from the group consisting of halogen, such as chlorine or fluorine, $C_1$-$C_4$-alkyl, such as methyl or ethyl, $C_1$-$C_4$-alkoxy, such as methoxy or ethoxy, $C_1$-$C_4$-haloalkoxy, such as difluoromethoxy or trifluoromethoxy, and $C_1$-$C_4$-haloalkyl, such as difluoromethyl, trifluoromethyl, 2,2-difluoroethyl, 2,2,2-trifluoroethyl or pentafluoroethyl, more preferably from halogen, $C_1$-$C_4$-alkyl and $C_1$-$C_4$-haloalkyl, even more preferably from fluorine, chlorine, $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl. Amongst the compounds of this particular group of embodiments, a particular sub-group of embodiments relates to compounds of the formula (I), to the stereoisomers, the tautomers and to the salts thereof, wherein Het is a radical of formula Het-1a

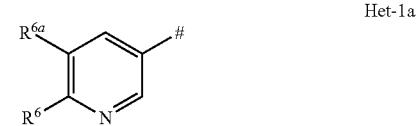

where
$R^6$ is as defined above and in particular selected from the group consisting of halogen, such as chlorine or fluorine, $C_1$-$C_4$-alkyl, such as methyl or ethyl, and $C_1$-$C_4$-haloalkyl, such as difluoromethyl, trifluoromethyl, 2,2-difluoroethyl, 2,2,2-trifluoroethyl or pentafluoroethyl, and even more preferably from fluorine, chlorine, $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl;

$R^{6a}$ is as defined above and in particular selected from the group consisting of hydrogen, halogen, such as chlorine or fluorine and $C_1$-$C_4$-alkyl, such as methyl or ethyl, more preferably is hydrogen.

A special embodiment of the radical Het-1a is 6-chloropyridin-3-yl, i.e. $R^{6a}$ is hydrogen and $R^6$ is chlorine. A further special embodiment of the radical Het-1a is 6-(trifluoromethyl)pyridin-3-yl, i.e. $R^{6a}$ is hydrogen and $R^6$ is trifluoromethyl.

Another particularly preferred group of embodiments relates to compounds of formula (I) to the stereoisomers, the tautomers and to the salts thereof, wherein Het is a radical of formula Het-11, where k is 0, 1 or 2, in particular 0 or 1, and where Het is in particular a radical of formula Het-1a,

Het 11a where $R^{6a}$ is as defined above and wherein $R^{6a}$ is in particular selected from the group consisting of hydrogen, halogen, such as chlorine or fluorine, $C_1$-$C_4$-alkyl, such as methyl or ethyl, $C_1$-$C_4$-alkoxy, such as methoxy or ethoxy, $C_1$-$C_4$-haloalkoxy, such as difluoromethoxy or trifluoromethoxy, and $C_1$-$C_4$-haloalkyl, such as difluoromethyl, trifluoromethyl, 2,2-difluoroethyl, 2,2,2-trifluoroethyl or pentafluoroethyl, more preferably from halogen, $C_1$-$C_4$-alkyl and $C_1$-$C_4$-haloalkyl, even more preferably from fluorine, chlorine, $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl. A special embodiment of the radical Het-11a is 2-chlorothiazol-5-yl, i.e. $R^{6a}$ is chlorine.

Another particularly preferred group of embodiments relates to compounds of formula (I) to the stereoisomers, the tautomers and to the salts thereof, wherein Het is a radical of formula Het-24, where k is 0, 1 or 2, in particular 0 or 1, and where $R^6$, if present, is as defined above and in particular selected from the group consisting of halogen, such as chlorine or fluorine, $C_1$-$C_4$-alkyl, such as methyl or ethyl, and $C_1$-$C_4$-haloalkyl, such as difluoromethyl, trifluoromethyl, 2,2-difluoroethyl, 2,2,2-trifluoroethyl or pentafluoroethyl, and even more preferably from fluorine, chlorine, $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl.

Preferred are compounds of formula (I), wherein $R^1$ and $R^2$ are independently from each other selected from the group consisting of hydrogen, halogen, such as fluorine or chlorine, CN, $C_1$-$C_6$-alkyl, in particular $C_1$-$C_4$-alkyl, such as methyl, ethyl, n-propyl or isopropyl, $C_3$-$C_6$-cycloalkyl, such as cyclopropyl or cyclobutyl, $C_1$-$C_6$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, or $C_3$-$C_6$-halocycloalkyl such as 1-fluorocyclopropyl or 2,2-difluorocyclopropyl.

Preferred are also compounds of formula (I), wherein $R^1$ and $R^2$ may together be =$CR^{13}R^{14}$.

Preferred are also compounds of formula (I), wherein $R^1$ and $R^2$ form, together with the carbon atom, which they attached to, a 3- to 5 membered saturated carbocyclic ring such as cyclopropyl, cyclobutyl or cyclopentyl.

Even more preferred are compounds of formula (I), wherein $R^1$ and $R^2$ are independently from each other selected from the group consisting of hydrogen, halogen, cyano, $C_1$-$C_3$-alkyl, such as methyl ethyl or isopropyl, or $C_1$-$C_3$-haloalkyl such as fluoromethyl, difluoromethyl, trifluoromethyl, 1,1-difluoroethyl, 2-fluoroethyl, 2,2-difluoroethyl or 2,2,2-trifluoroethyl.

Preferably at least one of the radicals $R^1$ and $R^2$ is hydrogen.

Especially more preferred are compounds of formula (I), wherein $R^1$ and $R^2$ are both hydrogen.

Especially more preferred are also compounds of formula (I), wherein one of $R^1$ and $R^2$ is methyl while the other is hydrogen.

According to a first group of embodiments A, compounds of formula (I) are preferred, wherein $R^3$ is selected from the group consisting of hydrogen, halogen, CN, $C_1$-$C_6$-alkyl, in particular $C_1$-$C_4$-alkyl, $C_1$-$C_6$-haloalkyl, in particular $C_1$-$C_4$-haloalkyl, $C_3$-$C_6$-cycloalkyl, such as cyclopropyl or cyclobutyl, $C_3$-$C_6$-halocycloalkyl, such as 1-fluorocyclopropyl, 2-fluorocyclopropyl, 2,2-difluorocyclopropyl, 2-chlorocyclopropyl, 2,2-dichlorocyclopropyl, 1-fluorocyclobutyl, 2-fluorocyclobutyl, 3-fluorocyclobutyl, 2,2-difluorocyclobutyl or 3,3-difluorocyclobutyl, $NR^{9a}R^{9b}$ and $NR^{9a}$—C(=O)$R^{7a}$.

In the context of $R^3$, the radicals $R^{7a}$ is preferably selected from the group consisting of hydrogen, $C_1$-$C_4$-alkyl, such as methyl, ethyl, n-propyl, isopropyl, n-butyl, 2-butyl or isobutyl, and $C_1$-$C_4$-haloalkyl, such as fluoromethyl, difluoromethyl, trifluoromethyl, 1,1-difluoroethyl, 2-fluoroethyl, 2,2-difluoroethyl or 2,2,2-trifluoroethyl. In the context of $R^3$, the radicals $R^{9a}$ and $R^{9b}$ are preferably selected from the group consisting of hydrogen, $C_1$-$C_4$-alkyl, such as methyl, ethyl, n-propyl, isopropyl, n-butyl, 2-butyl or isobutyl, and $C_1$-$C_4$-haloalkyl, such as fluoromethyl, difluoromethyl, trifluoromethyl, 1,1-difluoroethyl, 2-fluoroethyl, 2,2-difluoroethyl or 2,2,2-trifluoroethyl, or $NR^{9a}R^{9b}$ may also be a saturated N-bound 3-, 4-, 5- or 6-membered heterocycle, which in addition to the nitrogen atom may have 1 further heteroatom as ring members, which is selected from O and N and where the N-bound 3-, 4-, 5- or 6-membered heterocycle may be unsubstituted or carry 1, 2, 3 or 4 radicals selected from $C_1$-$C_4$-alkyl and $C_1$-$C_4$-haloalkyl. Examples of radicals $NR^{9a}R^{9b}$ include, but are not limited to methylamino, ethylamino, n-propylamino, isopropylamino, n-butylamino, 2-butylamino, isobutylamino, dimethylamino, diethylamino, di-n-propylamino, di-n-butylamino, N-methyl-N-ethylamino, N-methyl-N-propylamino, N-methyl-N-n-propylamino, N-methyl-N-isopropylamino, N-methyl-N-n-butylamino, N-methyl-N-2-butylamino, N-methyl-N-isobutylamino, 1-pyrrolidinyl, 1-piperidinyl, 1-piperazinly, 4-methyl-1-piperazinly and 4-morpholinyl. Examples of radicals $NR^{9a}C(=O)R^{7a}$ include, but are not limited NH—C(=O)H, NH—C(=O)CH$_3$, NH—C(=O)CH$_2$CH$_3$ and NH—C(=O)CH(CH$_3$)$_2$.

In this group of embodiments A, the radical $R^3$ is in particular selected from the group consisting of hydrogen, fluorine, chlorine, $C_1$-$C_4$-alkyl, such as methyl, ethyl, n-propyl, isopropyl or n-butyl, NHC(=O)—$C_1$-$C_4$-alkyl, such as NH—C(=O)H, NH—C(=O)CH$_3$, NH—C(=O)CH$_2$CH$_3$ or NH—C(=O)CH(CH$_3$)$_2$, and CN.

In this group of embodiments A, the radical $R^3$ is especially selected from the group consisting of hydrogen and $C_1$-$C_4$-alkyl, such as methyl, ethyl, n-propyl, isopropyl or n-butyl.

In this group of embodiments A, preference is given to compounds of formula (I), wherein $R^5$ is selected from the group consisting of hydrogen, halogen, CN, $NR^{9a}R^{9b}$, $C_1$-$C_6$-alkyl, in particular $C_1$-$C_4$-alkyl, $C_1$-$C_6$-haloalkyl, in particular $C_1$-$C_4$-haloalkyl, $C_3$-$C_6$-cycloalkyl, $C_3$-$C_6$-halocycloalkyl, C(=O)O$R^8$, C(=O)$NR^{9a}R^{9b}$, C(=S)$NR^{9a}R^{9b}$, C(=O)$R^{7a}$, C(=S)$R^{7a}$, Q-phenyl, where phenyl is unsubstituted or substituted with 1, 2, 3, 4 or 5 identical or different substituents $R^{10}$, or Q-Het$^\#$, where Het$^\#$ is unsubstituted or substituted with 1, 2, 3, 4 or 5 identical or different substituents $R^{10}$, and where Q, irrespectively of its occurrence, is a bond, $NR^{9a}$, such as NH or N(CH$_3$) $NR^{9a}$—C(=O), such as NH—C(=O)H, NH—C(=O)CH$_3$, NH—C(=O)CH$_2$CH$_3$ or NH—C(=O)CH(CH$_3$)$_2$, OC(=O), NR$^{9a}$CH$_2$, such as NHCH$_2$ or N(CH$_3$)CH$_2$, OC(=O)CH$_2$, or NR$^{9a}$C(=O)CH$_2$ such as NHC(=O)CH$_2$.

In context of R$^5$, Het$^\#$ is preferably 5- or 6-membered hetaryl such as pyridyl, thienyl, furyl, pyrrolyl, thiazolyl, isothiazolyl, pyrazolyl, imidazolyl, oxazolyl or isoxazolyl, which is unsubstituted or substituted by 1, 2 or 3 radicals R$^{10}$. In this context, R$^{10}$ is preferably selected from the group consisting of halogen, such as chlorine or fluorine, CN, C$_1$-C$_4$-alkyl, such as methyl, ethyl, n-propyl and isopropyl, C$_1$-C$_4$-haloalkyl, in particular C$_1$-C$_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, C$_1$-C$_4$-alkoxy, such as methoxy, ethoxy, n-propoxy and isopropoxy, and C$_1$-C$_4$-haloalkoxy, in particular C$_1$-C$_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

In context of R$^5$, the radical R$^{7a}$ is preferably selected from the group consisting of hydrogen, C$_1$-C$_4$-alkyl, C$_1$-C$_4$-haloalkyl, C$_3$-C$_6$-cycloalkyl, C$_3$-C$_6$-cycloalkyl-C$_1$-C$_4$-alkyl, phenyl and benzyl, where the phenyl ring in the last two radicals is unsubstituted or substituted by 1, 2 or 3 identical or different radicals selected from the group consisting of halogen, such as chlorine or fluorine, CN, C$_1$-C$_4$-alkyl, such as methyl, ethyl, n-propyl and isopropyl, C$_1$-C$_4$-haloalkyl, in particular C$_1$-C$_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, C$_1$-C$_4$-alkoxy, such as methoxy, ethoxy, n-propoxy and isopropoxy, and C$_1$-C$_4$-haloalkoxy, in particular C$_1$-C$_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy. R$^{7a}$ is in particular C$_1$-C$_4$-alkyl.

In context of R$^5$, the radical R$^8$ is preferably selected from the group consisting of C$_1$-C$_4$-alkyl, C$_1$-C$_4$-haloalkyl, C$_3$-C$_6$-cycloalkyl, C$_3$-C$_6$-cycloalkyl-C$_1$-C$_4$-alkyl, phenyl and benzyl, where the phenyl ring in the last two radicals is unsubstituted or substituted by 1, 2 or 3 identical or different radicals selected from the group consisting of halogen, such as chlorine or fluorine, CN, C$_1$-C$_4$-alkyl, such as methyl, ethyl, n-propyl and isopropyl, C$_1$-C$_4$-haloalkyl, in particular C$_1$-C$_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, C$_1$-C$_4$-alkoxy, such as methoxy, ethoxy, n-propoxy and isopropoxy, and C$_1$-C$_4$-haloalkoxy, in particular C$_1$-C$_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy. R$^8$ is in particular C$_1$-C$_4$-alkyl.

In context of R$^5$, the radicals R$^{9a}$ and R$^{9b}$ are preferably selected from the group consisting of hydrogen, C$_1$-C$_4$-alkyl, such as methyl, ethyl, n-propyl, isopropyl, n-butyl, 2-butyl or isobutyl, and C$_1$-C$_4$-haloalkyl, such as fluoromethyl, difluoromethyl, trifluoromethyl, 1,1-difluoroethyl, 2-fluoroethyl, 2,2-difluoroethyl or 2,2,2-trifluoroethyl, or NR$^{9a}$R$^{9b}$ may also be a saturated N-bound 3-, 4-, 5- or 6-membered heterocycle, which in addition to the nitrogen atom may have 1 further heteroatom as ring members, which is selected from O and N and where the N-bound 3-, 4-, 5- or 6-membered heterocycle may be unsubstituted or carry 1, 2, 3 or 4 radicals selected from C$_1$-C$_4$-alkyl and C$_1$-C$_4$-haloalkyl. Examples of such radicals NR$^{9a}$R$^{9b}$ include, but are not limited to methylamino, ethylamino, n-propylamino, isopropylamino, n-butylamino, 2-butylamino, isobutylamino, dimethylamino, diethylamino, di-n-propylamino, di-n-butylamino, N-methyl-N-ethylamino, N-methyl-N-propylamino, N-methyl-N-n-propylamino, N-methyl-N-isopropylamino, N-methyl-N-n-butylamino, N-methyl-N-2-butylamino, N-methyl-N-isobutylamino, 1-pyrrolidinyl, 1-piperidinyl, 1-piperazinly, 4-methyl-1-piperazinly and 4-morpholinyl.

In context of R$^5$, the radical R$^{10}$ is preferably selected from the group consisting of halogen, such as chlorine or fluorine, CN, C$_1$-C$_4$-alkyl, such as methyl, ethyl, n-propyl and isopropyl, C$_1$-C$_4$-haloalkyl, in particular C$_1$-C$_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, C$_1$-C$_4$-alkoxy, such as methoxy, ethoxy, n-propoxy and isopropoxy, and C$_1$-C$_4$-haloalkoxy, in particular C$_1$-C$_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

In this group of embodiments A, the radical R$^5$ is in particular selected from the group consisting of hydrogen, halogen, such as fluorine or chlorine, CN, C$_1$-C$_6$-alkyl, in particular C$_1$-C$_4$-alkyl, such as methyl, ethyl, n-propyl, isopropyl, n-butyl, 2-butyl or isobutyl, C$_1$-C$_6$-haloalkyl, in particular C$_1$-C$_4$-haloalkyl, such as fluoromethyl, difluoromethyl, trifluoromethyl, 1,1-difluoroethyl, 2-fluoroethyl, 2,2-difluoroethyl or 2,2,2-trifluoroethyl, C$_3$-C$_6$-cycloalkyl, such as cyclopropyl, cyclobutyl, cyclopentyl or cyclohexyl, C$_3$-C$_6$-halocycloalkyl, such as 1-fluorocyclopropyl, 2-fluorocyclopropyl, 2,2-difluorocyclopropyl, 2-chlorocyclopropyl, 2,2-dichlorocyclopropyl, 1-fluorocyclobutyl, 2-fluorocyclobutyl, 3-fluorocyclobutyl, 2,2-difluorocyclobutyl or 3,3-difluorocyclobutyl, and phenyl, which is unsubstituted or carries 1, 2, 3, 4 or 5 identical or different substituents R$^{10}$.

The variable m is preferably 0, 1 or 2, in particular with regard to the group of embodiments A.

If R$^{4a}$ and R$^{4b}$ are present, i.e. if m is different from 0 and in particular 1 or 2, and especially 1, the variables R$^{4a}$ and R$^{4b}$ are in particular selected, independently from one another, from the group consisting of hydrogen, C$_1$-C$_4$-alkyl, in particular methyl, and halogen, in particular fluorine or chlorine, or R$^{4a}$ and R$^{4b}$ together are =O.

According to a second group of embodiments B, compounds of formula (I) are preferred, wherein
R$^3$ and R$^5$ together with the carbon atom, to which they are bound, form a 3, 4, 5 or 6 membered saturated carbocycle, in particular a 3-membered carbocycle, wherein the carbocycle may be unsubstituted or may carry 1, 2, 3, 4, 5 or 6 radicals R$^{7b}$, wherein R$^{7b}$ is as defined above and wherein
R$^{7b}$ is in particular selected from the group consisting of halogen, C$_1$-C$_6$-alkyl, C$_1$-C$_6$-alkoxy, and C$_2$-C$_6$-alkynyl, and wherein the carbon atoms of the aforementioned aliphatic radicals may optionally be partly or completely halogenated and/or substituted by a radical selected from C$_1$-C$_4$-alkoxy, C$_1$-C$_4$-alkoxycarbonyl, C$_1$-C$_4$-alkylcarbonyloxy, C$_1$-C$_4$-alkoxy-C$_1$-C$_4$-alkoxy, C$_1$-C$_4$-alkylsulfanyl, C$_3$-C$_6$-cycloalkyl, C$_3$-C$_6$-cycloalkoxy, phenoxy, 5- or 6-membered saturated heterocyclyl having 1 heteroatom selected from O and S, such as tetrahydropyranyl, tetrahydrofuranyl and tetrahydrothiopyranyl, where the 5- or 6-membered saturated heterocyclyl may be unsubstituted or carry 1 or 2 radicals selected from C$_1$-C$_4$-alkyl and C$_1$-C$_4$-alkoxy, and wherein one or two radicals R$^{7b}$ may also be
C$_3$-C$_8$-cycloalkyl, in particular C$_3$-C$_6$-cycloalkyl, which is unsubstituted or carries 1, 2, 3, 4 or 5 radicals selected from fluorine, chlorine, $C_1$-$C_4$-alkyl such as methyl and $C_1$-$C_4$-alkoxycarbonyl such as methoxycarbonyl, $C_3$-$C_6$-cycloalkenyl, which is unsubstituted or carries 1, 2, 3, 4 or 5 radicals selected from fluorine, chlorine or $C_1$-$C_4$-alkyl such as methyl, phenyl, optionally substituted with 1, 2, 3, 4 or 5 identical or different substituents $R^{10b}$, or a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, such as tetrahydrofuryl, tetrahydropyranyl, tetrahydrothiopyranyl or thiazolyl, where the heterocyclic ring is optionally substituted with 1, 2, 3 or 4 identical or different substituents $R^{10b}$, and wherein the nitrogen and/or the sulfur atom(s) of the heterocyclic ring may optionally be oxidized, in particular a 5- or 6-membered hetaryl having 1 or 2 heteroatoms selected from O, S and N, where the 5- or 6-membered hetaryl is unsubstituted or carries 1, 2 or 3 identical or different substituents $R^{10b}$, or two of $R^{7b}$ present on one ring carbon may together form =O or =S, or two $R^{7b}$ together form a linear $C_2$-$C_7$ alkylene chain, thus forming, together with the carbon atom to which they are bound, a 3-, 4-, 5- or 6-membered spiro ring, where 1 or 2 $CH_2$ moieties of the alkylene chain may be replaced by 1 or 2 heteroatom moieties selected from O and S, and where the alkylene chain is unsubstituted or may be substituted with 1, 2, 3, 4, 5 or 6 radicals selected from the group consisting of halogen, $C_1$-$C_4$-alkyl, $C_1$-$C_4$-haloalkyl, $C_1$-$C_4$-alkoxy and $C_1$-$C_4$-haloalkoxy, where $R^{10b}$ has one of the meanings give for $R^{10}$ and where $R^{10b}$ is in particular selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy, in particular, wherein $R^3$ and $R^5$ together with the carbon atom, to which they are bound, form a 3, 4, 5 or 6 membered saturated carbocycle, in particular a 3-membered carbocycle, wherein the carbocycle may be unsubstituted or may carry 1, 2, 3, 4, 5 or 6 radicals $R^{7b}$, wherein $R^{7b}$ is as defined above and wherein $R^{7b}$ is in particular selected from the group consisting of halogen, $C_1$-$C_6$-alkyl, $C_1$-$C_6$-alkoxy, and $C_2$-$C_6$-alkynyl, and wherein the carbon atoms of the aforementioned aliphatic radicals may optionally be partly or completely halogenated, and wherein one or two radicals $R^{7b}$ may also be $C_3$-$C_8$-cycloalkyl, in particular $C_3$-$C_6$-cycloalkyl, which is unsubstituted or carries 1, 2, 3, 4 or 5 radicals selected from fluorine, chlorine or methyl, phenyl, optionally substituted with 1, 2, 3, 4 or 5 identical or different substituents $R^{10b}$, or a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, such as tetrahydrofuryl, tetrahydropyranyl, tetrahydrothiopyranyl or thiazolyl, where the heterocyclic ring is optionally substituted with 1, 2, 3 or 4 identical or different substituents $R^{10b}$, and wherein the nitrogen and/or the sulfur atom(s) of the heterocyclic ring may optionally be oxidized, in particular a 5- or 6-membered hetaryl having 1 or 2 heteroatoms selected from O, S and N, where the 5- or 6-membered hetaryl is unsubstituted or carries 1, 2 or 3 identical or different substituents $R^{10b}$, or two of $R^{7b}$ present on one ring carbon may together form =O or =S, or two $R^{7b}$ together form a linear $C_2$-$C_7$ alkylene chain, thus forming, together with the carbon atom to which they are bound, a 3-, 4-, 5- or 6-membered spiro ring, where 1 or 2 $CH_2$ moieties of the alkylene chain may be replaced by 1 or 2 heteroatom moieties selected from O and S, and where the alkylene chain is unsubstituted or may be substituted with 1, 2, 3, 4, 5 or 6 radicals selected from the group consisting of halogen, $C_1$-$C_4$-alkyl, $C_1$-$C_4$-haloalkyl, $C_1$-$C_4$-alkoxy and $C_1$-$C_4$-haloalkoxy, where $R^{10b}$ has one of the meanings give for $R^{10}$ and where $R^{10b}$ is in particular selected from the group consisting of halogen, $C_1$-$C_4$-alkyl, $C_1$-$C_4$-haloalkyl, $C_1$-$C_4$-alkoxy and $C_1$-$C_4$-haloalkoxy.

According to the second group of embodiments B, particular preference is given to compounds of formula (I), wherein $R^3$ and $R^5$ together with the carbon atom, to which they are bound, form a 3 or 4 membered saturated carbocycle, i.e. a 1,1-cyclopropylidene or 1,1-cyclobutylidene radical, in particular a 1,1-cyclopropylidene radical wherein the carbocycle may be unsubstituted or may carry 1, 2, 3, 4, 5 or 6 radicals $R^{7b}$, wherein $R^{7b}$ is as defined above and in particular selected from the group consisting of halogen, $C_1$-$C_6$-alkyl, $C_1$-$C_6$-haloalkyl, $C_1$-$C_4$-alkoxy-$C_1$-$C_4$-alkyl, $C_1$-$C_4$-alkoxycarbonyl, and wherein one radical $R^{7b}$ may also be $C_3$-$C_6$-cycloalkyl, which is unsubstituted or carries 1, 2, 3, 4 or 5 radicals selected from fluorine, chlorine, $C_1$-$C_4$-alkyl such as methyl, or $C_1$-$C_4$-alkoxycarbonyl, or phenyl, optionally substituted with 1, 2, 3, 4 or 5, in particular 1, 2 or 3, identical or different substituents $R^{10b}$, where $R^{10b}$ is as defined above, and in particular selected from the group consisting of halogen, such as fluorine or chlorine, $C_1$-$C_4$-alkyl, CN, $C_1$-$C_4$-haloalkyl, $C_1$-$C_4$-alkoxy and $C_1$-$C_4$-haloalkoxy.

According to the second group of embodiments B, more preference is given to compounds of formula (I), wherein $R^3$ and $R^5$ together with the carbon atom, to which they are bound, form a 3 or 4 membered saturated carbocycle, i.e. a 1,1-cyclopropylidene or 1,1-cyclobutylidene radical, in particular a 1,1-cyclopropylidene radical wherein each of the carbon atoms of the carbocycle may be unsubstituted or may carry 1, 2, 3, 4, 5 or 6 radicals $R^{7b}$, wherein $R^{7b}$ is as defined above and in particular selected from the group consisting of halogen, $C_1$-$C_4$-alkyl, and wherein one radical $R^{7b}$ may also be phenyl, optionally substituted with 1, 2, 3, 4 or 5, in particular 1, 2 or 3, identical or different substituents $R^{10b}$, where $R^{10b}$ is as defined above, and in particular selected from the group consisting of halogen, such as fluorine or chlorine, $C_1$-$C_4$-alkyl, CN, $C_1$-$C_4$-haloalkyl, $C_1$-$C_4$-alkoxy and $C_1$-$C_4$-haloalkoxy.

According to the second group of embodiments B, even more particular preference is given to compounds of formula (I), wherein $R^3$ and $R^5$ together form the following moieties: $CH_2$—$CH_2$, CHF—$CH_2$, $CF_2$—$CH_2$, CHF—CHF, $CF_2$—CHF, $CF_2$—$CF_2$, CHCl—$CH_2$, $CCl_2$—$CH_2$, CHCl—CHCl, $CCl_2$—$CHCl$, $CCl_2$—$CCl_2$, $CH(CH_3)$—$CH_2$, $C(CH_3)_2$—$CH_2$, $CH(CH_3)$—$CH(CH_3)$, $C(CH_3)_2$—$CH(CH_3)$, $C(CH_3)_2$—$C(CH_3)_2$, $CH(OCH_3)$—$CH_2$, $CH(CH_2CH_3)$—$CH_2$, $CH(CH_2CH_2CH_3)$—$CH_2$, $CH(CH_2CH_2CH_2CH_3)$—$CH_2$, $CH(CH_3)$—$CH_2$—$CH_2$, $CH_2$—$CH(CH_3)$—$CH_2$, $C(CH_3)_2$—$CH_2$—$CH_2$, $CH_2$—$C(CH_3)_2$—$CH_2$, $CH(CH_3)$—$CH(CH_3)$—$CH_2$, $CH(CH_3)$—$CH_2$—$CH(CH_3)$, $CH(CH_3)$—$CH(CH_3)$—$CH(CH_3)$, $CH(CH_3)$—$CH(CH_3)$, $C(CH_3)_2$—$CH(CH_3)$—$CH_2$, $CH(CH_3)$—$C(CH_3)_2$—$CH_2$, $C(CH_3)_2$—$CH_2$—$C(CH_3)_2$, $C(CH_3)_2$—$C(CH_3)_2$—$CH_2$, $C(CH_3)_2$—$C(CH_3)_2$—$C(CH_3)_2$, $CHF$—$CH_2$—$CH_2$, $CH_2$—$CHF$—$CH_2$, $CF_2$—$CH_2$—$CH_2$, $CH_2$—$CF_2$—$CH_2$, $CHF$—$CHF$—$CH_2$, $CHF$—$CH_2$—$CHF$, $CHF$—$CHF$—$CHF$, $CF_2$—$CHF$—$CH_2$, $CHF$—$CF_2$—$CH_2$, $CF_2$—$CH_2$—$CF_2$, $CF_2$—$CF_2$—$CH_2$, $CF_2$—$CF_2$—$CF_2$, $CHCl$—$CH_2$—$CH_2$, $CH_2$—$CHCl$—$CH_2$, $CCl_2$—$CH_2$—$CH_2$, $CH_2$—$CCl_2$—$CH_2$, $CHCl$—$CHCl$—$CH_2$, $CHCl$—$CH_2$—$CHCl$, $CHCl$—$CHCl$—$CHCl$, $CCl_2$—$CHCl$—$CH_2$, $CHCl$—$CCl_2$—$CH_2$, $CCl_2$—$CH_2$—$CCl_2$, $CCl_2$—$CCl_2$—$CH_2$, $CCl_2$—$CCl_2$—$CCl_2$, a radical $CH(R^{7bb})$—$CH_2$, where $R^{7bb}$ is selected from the group consisting of

- $C_2$-$C_{10}$-alkyl, such as ethyl, n-propyl, isopropyl, n-butyl, tert.butyl, 1-methylpropyl, 2-methylpropyl, 1,2-dimethylpropyl, 2,2-dimethylpropyl, 3,3-dimethylpropyl, 1-methylbutyl, 1,2-dimethylbutyl, 3,3-dimethylbutyl, n-pentyl, 1-ethylpentyl,
- $C_2$-$C_4$-haloalkyl, such as 2,2-difluoroethyl, 1,1-difluoroethyl or 2,2,2-trifluoroethyl,
- $C_1$-$C_6$-alkyl, which is substituted by 1 radical selected from $C_1$-$C_4$-alkoxy, $C_1$-$C_4$-alkylcarbonyloxy, $C_1$-$C_4$-alkoxy-$C_1$-$C_4$-alkoxy, $C_1$-$C_4$-alkylsulfanyl, $C_3$-$C_8$-cycloalkyl, $C_3$-$C_8$-cycloalkoxy, phenoxy and 5- or 6-membered saturated heterocyclyl having 1 heteroatom selected from O and S, such as tetrahydropyranyl, tetrahydrofuranyl, tetrahydrothiopyranyl, where $C_3$-$C_8$-cycloalkyl, $C_3$-$C_8$-cycloalkoxy and 5- or 6-membered saturated heterocyclyl may be unsubstituted or carry 1 or 2 radicals selected from $C_1$-$C_4$-alkyl and $C_1$-$C_4$-alkoxy, examples of substituted $C_1$-$C_6$-alkyl including 1-methoxyethyl, 2-methoxyethyl, 1-propoxyethyl, 2-propoxyethyl, 1-isopropoxyethyl, 2-isopropoxyethyl, 1-isobutoxyethyl, 2-isobutoxyethyl, 1-(cyclohexyloxy)ethyl, 2-phenoxyethyl, (4-isopropylcyclohexyl)methyl, 1-acetoxyethyl, 2-acetoxyethyl, 6-acetoxyhexyl, 2-methylsulfanylpropyl, 1-methyl-2-methylsulfanylethyl, tetrahydropyran-4-ylmethyl, tetrahydrothiopyran-4-ylmethyl,
- $C_2$-$C_{10}$-alkenyl, such as 3-nonenyl,
- $C_3$-$C_{10}$-cycloalkyl, optionally substituted by 1 or 2 $C_1$-$C_4$-alkyl, such as cyclopropyl, cyclobutyl, cyclopentyl, cyclohexyl, cycloheptyl, cyclooctyl, 4-methylcyclohexyl, 4-isopropylcyclohexyl, and 6,6-dimethylnorpinan-2-yl,
- $C_5$-$C_6$-cycloalkenyl, optionally substituted by 1 or 2 $C_1$-$C_4$-alkyl, such as 2-methylcyclohex-3-en-1-yl,
- 5- or 6-membered saturated heterocyclyl having 1 heteroatom selected from O and S, such as tetrahydropyranyl, tetrahydrofuranyl and tetrahydrothiopyranyl, where the 5- or 6-membered saturated heterocyclyl may be unsubstituted or carry 1 or 2 radicals selected from $C_1$-$C_4$-alkyl and $C_1$-$C_4$-alkoxy, examples including tetrahydrofuran-2-yl, tetrahydrofuran-3-yl, tetrahydropyran-3-yl, tetrahydropyran-4-yl, tehtrahydrothiopyran-3-yl, tetrahydrothiopyran-4-yl, 6-methoxy-3-methyltetrahydropyran-2-yl, and 5,5-dimethyltetrahydrofuran-2-yl,
- optionally substituted phenyl such as phenyl, 2-chloropheynl, 2-fluoropheynl, 2-methylphenyl, 2-methoxyphenyl, 2-cyanophenyl, 3-chloropheynl, 3-fluoropheynl, 3-methylphenyl, 3-methoxyphenyl, 3-cyanophenyl, 4-chloropheynl, 4-fluoropheynl, 4-methylphenyl, 4-methoxyphenyl, 3-nitrophenyl, 4-(trifluoromethyl)phenyl, 3-(trifluoromethyl)phenyl and 4-cyanophenyl,
- 5- or 6-membered hetaryl having 1 or 2 heteroatoms as ring members, selected from O, S and N and where the hetaryl is unsubstituted or subsisted by 1 or 2 radicals selected from halogen, $C_1$-$C_4$-alkyl, $C_1$-$C_4$-haloalkyl, $C_1$-$C_4$-alkoxy and $C_1$-$C_4$-haloalkoxy examples of hetaryl including 4-methylthiazol-5-yl, 2-pyridyl and 3-pyridyl,
- phenyl-$C_1$-$C_4$-alkyl, such as benzyl or phenethyl, and
- hetaryl-$C_1$-$C_4$-alkyl, where the hetaryl is 5- or 6-membered and has 1 or 2 heteroatoms as ring members, selected from O, S and N and where the hetaryl is unsubstituted or subistuted by 1 or 2 radicals selected from halogen, $C_1$-$C_4$-alkyl, $C_1$-$C_4$-haloalkyl, $C_1$-$C_4$-alkoxy and $C_1$-$C_4$-haloalkoxy examples of hetaryl-$C_1$-$C_4$-alkyl including 1,1-dimethyl-2-(3-pyridyl)ethyl, thereby forming, together with the carbon atom they are bound to, an unsubstituted or substituted 1,1-cyclopropylidene or 1,1-cyclobutylidene radical.

According to the second group of embodiments B, even more particular preference is given to compounds of formula (I), wherein $R^3$ and $R^5$ together form the following moieties:

$CH_2$—$CH_2$, $CHF$—$CH_2$, $CF_2$—$CH_2$, $CHF$—$CHF$, $CF_2$—$CHF$, $CF_2$—$CF_2$, $CHCl$—$CH_2$, $CCl_2$—$CH_2$, $CHCl$—$CHCl$, $CCl_2$—$CHCl$, $CCl_2$—$CCl_2$, $CH(CH_3)$—$CH_2$, $C(CH_3)_2$—$CH_2$, $CH(CH_3)$—$CH(CH_3)$, $C(CH_3)_2$—$CH(CH_3)$, $C(CH_3)_2$—$C(CH_3)_2$, $CH(OCH_3)$—$CH_2$, $CH(CH_2CH_3)$—$CH_2$, $CH(CH_2CH_2CH_3)$—$CH_2$, $CH(CH_2CH_2CH_2CH_3)$—$CH_2$, $CH(CH_3)$—$CH_2$—$CH_2$, $CH_2$—$CH(CH_3)$—$CH_2$, $C(CH_3)_2$—$CH_2$—$CH_2$, $CH_2$—$C(CH_3)_2$—$CH_2$, $CH(CH_3)$—$CH(CH_3)$—$CH_2$, $CH(CH_3)$—$CH_2$—$CH(CH_3)$, $CH(CH_3)$—$CH(CH_3)$—$CH(CH_3)$, $CH(CH_3)$—$CH(CH_3)$, $C(CH_3)_2$—$CH(CH_3)$—$CH_2$, $CH(CH_3)$—$C(CH_3)_2$—$CH_2$, $C(CH_3)_2$—$CH_2$—$C(CH_3)_2$, $C(CH_3)_2$—$C(CH_3)_2$—$CH_2$, $C(CH_3)_2$—$C(CH_3)_2$—$C(CH_3)_2$, $CHF$—$CH_2$—$CH_2$, $CH_2$—$CHF$—$CH_2$, $CF_2$—$CH_2$—$CH_2$, $CH_2$—$CF_2$—$CH_2$, $CHF$—$CHF$—$CH_2$, $CHF$—$CH_2$—$CHF$, $CHF$—$CHF$—$CHF$, $CF_2$—$CHF$—$CH_2$, $CHF$—$CF_2$—$CH_2$, $CF_2$—$CH_2$—$CF_2$, $CF_2$—$CF_2$—$CH_2$, $CF_2$—$CF_2$—$CF_2$, $CHCl$—$CH_2$—$CH_2$, $CH_2$—$CHCl$—$CH_2$, $CCl_2$—$CH_2$—$CH_2$, $CH_2$—$CCl_2$—$CH_2$, $CHCl$—$CHCl$—$CH_2$, $CHCl$—$CH_2$—$CHCl$, $CHCl$—$CHCl$—$CHCl$, $CCl_2$—$CHCl$—$CH_2$, $CHCl$—$CCl_2$—$CH_2$, $CCl_2$—$CH_2$—$CCl_2$, $CCl_2$—$CCl_2$—$CH_2$, $CCl_2$—$CCl_2$—$CCl_2$ or a radical $CH(Ar)$—$CH_2$, where Ar is selected from phenyl, 2-chloropheynl, 2-fluoropheynl, 2-methylphenyl, 2-methoxyphenyl, 2-cyanophenyl, 3-chloropheynl, 3-fluoropheynl, 3-methylphenyl, 3-methoxyphenyl, 3-cyanophenyl, 4-chloropehynl, 4-fluoropheynl, 4-methylphenyl, 4-methoxyphenyl and 4-cyanophenyl, thereby forming, together with the carbon atom they are bound to, an unsubstituted or substituted 1,1-cyclopropylidene or 1,1-cyclobutylidene radical.

According to the second group of embodiments B, special preference is given to compounds of formula (Ia) and (Ib),

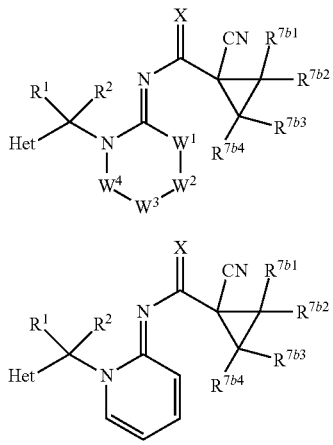

where Het, $W^1$, $W^2$, $W^3$, $W^4$, X, $R^1$ and $R^2$ are as defined above and in particular have the preferred meanings or the particularly preferred meanings;

$R^{7b1}$ is hydrogen or has one of the meanings given for $R^{7b}$;

$R^{7b2}$, $R^{7b3}$ and $R^{7b4}$ are hydrogen, methyl or halogen, in particular hydrogen.

In formulae (Ia) and (Ib), $R^{7b1}$ is in particular hydrogen or a radical selected from the group consisting of $C_1$-$C_{10}$-alkyl, such as methyl, ethyl, n-propyl, isopropyl, n-butyl, tert.butyl, 1-methylpropyl, 2-methylpropyl, 1,2-dimethylpropyl, 2,2-dimethylpropyl, 3,3-dimethylpropyl, 1-methylbutyl, 1,2-dimethylbutyl, 3,3-dimethylbutyl, n-pentyl, 1-ethylpentyl, $C_1$-$C_4$-haloalkyl, such as difluoromethyl, trifluoromethyl, 2,2-difluoroethyl, 1,1-difluoroethyl or 2,2,2-trifluoroethyl, $C_1$-$C_6$-alkyl, which is substituted by 1 radical selected from $C_1$-$C_4$-alkoxy, $C_1$-$C_4$-alkylcarbonyloxy, $C_1$-$C_4$-alkoxy-$C_1$-$C_4$-alkoxy, $C_1$-$C_4$-alkylsulfanyl, $C_3$-$C_8$-cycloalkyl, $C_3$-$C_8$-cycloalkoxy, phenoxy and 5- or 6-membered saturated heterocyclyl having 1 heteroatom selected from O and S, such as tetrahydropyranyl, tetrahydrofuranyl, tetrahydrothiopyranyl, where $C_3$-$C_8$-cycloalkyl, $C_3$-$C_8$-cycloalkoxy and 5- or 6-membered saturated heterocyclyl may be unsubstituted or carry 1 or 2 radicals selected from $C_1$-$C_4$-alkyl and $C_1$-$C_4$-alkoxy, examples of substituted $C_1$-$C_6$-alkyl including 1-methoxyethyl, 2-methoxyethyl, 1-propoxyethyl, 2-propoxyethyl, 1-isopropoxyethyl, 2-isopropoxyethyl, 1-isobutoxyethyl, 2-isobutoxyethyl, 1-(cyclohexyloxy)ethyl, 2-phenoxyethyl, (4-isopropylcyclohexyl)methyl, 1-acetoxyethyl, 2-acetoxyethyl, 6-acetoxyhexyl, 2-methylsulfanylpropyl, 1-methyl-2-methylsulfanylethyl, tetrahydropyran-4-ylmethyl, tetrahydrothiopyran-4-ylmethyl, $C_2$-$C_{10}$-alkenyl, such as 3-nonenyl, $C_3$-$C_{10}$-cycloalkyl, optionally substituted by 1 or 2 $C_1$-$C_4$-alkyl, such as cyclopropyl, cyclobutyl, cyclopentyl, cyclohexyl, cycloheptyl, cyclooctyl, 4-methylcyclohexyl, 4-isopropylcyclohexyl, and 6,6-dimethylnorpinan-2-yl, $C_5$-$C_6$-cycloalkenyl, optionally substituted by 1 or 2 $C_1$-$C_4$-alkyl, such as 2-methylcyclohex-3-en-1-yl, 5- or 6-membered saturated heterocyclyl having 1 heteroatom selected from O and S, such as tetrahydropyranyl, tetrahydrofuranyl and tetrahydrothiopyranyl, where the 5- or 6-membered saturated heterocyclyl may be unsubstituted or carry 1 or 2 radicals selected from $C_1$-$C_4$-alkyl and $C_1$-$C_4$-alkoxy, examples including tetrahydrofuran-2-yl, tetrahydrofuran-3-yl, tetrahydropyran-3-yl, tetrahydropyran-4-yl, tehtrahydrothiopyran-3-yl, tetrahydrothiopyran-4-yl, 6-methoxy-3-methyltetrahydropyran-2-yl, and 5,5-dimethyltetrahydrofuran-2-yl, optionally substituted phenyl such as phenyl, 2-chloropheynl, 2-fluoropheynl, 2-methylphenyl, 2-methoxyphenyl, 2-cyanophenyl, 3-chloropheynl, 3-fluoropheynl, 3-methylphenyl, 3-methoxyphenyl, 3-cyanophenyl, 4-chloropheynl, 4-fluoropheynl, 4-methylphenyl, 4-methoxyphenyl, 3-nitrophenyl, 4-(trifluoromethyl)phenyl, 3-(trifluoromethyl)phenyl and 4-cyanophenyl, 5- or 6-membered hetaryl having 1 or 2 heteroatoms as ring members, selected from O, S and N and where the hetaryl is unsubstituted or subistuted by 1 or 2 radicals selected from halogen, $C_1$-$C_4$-alkyl, $C_1$-$C_4$-haloalkyl, $C_1$-$C_4$-alkoxy and $C_1$-$C_4$-haloalkoxy examples of hetaryl including 4-methylthiazol-5-yl, 2-pyridyl and 3-pyridyl, phenyl-$C_1$-$C_4$-alkyl, such as benzyl or phenethyl, and hetaryl-$C_1$-$C_4$-alkyl, where the hetaryl is 5- or 6-membered and has 1 or 2 heteroatoms as ring members, selected from O, S and N and where the hetaryl is unsubstituted or subistuted by 1 or 2 radicals selected from halogen, $C_1$-$C_4$-alkyl, $C_1$-$C_4$-haloalkyl, $C_1$-$C_4$-alkoxy and $C_1$-$C_4$-haloalkoxy examples of hetaryl-$C_1$-$C_4$-alkyl including 1,1-dimethyl-2-(3-pyridyl)ethyl.

According to a third group of embodiments C, compounds of formula (I) are preferred, wherein $R^3$ and $R^5$ together with the carbon atom, to which they are bound, form a 3, 4, 5 or 6 membered saturated heterocycle having 1 or 2 non adjacent heteroatoms as ring members which are selected from O and S, wherein the heterocycle may be unsubstituted or may carry 1, 2, 3, 4, 5 or 6 radicals $R^{7b}$, wherein $R^{7b}$ is as defined above and in particular as defined for embodiment B and especially selected from the group consisting of halogen, $C_1$-$C_6$-alkyl, $C_1$-$C_6$-haloalkyl, $C_1$-$C_4$-alkoxy-$C_1$-$C_4$-alkyl, $C_1$-$C_4$-alkoxycarbonyl, and wherein one radical $R^{7b}$ may also be $C_3$-$C_6$-cycloalkyl, which is unsubstituted or carries 1, 2, 3, 4 or 5 radicals selected from fluorine, chlorine, $C_1$-$C_4$-alkyl such as methyl, or $C_1$-$C_4$-alkoxycarbonyl, or phenyl, optionally substituted with 1, 2, 3, 4 or 5, in particular 1, 2 or 3, identical or different substituents $R^{10b}$, where $R^{10b}$ is as defined above, and in particular selected from the group consisting of halogen, such as fluorine or chlorine, $C_1$-$C_4$-alkyl, CN, $C_1$-$C_4$-haloalkyl, $C_1$-$C_4$-alkoxy and $C_1$-$C_4$-haloalkoxy.

According to the third group of embodiments C, even more particular preference is given to compounds of formula (I), wherein $R^3$ and $R^5$ together form O—$C_1$-$C_3$-alkylene, wherein 1, 2, 3 or 4 of the hydrogen atoms in $C_1$-$C_3$-alkylene may be replaced by $R^{7b}$, thereby forming, together with the carbon atom they are bound to, an unsubstituted or substituted saturated 3-, 4- or 5-membered heterocyclic radical having 1 oxygen atom as ring member. According to the third group of embodiments C, even more particular preference is given to compounds of formula (I), wherein $R^3$ and $R^5$ together form O—$CH_2$ or O—$CH_2CH_2$, wherein 1, 2, 3 or 4 of the hydrogen atoms in $CH_2$ or $CH_2CH_2$, may be replaced by $R^{7b}$, thereby forming, together with the carbon atom they are bound to, an unsubstituted or substituted oxiran-2,2-diyl or oxetan-2,2-diyl.

According to a fourth group of embodiments D, compounds of formula (I) are preferred, wherein $R^3$ and $R^5$ together form =S or =O, in particular =O.

Preferred are compounds of formulae (I) and (Ia), wherein $W^1$-$W^2$-$W^3$-$W^4$ represents a carbon chain group connected to N and C=N, which is selected from the group consisting of $CR^{w6}$=$CR^{w5}$—$CR^{w4}$=$CR^{w3}$, $CR^{w6}$=$CR^{w5}$—$CHR^{w4}$—$CHR^{w3}$, $CHR^{w5}$—$CHR^{w5}$—$CHR^{w4}$—$CHR^{w3}$, $CHR^{w6}$—$CHR^{w5}$—$CR^{w4}$=$CR^{w3}$, and $CHR^{w6}$—$CHR^{w5}$—$CHR^{w4}$—$CHR^{w3}$, where in the five aforementioned radicals the carbon atom which carries $R^{w6}$ is bound to the nitrogen atom and where $R^{w3}$, $R^{w4}$, $R^{w5}$ and $R^{w6}$, independently of each other, have one of the meanings given for $R^w$. In this context, $R^w$ is preferably selected from the group consisting of hydrogen, halogen, such as fluorine or chlorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy. Preferably, at most one of $R^{w3}$, $R^{w4}$, $R^{w5}$ and $R^{w6}$ is different from hydrogen.

In a particularly preferred group of embodiments $R^{w3}$, $R^{w4}$ and $R^{w6}$ are hydrogen while $R^{w5}$ has one of the meanings given for $R^w$, and where $R^{w5}$ is in particular selected from the group consisting of hydrogen, halogen, such as fluorine or chlorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

In another particularly preferred group of embodiments $R^{w3}$, $R^{w4}$ and $R^{w5}$ are hydrogen while $R^{w6}$ has one of the meanings given for $R^w$, and where $R^{w6}$ is in particular selected from the group consisting of hydrogen, halogen, such as fluorine or chlorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

Especially, all of $R^{w3}$, $R^{w4}$, $R^{w5}$ and $R^{w6}$ are hydrogen.

Preferred are compounds of formulae (I) and (Ia), wherein the moiety of the formula (A)

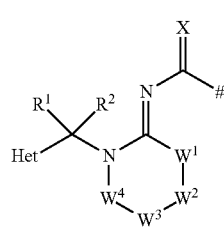

(A)

represents a radical selected from the group consisting of W.Het-1, W.Het-2, W.Het-3, W.Het-4, W.Het-5, W.Het-6, W.Het-7, W.Het-8, W.Het-9, W.Het-10, W.Het-11 and W.Het-12, in where the radical of formula (A) is in particular selected rom the radicals W.Het-1, W.Het-2, W.Het-5, W.Het-6, W.Het-9 and W.Het-10.

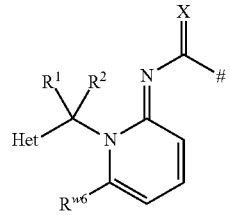

W.Het-1

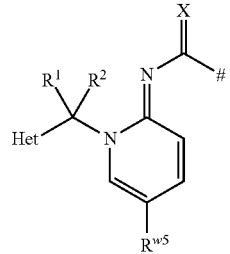

W.Het-2

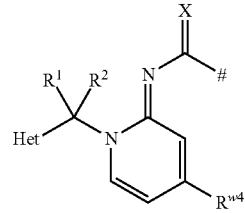

W.Het-3

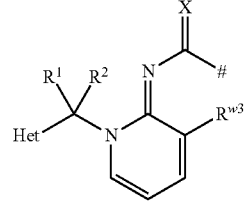

W.Het-4

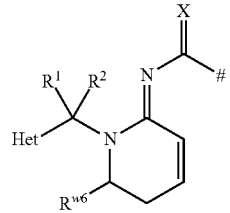

W.Het-5

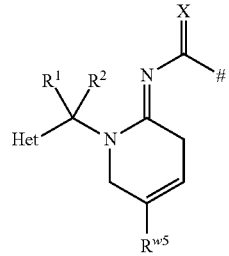

W.Het-6

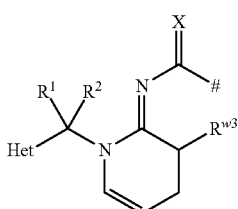
W.Het-7

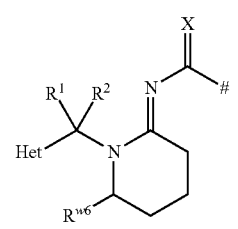
W.Het-8

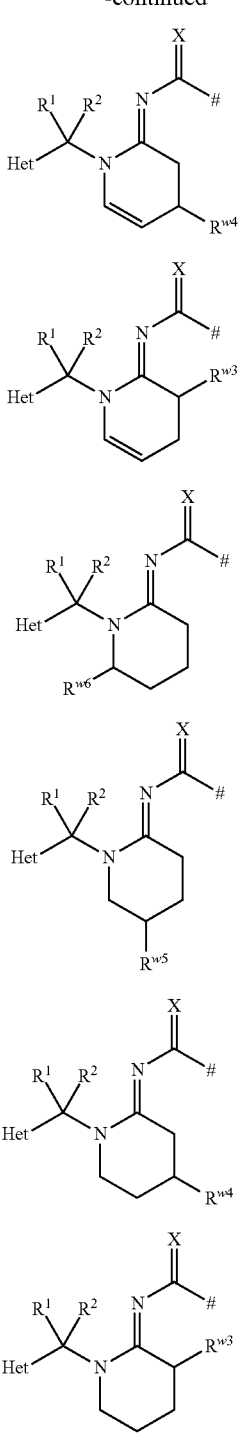
W.Het-9

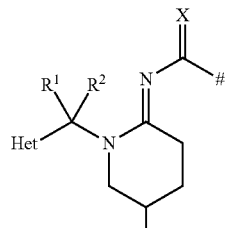
W.Het-10

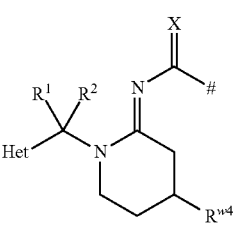
W.Het-11

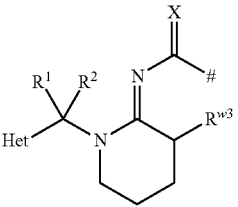
W.Het-12 wherein # denotes the bond to the remainder of the molecule and where $R^1$, $R^2$ and Het are as defined herein and where $R^1$, $R^2$ and Het, individually or in combination have the meanings given as preferred meanings, and wherein $R^{w3}$, $R^{w4}$, $R^{w5}$ and $R^{w6}$ are as defined above and in particular selected from the group consisting of hydrogen, halogen, such as fluorine or chlorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

Particularly preferred are compounds of formulae (I) and (Ia), wherein the moiety of the formula A is selected from the group consisting of W.Het-1, W.Het-5 and W.Het-9, wherein $R^{w6}$ is as defined above and in particular selected from the group consisting of hydrogen, halogen, such as fluorine or chlorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy and where $R^{w6}$ is especially hydrogen.

Likewise, particularly preferred are compounds of formulae (I) and (Ia), wherein the moiety of the formula A is selected from the group consisting of W.Het-2, W.Het-6 and W.Het-10, wherein $R^w$& is as defined above and in particular selected from the group consisting of hydrogen, halogen, such as fluorine or chlorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy and where $R^{w5}$ is especially hydrogen.

Likewise, particularly preferred are compounds of formulae (I) and (Ia), wherein the moiety of the formula A is selected from the group consisting of W.Het-1, W.Het-2, W.Het-3 and W.Het-4, especially from the group consisting of W.Het-1 and W.Het-2, wherein $R^{w3}$, $R^{w4}$, $R^{w5}$ and $R^{w6}$, independently of each other, are as defined above and in particular selected from the group consisting of hydrogen, halogen, such as fluorine or chlorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy and where at most one of $R^{w3}$, $R^{w4}$, $R^{w5}$ and $R^{w6}$ are especially hydrogen.

In the moieties W.Het-1, W.Het-2, W.Het-3, W.Het-4, W.Het-5, W.Het-6, W.Het-7, W.Het-8, W.Het-9, W.Het-10, W.Het-11 and W.Het-12, the heterocycle Het is in particular selected from the group consisting of the radicals of formulae Het-1 to Het-24, as defined above, and in particular selected from the group consisting of the radicals of the formulae Het-1 or Het-1a, Het-11a and Het-24.

In the moieties W.Het-1, W.Het-2, W.Het-3, W.Het-4, W.Het-5, W.Het-6, W.Het-7, W.Het-8, W.Het-9, W.Het-10, W.Het-11 and W.Het-12, the radicals $R^1$ and $R^2$ are, independently from each other, in particular selected from the group consisting of hydrogen, halogen, such as fluorine or chlorine, CN, $C_1$-$C_6$-alkyl, in particular $C_1$-$C_4$-alkyl, such as methyl, ethyl, n-propyl or isopropyl, $C_3$-$C_6$-cycloalkyl, such as cyclopropyl or cyclobutyl, $C_1$-$C_6$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, or $C_3$-$C_6$-halocycloalkyl such as 1-fluorocyclopropyl or 2,2-difluorocyclopropyl, or $R^1$ and $R^2$ may together be =$CR^{13}R^{14}$ or $R^1$ and $R^2$ form, together with the carbon atom, which they attached to, a 3- to 5 membered saturated carbocyclic ring such as cyclopropyl, cyclobutyl or cyclopentyl.

In particular embodiments of moieties W.Het-1, W.Het-2, W.Het-3, W.Het-4, W.Het-5, W.Het-6, W.Het-7, W.Het-8, W.Het-9, W.Het-10, W.Het-11 and W.Het-12, the radicals $R^1$ and $R^2$ are, independently from each other, more particularly selected from the group consisting of hydrogen, halogen, cyano, $C_1$-$C_3$-alkyl, such as methyl ethyl or isopropyl, or $C_1$-$C_3$-haloalkyl such as fluoromethyl, difluoromethyl, trifluoromethyl, 1,1-difluoroethyl, 2-fluoroethyl, 2,2-difluoroethyl or 2,2,2-trifluoroethyl, where in particular at least one of the radicals $R^1$ and $R^2$ is hydrogen.

Especially, $R^1$ and $R^2$ in the moieties W.Het-1, W.Het-2, W.Het-3, W.Het-4, W.Het-5, W.Het-6, W.Het-7, W.Het-8, W.Het-9, W.Het-10, W.Het-11 and W.Het-12 are both hydrogen.

A particular group 1 of embodiments relates to compounds of the formulae (I) and (Ia), to their stereoisomers, their tautomers and their salts, wherein the moiety of formula (A) represents a radical selected from the group consisting of W.Het-1, wherein Het is selected from the group consisting of radicals of formulae Het-1, Het-11a and Het-24.

A further particular group 2 of embodiments relates to compounds of the formulae (I) and (Ia), to their stereoisomers, their tautomers and their salts, wherein the moiety of formula (A) represents a radical selected from the group consisting of W.Het-2, wherein Het is selected from the group consisting of radicals of formulae Het-1, Het-11a and Het-24.

A further particular group 3 of embodiments relates to compounds of the formulae (I) and (Ia), to their stereoisomers, their tautomers and their salts, wherein the moiety of formula (A) represents a radical selected from the group consisting of W.Het-5, wherein Het is selected from the group consisting of radicals of formulae Het-1, Het-11a and Het-24.

A further particular group 4 of embodiments relates to compounds of the formulae (I) and (Ia), to their stereoisomers, their tautomers and their salts, wherein the moiety of formula (A) represents a radical selected from the group consisting of W.Het-6, wherein Het is selected from the group consisting of radicals of formulae Het-1, Het-11a and Het-24.

A further particular group 5 of embodiments relates to compounds of the formulae (I) and (Ia), to their stereoisomers, their tautomers and their salts, wherein the moiety of formula (A) represents a radical selected from the group consisting of W.Het-9, wherein Het is selected from the group consisting of radicals of formulae Het-1, Het-11a and Het-24.

A further particular group 6 of embodiments relates to compounds of the formulae (I) and (Ia), to their stereoisomers, their tautomers and their salts, wherein the moiety of formula (A) represents a radical selected from the group consisting of W.Het-10, wherein Het is selected from the group consisting of radicals of formulae Het-1, Het-11a and Het-24.

A special group 1a of embodiments relates to compounds of the formulae (I) and (Ia), to their stereoisomers, their tautomers and their salts, wherein the moiety of formula (A) represents a radical selected from the group consisting of W.Het-1, wherein Het is a radicals of formulae Het-1a.

A further special group 2a of embodiments relates to compounds of the formulae (I) and (Ia), to their stereoisomers, their tautomers and their salts, wherein the moiety of formula (A) represents a radical selected from the group consisting of W.Het-2, wherein Het is a radicals of formulae Het-1a.

A further special group 3a of embodiments relates to compounds of the formulae (I) and (Ia), to their stereoisomers, their tautomers and their salts, wherein the moiety of formula (A) represents a radical selected from the group consisting of W.Het-5, wherein Het is a radicals of formulae Het-1a.

A further special group 4a of embodiments relates to compounds of the formulae (I) and (Ia), to their stereoisomers, their tautomers and their salts, wherein the moiety of formula (A) represents a radical selected from the group consisting of W.Het-6, wherein Het is a radicals of formulae Het-1a.

A further special group 5a of embodiments relates to compounds of the formulae (I) and (Ia), to their stereoisomers, their tautomers and their salts, wherein the moiety of formula (A) represents a radical selected from the group consisting of W.Het-9, wherein Het is a radicals of formulae Het-1a.

A further special group 6a of embodiments relates to compounds of the formulae (I) and (Ia), to their stereoisomers, their tautomers and their salts, wherein the moiety of formula (A) represents a radical selected from the group consisting of W.Het-10, wherein Het is a radicals of formulae Het-1a.

In embodiments 1, 3, 5, 1a, 3a and 5a the radical $R^{w6}$ is as defined above and in particular selected from the group consisting of hydrogen, halogen, such as fluorine or chlorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy. In embodiments 1, 3, 5, 1a, 3a and 5a the radical $R^{w6}$ is especially hydrogen.

In embodiments 2, 4, 6, 2a, 4a and 6a the radical $R^{w5}$ is as defined above and in particular selected from the group consisting of hydrogen, halogen, such as fluorine or chlorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy. In embodiments 2, 4, 6, 2a, 4a and 6a the radical $R^{w5}$ is especially hydrogen.

In embodiments 1, 2, 3, 4, 5, 6, 1a, 2a, 3a, 4a, 5a and 6a the radicals $R^1$ and $R^2$ are, independently from each other, in particular selected from the group consisting of hydrogen, halogen, such as fluorine or chlorine, CN, $C_1$-$C_6$-alkyl, in particular $C_1$-$C_4$-alkyl, such as methyl, ethyl, n-propyl or isopropyl, $C_3$-$C_6$-cycloalkyl, such as cyclopropyl or cyclobutyl, $C_1$-$C_6$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, or $C_3$-$C_6$-halocycloalkyl such as 1-fluorocyclopropyl or 2,2-difluorocyclopropyl, or $R^1$ and $R^2$ may together be =$CR^{13}R^{14}$ or $R^1$ and $R^2$ form, together with the carbon atom, which they attached to, a 3- to 5 membered saturated carbocyclic ring such as cyclopropyl, cyclobutyl or cyclopentyl.

In embodiments 1, 2, 3, 4, 5, 6, 1a, 2a, 3a, 4a, 5a and 6a the radicals $R^1$ and $R^2$ are, independently from each other, more particularly selected from the group consisting of hydrogen, halogen, cyano, $C_1$-$C_3$-alkyl, such as methyl ethyl or isopropyl, or $C_1$-$C_3$-haloalkyl such as fluoromethyl, difluoromethyl, trifluoromethyl, 1,1-difluoroethyl, 2-fluoroethyl, 2,2-difluoroethyl or 2,2,2-trifluoroethyl, where in particular at least one of the radicals $R^1$ and $R^2$ is hydrogen and where especially both $R^1$ and $R^2$ are hydrogen.

In the compounds of formula (I), where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, the variables m, $R^1$, $R^2$, $R^3$, $R^{4a}$, $R^{4b}$ and $R^5$ are as defined above and in particular have the preferred meanings.

In the compounds of formula (I), where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, the variables m, $R^1$, $R^2$, $R^3$, $R^{4a}$, $R^{4b}$ and $R^5$, independently of each other or in particular in combination, in particular have the following meanings:

m is 0 or 1;

$R^1$ and $R^2$ are, independently from each other, selected from the group consisting of hydrogen, halogen, such as fluorine or chlorine, CN, $C_1$-$C_6$-alkyl, in particular $C_1$-$C_4$-alkyl, such as methyl, ethyl, n-propyl or isopropyl, $C_3$-$C_6$-cycloalkyl, such as cyclopropyl or cyclobutyl, $C_1$-$C_6$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, or $C_3$-$C_6$-halocycloalkyl such as 1-fluorocyclopropyl or 2,2-difluorocyclopropyl, or $R^1$ and $R^2$ may together be =$CR^{13}R^{14}$ or $R^1$ and $R^2$ form, together with the carbon atom, which they attached to, a 3- to 5 membered saturated carbocyclic ring such as cyclopropyl, cyclobutyl or cyclopentyl;

$R^3$ is selected from the group consisting of hydrogen, halogen, CN, $C_1$-$C_6$-alkyl, in particular $C_1$-$C_4$-alkyl, $C_1$-$C_6$-haloalkyl, in particular $C_1$-$C_4$-haloalkyl, $C_3$-$C_6$-cycloalkyl, such as cyclopropyl or cyclobutyl, $C_3$-$C_6$-halocycloalkyl, such as 1-fluorocyclopropyl, 2-fluorocyclopropyl, 2,2-difluorocyclopropyl, 2-chlorocyclopropyl, 2,2-dichlorocyclopropyl, 1-fluorocyclobutyl, 2-fluorocyclobutyl, 3-fluorocyclobutyl, 2,2-difluorocyclobutyl or 3,3-difluorocyclobutyl, $NR^{9a}R^{9b}$ and $NR^{9a}$—C(=O)$R^{7a}$, where $R^{7a}$, $R^{9a}$ and $R^{9b}$ are as defined above and in particular have the preferred meanings;

$R^5$ is selected from the group consisting of hydrogen, halogen, CN, $NR^{9a}R^{9b}$, $C_1$-$C_6$-alkyl, in particular $C_1$-$C_4$-alkyl, $C_1$-$C_6$-haloalkyl, in particular $C_1$-$C_4$-haloalkyl, $C_3$-$C_6$-cycloalkyl, $C_3$-$C_6$-halocycloalkyl, C(=O)$OR^8$, C(=O)$NR^{9a}R^{9b}$, C(=S)$NR^{9a}R^{9b}$, C(=O)$R^{7a}$, C(=S)$R^{7a}$, Q-phenyl, where phenyl is unsubstituted or substituted with 1, 2, 3, 4 or 5 identical or different substituents $R^{10}$, or Q-Het$^{\#}$, where Het$^{\#}$ is unsubstituted or substituted with 1, 2, 3, 4 or 5 identical or different substituents $R^{10}$, and where Q, irrespectively of its occurrence, is a bond, $NR^{9a}$, such as NH or $N(CH_3)$ $NR^{9a}$—C(=O), such as NH—C(=O)H, NH—C(=O)CH$_3$, NH—C(=O)CH$_2$CH$_3$ or NH—C(=O)CH(CH$_3$)$_2$, OC(=O), $NR^{9a}CH_2$, such as NHCH$_2$ or N(CH$_3$)CH$_2$, OC(=O)CH$_2$, or $NR^{9a}$C(=O)CH$_2$ such as NHC(=O)CH$_2$, where $R^{7a}$, $R^{9a}$, $R^{9b}$ and $R^{10}$ are as defined above and in particular have the preferred meanings;

and if m=1

$R^{4a}$ and $R^{4b}$ are selected, independently from one another, from the group consisting of hydrogen, $C_1$-$C_4$-alkyl, in particular methyl, and halogen, in particular fluorine or chlorine, or $R^{4a}$ and $R^{4b}$ together are =O.

In the compounds of formula (I), where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, the variables m, $R^1$, $R^2$, $R^3$, $R^{4a}$, $R^{4b}$ and $R^5$, independently of each other or in particular in combination, more particularly have the following meanings:

$R^1$ and $R^2$ are, independently from each other, selected from the group consisting of hydrogen, halogen, cyano, $C_1$-$C_3$-alkyl, such as methyl ethyl or isopropyl, or $C_1$-$C_3$-haloalkyl such as fluoromethyl, difluoromethyl, trifluoromethyl, 1,1-difluoroethyl, 2-fluoroethyl, 2,2-difluoroethyl or 2,2,2-trifluoroethyl, where in particular at least one of the radicals $R^1$ and $R^2$ is hydrogen and where especially both $R^1$ and $R^2$ are hydrogen;

$R^3$ is selected from the group consisting of hydrogen, fluorine, chlorine, $C_1$-$C_4$-alkyl, such as methyl, ethyl, n-propyl, isopropyl or n-butyl, NHC(=O)—$C_1$-$C_4$-alkyl, such as NH—C(=O)H, NH—C(=O)CH$_3$, NH—C(=O)CH$_2$CH$_3$ or NH—C(=O)CH(CH$_3$)$_2$, and CN, and in particular selected from the group of hydrogen and $C_1$-$C_4$-alkyl, such as methyl, ethyl, n-propyl, isopropyl or n-butyl;

$R^5$ is selected from the group consisting of hydrogen, halogen, such as fluorine or chlorine, CN, $C_1$-$C_6$-alkyl, in particular $C_1$-$C_4$-alkyl, such as methyl, ethyl, n-propyl, isopropyl, n-butyl, 2-butyl or isobutyl, $C_1$-$C_6$-haloalkyl, in particular $C_1$-$C_4$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_3$-$C_6$-cycloalkyl, such as cyclopropyl, cyclobutyl, cyclopentyl or cyclohexyl, $C_3$-$C_6$-halocycloalkyl, such as 1-fluorocyclopropyl, 2-fluorocyclopropyl, 2,2-difluorocyclopropyl, 2-chlorocyclopropyl, 2,2-dichlorocyclopropyl, 1-fluorocyclobutyl, 2-fluorocyclobutyl, 3-fluorocyclobutyl, 2,2-difluorocyclobutyl or 3,3-difluorocyclobutyl, and phenyl, which is unsubstituted or carries 1, 2, 3, 4 or 5 identical or different substituents $R^{10}$, where $R^{10}$ is as defined above and in particular selected from the group consisting of halogen, such as chlorine or fluorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy;

and if m=1

$R^{4a}$ and $R^{4b}$ are selected, independently from one another, from the group consisting of hydrogen and methyl or $R^{4a}$ and $R^{4b}$ together are =O.

In the compounds of formula (I), where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, where m=0, the variables $R^1$, $R^2$, $R^3$, and $R^5$, independently of each other or in particular in combination, in particular may also have the following meanings:

$R^1$ and $R^2$ are, independently from each other, selected from the group consisting of hydrogen, halogen, such as fluorine or chlorine, CN, $C_1$-$C_6$-alkyl, in particular $C_1$-$C_4$-alkyl, such as methyl, ethyl, n-propyl or isopropyl, $C_3$-$C_6$-cycloalkyl, such as cyclopropyl or cyclobutyl, $C_1$-$C_6$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, or $C_3$-$C_6$-halocycloalkyl such as 1-fluorocyclopropyl or 2,2-difluorocyclopropyl, or $R^1$ and $R^2$ may together be =$CR^{13}R^{14}$ or $R^1$ and $R^2$ form, together with the carbon atom, which they attached to, a 3- to 5 membered saturated carbocyclic ring such as cyclopropyl, cyclobutyl or cyclopentyl;

$R^3$ and $R^5$ together with the carbon atom, to which they are bound, form a 3, 4, 5 or 6 membered saturated carbocycle, wherein each of the carbon atoms of the carbocycle may be unsubstituted or may carry 1, 2, 3, 4, 5 or 6 radicals $R^{7b}$, wherein $R^{7b}$ is as defined above and wherein $R^{7b}$ is in particular selected from the group consisting of halogen, $C_1$-$C_6$-alkyl, $C_1$-$C_6$-alkoxy, and $C_2$-$C_6$-alkynyl, and wherein the carbon atoms of the aforementioned aliphatic radicals may optionally be partly or completely halogenated and/or substituted by a radical selected from $C_1$-$C_4$-alkoxy, $C_1$-$C_4$-alkoxycarbonyl, $C_1$-$C_4$-alkylcarbonyloxy, $C_1$-$C_4$-alkoxy-$C_1$-$C_4$-alkoxy, $C_1$-$C_4$-alkylsulfanyl, $C_3$-$C_6$-cycloalkyl, $C_3$-$C_6$-cycloalkoxy, phenoxy, 5- or 6-membered saturated heterocyclyl having 1 heteroatom selected from O and S, such as tetrahydropyranyl, tetrahydrofuranyl and tetrahydrothiopyranyl, where the 5- or 6-membered saturated heterocyclyl may be unsubstituted or carry 1 or 2 radicals selected from $C_1$-$C_4$-alkyl and $C_1$-$C_4$-alkoxy, and wherein one or two radicals $R^{7b}$ may also be $C_3$-$C_8$-cycloalkyl, in particular $C_3$-$C_6$-cycloalkyl, which is unsubstituted or carries 1, 2, 3, 4 or 5 radicals selected from fluorine, chlorine, $C_1$-$C_4$-alkyl such as methyl and $C_1$-$C_4$-alkoxycarbonyl such as methoxycarbonyl, $C_3$-$C_6$-cycloalkenyl, which is unsubstituted or carries 1, 2, 3, 4 or 5 radicals selected from fluorine, chlorine or $C_1$-$C_4$-alkyl such as methyl, phenyl, optionally substituted with 1, 2, 3, 4 or 5 identical or different substituents $R^{10b}$, or a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, such as tetrahydrofuryl, tetrahydropyranyl, tetrahydrothiopyranyl or thiazolyl, where the heterocyclic ring is optionally substituted with 1, 2, 3 or 4 identical or different substituents $R^{10b}$, and wherein the nitrogen and/or the sulfur atom(s) of the heterocyclic ring may optionally be oxidized, in particular a 5- or 6-membered hetaryl having 1 or 2 heteroatoms selected from O, S and N, where the 5- or 6-membered hetaryl is unsubstituted or carries 1, 2 or 3 identical or different substituents $R^{10b}$, or two of $R^{7b}$ present on one ring carbon may together form =O or =S, or two $R^{7b}$ together form a linear $C_2$-$C_7$ alkylene chain, thus forming, together with the carbon atom to which they are bound, a 3-, 4-, 5- or 6-membered spiro ring, where 1 or 2 $CH_2$ moieties of the alkylene chain may be replaced by 1 or 2 heteroatom moieties selected from O and S, and where the alkylene chain is unsubstituted or may be substituted with 1, 2, 3, 4, 5 or 6 radicals selected from the group consisting of halogen, $C_1$-$C_4$-alkyl, $C_1$-$C_4$-haloalkyl, $C_1$-$C_4$-alkoxy and $C_1$-$C_4$-haloalkoxy, where $R^{10b}$ has one of the meanings give for $R^{10}$ and where $R^{10b}$ is in particular selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy, $R^{7b}$ is more particularly selected from the group consisting of halogen, $C_1$-$C_6$-alkyl, $C_1$-$C_6$-alkoxy, and $C_2$-$C_6$-alkynyl, and wherein the carbon atoms of the aforementioned aliphatic radicals may optionally be partly or completely halogenated, and wherein one or two radicals $R^{7b}$ may also be $C_3$-$C_6$-cycloalkyl, which is unsubstituted or carries 1, 2, 3, 4 or 5 radicals selected from fluorine, chlorine or methyl, phenyl, optionally substituted with 1, 2, 3, 4 or 5 identical or different substituents $R^{10b}$, or a a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10b}$, and wherein the nitrogen and/or the sulfur atom(s) of the heterocyclic ring may optionally be oxidized, in particular a 5- or 6-membered hetaryl having 1 or 2 heteroatoms selected from O, S and N, where the 5- or 6-membered hetaryl is unsubstituted or carries 1, 2 or 3 identical or different substituents $R^{10a}$, or two of $R^{7b}$ present on one ring carbon may together form =O or =S, or two $R^{7b}$ together form a linear $C_2$-$C_7$ alkylene chain, thus forming, together with the carbon atom to which they are bound, a 3-, 4-, 5- or 6-membered spiro ring, where 1 or 2 $CH_2$ moieties of the alkylene chain may be replaced by 1 or 2 heteroatom moieties selected from O and S, and where the alkylene chain is unsubstituted or may be substituted with 1, 2, 3, 4, 5 or 6 radicals selected from the group consisting of halogen, $C_1$-$C_4$-alkyl, $C_1$-$C_4$-haloalkyl, $C_1$-$C_4$-alkoxy and $C_1$-$C_4$-haloalkoxy, where $R^{10b}$ has one of the meanings give for $R^{10}$ and where $R^{10b}$ is in particular selected from the group consisting of halogen, $C_1$-$C_4$-alkyl, $C_1$-$C_4$-haloalkyl, $C_1$-$C_4$-alkoxy and $C_1$-$C_4$-haloalkoxy.

In the compounds of formula (I), where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, where m=0, the variables $R^1$, $R^2$, $R^3$, and $R^5$, independently of each other or in particular in combination, more particular may also have the following meanings:

$R^1$ and $R^2$ are, independently from each other, selected from the group consisting of hydrogen, halogen, cyano, $C_1$-$C_3$-alkyl, such as methyl ethyl or isopropyl, or $C_1$-$C_3$-haloalkyl such as fluoromethyl, difluoromethyl, trifluoromethyl, 1,1-difluoroethyl, 2-fluoroethyl, 2,2-difluoroethyl or 2,2,2-trifluoroethyl, where in particular at least one of the radicals $R^1$ and $R^2$ is hydrogen and where especially both $R^1$ and $R^2$ are hydrogen;

$R^3$ and $R^5$ together with the carbon atom, to which they are bound, form a 3 or 4 membered saturated carbocycle, i.e. a 1,1-cyclopropylidene or 1,1-cyclobutylidene radical, wherein each of the carbon atoms of the carbocycle may be unsubstituted or may carry 1, 2, 3, 4, 5 or 6 radicals $R^{7b}$, wherein $R^{7b}$ is as defined above and in particular selected from the group consisting of halogen, $C_1$-$C_6$-alkyl, $C_1$-$C_6$-alkoxy, and $C_2$-$C_6$-alkynyl, and wherein the carbon atoms of the aforementioned aliphatic radicals may optionally be partly or completely halogenated and/or substituted by a radical selected from $C_1$-$C_4$-alkoxy, $C_1$-$C_4$-alkoxycarbonyl, $C_1$-$C_4$-alkylcarbonyloxy, $C_1$-$C_4$-alkoxy-$C_1$-$C_4$-alkoxy, $C_1$-$C_4$-alkylsulfanyl, $C_3$-$C_6$-cycloalkyl, $C_3$-$C_6$-cycloalkoxy, phenoxy, 5- or 6-membered saturated heterocyclyl having 1 heteroatom selected from O and S, such as tetrahydropyranyl, tetrahydrofuranyl and tetrahydrothiopyranyl, where the 5- or 6-membered saturated heterocyclyl may be unsubstituted or carry 1 or 2 radicals selected from $C_1$-$C_4$-alkyl and $C_1$-$C_4$-alkoxy, and wherein one or two radicals $R^{7b}$ may also be $C_3$-$C_8$-cycloalkyl, in particular $C_3$-$C_6$-cycloalkyl, which is unsubstituted or carries 1, 2, 3, 4 or 5 radicals selected from fluorine, chlorine, $C_1$-$C_4$-alkyl such as methyl and $C_1$-$C_4$-alkoxycarbonyl such as methoxycarbonyl, $C_3$-$C_6$-cycloalkenyl, which is unsubstituted or carries 1, 2, 3, 4 or 5 radicals selected from fluorine, chlorine or $C_1$-$C_4$-alkyl such as methyl, phenyl, optionally substituted with 1, 2, 3, 4 or 5 identical or different substituents $R^{10b}$, or a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, such as tetrahydrofuryl, tetrahydropyranyl, tetrahydrothiopyranyl or thiazolyl, where the heterocyclic ring is optionally substituted with 1, 2, 3 or 4 identical or different substituents $R^{10b}$, and wherein the nitrogen and/or the sulfur atom(s) of the heterocyclic ring may optionally be oxidized, in particular a 5- or 6-membered hetaryl having 1 or 2 heteroatoms selected from O, S and N, where the 5- or 6-membered hetaryl is unsubstituted or carries 1, 2 or 3 identical or different substituents $R^{10b}$, or two of $R^{7b}$ present on one ring carbon may together form =O or =S, or two $R^{7b}$ together form a linear $C_2$-$C_7$ alkylene chain, thus forming, together with the carbon atom to which they are bound, a 3-, 4-, 5- or 6-membered spiro ring, where 1 or 2 $CH_2$ moieties of the alkylene chain may be replaced by 1 or 2 heteroatom moieties selected from O and S, and where the alkylene chain is unsubstituted or may be substituted with 1, 2, 3, 4, 5 or 6 radicals selected from the group consisting of halogen, $C_1$-$C_4$-alkyl, $C_1$-$C_4$-haloalkyl, $C_1$-$C_4$-alkoxy and $C_1$-$C_4$-haloalkoxy, where $R^{10b}$ has one of the meanings give for $R^{10}$ and where $R^{10b}$ is in particular selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy, or $R^{7b}$ is especially selected from the group consisting of particular selected from the group consisting of halogen, $C_1$-$C_4$-alkyl, and wherein one radical $R^{7b}$ may also be phenyl, optionally substituted with 1, 2, 3, 4 or 5, in particular 1, 2 or 3, identical or different substituents $R^{10b}$, where $R^{10b}$ is as defined above, and in particular selected from the group consisting of halogen, such as fluorine or chlorine, $C_1$-$C_4$-alkyl, CN, $C_1$-$C_4$-haloalkyl, $C_1$-$C_4$-alkoxy and $C_1$-$C_4$-haloalkoxy.

In the compounds of formula (I), where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, where m=0, the variables $R^1$, $R^2$, $R^3$, and $R^5$, independently of each other or in particular in combination, especially may also have the following meanings:

$R^1$ and $R^2$ are are hydrogen or one of $R^1$ and $R^2$ is hydrogen and the other of $R^1$ and $R^2$ is methyl;

$R^3$ and $R^5$ together form the following moieties:
$CH_2$—$CH_2$, CHF—$CH_2$, $CF_2$—$CH_2$, CHF—CHF, $CF_2$—CHF, $CF_2$—$CF_2$, CHCl—$CH_2$, $CCl_2$—$CH_2$, CHCl—CHCl, $CCl_2$—CHCl, $CCl_2$—$CCl_2$, $CH(CH_3)$—$CH_2$, $C(CH_3)_2$—$CH_2$, $CH(CH_3)$—$CH(CH_3)$, $C(CH_3)_2$—$CH(CH_3)$, $C(CH_3)_2$—$C(CH_3)_2$, $CH(OCH_3)$—$CH_2$, $CH(CH_2CH_3)$—$CH_2$, $CH(CH_2CH_2CH_3)$—$CH_2$, $CH(CH_2CH_2CH_2CH_3)$—$CH_2$, $CH(CH_3)$—$CH_2$—$CH_2$, $CH_2$—$CH(CH_3)$—$CH_2$, $C(CH_3)_2$—$CH_2$—$CH_2$, $CH_2$—$C(CH_3)_2$—$CH_2$, $CH(CH_3)$—$CH(CH_3)$—$CH_2$, $CH(CH_3)$—$CH_2$—$CH(CH_3)$, $CH(CH_3)$—$CH(CH_3)$—$CH(CH_3)$, $C(CH_3)_2$—$CH(CH_3)$—$CH_2$, $CH(CH_3)$—$C(CH_3)_2$—$CH_2$, $C(CH_3)_2$—$CH_2$—$C(CH_3)_2$, $C(CH_3)_2$—$C(CH_3)_2$—$CH_2$, $C(CH_3)_2$—$C(CH_3)_2$—$C(CH_3)_2$—$C(CH_3)_2$, CHF—$CH_2$—$CH_2$, $CH_2$—CHF—$CH_2$, $CF_2$—$CH_2$—$CH_2$, $CH_2$—$CF_2$—$CH_2$, CHF—CHF—$CH_2$, CHF—$CH_2$—CHF, CHF—CHF—CHF, $CF_2$—CHF—$CH_2$, CHF—$CF_2$—$CH_2$, $CF_2$—$CH_2$—$CF_2$, $CF_2$—$CF_2$—$CH_2$, $CF_2$—$CF_2$—$CF_2$, CHCl—$CH_2$—$CH_2$, $CH_2$—CHCl—$CH_2$, $CCl_2$—$CH_2$—$CH_2$, $CH_2$—$CCl_2$—$CH_2$, CHCl—CHCl—$CH_2$, CHCl—$CH_2$—CHCl, CHCl—CHCl—CHCl, $CCl_2$—CHCl—$CH_2$, CHCl—$CCl_2$—$CH_2$, $CCl_2$—$CH_2$—$CCl_2$, $CCl_2$—$CCl_2$—$CH_2$, $CCl_2$—$CCl_2$—$CCl_2$, or a radical $CH(R^{7bb})$—$CH_2$, where $R^{7bb}$ is selected from the group consisting of
$C_2$-$C_{10}$-alkyl, such as ethyl, n-propyl, isopropyl, n-butyl, tert.butyl, 1-methylpropyl, 2-methylpropyl, 1,2-dimethylpropyl, 2,2-dimethylpropyl, 3,3-dimethylpropyl, 1-methylbutyl, 1,2-dimethylbutyl, 3,3-dimethylbutyl, n-pentyl, 1-ethylpentyl, $C_2$-$C_4$-haloalkyl, such as 2,2-difluoroethyl, 1,1-difluoroethyl or 2,2,2-trifluoroethyl, $C_1$-$C_6$-alkyl, which is substituted by 1 radical selected from $C_1$-$C_4$-alkoxy, $C_1$-$C_4$-alkylcarbonyloxy, $C_1$-$C_4$-alkoxy-$C_1$-$C_4$-alkoxy, $C_1$-$C_4$-alkylsulfanyl, $C_3$-$C_8$-cycloalkyl, $C_3$-$C_8$-cycloalkoxy, phenoxy and 5- or 6-membered saturated heterocyclyl having 1 heteroatom selected from O and S, such as tetrahydropyranyl, tetrahydrofuranyl, tetrahydrothiopyranyl, where $C_3$-$C_8$-cycloalkyl, $C_3$-$C_8$-cycloalkoxy and 5- or 6-membered saturated heterocyclyl may be unsubstituted or carry 1 or 2 radicals selected from $C_1$-$C_4$-alkyl and $C_1$-$C_4$-alkoxy, examples of substituted $C_1$-$C_6$-alkyl including 1-methoxyethyl, 2-methoxyethyl, 1-propoxyethyl, 2-propoxyethyl, 1-isopropoxyethyl, 2-isopropoxyethyl, 1-isobutoxyethyl, 2-isobutoxyethyl, 1-(cyclohexyloxy)ethyl, 2-phenoxyethyl, (4-isopropylcyclohexyl)methyl, 1-acetoxyethyl, 2-acetoxyethyl, 6-acetoxyhexyl, 2-methylsulfanylpropyl, 1-methyl-2-methylsulfanylethyl, tetrahydropyran-4-ylmethyl, tetrahydrothiopyran-4-ylmethyl, $C_2$-$C_{10}$-alkenyl, such as 3-nonenyl, $C_3$-$C_{10}$-cycloalkyl, optionally substituted by 1 or 2 $C_1$-$C_4$-alkyl, such as cyclopropyl, cyclobutyl, cyclopentyl, cyclohexyl, cycloheptyl, cyclooctyl, 4-methylcyclohexyl, 4-isopropylcyclohexyl, and 6,6-dimethylnorpinan-2-yl, $C_5$-$C_6$-cycloalkenyl, optionally substituted by 1 or 2 $C_1$-$C_4$-alkyl, such as 2-methylcyclohex-3-en-1-yl, 5- or 6-membered saturated heterocyclyl having 1 heteroatom selected from O and S, such as tetrahydropyranyl, tetrahydrofuranyl and tetrahydrothiopyranyl, where the 5- or 6-membered saturated heterocyclyl may be unsubstituted or carry 1 or 2 radicals selected from $C_1$-$C_4$-alkyl and $C_1$-$C_4$-alkoxy, examples including tetrahydrofuran-2-yl, tetrahydrofuran-3-yl, tetrahydropyran-3-yl, tetrahydropyran-4-yl, tehtrahydrothiopyran-3-yl, tetrahydrothiopyran-4-yl, 6-methoxy-3-methyltetrahydropyran-2-yl, and 5,5-dimethyltetrahydrofuran-2-yl, optionally substituted phenyl such as phenyl, 2-chlropheynl, 2-fluoropheynl, 2-methylphenyl, 2-methoxyphenyl, 2-cyanophenyl, 3-chloropheynl, 3-fluoropheynl, 3-methylphenyl, 3-methoxyphenyl, 3-cyanophenyl, 4-chloropheynl, 4-fluoropheynl, 4-methylphenyl, 4-methoxyphenyl, 3-nitrophenyl, 4-(trifluoromethyl)phenyl, 3-(trifluoromethyl)phenyl and 4-cyanophenyl, 5- or 6-membered hetaryl having 1 or 2 heteroatoms as ring members, selected from O, S and N and where the hetaryl is unsubstituted or subistuted by 1 or 2 radicals selected from halogen, $C_1$-$C_4$-alkyl, $C_1$-$C_4$-haloalkyl, $C_1$-$C_4$-alkoxy and $C_1$-$C_4$-haloalkoxy examples of hetaryl including 4-methylthiazol-5-yl, 2-pyridyl and 3-pyridyl, phenyl-$C_1$-$C_4$-alkyl, such as benzyl or phenethyl, and hetaryl-$C_1$-$C_4$-alkyl, where the hetaryl is 5- or 6-membered and has 1 or 2 heteroatoms as ring members, selected from O, S and N and where the hetaryl is unsubstituted or subistuted by 1 or 2 radicals selected from halogen, $C_1$-$C_4$-alkyl, $C_1$-$C_4$-haloalkyl, $C_1$-$C_4$-alkoxy and $C_1$-$C_4$-haloalkoxy examples of hetaryl-$C_1$-$C_4$-alkyl including 1,1-dimethyl-2-(3-pyridyl)ethyl, thereby forming, together with the carbon atom they are bound to, an unsubstituted or substituted 1,1-cyclopropylidene or 1,1-cyclobutylidene radical.

In the compounds of formula (I), where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, where m=0, the variables $R^1$, $R^2$, $R^3$, and $R^5$, independently of each other or in particular in combination, especially may also have the following meanings:

$R^1$ and $R^2$ are are hydrogen or one of $R^1$ and $R^2$ is hydrogen and the other of $R^1$ and $R^2$ is methyl;

$R^3$ and $R^5$ together form a moiety selected from the group consisting of:

$CH_2$—$CH_2$, $CHF$—$CH_2$, $CF_2$—$CH_2$, $CHF$—$CHF$, $CF_2$—$CHF$, $CF_2$—$CF_2$, $CHCl$—$CH_2$, $CCl_2$—$CH_2$, $CHCl$—$CHCl$, $CCl_2$—$CHCl$, $CCl_2$—$CCl_2$, $CH(CH_3)$—$CH_2$, $C(CH_3)_2$—$CH_2$, $CH(CH_3)$—$CH(CH_3)$, $C(CH_3)_2$—$CH(CH_3)$, $C(CH_3)_2$—$C(CH_3)_2$, $CH(OCH_3)$—$CH_2$, $CH(CH_2CH_3)$—$CH_2$, $CH(CH_2CH_2CH_3)$—$CH_2$, $CH(CH_2CH_2CH_2CH_3)$—$CH_2$, $CH(CH_3)$—$CH_2$—$CH_2$, $CH_2$—$CH(CH_3)$—$CH_2$, $C(CH_3)_2$—$CH_2$—$CH_2$, $CH_2$—$C(CH_3)_2$—$CH_2$, $CH(CH_3)$—$CH(CH_3)$—$CH_2$, $CH(CH_3)$—$CH_2$—$CH(CH_3)$, $CH(CH_3)$—$CH(CH_3)$—$CH(CH_3)$, $C(CH_3)_2$—$CH(CH_3)$—$CH_2$, $CH(CH_3)$—$C(CH_3)_2$—$CH_2$, $C(CH_3)_2$—$CH_2$—$C(CH_3)_2$, $C(CH_3)_2$—$C(CH_3)_2$—$CH_2$, $C(CH_3)_2$—$C(CH_3)_2$—$C(CH_3)_2$, $CHF$—$CH_2$—$CH_2$, $CH_2$—$CHF$—$CH_2$, $CF_2$—$CH_2$—$CH_2$, $CH_2$—$CF_2$—$CH_2$, $CHF$—$CHF$—$CH_2$, $CHF$—$CH_2$—$CHF$, $CHF$—$CHF$—$CHF$, $CF_2$—$CHF$—$CH_2$, $CHF$—$CF_2$—$CH_2$, $CF_2$—$CH_2$—$CF_2$, $CF_2$—$CF_2$—$CH_2$, $CF_2$—$CF_2$—$CF_2$, $CHCl$—$CH_2$—$CH_2$, $CH_2$—$CHCl$—$CH_2$, $CCl_2$—$CH_2$—$CH_2$, $CH_2$—$CCl_2$—$CH_2$, $CHCl$—$CHCl$—$CH_2$, $CHCl$—$CH_2$—$CHCl$, $CHCl$—$CHCl$—$CHCl$, $CCl_2$—$CHCl$—$CH_2$, $CHCl$—$CCl_2$—$CH_2$, $CCl_2$—$CH_2$—$CCl_2$, $CCl_2$—$CCl_2$—$CH_2$, $CCl_2$—$CCl_2$—$CCl_2$ or a radical $CH(Ar)$—$CH_2$, where Ar is selected from phenyl, 2-chloropheynl, 2-fluoropheynl, 2-methylphenyl, 2-methoxyphenyl, 2-cyanophenyl, 3-chloropheynl, 3-fluoropheynl, 3-methylphenyl, 3-methoxyphenyl, 3-cyanophenyl, 4-chloropheynl, 4-fluoropehynl, 4-methylphenyl, 4-methoxyphenyl and 4-cyanophenyl, thereby forming, together with the carbon atom they are bound to, an unsubstituted or substituted 1,1-cyclopropylidene or 1,1-cyclobutylidene radical.

Special preference is given to compounds of formula (Ia) and (Ib),

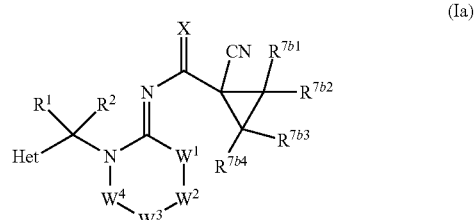

(Ia)

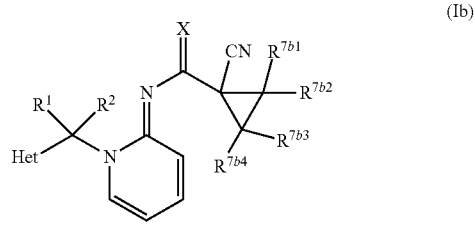

(Ib)

where Het, $W^1$, $W^2$, $W^3$, $W^4$ and X, are as defined above and in particular have the preferred meanings or the particularly preferred meanings;

$R^1$ and $R^2$ are, independently from each other, selected from the group consisting of hydrogen, halogen, cyano, $C_1$-$C_3$- alkyl, such as methyl ethyl or isopropyl, or $C_1$-$C_3$-haloalkyl such as fluoromethyl, difluoromethyl, trifluoromethyl, 1,1-difluoroethyl, 2-fluoroethyl, 2,2-difluoroethyl or 2,2,2-trifluoroethyl, where in particular at least one of the radicals $R^1$ and $R^2$ is hydrogen and where especially both $R^1$ and $R^2$ are hydrogen;

$R^{7b1}$ is hydrogen or has one of the meanings given for $R^{7b}$;

$R^{7b2}$, $R^{7b3}$ and $R^{7b4}$ are hydrogen, methyl or halogen, in particular hydrogen and where $R^{7b1}$ is in particular hydrogen or a radical selected from the group consisting of $C_1$-$C_{10}$-alkyl, such as methyl, ethyl, n-propyl, isopropyl, n-butyl, tert.butyl, 1-methylpropyl, 2-methylpropyl, 1,2-dimethylpropyl, 2,2-dimethylpropyl, 3,3-dimethylpropyl, 1-methylbutyl, 1,2-dimethylbutyl, 3,3-dimethylbutyl, n-pentyl, 1-ethylpentyl, $C_1$-$C_4$-haloalkyl, such as difluoromethyl, trifluoromethyl, 2,2-difluoroethyl, 1,1-difluoroethyl or 2,2,2-trifluoroethyl, $C_1$-$C_6$-alkyl, which is substituted by 1 radical selected from $C_1$-$C_4$-alkoxy, $C_1$-$C_4$-alkylcarbonyloxy, $C_1$-$C_4$-alkoxy-$C_1$-$C_4$-alkoxy, $C_1$-$C_4$-alkylsulfanyl, $C_3$-$C_8$-cycloalkyl, $C_3$-$C_8$-cycloalkoxy, phenoxy and 5- or 6-membered saturated heterocyclyl having 1 heteroatom selected from O and S, such as tetrahydropyranyl, tetrahydrofuranyl, tetrahydrothiopyranyl, where $C_3$-$C_8$-cycloalkyl, $C_3$-$C_8$-cycloalkoxy and 5- or 6-membered saturated heterocyclyl may be unsubstituted or carry 1 or 2 radicals selected from $C_1$-$C_4$-alkyl and $C_1$-$C_4$-alkoxy, examples of substituted $C_1$-$C_6$-alkyl including 1-methoxyethyl, 2-methoxyethyl, 1-propoxyethyl, 2-propoxyethyl, 1-isopropoxyethyl, 2-isopropoxyethyl, 1-isobutoxyethyl, 2-isobutoxyethyl, 1-(cyclohexyloxy)ethyl, 2-phenoxyethyl, (4-isopropylcyclohexyl)methyl, 1-acetoxyethyl, 2-acetoxyethyl, 6-acetoxyhexyl, 2-methylsulfanylpropyl, 1-methyl-2-methylsulfanylethyl, tetrahydropyran-4-ylmethyl, tetrahydrothiopyran-4-ylmethyl, $C_2$-$C_{10}$-alkenyl, such as 3-nonenyl, $C_3$-$C_{10}$-cycloalkyl, optionally substituted by 1 or 2 $C_1$-$C_4$-alkyl, such as cyclopropyl, cyclobutyl, cyclopentyl, cyclohexyl, cycloheptyl, cyclooctyl, 4-methylcyclohexyl, 4-isopropylcyclohexyl, and 6,6-dimethylnorpinan-2-yl, $C_5$-$C_6$-cycloalkenyl, optionally substituted by 1 or 2 $C_1$-$C_4$-alkyl, such as 2-methylcyclohex-3-en-1-yl, 5- or 6-membered saturated heterocyclyl having 1 heteroatom selected from O and S, such as tetrahydropyranyl, tetrahydrofuranyl and tetrahydrothiopyranyl, where the 5- or 6-membered saturated heterocyclyl may be unsubstituted or carry 1 or 2 radicals selected from $C_1$-$C_4$-alkyl and $C_1$-$C_4$-alkoxy, examples including tetrahydrofuran-2-yl, tetrahydrofuran-3-yl, tetrahydropyran-3-yl, tetrahydropyran-4-yl, tehtrahydrothiopyran-3-yl, tetrahydrothiopyran-4-yl, 6-methoxy-3-methyltetrahydropyran-2-yl, and 5,5-dimethyltetrahydrofuran-2-yl, optionally substituted phenyl such as phenyl, 2-chloropheynl, 2-fluoropheynl, 2-methylphenyl, 2-methoxyphenyl, 2-cyanophenyl, 3-chloropheynl, 3-fluoropheynl, 3-methylphenyl, 3-methoxyphenyl, 3-cyanophenyl, 4-chloropheynl, 4-fluoropheynl, 4-methylphenyl, 4-methoxyphenyl, 3-nitrophenyl, 4-(trifluoromethyl)phenyl, 3-(trifluoromethyl)phenyl and 4-cyanophenyl, 5- or 6-membered hetaryl having 1 or 2 heteroatoms as ring members, selected from O, S and N and where the hetaryl is unsubstituted or subistuted by 1 or 2 radicals selected from halogen, $C_1$-$C_4$-alkyl, $C_1$-$C_4$-haloalkyl, $C_1$-$C_4$-alkoxy and $C_1$-$C_4$-haloalkoxy examples of hetaryl including 4-methylthiazol-5-yl, 2-pyridyl and 3-pyridyl, phenyl-$C_1$-$C_4$-alkyl, such as benzyl or phenethyl, and hetaryl-$C_1$-$C_4$-alkyl, where the hetaryl is 5- or 6-membered and has 1 or 2 heteroatoms as ring members, selected from O, S and N and where the hetaryl is unsubstituted or subistuted by 1 or 2 radicals selected from halogen, $C_1$-$C_4$-alkyl, $C_1$-$C_4$-haloalkyl, $C_1$-$C_4$-alkoxy and $C_1$-$C_4$-haloalkoxy examples of hetaryl-$C_1$-$C_4$-alkyl including 1,1-dimethyl-2-(3-pyridyl)ethyl.

In the compounds of formula (I), where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, where m=0, the variables $R^1$, $R^2$, $R^3$, and $R^5$, independently of each other or in particular in combination, in particular may also have the following meanings:

$R^1$ and $R^2$ are, independently from each other, selected from the group consisting of hydrogen, halogen, such as fluorine or chlorine, CN, $C_1$-$C_6$-alkyl, in particular $C_1$-$C_4$-alkyl, such as methyl, ethyl, n-propyl or isopropyl, $C_3$-$C_6$-cycloalkyl, such as cyclopropyl or cyclobutyl, $C_1$-$C_6$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, or $C_3$-$C_6$-halocycloalkyl such as 1-fluorocyclopropyl or 2,2-difluorocyclopropyl, or $R^1$ and $R^2$ may together be =$CR^{13}R^{14}$ or $R^1$ and $R^2$ form, together with the carbon atom, which they attached to, a 3- to 5 membered saturated carbocyclic ring such as cyclopropyl, cyclobutyl or cyclopentyl;

$R^3$ and $R^5$ together with the carbon atom, to which they are bound, form a 3, 4, 5 or 6 membered saturated heterocycle having 1 or 2 non adjacent heteroatoms as ring members which are selected from O and S, in particular a 3 or 4 membered saturated heterocycle having 1 oxygen atom as ring member wherein the heterocycle may be unsubstituted or may carry 1, 2, 3, 4, 5 or 6 radicals $R^{7b}$, wherein $R^{7b}$, if present, is as defined above and wherein $R^{7b}$ if present, is in particular selected from the group consisting of halogen, $C_1$-$C_6$-alkyl, $C_1$-$C_6$-alkoxy, and $C_2$-$C_6$-alkynyl, and wherein the carbon atoms of the aforementioned aliphatic radicals may optionally be partly or completely halogenated and/or substituted by a radical selected from $C_1$-$C_4$-alkoxy, $C_1$-$C_4$-alkoxycarbonyl, $C_1$-$C_4$-alkylcarbonyloxy, $C_1$-$C_4$-alkoxy-$C_1$-$C_4$-alkoxy, $C_1$-$C_4$-alkylsulfanyl, $C_3$-$C_6$-cycloalkyl, $C_3$-$C_6$-cycloalkoxy, phenoxy, 5- or 6-membered saturated heterocyclyl having 1 heteroatom selected from O and S, such as tetrahydropyranyl, tetrahydrofuranyl and tetrahydrothiopyranyl, where the 5- or 6-membered saturated heterocyclyl may be unsubstituted or carry 1 or 2 radicals selected from $C_1$-$C_4$-alkyl and $C_1$-$C_4$-alkoxy, and wherein one or two radicals $R^{7b}$ may also be $C_3$-$C_8$-cycloalkyl, in particular $C_3$-$C_6$-cycloalkyl, which is unsubstituted or carries 1, 2, 3, 4 or 5 radicals selected from fluorine, chlorine, $C_1$-$C_4$-alkyl such as methyl and $C_1$-$C_4$-alkoxycarbonyl such as methoxycarbonyl, $C_3$-$C_6$-cycloalkenyl, which is unsubstituted or carries 1, 2, 3, 4 or 5 radicals selected from fluorine, chlorine or $C_1$-$C_4$-alkyl such as methyl, phenyl, optionally substituted with 1, 2, 3, 4 or 5 identical or different substituents $R^{10b}$, or a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, such as tetrahydrofuryl, tetrahydropyranyl, tetrahydrothiopyranyl or thiazolyl, where the heterocyclic ring is optionally substituted with 1, 2, 3 or 4 identical or different substituents $R^{10b}$, and wherein the nitrogen and/or the sulfur atom(s) of the heterocyclic ring may optionally be oxidized, in particular a 5- or 6-membered hetaryl having 1 or 2 heteroatoms selected from O, S and N, where the 5- or 6-membered hetaryl is unsubstituted or carries 1, 2 or 3 identical or different substituents $R^{10b}$, or two of $R^{7b}$ present on one ring carbon may together form =O or =S, or two $R^{7b}$ together form a linear $C_2$-$C_7$ alkylene chain, thus forming, together with the carbon atom to which they are bound, a 3-, 4-, 5- or 6-membered spiro ring, where 1 or 2 $CH_2$ moieties of the alkylene chain may be replaced by 1 or 2 heteroatom moieties selected from O and S, and where the alkylene chain is unsubstituted or may be substituted with 1, 2, 3, 4, 5 or 6 radicals selected from the group consisting of halogen, $C_1$-$C_4$-alkyl, $C_1$-$C_4$-haloalkyl, $C_1$-$C_4$-alkoxy and $C_1$-$C_4$-haloalkoxy, where $R^{10b}$ has one of the meanings give for $R^{10}$ and where $R^{10b}$ is in particular selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy, $R^{7b}$ is more particularly selected from the group consisting of halogen, $C_1$-$C_6$-alkyl, $C_1$-$C_6$-alkoxy, and $C_2$-$C_6$-alkynyl, and wherein the carbon atoms of the aforementioned aliphatic radicals may optionally be partly or completely halogenated, and wherein one or two radicals $R^{7b}$ may also be $C_3$-$C_6$-cycloalkyl, which is unsubstituted or carries 1, 2, 3, 4 or 5 radicals selected from fluorine, chlorine or methyl, phenyl, optionally substituted with 1, 2, 3, 4 or 5 identical or different substituents $R^{10b}$, or a a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10b}$, and wherein the nitrogen and/or the sulfur atom(s) of the heterocyclic ring may optionally be oxidized, in particular a 5- or 6-membered hetaryl having 1 or 2 heteroatoms selected from O, S and N, where the 5- or 6-membered hetaryl is unsubstituted or carries 1, 2 or 3 identical or different substituents $R^{10a}$, or two of $R^{7b}$ present on one ring carbon may together form =O or =S, or two $R^{7b}$ together form a linear $C_2$-$C_7$ alkylene chain, thus forming, together with the carbon atom to which they are bound, a 3-, 4-, 5- or 6-membered spiro ring, where 1 or 2 $CH_2$ moieties of the alkylene chain may be replaced by 1 or 2 heteroatom moieties selected from O and S, and where the alkylene chain is unsubstituted or may be substituted with 1, 2, 3, 4, 5 or 6 radicals selected from the group consisting of halogen, $C_1$-$C_4$-alkyl, $C_1$-$C_4$-haloalkyl, $C_1$-$C_4$-alkoxy and $C_1$-$C_4$-haloalkoxy, where $R^{10b}$ has one of the meanings give for $R^{10}$ and where $R^{10b}$ is in particular selected from the group consisting of halogen, $C_1$-$C_4$-alkyl, $C_1$-$C_4$-haloalkyl, $C_1$-$C_4$-alkoxy and $C_1$-$C_4$-haloalkoxy.

In the compounds of formula (I), where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, where m=0, the variables $R^1$, $R^2$, $R^3$, and $R^5$, independently of each other or in particular in combination, more particular may also have the following meanings:

$R^1$ and $R^2$ are, independently from each other, selected from the group consisting of hydrogen, halogen, cyano, $C_1$-$C_3$-alkyl, such as methyl ethyl or isopropyl, or $C_1$-$C_3$-haloalkyl such as fluoromethyl, difluoromethyl, trifluoromethyl, 1,1-difluoroethyl, 2-fluoroethyl, 2,2-difluoroethyl or 2,2,2-trifluoroethyl, where in particular at least one of the radicals $R^1$ and $R^2$ is hydrogen and where especially both $R^1$ and $R^2$ are hydrogen;

$R^3$ and $R^5$ together with the carbon atom, to which they are bound, form a 3, 4, 5 or 6 membered saturated heterocycle having 1 or 2 non adjacent heteroatoms as ring members which are selected from O and S, in particular a 3 or 4 membered saturated heterocycle having 1 oxygen atom as ring member wherein the heterocycle may be unsubstituted or may carry 1, 2, 3, 4, 5 or 6 radicals $R^{7b}$, wherein $R^{7b}$, if present, is as defined above and wherein $R^{7b}$ is as defined above and in particular selected from the group consisting of halogen, $C_1$-$C_6$-alkyl, $C_1$-$C_6$-alkoxy, and $C_2$-$C_6$-alkynyl, and wherein the carbon atoms of the aforementioned aliphatic radicals may optionally be partly or completely halogenated and/or substituted by a radical selected from $C_1$-$C_4$-alkoxy, $C_1$-$C_4$-alkoxycarbonyl, $C_1$-$C_4$-alkylcarbonyloxy, $C_1$-$C_4$-alkoxy-$C_1$-$C_4$-alkoxy, $C_1$-$C_4$-alkylsulfanyl, $C_3$-$C_6$-cycloalkyl, $C_3$-$C_6$-cycloalkoxy, phenoxy, 5- or 6-membered saturated heterocyclyl having 1 heteroatom selected from O and S, such as tetrahydropyranyl, tetrahydrofuranyl and tetrahydrothiopyranyl, where the 5- or 6-membered saturated heterocyclyl may be unsubstituted or carry 1 or 2 radicals selected from $C_1$-$C_4$-alkyl and $C_1$-$C_4$-alkoxy, and wherein one or two radicals $R^{7b}$ may also be $C_3$-$C_8$-cycloalkyl, in particular $C_3$-$C_6$-cycloalkyl, which is unsubstituted or carries 1, 2, 3, 4 or 5 radicals selected from fluorine, chlorine, $C_1$-$C_4$-alkyl such as methyl and $C_1$-$C_4$-alkoxycarbonyl such as methoxycarbonyl, $C_3$-$C_6$-cycloalkenyl, which is unsubstituted or carries 1, 2, 3, 4 or 5 radicals selected from fluorine, chlorine or $C_1$-$C_4$-alkyl such as methyl, phenyl, optionally substituted with 1, 2, 3, 4 or 5 identical or different substituents $R^{10b}$, or a 3-, 4-, 5-, 6- or 7-membered saturated, partly saturated or unsaturated aromatic heterocyclic ring comprising 1, 2 or 3 heteroatoms as ring members, which are identical or different and selected from oxygen, nitrogen and sulfur, such as tetrahydrofuryl, tetrahydropyranyl, tetrahydrothiopyranyl or thiazolyl, where the heterocyclic ring is optionally substituted with 1, 2, 3 or 4 identical or different substituents $R^{10b}$, and wherein the nitrogen and/or the sulfur atom(s) of the heterocyclic ring may optionally be oxidized, in particular a 5- or 6-membered hetaryl having 1 or 2 heteroatoms selected from O, S and N, where the 5- or 6-membered hetaryl is unsubstituted or carries 1, 2 or 3 identical or different substituents $R^{10b}$, or two of $R^{7b}$ present on one ring carbon may together form =O or =S, or two $R^{7b}$ together form a linear $C_2$-$C_7$ alkylene chain, thus forming, together with the carbon atom to which they are bound, a 3-, 4-, 5- or 6-membered spiro ring, where 1 or 2 $CH_2$ moieties of the alkylene chain may be replaced by 1 or 2 heteroatom moieties selected from O and S, and where the alkylene chain is unsubstituted or may be substituted with 1, 2, 3, 4, 5 or 6 radicals selected from the group consisting of halogen, $C_1$-$C_4$-alkyl, $C_1$-$C_4$-haloalkyl, $C_1$-$C_4$-alkoxy and $C_1$-$C_4$-haloalkoxy, where $R^{10b}$ has one of the meanings give for $R^{10}$ and where $R^{10b}$ is in particular selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy, or $R^{7b}$ is especially selected from the group consisting of particular selected from the group consisting of halogen, $C_1$-$C_4$-alkyl, and wherein one radical $R^{7b}$ may also be phenyl, optionally substituted with 1, 2, 3, 4 or 5, in particular 1, 2 or 3, identical or different substituents $R^{10b}$, where $R^{10b}$ is as defined above, and in particular selected from the group consisting of halogen, such as fluorine or chlorine, $C_1$-$C_4$-alkyl, CN, $C_1$-$C_4$-haloalkyl, $C_1$-$C_4$-alkoxy and $C_1$-$C_4$-haloalkoxy.

In the compounds of formula (I), where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, where m=0, the variables $R^1$, $R^2$, $R^3$, and $R^5$, independently of each other or in particular in combination, especially may also have the following meanings:

$R^1$ and $R^2$ are are hydrogen or one of $R^1$ and $R^2$ is hydrogen and the other of $R^1$ and $R^2$ is methyl;

$R^3$ and $R^5$ together form O—$CH_2$ or O—$CH_2$—$CH_2$, where 1, 2, 3 or 4 of the hydrogen atoms of $CH_2$ and $CH_2$—$CH_2$, respectively, may be replaced by a radical $R^{7b}$, thereby forming, together with the carbon atom they are bound to, an unsubstituted or substituted 1,1-cyclopropylidene or 1,1-cyclobutylidene radical.

In the compounds of formulae (I) and (Ia), in particular in those compounds of formula (I) where the moiety of formula (A) is selected from the moieties of formulae W.Het-1, W.Het-2, W.Het-3, W.Het-4, W.Het-5, W.Het-6, W.Het-7, W.Het-8, W.Het-9, W.Het-10, W.Het-11 and W.Het-12 and likewise in the embodiments 1, 2, 3, 4, 5, 6, 1a, 2a, 3a, 4a, 5a and 6a, the variable X is in particular O.

Apart from that, the variables $Het^{\#}$, Q, $R^v$, $R^w$, $R^6$, $R^7$, $R^{7a}$, $R^8$, $R^{8a}$, $R^9$, $R^{9a}$, $R^{9b}$, $R^{9c}$, $R^{9d}$, $R^{10}$, $R^{10a}$, $R^{11}$, $R^{12}$, $R^{13}$, $R^{14}$, $R^{15}$, $R^{16}$, $R^{17}$, $R^{17a}$, $R^{17b}$ and $R^{17c}$, irrespectively of their occurrence, in particular have the following meanings, if not stated otherwise:

$Het^{\#}$ irrespectively of its occurrence, is 5- or 6-membered hetaryl such as pyridyl, thienyl, furyl, pyrrolyl, thiazolyl, isothiazolyl, pyrazolyl, imidazolyl, oxazolyl or isoxazolyl, which is unsubstituted or substituted by 1, 2 or 3 radicals $R^{10}$.

Q is, irrespectively of its occurrence, selected from a single bond, $NR^{9a}$, $CH_2$, and $NR^{9a}CH_2$, and it is in particular a single bond, NH, $N(C_1$-$C_4$-alkyl), $CH_2$, $NHCH_2$ or $N(C_1$-$C_4$-alkyl)$CH_2$.

$R^v$ is hydrogen or together with an $R^v$, which is bound to an adjacent carbon atom, forms together with the existing bound a C=C-double bond.

$R^w$ irrespectively of its occurrence, is selected from the group consisting of hydrogen, halogen, such as fluorine or chlorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy. $R^w$ is more particularly hydrogen, chlorine, fluorine or methyl and especially hydrogen.

$R^6$ irrespectively of its occurrence, is selected from the group consisting of halogen, such as chlorine or fluorine, $C_1$-$C_4$-alkyl, such as methyl or ethyl, $C_1$-$C_4$-alkoxy, such as methoxy or ethoxy, $C_1$-$C_4$-haloalkoxy, such as difluoromethoxy or trifluormethoxy, and $C_1$-$C_4$-haloalkyl, such as difluoromethyl, trifluoromethyl, 2,2-difluoroethyl, 2,2,2-trifluoroethyl or pentafluoroethyl, more preferably from halogen, $C_1$-$C_4$-alkyl and $C_1$-$C_4$-haloalkyl, even more preferably from fluorine, chlorine, $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl.

$R^7$ irrespectively of its occurrence, is selected from the group consisting of CN, $C_1$-$C_4$-alkoxy, such as methoxy or ethoxy, $C_1$-$C_4$-haloalkoxy, such as difluoromethoxy or trifluormethoxy, such as difluoromethyl, trifluoromethyl, 2,2-difluoroethyl, 2,2,2-trifluoroethyl or pentafluoroethyl, more preferably from halogen, $C_1$-$C_4$-alkyl and $C_1$-$C_4$-haloalkyl, even more preferably from fluorine, chlorine, $C_1$-$C_2$-alkyl, such as methyl or ethyl and $C_1$-$C_2$-haloalkyl such as difluoromethyl, trifluoromethyl, 2,2-difluoroethyl, 2,2,2-trifluoroethyl or pentafluoroethyl, $C_3$-$C_6$-cycloalkyl such as cyclopropyl, cyclobutyl or cyclopropyl, and $C_3$-$C_6$-halocycloalkyl.

$R^{7a}$ irrespectively of its occurrence, is selected from the group consisting of hydrogen, $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl, where the phenyl ring in the last two radicals is unsubstituted or substituted by 1, 2 or 3 identical or different radicals selected from the group consisting of halogen, such as chlorine or fluorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

$R^8$ irrespectively of its occurrence, is selected from the group consisting of $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl, where the phenyl ring in the last two radicals is unsubstituted or substituted by 1, 2 or 3 identical or different radicals selected from the group consisting of halogen, such as chlorine or fluorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

$R^{8a}$ irrespectively of its occurrence, is selected from the group consisting of $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl, where the phenyl ring in the last two radicals is unsubstituted or substituted by 1, 2 or 3 identical or different radicals selected from the group consisting of halogen, such as chlorine or fluorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

$R^9$ irrespectively of its occurrence, is selected from the group consisting of $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl, where the phenyl ring in the last two radicals is unsubstituted or substituted by 1, 2 or 3 identical or different radicals selected from the group consisting of halogen, such as chlorine or fluorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

$R^{9a}$ and $R^{9b}$ irrespectively of their occurrence, are preferably selected from the group consisting of hydrogen, $C_1$-$C_4$-alkyl, such as methyl, ethyl, n-propyl, isopropyl, n-butyl, 2-butyl or isobutyl, and $C_1$-$C_4$-haloalkyl, such as fluoromethyl, difluoromethyl, trifluoromethyl, 1,1-difluoroethyl, 2-fluoroethyl, 2,2-difluoroethyl or 2,2,2-trifluoroethyl, or $NR^{9a}R^{9b}$ may also be a saturated N-bound 3-, 4-, 5- or 6-membered heterocycle, which in addition to the nitrogen atom may have 1 further heteroatom as ring members, which is selected from O and N and where the N-bound 3-, 4-, 5- or 6-membered heterocycle may be unsubstituted or carry 1, 2, 3 or 4 radicals selected from $C_1$-$C_4$-alkyl and $C_1$-$C_4$-haloalkyl. Examples of such radicals $NR^{9a}R^{9b}$ include, but are not limited to methylamino, ethylamino, n-propylamino, isopropylamino, n-butylamino, 2-butylamino, isobutylamino, dimethylamino, diethylamino, di-n-propylamino, di-n-butylamino, N-methyl-N-ethylamino, N-methyl-N-propylamino, N-methyl-N-n-propylamino, N-methyl-N-isopropylamino, N-methyl-N-n-butylamino, N-methyl-N-2-butylamino, N-methyl-N-isobutylamino, 1-pyrrolidinyl, 1-piperidinyl, 1-piperazinly, 4-methyl-1-piperazinly and 4-morpholinyl.

$R^{9c}$ and $R^{9d}$ irrespectively of their occurrence, are preferably selected from the group consisting of hydrogen, $C_1$-$C_4$-alkyl, such as methyl, ethyl, n-propyl, isopropyl, n-butyl, 2-butyl or isobutyl, and $C_1$-$C_4$-haloalkyl, such as fluoromethyl, difluoromethyl, trifluoromethyl, 1,1-difluoroethyl, 2-fluoroethyl, 2,2-difluoroethyl or 2,2,2-trifluoroethyl. Examples of such radicals $NR^{9c}R^{9d}$ include, but are not limited to methylamino, ethylamino, n-propylamino, isopropylamino, n-butylamino, 2-butylamino, isobutylamino, dimethylamino, diethylamino, di-n-propylamino, di-n-butylamino, N-methyl-N-ethylamino, N-methyl-N-propylamino, N-methyl-N-n-propylamino, N-methyl-N-isopropylamino, N-methyl-N-n-butylamino, N-methyl-N-2-butylamino and N-methyl-N-isobutylamino.

$R^{10}$ irrespectively of its occurrence, is selected from the group consisting of halogen, such as chlorine or fluorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy. $R^{10a}$ irrespectively of its occurrence, is selected from the group consisting of halogen, cyano, $NO_2$, $C_1$-$C_6$-alkyl, $C_1$-$C_6$-haloalkyl, $C_3$-$C_8$-cycloalkyl, $C_3$-$C_8$-halocycloalkyl, phenyl, optionally substituted with 1, 2, 3, 4 or 5 identical or different radicals selected from OH, halogen, cyano, nitro, $C_1$-$C_6$-alkyl, $C_1$-$C_6$-haloalkyl, $C_1$-$C_6$-alkoxy and $C_1$-$C_6$-haloalkoxy.

$R^{11}$, $R^{12}$ independently of their occurrence, are selected from the group consisting of $C_1$-$C_6$-alkyl, $C_1$-$C_6$-alkoxy, $C_3$-$C_8$-cycloalkyl, $C_3$-$C_8$-cycloalkyl-$C_1$-$C_4$-alkyl, phenyl and benzyl, where the phenyl ring in last two radicals are unsubstituted or substituted with 1, 2, or 3 identical or different radicals selected from fluorine, chlorine, $C_1$-$C_3$-alkyl, $C_1$-$C_2$-haloalkyl, $C_1$-$C_2$-alkoxy and $C_1$-$C_2$-haloalkoxy.

$R^{13}$, $R^{14}$ independently of their occurrence, are selected from the group consisting of hydrogen, fluorine, chlorine, CN, $C_1$-$C_4$-alkyl, such as methyl, ethyl, n-propyl or n-butyl, $C_3$-$C_6$-cycloalkyl, such as cyclopropyl, cyclobutyl or cyclopentyl, and phenyl.

$R^{15}$ irrespectively of its occurrence, is selected from the group consisting of hydrogen, $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl, where the phenyl ring in the last two radicals is unsubstituted or substituted by 1, 2 or 3 identical or different radicals selected from the group consisting of halogen, such as chlorine or fluorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

$R^{16}$ irrespectively of its occurrence, is selected from the group consisting of $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl, where the phenyl ring in the last two radicals is unsubstituted or substituted by 1, 2 or 3 identical or different radicals selected from the group consisting of halogen, such as chlorine or fluorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

$R^{17}$ irrespectively of its occurrence, is selected from the group consisting of hydrogen, $C_1$-$C_6$-alkyl, $C_1$-$C_4$-haloalkyl, $C_1$-$C_6$-alkoxy, $C_1$-$C_4$-haloalkoxy, $C_3$-$C_6$-alkenyl, $C_3$-$C_6$-cycloalkyl-$C_1$-$C_4$-alkyl, phenyl and benzyl, where the phenyl ring in the last two radicals is unsubstituted or substituted by 1, 2 or 3 identical or different radicals selected from the group consisting of halogen, such as chlorine or fluorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

$R^{17a}$ and $R^{17b}$ irrespectively of their occurrence, are preferably selected from the group consisting of hydrogen, $C_1$-$C_4$-alkyl, such as methyl, ethyl, n-propyl, isopropyl, n-butyl, 2-butyl or isobutyl, and $C_1$-$C_4$-haloalkyl, such as fluoromethyl, difluoromethyl, trifluoromethyl, 1,1-difluoroethyl, 2-fluoroethyl, 2,2-difluoroethyl or 2,2,2-trifluoroethyl, or $NR^{9a}R^{9b}$ may also be a saturated N-bound 3-, 4-, 5- or 6-membered heterocycle, which in addition to the nitrogen atom may have 1 further heteroatom as ring members, which is selected from O and N and where the N-bound 3-, 4-, 5- or 6-membered heterocycle may be unsubstituted or carry 1, 2, 3 or 4 radicals selected from $C_1$-$C_4$-alkyl and $C_1$-$C_4$-haloalkyl. Examples of such radicals $NR^{9a}R^{9b}$ include, but are not limited to methylamino, ethylamino, n-propylamino, isopropylamino, n-butylamino, 2-butylamino, isobutylamino, dimethylamino, diethylamino, di-n-propylamino, di-n-butylamino, N-methyl-N-ethylamino, N-methyl-N-propylamino, N-methyl-N-n-propylamino, N-methyl-N-isopropylamino, N-methyl-N-n-butylamino, N-methyl-N-2-butylamino, N-methyl-N-isobutylamino, 1-pyrrolidinyl, 1-piperidinyl, 1-piperazinly, 4-methyl-1-piperazinly and 4-morpholinyl.

$R^{17c}$ irrespectively of its occurrence, is selected from the group consisting of hydrogen, $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl, where the phenyl ring in the last two radicals is unsubstituted or substituted by 1, 2 or 3 identical or different radicals selected from the group consisting of halogen, such as chlorine or fluorine, CN, $C_1$-$C_4$-alkyl, such as methyl, ethyl, n-propyl and isopropyl, $C_1$-$C_4$-haloalkyl, in particular $C_1$-$C_2$-haloalkyl, such as fluoromethyl, difluoromethyl, trifluoromethyl, 1,1-difluoroethyl, 2-fluoroethyl, 2,2-difluoroethyl or 2,2,2-trifluoroethyl, $C_1$-$C_4$-alkoxy, such as methoxy, ethoxy, n-propoxy and isopropoxy, and $C_1$-$C_4$-haloalkoxy, in particular $C_1$-$C_2$-haloalkoxy, such as fluoromethoxy, difluoromethoxy, trifluoromethoxy, 1,1-difluoroethoxy, 2-fluoroethoxy, 2,2-difluoroethoxy or 2,2,2-trifluoroethoxy.

A special group of embodiments relates to the compounds of formula (I)-A.1a, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.2a, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.1b, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.2b, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.1c, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.2c, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.1d, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.2d, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.3a, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.4a, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.3b, to their tautomers, to their stereoisomers and to their salts, where m, $R^1$, $R^3$, $R^{4a}$, $R^{4b}$ and $R^5$ are as defined above and where $R^1$, $R^3$, $R[CR^{4a}R^{4b}]_m{}^4$ and $R^5$ have in particular one of the meanings given in any of lines 1 to 872 of the following table A.

A further special group of embodiments relates to the compounds of formula (I)-A.4b, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.3c, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.4c, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.3d, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.4d, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.5a, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.5b, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.5c, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A further special group of embodiments relates to the compounds of formula (I)-A.5d, to their tautomers, to their stereoisomers and to their salts, where m, $R^1$, $R^3$, $R^{4a}$, $R^{4b}$ and $R^5$ are as defined above and where $R^1$, $R^3$, $[CR^{4a}R^{4b}]_m$ and $R^5$ have in particular one of the meanings given in any of lines 1 to 872 of the following table A.

A skilled person will readily appreciate that the compounds of formulae (I)-A.1a, (I)-A.2a, (I)-A.3a, (I)-A.4a, (I)-A.1b, (I)-A.2b, (I)-A.3b, (I)-A.4b, (I)-A.1c, (I)-A.2c, (I)-A.3c, (I)-A.4c, (I)-A.1d, (I)-A.2d, (I)-A.3d, (I)-A.4d, (I)-A.5a, (I)-A.5b, (I)-A.5c and (I)-A.5d, where $R^1$, $R^3$, $[CR^{4a}R^{4b}]_m$ and $R^5$ have the meanings given in one of lines 6 to 164, 168 to 308, 333 to 436, 442 to 744 or 769 to 872 of the following table A may have S- or R-configuration with regard to the carbon atom carrying the radical $R^3$. A skilled person will also readily appreciate that the compounds of formulae (I)-A.1a, (I)-A.2a, (I)-A.3a, (I)-A.4a, (I)-A.1b, (I)-A.2b, (I)-A.3b, (I)-A.4b, (I)-A.1c, (I)-A.2c, (I)-A.3c, (I)-A.4c, (I)-A.1d, (I)-A.2d, (I)-A.3d, (I)-A.4d, (I)-A.5a, (I)-A.5b, (I)-A.5c and (I)-A.5d, where $R^1$, $R^3$, $[CR^{4a}R^{4b}]_m$ and $R^5$ have the meanings given in one of lines 437 to 872 of the following table A may have S- or R-configuration with regard to the carbon atom carrying the radical $R^1$. A skilled person will also readily appreciate that the compounds of formulae (I)-A.1a, (I)A.2a, (I)-A.3a, (I)-A.4a, (I)-A.1b, (I)-A.2b, (I)-A.3b, (I)-A.4b, (I)-A.1c, (I)-A.2c, (I)-A.3c, (I)-A.4c, (I)-A.1d, (I)-A.2d, (I)-A.3d, (I)-A.4d, (I)-A.5a, (I)-A.5b, (I)-A.5c and (I)-A.5d, where $R^1$, $R^3$, $[CR^{4a}R^{4b}]_m$ and $R^5$ have the meanings given in one of lines 442 to 744 or 769 to 872 of the following table A will form diastereomeric mixtures. The aforementioned embodiments include both the S-enantiomers and the R-enantiomers as well as mixtures of these enantiomers, in particular racemic mixtures and also pure diastereomers and mixtures of said diastereomers.

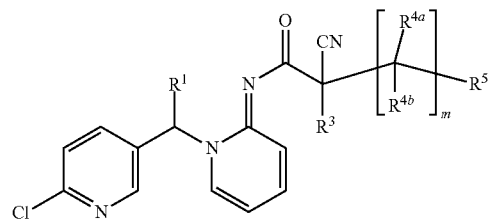

I-A.1a

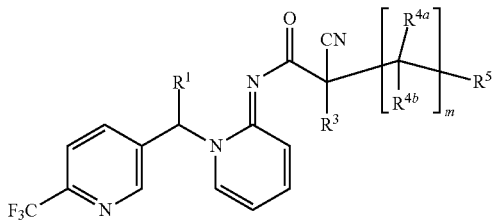

I-A.2a

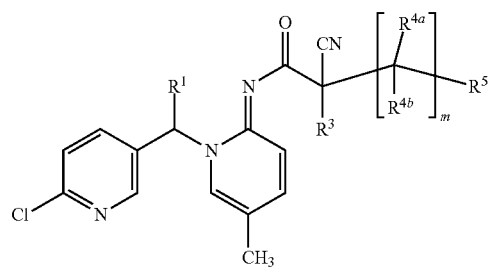

I-A.1b

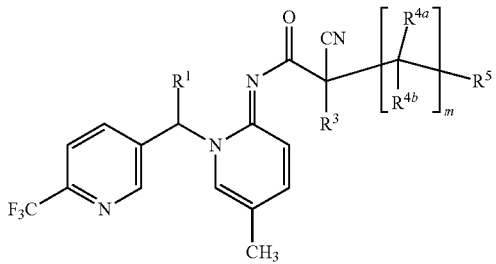

I-A.2b

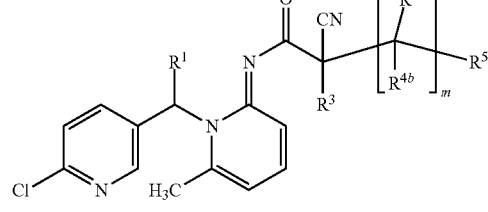

I-A.1c

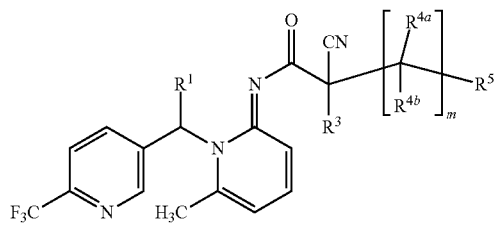
I-A.2c
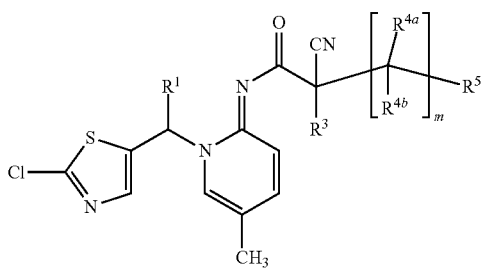
I-A.4b
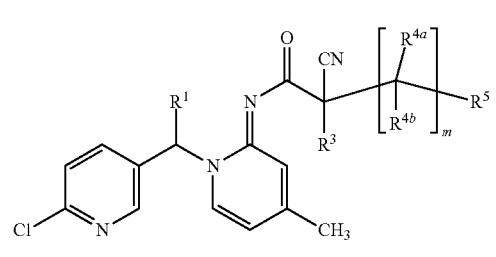
I-A.1d
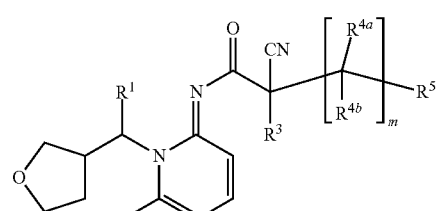
I-A.3c
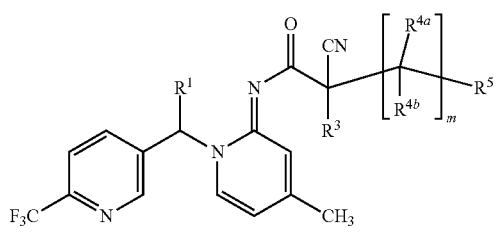
I-A.2d
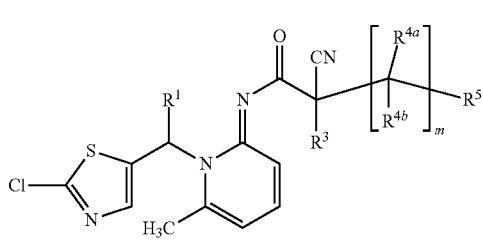
I-A.4c
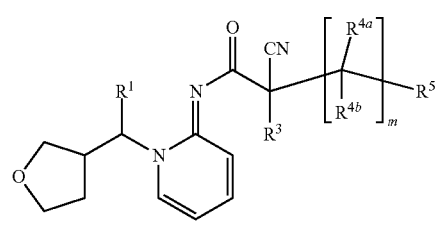
I-A.3a
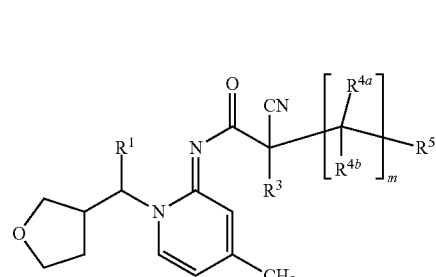
I-A.3d
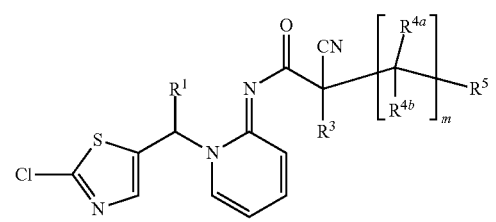
I-A.4a
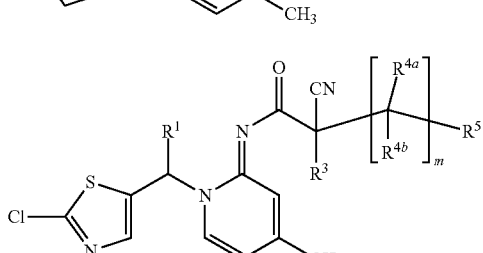
I-A.4d
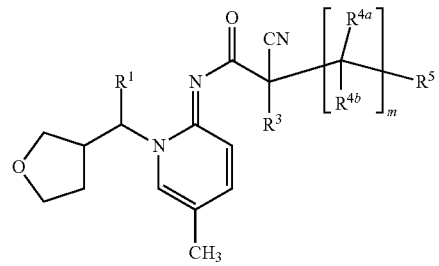
I-A.3b
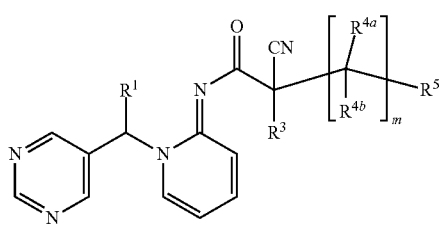
I-A.5a

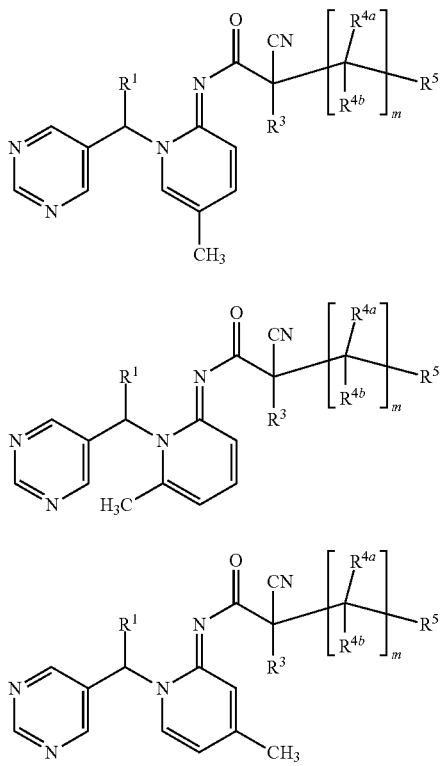

I-A.5b

I-A.5c

I-A.5d

TABLE A

| # | R¹ | R³ | R⁵ | [CR⁴ᵃR⁴ᵇ]ₘ |
|---|---|---|---|---|
| 1. | H | H | H | — |
| 2. | H | CH₃ | CH₃ | — |
| 3. | H | CH₂CH₃ | CH₂CH₃ | — |
| 4. | H | F | F | — |
| 5. | H | Cl | Cl | — |
| 6. | H | H | F | — |
| 7. | H | H | Cl | — |
| 8. | H | H | Br | — |
| 9. | H | CH₃ | F | — |
| 10. | H | CH₃ | Cl | — |
| 11. | H | CH₃ | Br | — |
| 12. | H | H | CH₃ | — |
| 13. | H | H | CH₂CH₃ | — |
| 14. | H | H | CH₂CH₂CH₃ | — |
| 15. | H | H | CH(CH₃)₂ | — |
| 16. | H | H | CH₂CH₂CH₂CH₃ | — |
| 17. | H | H | CH(CH₃)CH₂CH₃ | — |
| 18. | H | H | CH₂CH(CH₃)₂ | — |
| 19. | H | H | CN | — |
| 20. | H | H | c-C₃H₅ | — |
| 21. | H | H | c-C₄H₇ | — |
| 22. | H | H | c-C₅H₉ | — |
| 23. | H | H | c-C₆H₁₁ | — |
| 24. | H | H | C₆H₅ | — |
| 25. | H | H | 4-Cl—C₆H₄ | — |
| 26. | H | H | 4-F—C₆H₄ | — |
| 27. | H | H | 4-Br—C₆H₄ | — |
| 28. | H | H | 3-Cl—C₆H₄ | — |
| 29. | H | H | 3-F—C₆H₄ | — |
| 30. | H | H | 3-Br—C₆H₄ | — |
| 31. | H | H | 2-Cl—C₆H₄ | — |
| 32. | H | H | 2-F—C₆H₄ | — |
| 33. | H | H | 2-Br—C₆H₄ | — |
| 34. | H | H | 2-CN—C₆H₄ | — |
| 35. | H | H | 3-CN—C₆H₄ | — |
| 36. | H | H | 4-CN—C₆H₄ | — |
| 37. | H | H | 3-CH₃O—C₆H₄ | — |
| 38. | H | H | 4-CH₃—O—C₆H₄ | — |
| 39. | H | H | 3,4-(CH₃O)₂—C₆H₃ | — |
| 40. | H | H | 3,4,5-(CH₃O)₃—C₆H₂ | — |
| 41. | H | H | 3-CH₃O-4-F—C₆H₃ | — |
| 42. | H | H | 4-CH₃O-3-F—C₆H₃ | — |
| 43. | H | H | 2-CH₃—C₆H₄ | — |
| 44. | H | H | 3-CH₃—C₆H₄ | — |
| 45. | H | H | 4-CH₃—C₆H₄ | — |
| 46. | H | H | 2-CF₃—C₆H₄ | — |
| 47. | H | H | 3-CF₃—C₆H₄ | — |
| 48. | H | H | 4-CF₃—C₆H₄ | — |
| 49. | H | H | 3,4-Cl₂—C₆H₃ | — |
| 50. | H | H | 2,3-Cl₂—C₆H₃ | — |
| 51. | H | H | 3,5-Cl₂—C₆H₃ | — |
| 52. | H | H | 2,4-Cl₂—C₆H₃ | — |
| 53. | H | H | 2,5-Cl₂—C₆H₃ | — |
| 54. | H | H | 2,6-Cl₂—C₆H₃ | — |
| 55. | H | H | 3,4-F₂—C₆H₃ | — |
| 56. | H | H | 3,5-F₂—C₆H₃ | — |
| 57. | H | H | 2,3-F₂—C₆H₃ | — |
| 58. | H | H | 2,4-F₂—C₆H₃ | — |
| 59. | H | H | 2,5-F₂—C₆H₃ | — |
| 60. | H | H | 2,6-F₂—C₆H₃ | — |
| 61. | H | H | 3-Cl-4-F—C₆H₃ | — |
| 62. | H | H | 4-Cl-3-F—C₆H₃ | — |
| 63. | H | H | 3-Br-4-F—C₆H₃ | — |
| 64. | H | H | 4-Br-3-F—C₆H₃ | — |
| 65. | H | H | 3-Br-4-Cl—C₆H₃ | — |
| 66. | H | H | 4-Br-3-Cl—C₆H₃ | — |
| 67. | H | H | 2-Cl-5-NO₂—C₆H₃ | — |
| 68. | H | CH₃ | CH₂CH₃ | — |
| 69. | H | CH₃ | CH₂CH₂CH₃ | — |
| 70. | H | CH₃ | CH(CH₃)₂ | — |
| 71. | H | CH₃ | CH₂CH₂CH₂CH₃ | — |
| 72. | H | CH₃ | CH(CH₃)CH₂CH₃ | — |
| 73. | H | CH₃ | CH₂CH(CH₃)₂ | — |
| 74. | H | CH₃ | CN | — |
| 75. | H | CH₃ | c-C₃H₅ | — |
| 76. | H | CH₃ | c-C₄H₇ | — |
| 77. | H | CH₃ | c-C₅H₉ | — |
| 78. | H | CH₃ | c-C₆H₁₁ | — |
| 79. | H | CH₃ | C₆H₅ | — |
| 80. | H | CH₃ | 4-Cl—C₆H₄ | — |
| 81. | H | CH₃ | 4-F—C₆H₄ | — |
| 82. | H | CH₃ | 4-Br—C₆H₄ | — |
| 83. | H | CH₃ | 3-Cl—C₆H₄ | — |
| 84. | H | CH₃ | 3-F—C₆H₄ | — |
| 85. | H | CH₃ | 3-Br—C₆H₄ | — |
| 86. | H | CH₃ | 2-Cl—C₆H₄ | — |
| 87. | H | CH₃ | 2-F—C₆H₄ | — |
| 88. | H | CH₃ | 2-Br—C₆H₄ | — |
| 89. | H | CH₃ | 2-CN—C₆H₄ | — |
| 90. | H | CH₃ | 3-CN—C₆H₄ | — |
| 91. | H | CH₃ | 4-CN—C₆H₄ | — |
| 92. | H | CH₃ | 3-CH₃O—C₆H₄ | — |
| 93. | H | CH₃ | 4-CH₃—O—C₆H₄ | — |
| 94. | H | CH₃ | 3,4-(CH₃O)₂—C₆H₃ | — |
| 95. | H | CH₃ | 3,4,5-(CH₃O)₃—C₆H₂ | — |
| 96. | H | CH₃ | 3-CH₃O-4-F—C₆H₃ | — |
| 97. | H | CH₃ | 4-CH₃O-3-F—C₆H₃ | — |
| 98. | H | CH₃ | 2-CH₃—C₆H₄ | — |
| 99. | H | CH₃ | 3-CH₃—C₆H₄ | — |
| 100. | H | CH₃ | 4-CH₃—C₆H₄ | — |
| 101. | H | CH₃ | 2-CF₃—C₆H₄ | — |
| 102. | H | CH₃ | 3-CF₃—C₆H₄ | — |
| 103. | H | CH₃ | 4-CF₃—C₆H₄ | — |
| 104. | H | CH₃ | 3,4-Cl₂—C₆H₃ | — |
| 105. | H | CH₃ | 2,3-Cl₂—C₆H₃ | — |
| 106. | H | CH₃ | 3,5-Cl₂—C₆H₃ | — |
| 107. | H | CH₃ | 2,4-Cl₂—C₆H₃ | — |
| 108. | H | CH₃ | 2,5-Cl₂—C₆H₃ | — |
| 109. | H | CH₃ | 2,6-Cl₂—C₆H₃ | — |
| 110. | H | CH₃ | 3,4-F₂—C₆H₃ | — |
| 111. | H | CH₃ | 3,5-F₂—C₆H₃ | — |
| 112. | H | CH₃ | 2,3-F₂—C₆H₃ | — |
| 113. | H | CH₃ | 2,4-F₂—C₆H₃ | — |
| 114. | H | CH₃ | 2,5-F₂—C₆H₃ | — |
| 115. | H | CH₃ | 2,6-F₂—C₆H₃ | — |

TABLE A-continued

| # | R¹ | R³ | R⁵ | [CR⁴ᵃR⁴ᵇ]ₘ |
|---|---|---|---|---|
| 116. | H | CH₃ | 3-Cl-4-F—C₆H₃ | — |
| 117. | H | CH₃ | 4-Cl-3-F—C₆H₃ | — |
| 118. | H | CH₃ | 3-Br-4-F—C₆H₃ | — |
| 119. | H | CH₃ | 4-Br-3-F—C₆H₃ | — |
| 120. | H | CH₃ | 3-Br-4-Cl—C₆H₃ | — |
| 121. | H | CH₃ | 4-Br-3-Cl—C₆H₃ | — |
| 122. | H | C₂H₅ | C₆H₅ | — |
| 123. | H | C₂H₅ | 4-Cl—C₆H₄ | — |
| 124. | H | C₂H₅ | 4-F—C₆H₄ | — |
| 125. | H | C₂H₅ | 4-Br—C₆H₄ | — |
| 126. | H | C₂H₅ | 3-Cl—C₆H₄ | — |
| 127. | H | C₂H₅ | 3-F—C₆H₄ | — |
| 128. | H | C₂H₅ | 3-Br—C₆H₄ | — |
| 129. | H | C₂H₅ | 2-Cl—C₆H₄ | — |
| 130. | H | C₂H₅ | 2-F—C₆H₄ | — |
| 131. | H | C₂H₅ | 2-Br—C₆H₄ | — |
| 132. | H | C₂H₅ | 2-CN—C₆H₄ | — |
| 133. | H | C₂H₅ | 3-CN—C₆H₄ | — |
| 134. | H | C₂H₅ | 4-CN—C₆H₄ | — |
| 135. | H | C₂H₅ | 3-CH₃O—C₆H₄ | — |
| 136. | H | C₂H₅ | 4-CH₃—O—C₆H₄ | — |
| 137. | H | C₂H₅ | 3,4-(CH₃O)₂—C₆H₃ | — |
| 138. | H | C₂H₅ | 3,4,5-(CH₃O)₃—C₆H₂ | — |
| 139. | H | C₂H₅ | 3-CH₃O-4-F—C₆H₃ | — |
| 140. | H | C₂H₅ | 4-CH₃O-3-F—C₆H₃ | — |
| 141. | H | C₂H₅ | 2-CH₃—C₆H₄ | — |
| 142. | H | C₂H₅ | 3-CH₃—C₆H₄ | — |
| 143. | H | C₂H₅ | 4-CH₃—C₆H₄ | — |
| 144. | H | C₂H₅ | 2-CF₃—C₆H₄ | — |
| 145. | H | C₂H₅ | 3-CF₃—C₆H₄ | — |
| 146. | H | C₂H₅ | 4-CF₃—C₆H₄ | — |
| 147. | H | C₂H₅ | 3,4-Cl₂—C₆H₃ | — |
| 148. | H | C₂H₅ | 2,3-Cl₂—C₆H₃ | — |
| 149. | H | C₂H₅ | 3,5-Cl₂—C₆H₃ | — |
| 150. | H | C₂H₅ | 2,4-Cl₂—C₆H₃ | — |
| 151. | H | C₂H₅ | 2,5-Cl₂—C₆H₃ | — |
| 152. | H | C₂H₅ | 2,6-Cl₂—C₆H₃ | — |
| 153. | H | C₂H₅ | 3,4-F₂—C₆H₃ | — |
| 154. | H | C₂H₅ | 3,5-F₂—C₆H₃ | — |
| 155. | H | C₂H₅ | 2,3-F₂—C₆H₃ | — |
| 156. | H | C₂H₅ | 2,4-F₂—C₆H₃ | — |
| 157. | H | C₂H₅ | 2,5-F₂—C₆H₃ | — |
| 158. | H | C₂H₅ | 2,6-F₂—C₆H₃ | — |
| 159. | H | C₂H₅ | 3-Cl-4-F—C₆H₃ | — |
| 160. | H | C₂H₅ | 4-Cl-3-F—C₆H₃ | — |
| 161. | H | C₂H₅ | 3-Br-4-F—C₆H₃ | — |
| 162. | H | C₂H₅ | 4-Br-3-F—C₆H₃ | — |
| 163. | H | C₂H₅ | 3-Br-4-Cl—C₆H₃ | — |
| 164. | H | C₂H₅ | 4-Br-3-Cl—C₆H₃ | — |
| 165. | H | CH₂CH=CH₂ | CH₂CH=CH₂ | — |
| 166. | H | CH₂C(CH₃)=CH₂ | CH₂C(CH₃)=CH₂ | — |
| 167. | H | (CH₃)₂C=CHCH₂ | (CH₃)₂C=CHCH₂ | — |
| 168. | H | H | (CH₃)₂C=CHCH₂ | — |
| 169. | H | H | CH₂CH=CH₂ | — |
| 170. | H | H | c-C₃H₅ | CH₂ |
| 171. | H | H | c-C₄H₇ | CH₂ |
| 172. | H | H | c-C₅H₉ | CH₂ |
| 173. | H | H | c-C₆H₁₁ | CH₂ |
| 174. | H | H | C₆H₅ | CH₂ |
| 175. | H | H | 4-Cl—C₆H₄ | CH₂ |
| 176. | H | H | 4-F—C₆H₄ | CH₂ |
| 177. | H | H | 4-Br—C₆H₄ | CH₂ |
| 178. | H | H | 3-Cl—C₆H₄ | CH₂ |
| 179. | H | H | 3-F—C₆H₄ | CH₂ |
| 180. | H | H | 3-Br—C₆H₄ | CH₂ |
| 181. | H | H | 2-Cl—C₆H₄ | CH₂ |
| 182. | H | H | 2-F—C₆H₄ | CH₂ |
| 183. | H | H | 2-Br—C₆H₄ | CH₂ |
| 184. | H | H | 2-CN—C₆H₄ | CH₂ |
| 185. | H | H | 3-CN—C₆H₄ | CH₂ |
| 186. | H | H | 4-CN—C₆H₄ | CH₂ |
| 187. | H | H | 3-CH₃O—C₆H₄ | CH₂ |
| 188. | H | H | 4-CH₃—O—C₆H₄ | CH₂ |
| 189. | H | H | 3,4-(CH₃O)₂—C₆H₃ | CH₂ |
| 190. | H | H | 3,4,5-(CH₃O)₃—C₆H₂ | CH₂ |
| 191. | H | H | 3-CH₃O-4-F—C₆H₃ | CH₂ |
| 192. | H | H | 4-CH₃O-3-F—C₆H₃ | CH₂ |
| 193. | H | H | 2-CH₃—C₆H₄ | CH₂ |
| 194. | H | H | 3-CH₃—C₆H₄ | CH₂ |
| 195. | H | H | 4-CH₃—C₆H₄ | CH₂ |
| 196. | H | H | 2-CF₃—C₆H₄ | CH₂ |
| 197. | H | H | 3-CF₃—C₆H₄ | CH₂ |
| 198. | H | H | 4-CF₃—C₆H₄ | CH₂ |
| 199. | H | H | 3,4-Cl₂—C₆H₃ | CH₂ |
| 200. | H | H | 2,3-Cl₂—C₆H₃ | CH₂ |
| 201. | H | H | 3,5-Cl₂—C₆H₃ | CH₂ |
| 202. | H | H | 2,4-Cl₂—C₆H₃ | CH₂ |
| 203. | H | H | 2,5-Cl₂—C₆H₃ | CH₂ |
| 204. | H | H | 2,6-Cl₂—C₆H₃ | CH₂ |
| 205. | H | H | 3,4-F₂—C₆H₃ | CH₂ |
| 206. | H | H | 3,5-F₂—C₆H₃ | CH₂ |
| 207. | H | H | 2,3-F₂—C₆H₃ | CH₂ |
| 208. | H | H | 2,4-F₂—C₆H₃ | CH₂ |
| 209. | H | H | 2,5-F₂—C₆H₃ | CH₂ |
| 210. | H | H | 2,6-F₂—C₆H₃ | CH₂ |
| 211. | H | H | 3-Cl-4-F—C₆H₃ | CH₂ |
| 212. | H | H | 4-Cl-3-F—C₆H₃ | CH₂ |
| 213. | H | H | 3-Br-4-F—C₆H₃ | CH₂ |
| 214. | H | H | 4-Br-3-F—C₆H₃ | CH₂ |
| 215. | H | H | 3-Br-4-Cl—C₆H₃ | CH₂ |
| 216. | H | H | 4-Br-3-Cl—C₆H₃ | CH₂ |
| 217. | H | H | 2-Cl-5-NO₂—C₆H₃ | CH₂ |
| 218. | H | H | 2-methyl-1,3-dioxolan-2-yl | CH₂ |
| 219. | H | H | c-C₃H₅ | C=O |
| 220. | H | H | c-C₄H₇ | C=O |
| 221. | H | H | c-C₅H₉ | C=O |
| 222. | H | H | c-C₆H₁₁ | C=O |
| 223. | H | H | C₆H₅ | C=O |
| 224. | H | H | 4-Cl—C₆H₄ | C=O |
| 225. | H | H | 4-F—C₆H₄ | C=O |
| 226. | H | H | 4-Br—C₆H₄ | C=O |
| 227. | H | H | 3-Cl—C₆H₄ | C=O |
| 228. | H | H | 3-F—C₆H₄ | C=O |
| 229. | H | H | 3-Br—C₆H₄ | C=O |
| 230. | H | H | 2-Cl—C₆H₄ | C=O |
| 231. | H | H | 2-F—C₆H₄ | C=O |
| 232. | H | H | 2-Br—C₆H₄ | C=O |
| 233. | H | H | 2-CN—C₆H₄ | C=O |
| 234. | H | H | 3-CN—C₆H₄ | C=O |
| 235. | H | H | 4-CN—C₆H₄ | C=O |
| 236. | H | H | 3-CH₃O—C₆H₄ | C=O |
| 237. | H | H | 4-CH₃—O—C₆H₄ | C=O |
| 238. | H | H | 3,4-(CH₃O)₂—C₆H₃ | C=O |
| 239. | H | H | 3,4,5-(CH₃O)₃—C₆H₂ | C=O |
| 240. | H | H | 3-CH₃O-4-F—C₆H₃ | C=O |
| 241. | H | H | 4-CH₃O-3-F—C₆H₃ | C=O |
| 242. | H | H | 2-CH₃—C₆H₄ | C=O |
| 243. | H | H | 3-CH₃—C₆H₄ | C=O |
| 244. | H | H | 4-CH₃—C₆H₄ | C=O |
| 245. | H | H | 2-CF₃—C₆H₄ | C=O |
| 246. | H | H | 3-CF₃—C₆H₄ | C=O |
| 247. | H | H | 4-CF₃—C₆H₄ | C=O |
| 248. | H | H | 3,4-Cl₂—C₆H₃ | C=O |
| 249. | H | H | 2,3-Cl₂—C₆H₃ | C=O |
| 250. | H | H | 3,5-Cl₂—C₆H₃ | C=O |
| 251. | H | H | 2,4-Cl₂—C₆H₃ | C=O |
| 252. | H | H | 2,5-Cl₂—C₆H₃ | C=O |
| 253. | H | H | 2,6-Cl₂—C₆H₃ | C=O |
| 254. | H | H | 3,4-F₂—C₆H₃ | C=O |
| 255. | H | H | 3,5-F₂—C₆H₃ | C=O |
| 256. | H | H | 2,3-F₂—C₆H₃ | C=O |
| 257. | H | H | 2,4-F₂—C₆H₃ | C=O |
| 258. | H | H | 2,5-F₂—C₆H₃ | C=O |
| 259. | H | H | 2,6-F₂—C₆H₃ | C=O |
| 260. | H | H | 3-Cl-4-F—C₆H₃ | C=O |
| 261. | H | H | 4-Cl-3-F—C₆H₃ | C=O |
| 262. | H | H | 3-Br-4-F—C₆H₃ | C=O |
| 263. | H | H | 4-Br-3-F—C₆H₃ | C=O |
| 264. | H | H | 3-Br-4-Cl—C₆H₃ | C=O |
| 265. | H | H | 4-Br-3-Cl—C₆H₃ | C=O |
| 266. | H | H | C₆H₅ | CH(CH₃) |
| 267. | H | H | 4-Cl—C₆H₄ | CH(CH₃) |
| 268. | H | H | 4-F—C₆H₄ | CH(CH₃) |
| 269. | H | H | 4-Br—C₆H₄ | CH(CH₃) |
| 270. | H | H | 3-Cl—C₆H₄ | CH(CH₃) |

TABLE A-continued

| # | R¹ | R³ | R⁵ | $[CR^{4a}R^{4b}]_m$ |
|---|----|----|----|----|
| 271. | H | H | 3-F—C₆H₄ | CH(CH₃) |
| 272. | H | H | 3-Br—C₆H₄ | CH(CH₃) |
| 273. | H | H | 2-Cl—C₆H₄ | CH(CH₃) |
| 274. | H | H | 2-F—C₆H₄ | CH(CH₃) |
| 275. | H | H | 2-Br—C₆H₄ | CH(CH₃) |
| 276. | H | H | 2-CN—C₆H₄ | CH(CH₃) |
| 277. | H | H | 3-CN—C₆H₄ | CH(CH₃) |
| 278. | H | H | 4-CN—C₆H₄ | CH(CH₃) |
| 279. | H | H | 3-CH₃O—C₆H₄ | CH(CH₃) |
| 280. | H | H | 4-CH₃—O—C₆H₄ | CH(CH₃) |
| 281. | H | H | 3,4-(CH₃O)₂—C₆H₃ | CH(CH₃) |
| 282. | H | H | 3,4,5-(CH₃O)₃—C₆H₂ | CH(CH₃) |
| 283. | H | H | 3-CH₃O-4-F—C₆H₃ | CH(CH₃) |
| 284. | H | H | 4-CH₃O-3-F—C₆H₃ | CH(CH₃) |
| 285. | H | H | 2-CH₃—C₆H₄ | CH(CH₃) |
| 286. | H | H | 3-CH₃—C₆H₄ | CH(CH₃) |
| 287. | H | H | 4-CH₃—C₆H₄ | CH(CH₃) |
| 288. | H | H | 2-CF₃—C₆H₄ | CH(CH₃) |
| 289. | H | H | 3-CF₃—C₆H₄ | CH(CH₃) |
| 290. | H | H | 4-CF₃—C₆H₄ | CH(CH₃) |
| 291. | H | H | 3,4-Cl₂—C₆H₃ | CH(CH₃) |
| 292. | H | H | 2,3-Cl₂—C₆H₃ | CH(CH₃) |
| 293. | H | H | 3,5-Cl₂—C₆H₃ | CH(CH₃) |
| 294. | H | H | 2,4-Cl₂—C₆H₃ | CH(CH₃) |
| 295. | H | H | 2,5-Cl₂—C₆H₃ | CH(CH₃) |
| 296. | H | H | 2,6-Cl₂—C₆H₃ | CH(CH₃) |
| 297. | H | H | 3,4-F₂—C₆H₃ | CH(CH₃) |
| 298. | H | H | 3,5-F₂—C₆H₃ | CH(CH₃) |
| 299. | H | H | 2,3-F₂—C₆H₃ | CH(CH₃) |
| 300. | H | H | 2,4-F₂—C₆H₃ | CH(CH₃) |
| 301. | H | H | 2,5-F₂—C₆H₃ | CH(CH₃) |
| 302. | H | H | 2,6-F₂—C₆H₃ | CH(CH₃) |
| 303. | H | H | 3-Cl-4-F—C₆H₃ | CH(CH₃) |
| 304. | H | H | 4-Cl-3-F—C₆H₃ | CH(CH₃) |
| 305. | H | H | 3-Br-4-F—C₆H₃ | CH(CH₃) |
| 306. | H | H | 4-Br-3-F—C₆H₃ | CH(CH₃) |
| 307. | H | H | 3-Br-4-Cl—C₆H₃ | CH(CH₃) |
| 308. | H | H | 4-Br-3-Cl—C₆H₃ | CH(CH₃) |
| 309. | H | | CH₂—CH₂ | — |
| 310. | H | | CHF—CHF | — |
| 311. | H | | CF₂—CF₂ | — |
| 312. | H | | CHCl—CHCl | — |
| 313. | H | | CCl₂—CCl₂ | — |
| 314. | H | | CH(CH₃)—CH(CH₃) | — |
| 315. | H | | C(CH₃)₂—C(CH₃)₂ | — |
| 316. | H | | CH₂—CH₂—CH₂ | — |
| 317. | H | | CH₂—CHF—CH₂ | — |
| 318. | H | | CHF—CH₂—CHF | — |
| 319. | H | | CHF—CHF—CHF | — |
| 320. | H | | CH₂—CF₂—CH₂ | — |
| 321. | H | | CH₂—CHCl—CH₂ | — |
| 322. | H | | CH₂—CCl₂—CH₂ | — |
| 323. | H | | CHCl—CH₂—CHCl | — |
| 324. | H | | CHCl—CHCl—CHCl | — |
| 325. | H | | CCl₂—CH₂—CCl₂ | — |
| 326. | H | | CCl₂—CCl₂—CCl₂ | — |
| 327. | H | | CH(CH₃)—CH₂—CH(CH₃) | — |
| 328. | H | | CH(CH₃)—CH(CH₃)—CH(CH₃) | — |
| 329. | H | | C(CH₃)₂—CH₂—C(CH₃)₂ | — |
| 330. | H | | C(CH₃)₂—C(CH₃)₂—C(CH₃)₂ | — |
| 331. | H | | CH₂—CH(CH₃)—CH₂ | — |
| 332. | H | | CH₂—C(CH₃)₂—CH₂ | — |
| 333. | H | | CHF—CH₂ | — |
| 334. | H | | CF₂—CH₂ | — |
| 335. | H | | CF₂—CHF | — |
| 336. | H | | CHCl—CH₂ | — |
| 337. | H | | CCl₂—CH₂ | — |
| 338. | H | | CCl₂—CHCl | — |
| 339. | H | | CH(CH₃)—CH₂ | — |
| 340. | H | | C(CH₃)₂—CH₂ | — |
| 341. | H | | C(CH₃)₂—CH(CH₃) | — |
| 342. | H | | CH(OCH₃)—CH₂ | — |
| 343. | H | | CH(CH₃)—CH₂ | — |
| 344. | H | | CH(CH₂CH₂CH₃)—CH₂ | — |
| 345. | H | | CH(CH₂CH₂CH₂CH₃)—CH₂ | — |
| 346. | H | | CH(C₆H₅)—CH₂ | — |
| 347. | H | | CH(2-Cl—C₆H₄)—CH₂ | — |
| 348. | H | | CH(2-F—C₆H₄)—CH₂ | — |
| 349. | H | | CH(2-CN—C₆H₄)—CH₂ | — |
| 350. | H | | CH(2-CH₃—C₆H₄)—CH₂ | — |
| 351. | H | | CH(2-OCH₃—C₆H₄)—CH₂ | — |
| 352. | H | | CH(3-Cl—C₆H₄)—CH₂ | — |
| 353. | H | | CH(3-F—C₆H₄)—CH₂ | — |
| 354. | H | | CH(3-CN—C₆H₄)—CH₂ | — |
| 355. | H | | CH(3-CH₃—C₆H₄)—CH₂ | — |
| 356. | H | | CH(3-OCH₃—C₆H₄)—CH₂ | — |
| 357. | H | | CH(4-Cl—C₆H₄)—CH₂ | — |
| 358. | H | | CH(4-F—C₆H₄)—CH₂ | — |
| 359. | H | | CH(4-CN—C₆H₄)—CH₂ | — |
| 360. | H | | CH(4-CH₃—C₆H₄)—CH₂ | — |
| 361. | H | | CH(4-OCH₃—C₆H₄)—CH₂ | — |
| 362. | H | | CH(CH₃)—CH₂—CH₂ | — |
| 363. | H | | C(CH₃)₂—CH₂—CH₂ | — |
| 364. | H | | CH(CH₃)—CH(CH₃)—CH₂ | — |
| 365. | H | | C(CH₃)₂—CH(CH₃)—CH₂ | — |
| 366. | H | | CH(CH₃)—C(CH₃)₂—CH₂ | — |
| 367. | H | | C(CH₃)₂—C(CH₃)₂—CH₂ | — |
| 368. | H | | CHF—CH₂—CH₂ | — |
| 369. | H | | CF₂—CH₂—CH₂ | — |
| 370. | H | | CHF—CHF—CH₂ | — |
| 371. | H | | CF₂—CHF—CH₂ | — |
| 372. | H | | CHF—CF₂—CH₂ | — |
| 373. | H | | CF₂—CH₂—CF₂ | — |
| 374. | H | | CF₂—CF₂—CH₂ | — |
| 375. | H | | CF₂—CF₂—CF₂ | — |
| 376. | H | | CHCl—CH₂—CH₂ | — |
| 377. | H | | CCl₂—CH₂—CH₂ | — |
| 378. | H | | CHCl—CHCl—CH₂ | — |
| 379. | H | | CCl₂—CHCl—CH₂ | — |
| 380. | H | | CHCl—CCl₂—CH₂ | — |
| 381. | H | | CCl₂—CCl₂—CH₂ | — |
| 382. | H | | CH₂CH=CHCH₂ | — |
| 383. | H | | CH₂OCH₂ | — |
| 384. | H | | CH₂CH₂CH₂CH₂ | — |
| 385. | H | | OCH₂ | — |
| 386. | H | | OCH₂CH₂ | — |
| 387. | H | | CH₂OCH₂ | — |
| 388. | H | | CH(CH(CH₃)₂)—CH₂ | — |
| 389. | H | | CH(c-C₃H₅)—CH₂ | — |
| 390. | H | | CH(c-C₅H₇)—CH₂ | — |
| 391. | H | | CH(c-C₆H₁₁)—CH₂ | — |
| 392. | H | | CH(c-C₇H₁₃)—CH₂ | — |
| 393. | H | | CH(c-C₈H₁₅)—CH₂ | — |
| 394. | H | | CH(CH(CH₃)CH₂CH₂CH₃)—CH₂ | — |
| 395. | H | | CH(CH₂C(CH₃)₃)—CH₂ | — |
| 396. | H | | CH(CH₂CH(CH₃)₂)—CH₂ | — |
| 397. | H | | CH(CH₂CH₂C₆H₅)—CH₂ | — |
| 398. | H | | CH(CH(CH₃)CH(CH₃)CH₂CH₃)—CH₂ | — |
| 399. | H | | CH(CH₂CH₂CH₂CH₂CH₃)—CH₂ | — |
| 400. | H | | CH(CH₂CH₂C(CH₃)₃)—CH₂ | — |
| 401. | H | | CH(4-THP)—CH₂ | — |
| 402. | H | | CH(CH(C₂H₅)CH₂CH₂CH₂CH₃)—CH₂ | — |
| 403. | H | | CH(C(CH₃)₃)—CH₂ | — |
| 404. | H | | CH(non-3-enyl)—CH₂ | — |
| 405. | H | | CH(C(CH₃)₂CH₂-3-Py)—CH₂ | — |
| 406. | H | | CH(CF₃)—CH₂ | — |
| 407. | H | | 6,6-DM-2-N | — |
| 408. | H | | CH(3-THTP)—CH₂ | — |
| 409. | H | | CH(1-AOE)—CH₂ | — |
| 410. | H | | CH(CH(CH₃)OCH(CH₃)₂)—CH₂ | — |
| 411. | H | | CH(CH(CH₃)CH₂SCH₃)—CH₂ | — |
| 412. | H | | CH(CH₂CH₂OCH₂CH₂CH₃)—CH₂ | — |
| 413. | H | | CH(2-Me-c-C₆H₈)—CH₂ | — |
| 414. | H | | CH(4-Me-c-C₆H₁₀)—CH₂ | — |
| 415. | H | | CH(5,5-DM-2-THF)—CH₂ | — |
| 416. | H | | CH(CH₂-4-THP)—CH₂ | — |
| 417. | H | | CH(CH₂CH₂OCH₂CH(CH₃)₂)—CH₂ | — |
| 418. | H | | CH(CH(CH₃)OCH₂CH₂OCH₃)—CH₂ | — |
| 419. | H | | CH(2-EC-c-C₃H₅)—CH₂ | — |
| 420. | H | | CH(CH(CH₃)OCH₃)—CH₂ | — |
| 421. | H | | CH(CH(CH₃)CH(CH₃)₂)—CH₂ | — |
| 422. | H | | CH(4-Me-5-TZ)—CH₂ | — |
| 423. | H | | CH(3-THP)—CH₂ | — |
| 424. | H | | CH(CH₂-4-THTP)—CH₂ | — |
| 425. | H | | CH(CH(CH₃)OC₆H₅)—CH₂ | — |
| 426. | H | | CH(CH(CH₃)O—c-C₆H₁₁)—CH₂ | — |

TABLE A-continued

| # | R¹ | R³ | R⁵ | $[CR^{4a}R^{4b}]_m$ |
|---|---|---|---|---|
| 427. | H | | CH(4-Ip-c-C₆H₁₀)—CH₂ | — |
| 428. | H | | CH(6-Ac—O—C₆H₁₂)—CH₂ | — |
| 429. | H | | CH(3-CF₃—C₆H₄)—CH₂ | — |
| 430. | H | | CH(3-NO₂—C₆H₄)—CH₂ | — |
| 431. | H | | CH(2-Py)—CH₂ | — |
| 432. | H | | CH(4-CF₃—C₆H₄)—CH₂ | — |
| 433. | H | | CH(CH₃—O—C(O))—CH₂ | — |
| 434. | H | | CH(Bz)—CH₂ | — |
| 435. | H | | CH(CH₂CF₃)—CH₂ | — |
| 436. | H | | CH(3-THF)—CH₂ | — |
| 437. | CH₃ | H | H | — |
| 438. | CH₃ | CH₃ | CH₃ | — |
| 439. | CH₃ | CH₂CH₃ | CH₂CH₃ | — |
| 440. | CH₃ | F | F | — |
| 441. | CH₃ | Cl | Cl | — |
| 442. | CH₃ | H | F | — |
| 443. | CH₃ | H | Cl | — |
| 444. | CH₃ | H | Br | — |
| 445. | CH₃ | CH₃ | F | — |
| 446. | CH₃ | CH₃ | Cl | — |
| 447. | CH₃ | CH₃ | Br | — |
| 448. | CH₃ | H | CH₃ | — |
| 449. | CH₃ | H | CH₂CH₃ | — |
| 450. | CH₃ | H | CH₂CH₂CH₃ | — |
| 451. | CH₃ | H | CH(CH₃)₂ | — |
| 452. | CH₃ | H | CH₂CH₂CH₂CH₃ | — |
| 453. | CH₃ | H | CH(CH₃)CH₂CH₃ | — |
| 454. | CH₃ | H | CH₂CH(CH₃)₂ | — |
| 455. | CH₃ | H | CN | — |
| 456. | CH₃ | H | c-C₃H₅ | — |
| 457. | CH₃ | H | c-C₄H₇ | — |
| 458. | CH₃ | H | c-C₅H₉ | — |
| 459. | CH₃ | H | c-C₆H₁₁ | — |
| 460. | CH₃ | H | C₆H₅ | — |
| 461. | CH₃ | H | 4-Cl—C₆H₄ | — |
| 462. | CH₃ | H | 4-F—C₆H₄ | — |
| 463. | CH₃ | H | 4-Br—C₆H₄ | — |
| 464. | CH₃ | H | 3-Cl—C₆H₄ | — |
| 465. | CH₃ | H | 3-F—C₆H₄ | — |
| 466. | CH₃ | H | 3-Br—C₆H₄ | — |
| 467. | CH₃ | H | 2-Cl—C₆H₄ | — |
| 468. | CH₃ | H | 2-F—C₆H₄ | — |
| 469. | CH₃ | H | 2-Br—C₆H₄ | — |
| 470. | CH₃ | H | 2-CN—C₆H₄ | — |
| 471. | CH₃ | H | 3-CN—C₆H₄ | — |
| 472. | CH₃ | H | 4-CN—C₆H₄ | — |
| 473. | CH₃ | H | 3-CH₃O—C₆H₄ | — |
| 474. | CH₃ | H | 4-CH₃—O—C₆H₄ | — |
| 475. | CH₃ | H | 3,4-(CH₃O)₂—C₆H₃ | — |
| 476. | CH₃ | H | 3,4,5-(CH₃O)₃—C₆H₂ | — |
| 477. | CH₃ | H | 3-CH₃O-4-F—C₆H₃ | — |
| 478. | CH₃ | H | 4-CH₃O-3-F—C₆H₃ | — |
| 479. | CH₃ | H | 2-CH₃—C₆H₄ | — |
| 480. | CH₃ | H | 3-CH₃—C₆H₄ | — |
| 481. | CH₃ | H | 4-CH₃—C₆H₄ | — |
| 482. | CH₃ | H | 2-CF₃—C₆H₄ | — |
| 483. | CH₃ | H | 3-CF₃—C₆H₄ | — |
| 484. | CH₃ | H | 4-CF₃—C₆H₄ | — |
| 485. | CH₃ | H | 3,4-Cl₂—C₆H₃ | — |
| 486. | CH₃ | H | 2,3-Cl₂—C₆H₃ | — |
| 487. | CH₃ | H | 3,5-Cl₂—C₆H₃ | — |
| 488. | CH₃ | H | 2,4-Cl₂—C₆H₃ | — |
| 489. | CH₃ | H | 2,5-Cl₂—C₆H₃ | — |
| 490. | CH₃ | H | 2,6-Cl₂—C₆H₃ | — |
| 491. | CH₃ | H | 3,4-F₂—C₆H₃ | — |
| 492. | CH₃ | H | 3,5-F₂—C₆H₃ | — |
| 493. | CH₃ | H | 2,3-F₂—C₆H₃ | — |
| 494. | CH₃ | H | 2,4-F₂—C₆H₃ | — |
| 495. | CH₃ | H | 2,5-F₂—C₆H₃ | — |
| 496. | CH₃ | H | 2,6-F₂—C₆H₃ | — |
| 497. | CH₃ | H | 3-Cl-4-F—C₆H₃ | — |
| 498. | CH₃ | H | 4-Cl-3-F—C₆H₃ | — |
| 499. | CH₃ | H | 3-Br-4-F—C₆H₃ | — |
| 500. | CH₃ | H | 4-Br-3-F—C₆H₃ | — |
| 501. | CH₃ | H | 3-Br-4-Cl—C₆H₃ | — |
| 502. | CH₃ | H | 4-Br-3-Cl—C₆H₃ | — |
| 503. | CH₃ | H | 2-Cl-5-NO₂—C₆H₃ | — |
| 504. | CH₃ | CH₃ | CH₂CH₃ | — |
| 505. | CH₃ | CH₃ | CH₂CH₂CH₃ | — |
| 506. | CH₃ | CH₃ | CH(CH₃)₂ | — |
| 507. | CH₃ | CH₃ | CH₂CH₂CH₂CH₃ | — |
| 508. | CH₃ | CH₃ | CH(CH₃)CH₂CH₃ | — |
| 509. | CH₃ | CH₃ | CH₂CH(CH₃)₂ | — |
| 510. | CH₃ | CH₃ | CN | — |
| 511. | CH₃ | CH₃ | c-C₃H₅ | — |
| 512. | CH₃ | CH₃ | c-C₄H₇ | — |
| 513. | CH₃ | CH₃ | c-C₅H₉ | — |
| 514. | CH₃ | CH₃ | c-C₆H₁₁ | — |
| 515. | CH₃ | CH₃ | C₆H₅ | — |
| 516. | CH₃ | CH₃ | 4-Cl—C₆H₄ | — |
| 517. | CH₃ | CH₃ | 4-F—C₆H₄ | — |
| 518. | CH₃ | CH₃ | 4-Br—C₆H₄ | — |
| 519. | CH₃ | CH₃ | 3-Cl—C₆H₄ | — |
| 520. | CH₃ | CH₃ | 3-F—C₆H₄ | — |
| 521. | CH₃ | CH₃ | 3-Br—C₆H₄ | — |
| 522. | CH₃ | CH₃ | 2-Cl—C₆H₄ | — |
| 523. | CH₃ | CH₃ | 2-F—C₆H₄ | — |
| 524. | CH₃ | CH₃ | 2-Br—C₆H₄ | — |
| 525. | CH₃ | CH₃ | 2-CN—C₆H₄ | — |
| 526. | CH₃ | CH₃ | 3-CN—C₆H₄ | — |
| 527. | CH₃ | CH₃ | 4-CN—C₆H₄ | — |
| 528. | CH₃ | CH₃ | 3-CH₃O—C₆H₄ | — |
| 529. | CH₃ | CH₃ | 4-CH₃—O—C₆H₄ | — |
| 530. | CH₃ | CH₃ | 3,4-(CH₃O)₂—C₆H₃ | — |
| 531. | CH₃ | CH₃ | 3,4,5-(CH₃O)₃—C₆H₂ | — |
| 532. | CH₃ | CH₃ | 3-CH₃O-4-F—C₆H₃ | — |
| 533. | CH₃ | CH₃ | 4-CH₃O-3-F—C₆H₃ | — |
| 534. | CH₃ | CH₃ | 2-CH₃—C₆H₄ | — |
| 535. | CH₃ | CH₃ | 3-CH₃—C₆H₄ | — |
| 536. | CH₃ | CH₃ | 4-CH₃—C₆H₄ | — |
| 537. | CH₃ | CH₃ | 2-CF₃—C₆H₄ | — |
| 538. | CH₃ | CH₃ | 3-CF₃—C₆H₄ | — |
| 539. | CH₃ | CH₃ | 4-CF₃—C₆H₄ | — |
| 540. | CH₃ | CH₃ | 3,4-Cl₂—C₆H₃ | — |
| 541. | CH₃ | CH₃ | 2,3-Cl₂—C₆H₃ | — |
| 542. | CH₃ | CH₃ | 3,5-Cl₂—C₆H₃ | — |
| 543. | CH₃ | CH₃ | 2,4-Cl₂—C₆H₃ | — |
| 544. | CH₃ | CH₃ | 2,5-Cl₂—C₆H₃ | — |
| 545. | CH₃ | CH₃ | 2,6-Cl₂—C₆H₃ | — |
| 546. | CH₃ | CH₃ | 3,4-F₂—C₆H₃ | — |
| 547. | CH₃ | CH₃ | 3,5-F₂—C₆H₃ | — |
| 548. | CH₃ | CH₃ | 2,3-F₂—C₆H₃ | — |
| 549. | CH₃ | CH₃ | 2,4-F₂—C₆H₃ | — |
| 550. | CH₃ | CH₃ | 2,5-F₂—C₆H₃ | — |
| 551. | CH₃ | CH₃ | 2,6-F₂—C₆H₃ | — |
| 552. | CH₃ | CH₃ | 3-Cl-4-F—C₆H₃ | — |
| 553. | CH₃ | CH₃ | 4-Cl-3-F—C₆H₃ | — |
| 554. | CH₃ | CH₃ | 3-Br-4-F—C₆H₃ | — |
| 555. | CH₃ | CH₃ | 4-Br-3-F—C₆H₃ | — |
| 556. | CH₃ | CH₃ | 3-Br-4-Cl—C₆H₃ | — |
| 557. | CH₃ | CH₃ | 4-Br-3-Cl—C₆H₃ | — |
| 558. | CH₃ | C₂H₅ | C₆H₅ | — |
| 559. | CH₃ | C₂H₅ | 4-Cl—C₆H₄ | — |
| 560. | CH₃ | C₂H₅ | 4-F—C₆H₄ | — |
| 561. | CH₃ | C₂H₆ | 4-Br—C₆H₄ | — |
| 562. | CH₃ | C₂H₅ | 3-Cl—C₆H₄ | — |
| 563. | CH₃ | C₂H₅ | 3-F—C₆H₄ | — |
| 564. | CH₃ | C₂H₅ | 3-Br—C₆H₄ | — |
| 565. | CH₃ | C₂H₅ | 2-Cl—C₆H₄ | — |
| 566. | CH₃ | C₂H₅ | 2-F—C₆H₄ | — |
| 567. | CH₃ | C₂H₅ | 2-Br—C₆H₄ | — |
| 568. | CH₃ | C₂H₅ | 2-CN—C₆H₄ | — |
| 569. | CH₃ | C₂H₅ | 3-CN—C₆H₄ | — |
| 570. | CH₃ | C₂H₅ | 4-CN—C₆H₄ | — |
| 571. | CH₃ | C₂H₅ | 3-CH₃O—C₆H₄ | — |
| 572. | CH₃ | C₂H₅ | 4-CH₃—O—C₆H₄ | — |
| 573. | CH₃ | C₂H₅ | 3,4-(CH₃O)₂—C₆H₃ | — |
| 574. | CH₃ | C₂H₅ | 3,4,5-(CH₃O)₃—C₆H₂ | — |
| 575. | CH₃ | C₂H₅ | 3-CH₃O-4-F—C₆H₃ | — |
| 576. | CH₃ | C₂H₅ | 4-CH₃O-3-F—C₆H₃ | — |
| 577. | CH₃ | C₂H₅ | 2-CH₃—C₆H₄ | — |
| 578. | CH₃ | C₂H₅ | 3-CH₃—C₆H₄ | — |
| 579. | CH₃ | C₂H₅ | 4-CH₃—C₆H₄ | — |
| 580. | CH₃ | C₂H₅ | 2-CF₃—C₆H₄ | — |
| 581. | CH₃ | C₂H₅ | 3-CF₃—C₆H₄ | — |
| 582. | CH₃ | C₂H₅ | 4-CF₃—C₆H₄ | — |

TABLE A-continued

| # | R¹ | R³ | R⁵ | $[CR^{4a}R^{4b}]_m$ |
|---|---|---|---|---|
| 583. | CH₃ | C₂H₅ | 3,4-Cl₂—C₆H₃ | — |
| 584. | CH₃ | C₂H₅ | 2,3-Cl₂—C₆H₃ | — |
| 585. | CH₃ | C₂H₅ | 3,5-Cl₂—C₆H₃ | — |
| 586. | CH₃ | C₂H₅ | 2,4-Cl₂—C₆H₃ | — |
| 587. | CH₃ | C₂H₅ | 2,5-Cl₂—C₆H₃ | — |
| 588. | CH₃ | C₂H₅ | 2,6-Cl₂—C₆H₃ | — |
| 589. | CH₃ | C₂H₅ | 3,4-F₂—C₆H₃ | — |
| 590. | CH₃ | C₂H₅ | 3,5-F₂—C₆H₃ | — |
| 591. | CH₃ | C₂H₅ | 2,3-F₂—C₆H₃ | — |
| 592. | CH₃ | C₂H₅ | 2,4-F₂—C₆H₃ | — |
| 593. | CH₃ | C₂H₅ | 2,5-F₂—C₆H₃ | — |
| 594. | CH₃ | C₂H₅ | 2,6-F₂—C₆H₃ | — |
| 595. | CH₃ | C₂H₅ | 3-Cl-4-F—C₆H₃ | — |
| 596. | CH₃ | C₂H₅ | 4-Cl-3-F—C₆H₃ | — |
| 597. | CH₃ | C₂H₅ | 3-Br-4-F—C₆H₃ | — |
| 598. | CH₃ | C₂H₅ | 4-Br-3-F—C₆H₃ | — |
| 599. | CH₃ | C₂H₅ | 3-Br-4-Cl—C₆H₃ | — |
| 600. | CH₃ | C₂H₅ | 4-Br-3-Cl—C₆H₃ | — |
| 601. | CH₃ | H | CH₂CHCH₂ | — |
| 602. | CH₃ | CH₂CH=CH₂ | CH₂CH=CH₂ | — |
| 603. | CH₃ | CH₂C(CH₃)=CH₂ | CH₂C(CH₃)=CH₂ | — |
| 604. | CH₃ | H | (CH₃)₂C=CHCH₂ | — |
| 605. | CH₃ | (CH₃)₂C=CHCH₂ | (CH₃)₂C=CHCH₂ | — |
| 606. | CH₃ | H | c-C₃H₅ | CH₂ |
| 607. | CH₃ | H | c-C₄H₇ | CH₂ |
| 608. | CH₃ | H | c-C₅H₉ | CH₂ |
| 609. | CH₃ | H | c-C₆H₁₁ | CH₂ |
| 610. | CH₃ | H | C₆H₅ | CH₂ |
| 611. | CH₃ | H | 4-Cl—C₆H₄ | CH₂ |
| 612. | CH₃ | H | 4-F—C₆H₄ | CH₂ |
| 613. | CH₃ | H | 4-Br—C₆H₄ | CH₂ |
| 614. | CH₃ | H | 3-Cl—C₆H₄ | CH₂ |
| 615. | CH₃ | H | 3-F—C₆H₄ | CH₂ |
| 616. | CH₃ | H | 3-Br—C₆H₄ | CH₂ |
| 617. | CH₃ | H | 2-Cl—C₆H₄ | CH₂ |
| 618. | CH₃ | H | 2-F—C₆H₄ | CH₂ |
| 619. | CH₃ | H | 2-Br—C₆H₄ | CH₂ |
| 620. | CH₃ | H | 2-CN—C₆H₄ | CH₂ |
| 621. | CH₃ | H | 3-CN—C₆H₄ | CH₂ |
| 622. | CH₃ | H | 4-CN—C₆H₄ | CH₂ |
| 623. | CH₃ | H | 3-CH₃O—C₆H₄ | CH₂ |
| 624. | CH₃ | H | 4-CH₃—O—C₆H₄ | CH₂ |
| 625. | CH₃ | H | 3,4-(CH₃O)₂—C₆H₃ | CH₂ |
| 626. | CH₃ | H | 3,4,5-(CH₃O)₃—C₆H₂ | CH₂ |
| 627. | CH₃ | H | 3-CH₃O-4-F—C₆H₃ | CH₂ |
| 628. | CH₃ | H | 4-CH₃O-3-F—C₆H₃ | CH₂ |
| 629. | CH₃ | H | 2-CH₃—C₆H₄ | CH₂ |
| 630. | CH₃ | H | 3-CH₃—C₆H₄ | CH₂ |
| 631. | CH₃ | H | 4-CH₃—C₆H₄ | CH₂ |
| 632. | CH₃ | H | 2-CF₃—C₆H₄ | CH₂ |
| 633. | CH₃ | H | 3-CF₃—C₆H₄ | CH₂ |
| 634. | CH₃ | H | 4-CF₃—C₆H₄ | CH₂ |
| 635. | CH₃ | H | 3,4-Cl₂—C₆H₃ | CH₂ |
| 636. | CH₃ | H | 2,3-Cl₂—C₆H₃ | CH₂ |
| 637. | CH₃ | H | 3,5-Cl₂—C₆H₃ | CH₂ |
| 638. | CH₃ | H | 2,4-Cl₂—C₆H₃ | CH₂ |
| 639. | CH₃ | H | 2,5-Cl₂—C₆H₃ | CH₂ |
| 640. | CH₃ | H | 2,6-Cl₂—C₆H₃ | CH₂ |
| 641. | CH₃ | H | 3,4-F₂—C₆H₃ | CH₂ |
| 642. | CH₃ | H | 3,5-F₂—C₆H₃ | CH₂ |
| 643. | CH₃ | H | 2,3-F₂—C₆H₃ | CH₂ |
| 644. | CH₃ | H | 2,4-F₂—C₆H₃ | CH₂ |
| 645. | CH₃ | H | 2,5-F₂—C₆H₃ | CH₂ |
| 646. | CH₃ | H | 2,6-F₂—C₆H₃ | CH₂ |
| 647. | CH₃ | H | 3-Cl-4-F—C₆H₃ | CH₂ |
| 648. | CH₃ | H | 4-Cl-3-F—C₆H₃ | CH₂ |
| 649. | CH₃ | H | 3-Br-4-F—C₆H₃ | CH₂ |
| 650. | CH₃ | H | 4-Br-3-F—C₆H₃ | CH₂ |
| 651. | CH₃ | H | 3-Br-4-Cl—C₆H₃ | CH₂ |
| 652. | CH₃ | H | 4-Br-3-Cl—C₆H₃ | CH₂ |
| 653. | CH₃ | H | 2-Cl-5-NO₂—C₆H₃ | CH₂ |
| 654. | CH₃ | H | 2-methyl-1,3-dioxolan-2-yl | CH₂ |
| 655. | CH₃ | H | c-C₃H₅ | C=O |
| 656. | CH₃ | H | c-C₄H₇ | C=O |
| 657. | CH₃ | H | c-C₅H₉ | C=O |
| 658. | CH₃ | H | c-C₆H₁₁ | C=O |
| 659. | CH₃ | H | C₆H₅ | C=O |
| 660. | CH₃ | H | 4-Cl—C₆H₄ | C=O |
| 661. | CH₃ | H | 4-F—C₆H₄ | C=O |
| 662. | CH₃ | H | 4-Br—C₆H₄ | C=O |
| 663. | CH₃ | H | 3-Cl—C₆H₄ | C=O |
| 664. | CH₃ | H | 3-F—C₆H₄ | C=O |
| 665. | CH₃ | H | 3-Br—C₆H₄ | C=O |
| 666. | CH₃ | H | 2-Cl—C₆H₄ | C=O |
| 667. | CH₃ | H | 2-F—C₆H₄ | C=O |
| 668. | CH₃ | H | 2-Br—C₆H₄ | C=O |
| 669. | CH₃ | H | 2-CN—C₆H₄ | C=O |
| 670. | CH₃ | H | 3-CN—C₆H₄ | C=O |
| 671. | CH₃ | H | 4-CN—C₆H₄ | C=O |
| 672. | CH₃ | H | 3-CH₃O—C₆H₄ | C=O |
| 673. | CH₃ | H | 4-CH₃—O—C₆H₄ | C=O |
| 674. | CH₃ | H | 3,4-(CH₃O)₂—C₆H₃ | C=O |
| 675. | CH₃ | H | 3,4,5-(CH₃O)₃—C₆H₂ | C=O |
| 676. | CH₃ | H | 3-CH₃O-4-F—C₆H₃ | C=O |
| 677. | CH₃ | H | 4-CH₃O-3-F—C₆H₃ | C=O |
| 678. | CH₃ | H | 2-CH₃—C₆H₄ | C=O |
| 679. | CH₃ | H | 3-CH₃—C₆H₄ | C=O |
| 680. | CH₃ | H | 4-CH₃—C₆H₄ | C=O |
| 681. | CH₃ | H | 2-CF₃—C₆H₄ | C=O |
| 682. | CH₃ | H | 3-CF₃—C₆H₄ | C=O |
| 683. | CH₃ | H | 4-CF₃—C₆H₄ | C=O |
| 684. | CH₃ | H | 3,4-Cl₂—C₆H₃ | C=O |
| 685. | CH₃ | H | 2,3-Cl₂—C₆H₃ | C=O |
| 686. | CH₃ | H | 3,5-Cl₂—C₆H₃ | C=O |
| 687. | CH₃ | H | 2,4-Cl₂—C₆H₃ | C=O |
| 688. | CH₃ | H | 2,5-Cl₂—C₆H₃ | C=O |
| 689. | CH₃ | H | 2,6-Cl₂—C₆H₃ | C=O |
| 690. | CH₃ | H | 3,4-F₂—C₆H₃ | C=O |
| 691. | CH₃ | H | 3,5-F₂—C₆H₃ | C=O |
| 692. | CH₃ | H | 2,3-F₂—C₆H₃ | C=O |
| 693. | CH₃ | H | 2,4-F₂—C₆H₃ | C=O |
| 694. | CH₃ | H | 2,5-F₂—C₆H₃ | C=O |
| 695. | CH₃ | H | 2,6-F₂—C₆H₃ | C=O |
| 696. | CH₃ | H | 3-Cl-4-F—C₆H₃ | C=O |
| 697. | CH₃ | H | 4-Cl-3-F—C₆H₃ | C=O |
| 698. | CH₃ | H | 3-Br-4-F—C₆H₃ | C=O |
| 699. | CH₃ | H | 4-Br-3-F—C₆H₃ | C=O |
| 700. | CH₃ | H | 3-Br-4-Cl—C₆H₃ | C=O |
| 701. | CH₃ | H | 4-Br-3-Cl—C₆H₃ | C=O |
| 702. | CH₃ | H | C₆H₅ | CH(CH₃) |
| 703. | CH₃ | H | 4-Cl—C₆H₄ | CH(CH₃) |
| 704. | CH₃ | H | 4-F—C₆H₄ | CH(CH₃) |
| 705. | CH₃ | H | 4-Br—C₆H₄ | CH(CH₃) |
| 706. | CH₃ | H | 3-Cl—C₆H₄ | CH(CH₃) |
| 707. | CH₃ | H | 3-F—C₆H₄ | CH(CH₃) |
| 708. | CH₃ | H | 3-Br—C₆H₄ | CH(CH₃) |
| 709. | CH₃ | H | 2-Cl—C₆H₄ | CH(CH₃) |
| 710. | CH₃ | H | 2-F—C₆H₄ | CH(CH₃) |
| 711. | CH₃ | H | 2-Br—C₆H₄ | CH(CH₃) |
| 712. | CH₃ | H | 2-CN—C₆H₄ | CH(CH₃) |
| 713. | CH₃ | H | 3-CN—C₆H₄ | CH(CH₃) |
| 714. | CH₃ | H | 4-CN—C₆H₄ | CH(CH₃) |
| 715. | CH₃ | H | 3-CH₃O—C₆H₄ | CH(CH₃) |
| 716. | CH₃ | H | 4-CH₃—O—C₆H₄ | CH(CH₃) |
| 717. | CH₃ | H | 3,4-(CH₃O)₂—C₆H₃ | CH(CH₃) |
| 718. | CH₃ | H | 3,4,5-(CH₃O)₃—C₆H₂ | CH(CH₃) |
| 719. | CH₃ | H | 3-CH₃O-4-F—C₆H₃ | CH(CH₃) |
| 720. | CH₃ | H | 4-CH₃O-3-F—C₆H₃ | CH(CH₃) |
| 721. | CH₃ | H | 2-CH₃—C₆H₄ | CH(CH₃) |
| 722. | CH₃ | H | 3-CH₃—C₆H₄ | CH(CH₃) |
| 723. | CH₃ | H | 4-CH₃—C₆H₄ | CH(CH₃) |
| 724. | CH₃ | H | 2-CF₃—C₆H₄ | CH(CH₃) |
| 725. | CH₃ | H | 3-CF₃—C₆H₄ | CH(CH₃) |
| 726. | CH₃ | H | 4-CF₃—C₆H₄ | CH(CH₃) |
| 727. | CH₃ | H | 3,4-Cl₂—C₆H₃ | CH(CH₃) |
| 728. | CH₃ | H | 2,3-Cl₂—C₆H₃ | CH(CH₃) |
| 729. | CH₃ | H | 3,5-Cl₂—C₆H₃ | CH(CH₃) |
| 730. | CH₃ | H | 2,4-Cl₂—C₆H₃ | CH(CH₃) |
| 731. | CH₃ | H | 2,5-Cl₂—C₆H₃ | CH(CH₃) |
| 732. | CH₃ | H | 2,6-Cl₂—C₆H₃ | CH(CH₃) |
| 733. | CH₃ | H | 3,4-F₂—C₆H₃ | CH(CH₃) |
| 734. | CH₃ | H | 3,5-F₂—C₆H₃ | CH(CH₃) |
| 735. | CH₃ | H | 2,3-F₂—C₆H₃ | CH(CH₃) |
| 736. | CH₃ | H | 2,4-F₂—C₆H₃ | CH(CH₃) |
| 737. | CH₃ | H | 2,5-F₂—C₆H₃ | CH(CH₃) |

TABLE A-continued

| # | R¹ | R³ | R⁵ | $[CR^{4a}R^{4b}]_m$ |
|---|---|---|---|---|
| 738. | CH₃ | H | 2,6-F₂—C₆H₃ | CH(CH₃) |
| 739. | CH₃ | H | 3-Cl-4-F—C₆H₃ | CH(CH₃) |
| 740. | CH₃ | H | 4-Cl-3-F—C₆H₃ | CH(CH₃) |
| 741. | CH₃ | H | 3-Br-4-F—C₆H₃ | CH(CH₃) |
| 742. | CH₃ | H | 4-Br-3-F—C₆H₃ | CH(CH₃) |
| 743. | CH₃ | H | 3-Br-4-Cl—C₆H₃ | CH(CH₃) |
| 744. | CH₃ | H | 4-Br-3-Cl—C₆H₃ | CH(CH₃) |
| 745. | CH₃ | | CH₂—CH₂ | — |
| 746. | CH₃ | | CHF—CHF | — |
| 747. | CH₃ | | CF₂—CF₂ | — |
| 748. | CH₃ | | CHCl—CHCl | — |
| 749. | CH₃ | | CCl₂—CCl₂ | — |
| 750. | CH₃ | | CH(CH₃)—CH(CH₃) | — |
| 751. | CH₃ | | C(CH₃)₂—C(CH₃)₂ | — |
| 752. | CH₃ | | CH₂—CH₂—CH₂ | — |
| 753. | CH₃ | | CH₂—CHF—CH₂ | — |
| 754. | CH₃ | | CHF—CH₂—CHF | — |
| 755. | CH₃ | | CHF—CHF—CHF | — |
| 756. | CH₃ | | CH₂—CF₂—CH₂ | — |
| 757. | CH₃ | | CH₂—CHCl—CH₂ | — |
| 758. | CH₃ | | CH₂—CCl₂—CH₂ | — |
| 759. | CH₃ | | CHCl—CH₂—CHCl | — |
| 760. | CH₃ | | CHCl—CHCl—CHCl | — |
| 761. | CH₃ | | CCl₂—CCl₂—CCl₂ | — |
| 762. | CH₃ | | CCl₂—CCl₂—CCl₂ | — |
| 763. | CH₃ | | CH(CH₃)—CH₂—CH(CH₃) | — |
| 764. | CH₃ | | CH(CH₃)—CH(CH₃)—CH(CH₃) | — |
| 765. | CH₃ | | C(CH₃)₂—CH₂—C(CH₃)₂ | — |
| 766. | CH₃ | | C(CH₃)₂—C(CH₃)₂—C(CH₃)₂ | — |
| 767. | CH₃ | | CH₂—CH(CH₃)—CH₂ | — |
| 768. | CH₃ | | CH₂—C(CH₃)₂—CH₂ | — |
| 769. | CH₃ | | CHF—CH₂ | — |
| 770. | CH₃ | | CF₂—CH₂ | — |
| 771. | CH₃ | | CF₂—CHF | — |
| 772. | CH₃ | | CHCl—CH₂ | — |
| 773. | CH₃ | | CCl₂—CH₂ | — |
| 774. | CH₃ | | CCl₂—CHCl | — |
| 775. | CH₃ | | CH(CH₃)—CH₂ | — |
| 776. | CH₃ | | C(CH₃)₂—CH₂ | — |
| 777. | CH₃ | | C(CH₃)₂—CH(CH₃) | — |
| 778. | CH₃ | | CH(OCH₃)—CH₂ | — |
| 779. | CH₃ | | CH(CH₂CH₃)—CH₂ | — |
| 780. | CH₃ | | CH(CH₂CH₂CH₃)—CH₂ | — |
| 781. | CH₃ | | CH(CH₂CH₂CH₂CH₃)—CH₂ | — |
| 782. | CH₃ | | CH(C₆H₅)—CH₂ | — |
| 783. | CH₃ | | CH(2-Cl—C₆H₄)—CH₂ | — |
| 784. | CH₃ | | CH(2-F—C₆H₄)—CH₂ | — |
| 785. | CH₃ | | CH(2-CN—C₆H₄)—CH₂ | — |
| 786. | CH₃ | | CH(2-CH₃—C₆H₄)—CH₂ | — |
| 787. | CH₃ | | CH(2-OCH₃—C₆H₄)—CH₂ | — |
| 788. | CH₃ | | CH(3-Cl—C₆H₄)—CH₂ | — |
| 789. | CH₃ | | CH(3-F—C₆H₄)—CH₂ | — |
| 790. | CH₃ | | CH(3-CN—C₆H₄)—CH₂ | — |
| 791. | CH₃ | | CH(3-CH₃—C₆H₄)—CH₂ | — |
| 792. | CH₃ | | CH(3-OCH₃—C₆H₄)—CH₂ | — |
| 793. | CH₃ | | CH(4-Cl—C₆H₄)—CH₂ | — |
| 794. | CH₃ | | CH(4-F—C₆H₄)—CH₂ | — |
| 795. | CH₃ | | CH(4-CN—C₆H₄)—CH₂ | — |
| 796. | CH₃ | | CH(4-CH₃—C₆H₄)—CH₂ | — |
| 797. | CH₃ | | CH(4-OCH₃—C₆H₄)—CH₂ | — |
| 798. | CH₃ | | CH(CH₃)—CH₂—CH₂ | — |
| 799. | CH₃ | | C(CH₃)₂—CH₂—CH₂ | — |
| 800. | CH₃ | | CH(CH₃)—CH(CH₃)—CH₂ | — |
| 801. | CH₃ | | C(CH₃)₂—CH(CH₃)—CH₂ | — |
| 802. | CH₃ | | CH(CH₃)—C(CH₃)₂—CH₂ | — |
| 803. | CH₃ | | C(CH₃)₂—C(CH₃)₂—CH₂ | — |
| 804. | CH₃ | | CHF—CH₂—CH₂ | — |
| 805. | CH₃ | | CF₂—CH₂—CH₂ | — |
| 806. | CH₃ | | CHF—CHF—CH₂ | — |
| 807. | CH₃ | | CF₂—CHF—CH₂ | — |
| 808. | CH₃ | | CHF—CF₂—CH₂ | — |
| 809. | CH₃ | | CF₂—CH₂—CF₂ | — |
| 810. | CH₃ | | CF₂—CF₂—CH₂ | — |
| 811. | CH₃ | | CF₂—CF₂—CF₂ | — |
| 812. | CH₃ | | CHCl—CH₂—CH₂ | — |
| 813. | CH₃ | | CCl₂—CH₂—CH₂ | — |
| 814. | CH₃ | | CHCl—CHCl—CH₂ | — |
| 815. | CH₃ | | CCl₂—CHCl—CH₂ | — |
| 816. | CH₃ | | CHCl—CCl₂—CH₂ | — |
| 817. | CH₃ | | CCl₂—CCl₂—CH₂ | — |
| 818. | CH₃ | | CH₂CH=CHCH₂ | — |
| 819. | CH₃ | | CH₂OCH₂ | — |
| 820. | CH₃ | | CH₂CH₂CH₂CH₂ | — |
| 821. | CH₃ | | OCH₂ | — |
| 822. | CH₃ | | OCH₂CH₂ | — |
| 823. | CH₃ | | CH₂OCH₂ | — |
| 824. | CH₃ | | CH(CH(CH₃)₂)—CH₂ | — |
| 825. | CH₃ | | CH(c-C₃H₅)—CH₂ | — |
| 826. | CH₃ | | CH(c-C₅H₇)—CH₂ | — |
| 827. | CH₃ | | CH(c-C₆H₁₁)—CH₂ | — |
| 828. | CH₃ | | CH(c-C₇H₁₃)—CH₂ | — |
| 829. | CH₃ | | CH(c-C₈H₁₅)—CH₂ | — |
| 830. | CH₃ | | CH(CH(CH₃)CH₂CH₂CH₃)—CH₂ | — |
| 831. | CH₃ | | CH(CH₂C(CH₃)₃)—CH₂ | — |
| 832. | CH₃ | | CH(CH₂CH(CH₃)₂)—CH₂ | — |
| 833. | CH₃ | | CH(CH₂CH₂C₆H₅)—CH₂ | — |
| 834. | CH₃ | | CH(CH(CH₃)CH(CH₃)CH₂CH₃)—CH₂ | — |
| 835. | CH₃ | | CH(CH₂CH₂CH₂CH₂CH₃)—CH₂ | — |
| 836. | CH₃ | | CH(CH₂CH₂C(CH₃)₃)—CH₂ | — |
| 837. | CH₃ | | CH(4-THP)—CH₂ | — |
| 838. | CH₃ | | CH(CH(C₂H₅)CH₂CH₂CH₂CH₃)—CH₂ | — |
| 839. | CH₃ | | CH(C(CH₃)₃)—CH₂ | — |
| 840. | CH₃ | | CH(non-3-enyl)—CH₂ | — |
| 841. | CH₃ | | CH(C(CH₃)₂CH₂-3-Py)—CH₂ | — |
| 842. | CH₃ | | CH(CF₃)—CH₂ | — |
| 843. | CH₃ | | 6,6-DM-2-N | — |
| 844. | CH₃ | | CH(3-THTP)—CH₂ | — |
| 845. | CH₃ | | CH(1-AOE)—CH₂ | — |
| 846. | CH₃ | | CH(CH(CH₃)OCH(CH₃)₂)—CH₂ | — |
| 847. | CH₃ | | CH(CH(CH₃)CH₂SCH₃)—CH₂ | — |
| 848. | CH₃ | | CH(CH₂CH₂OCH₂CH₂CH₃)—CH₂ | — |
| 849. | CH₃ | | CH(2-Me—c-C₆H₈)—CH₂ | — |
| 850. | CH₃ | | CH(4-Me—c-C₆H₁₀)—CH₂ | — |
| 851. | CH₃ | | CH(5,5-DM-2-THF)—CH₂ | — |
| 852. | CH₃ | | CH(CH₂-4-THP)—CH₂ | — |
| 853. | CH₃ | | CH(CH₂CH₂OCH(CH₃)₂)—CH₂ | — |
| 854. | CH₃ | | CH(CH(CH₃)OCH₂CH₂OCH₃)—CH₂ | — |
| 855. | CH₃ | | CH(2-EC-c-C₃H₅)—CH₂ | — |
| 856. | CH₃ | | CH(CH(CH₃)OCH₃)—CH₂ | — |
| 857. | CH₃ | | CH(CH(CH₃)CH(CH₃)₂)—CH₂ | — |
| 858. | CH₃ | | CH(4-Me-5-TZ)—CH₂ | — |
| 859. | CH₃ | | CH(3-THP)—CH₂ | — |
| 860. | CH₃ | | CH(CH₂-4-THTP)—CH₂ | — |
| 861. | CH₃ | | CH(CH(CH₃)OC₆H₅)—CH₂ | — |
| 862. | CH₃ | | CH(CH(CH₃)O—c-C₆H₁₁)—CH₂ | — |
| 863. | CH₃ | | CH(4-Ip-c-C₆H₁₀)—CH₂ | — |
| 864. | CH₃ | | CH(6-Ac—O—C₆H₁₂)—CH₂ | — |
| 865. | CH₃ | | CH(3-CF₃—C₆H₄)—CH₂ | — |
| 866. | CH₃ | | CH(3-NO₂—C₆H₄)—CH₂ | — |
| 867. | CH₃ | | CH(2-Py)—CH₂ | — |
| 868. | CH₃ | | CH(4-CF₃—C₆H₄)—CH₂ | — |
| 869. | CH₃ | | CH(CH₃—O—C(O))—CH₂ | — |
| 870. | CH₃ | | CH(Bz)—CH₂ | — |
| 871. | CH₃ | | CH(CH₂CF₃)—CH₂ | — |
| 872. | CH₃ | | CH(3-THF)—CH₂ | — |

In table A, the following abbreviations are used:
In the last column "-" indicates that m=0, i.e. $[CR^{4a}R^{4b}]$ is absent.
c-C₃H₅: cyclopropyl
c-C₄H₇: cyclobutyl
c-C₅H₉: cyclopentyl
c-C₆H₁₁: cyclohexyl
2-Me-c-C₆H₈: 2-methylcyclohexen-3-yl
4-Me-c-C₆H₁₀: 4-methylcyclohexyl
c-C₇H₁₃: cycloheptyl
c-C₈H₁₅: cyclooctyl
C₆H₅: phenyl
CH₂—C₆H₅: benzyl
CH₂CH₂—C₆H₅: phenetyl
2-Cl—C₆H₄: 2-chlorophenyl
2-F—C₆H₄: 2-fluorophenyl 2-Br—$C_6H_4$: 2-bromophenyl
4-Cl—$C_6H_4$: 4-chlorophenyl
4-F—$C_6H_4$: 4-fluorophenyl
4-Br—$C_6H_4$: 4-bromophenyl
3-Cl—$C_6H_4$: 3-chlorophenyl
3-F—$C_6H_4$: 3-fluorophenyl
3-Br—$C_6H_4$: 3-bromophenyl
2-$CH_3$—$C_6H_4$: 2-methylphenyl
3-$CH_3$—$C_6H_4$: 3-methylphenyl
4-$CH_3$—$C_6H_4$: 4-methylphenyl
2-$CF_3$—$C_6H_4$: 2-trifluoromethylphenyl
3-$CF_3$—$C_6H_4$: 3-trifluoromethylphenyl
4-$CF_3$—$C_6H_4$: 4-trifluoromethylphenyl
2-CN—$C_6H_4$: 2-cyanophenyl
3-CN—$C_6H_4$: 3-cyanophenyl
4-CN—$C_6H_4$: 4-cyanophenyl
3-$CF_3$—$C_6H_4$: 3-trifluoromethylphenyl
4-$CF_3$—$C_6H_4$: 4-trifluoromethylphenyl
3-$NO_2$—$C_6H_4$: 3-nitrophenyl
2-$OCH_3$—$C_6H_4$: 2-methoxyphenyl
3-$OCH_3$—$C_6H_4$: 3-methoxyphenyl
4-$OCH_3$—$C_6H_4$: 4-methoxyphenyl
3,4-$Cl_2$—$C_6H_3$: 3,4-dichlorophenyl
3,5-$Cl_2$—$C_6H_3$: 3,5-dichlorophenyl
2,3-$Cl_2$—$C_6H_3$: 2,3-dichlorophenyl
2,4-$Cl_2$—$C_6H_3$: 2,4-dichlorophenyl
2,5-$Cl_2$—$C_6H_3$: 2,5-dichlorophenyl
2,6-$Cl_2$—$C_6H_3$: 2,6-dichlorophenyl
3,4-$F_2$—$C_6H_3$: 3,4-difluorophenyl
3,5-$F_2$—$C_6H_3$: 3,5-difluorophenyl
2,3-$F_2$—$C_6H_3$: 2,3-difluorophenyl
2,4-$F_2$—$C_6H_3$: 2,4-dichlorophenyl
2,5-$F_2$—$C_6H_3$: 2,5-difluorophenyl
2,6-$F_2$—$C_6H_3$: 2,6-difluorophenyl
3-Cl-4-F—$C_6H_3$: 3-chloro-4-fluorophenyl
4-Cl-3-F—$C_6H_3$: 4-chloro-3-fluorophenyl
3-Br-4-F—$C_6H_3$: 3-bromo-4-fluorophenyl
4-Br-3-F—$C_6H_3$: 4-bromo-3-fluorophenyl
3-Br-4-Cl—$C_6H_3$: 3-bromo-4-chlorophenyl
4-Br-3-Cl—$C_6H_3$: 4-bromo-3-chlorophenyl
3-OH—$C_6H_4$: 3-hydroxyphenyl
3,4,5-(($OCH_3$)$_3C_6H_2$): 3,4,5-trimethoxyphenyl
3,4-($CH_3O$)$_2$—$C_6H_3$: 3,4-dimethoxyphenyl
3-$CH_3O$-4-F—$C_6H_3$: 4-fluoro-3-methoxyphenyl
4-$CH_3O$-3-F—$C_6H_3$: 3-fluoro-4-methoxyphenyl
2-Cl-5-$NO_2$—$C_6H_3$: 2-chloro-5-nitrophenyl
$CH_2CHCH_2$: allyl
$CH_2C(CH_3)CH_2$: 2-methallyl
($CH_3$)$_2$C=$CHCH_2$: 3-methylbut-2-enyl
2-Py: 2-pyridyl
3-Py: 3-pyridyl
3-THF: tetrahydrofuran-3-yl
3-THP: tetrahydropyran-3-yl
4-THP: tetrahydropyran-4-yl
$CH_2$-4-THP: tetrahydropyran-4-yl-methyl
3-THTP: tetrahydrothiopyran-3-yl
4-THTP: tetrahydrothiopyran-4-yl
$CH_2$-4-THTP: tetrahydrothiopyran-4-yl-methyl
4-Me-5-TZ: 4-methylthiazol-5-yl
6,6-DM-2-N: 6,6-dimethylnorpinan-2-yl
5,5-DM-2-THF: 5,5-dimethyltetrahydrofuran-2-yl
Bz: Benzyl
1-AOE: 1-acetoxyethyl
$CH(CH_3)OCH_3$: 1-methoxyethyl
$CH(CH_3)OCH(CH_3)_2$: 1-isopropoxyethyl
$CH(CH_3)CH_2SCH_3$: 1-methyl-2-methylsulfanylethyl
$CH_2CH_2OCH_2CH_2CH_3$: 2-propoxyethyl
$CH_2CH_2OCH_2CH(CH_3)_2$: 2-isobutoxyethyl
$CH(CH_3)OCH_2CH_2OCH_3$: 1-(2-methoxyethoxy)ethyl
$CH(CH_3)OC_6H_5$: 1-(phenoxy)ethyl
$CH(CH_3)$O-c-$C_6H_{11}$: 1-(cyclohexyloxy)ethyl
2-EC-c-$C_3H_5$: 2-ethoxycarbonylcyclopropyl
$CH(CH_3)CH(CH_3)_2$: 1,2-dimethylpropyl
4-Ip-c-$C_6H_{10}$: 4-isopropylcyclohexyl
6-Ac-O—$C_6H_{12}$: 6-acetoxyhexyl
$CH_3$—O—C(O): methoxycarbonyl
$CH_2CF_3$: 2,2,2-trifluoroethyl Compounds of formula (I) according to the present invention can be prepared e.g. according to the preparation methods and preparation schemes as described below.

Compounds of formula (I) according to the present invention can be prepared by standard methods of organic chemistry e.g. by the preparation methods and preparation schemes as described below and in the experimental part of this application. The definition of m, Het, X, $W^1$, $W^2$, $W^3$, $W^4$, $R^1$, $R^2$, $R^3$, $R^{4a}$, $R^{4b}$ and $R^5$ of the molecular structures given in the schemes below are as defined above. Room temperature means a temperature range between about 20 and 25° C.

An example of a general method for the preparation of compounds of formula (I) is shown below in Scheme A. Thus, construction of the heterocyclic element 3 present in compounds of formula (I) can be achieved, for example, by alkylation of the appropriate 2-amino heterocycle precursor 1 with the appropriate reagent of formula 2. The transformation is preferably carried out in polar solvents such as acetonitrile, acetone, dichloromethane, 1,4-dioxane, tetrahydrofuran, N,N-dimethylformamide, N,N-dimethylacetamide, N-methylpyrolidinone or a $C_1$-$C_6$ alcohol at a temperature ranging between room temperature and the reflux temperature of the solvent. Representative reaction conditions for the alkylation of compounds analogous to formula 1 are given in Tett. Lett. 2011, 52(23), 3033-3037. The synthesis of compounds of formula 5 can be achieved by acylation of the amine functionality in compounds of formula 3 using carboxylic acid derivatives 4 which are activated in situ. The transformation is preferably carried out in polar solvents such as acetonitrile, acetone, 1,4-dioxane, tetrahydrofuran, N,N-dimethylformamide, N,N-dimethylacetamide, N-methylpyrolidinone or in an inert solvent such as dichloromethane, 1,2-dichloroethane, or 1,2-dimethoxyethane at temperatures ranging between room temperature and the reflux temperature of the solvent. A representative procedure condition for the acylation is given in Journal of Medicinal Chemistry, 2012, 55, 7378-7391. Examples of suitable leaving groups (LG) in formula 2 include, but are not limited to: halogen, alkyl sulfonate, haloalkyl sulfonate, aryl sulfonate, alkyl phosphonate. Examples of suitable leaving groups ($LG^2$) in formula 4 include, but are not limited to: halogen, alkyl sulfonate, haloalkyl sulfonate, aryl sulfonate, alkyl phosphonate and various activated esters derived from the reaction of a free carboxylic acid with a peptide coupling reagent in the presence of an amine base (*Chem. Rev.*, 2011, 111(11), 6557-6602). A reversal of the order of these two steps would also result in an acceptable synthesis of the desired compounds.

Scheme A

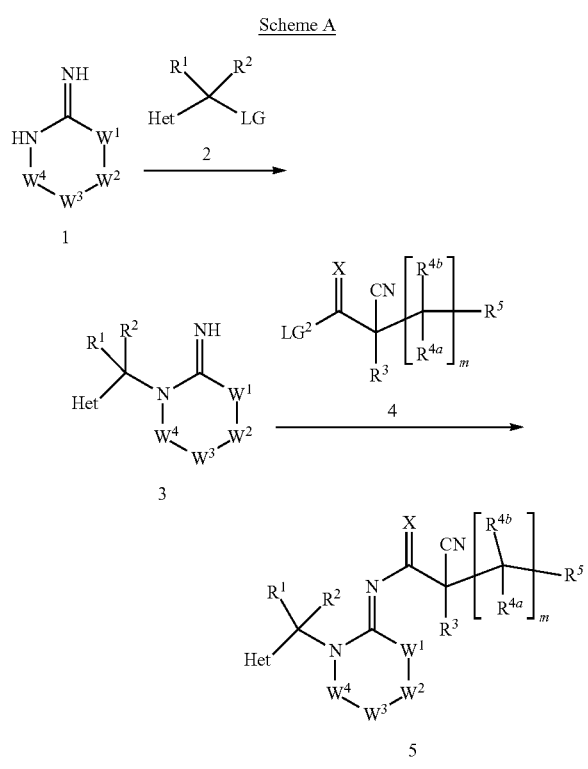

Compounds of formula (I) can also be prepared using an alternative strategy to install the cyano group as is shown below in Scheme B. Thus, construction of intermediate 3 proceeds as described in Scheme A, and amine functionality present in intermediates of type 3 can then be acylated with a reagent of type 6. The transformation is preferably carried out in polar solvents such as acetonitrile, acetone, tetrahydrofuran, 1,4-dioxane, N,N-dimethylformamide, N,N-dimethylacetamide, N-methylpyrolidinone or in an inert solvent such as dichloromethane, 1,2-dichloroethane, or 1,2-dimethoxyethane at temperatures ranging between room temperature and the reflux temperature of the solvent. Representative procedure conditions for the acylation of 3 are given in Journal of Medicinal Chemistry, 1988, 31, 4, 807-814. In reagent 6, suitable examples of substitutent Z are: halogen, alkyl sulfonate, halo alkyl sulfonate, aryl sulfonate, phosphate, phosphonate. Examples of suitable leaving groups ($LG^3$) in formula 6 include, but are not limited to: halogen, alkyl sulfonate or haloalkyl sulfonate, alkyl phosphonate, and various activated esters derived from the reaction of the free carbonic acid with a peptide coupling reagent in the presence of an amine base (*Chem. Rev.*, 2011, 111(11), 6557-6602). In the next step, Z is displaced through the action of a cyanide containing compound 8 to afford the desired compound 5. The transformation is preferably carried out in polar solvents such as acetonitrile, acetone, tetrahydrofuran, 1,4-dioxane, N,N-dimethylformamide, N,N-dimethylacetamide, N-methylpyrolidinone, a $C_1$-$C_6$ alcohol or in an inert solvent such as dichloromethane, 1,2-dichloroethane, 1,2-dimethoxyethane, benzene, toluene, mesitylene, cymenes, or xylenes at temperatures ranging between room temperature and the reflux temperature of the solvent. Examples of suitable Y in formula 8 include, but are not limited to: a metal of group 1, 2, 11 or 12 of the peridodic table (by modern IUPAC numbering), hydrogen, Si($C_1$-$C_4$-alkyl)$_3$ or C(CH$_3$)$_2$OH. Examples of suitable cyanide containing compounds 8 are: LiCN, NaCN, KCN, CuCN, Cu(CN)$_2$, Zn(CN)$_2$, HCN, TMS-CN (trimethylsilylcyanide), and acetone cyanohydrin. Representative procedure conditions for such a reaction are given in Journal of Medicinal Chemistry, 1989, 32, 1673-1681. A reversal of the order of these steps would also result in an acceptable synthesis of the desired compounds of formula (I).

Scheme B

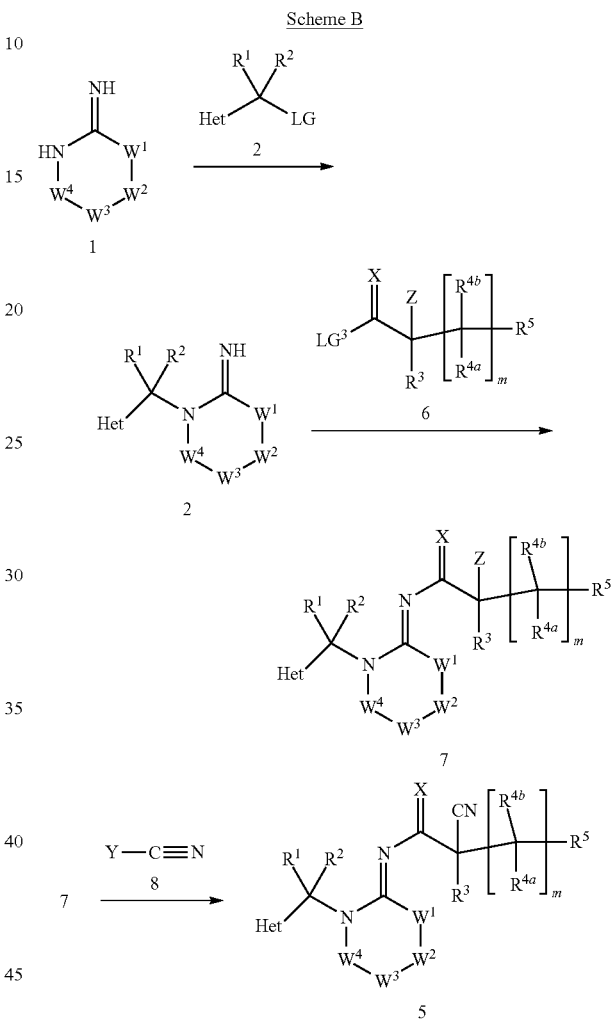

In cases where X is a sulfur atom, the sulfur atom is best installed in a subsequent step from the compound where X is an oxygen atom as detailed in Scheme C.

Scheme C

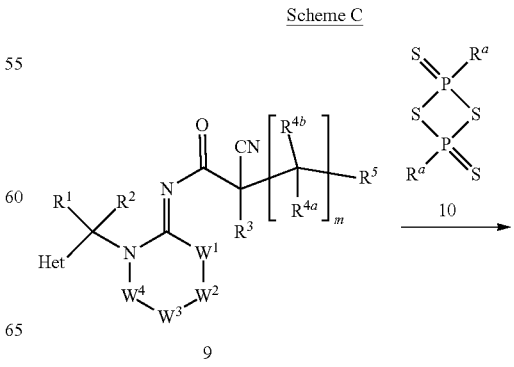

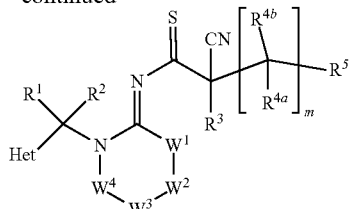

11

Here C=O containing compound 9 is transformed into C=S containing compound 11. The transformation is preferably carried out using a reagent of substructure 10 in polar solvents such as acetonitrile, acetone, tetrahydrofuran, N,N-dimethylformamide, or in an inert solvent such as dichloromethane, 1,2-dichloroethane, or 1,2-dimethoxyethane at temperatures ranging between room temperature and the reflux temperature of the solvent. Suitable $R^a$ groups in compounds of formula 10 are: thio, alkyl, aryl or substituted aryl. Representative reaction conditions for thionation analogous substrates are given in European Journal of Organic Chemistry, 2000, 3273-3278.

The compounds of the formula (I), and their salts are in particular suitable for efficiently controlling arthropodal pests such as arachnids, myriapedes and insects as well as nematodes.

The compounds of the formula (I) are especially suitable for efficiently combating insects, in particular the following pests:

Insects from the order of the lepidopterans (Lepidoptera), for example *Acronicta major, Adoxophyes orana, Aedia leucomelas, Agrotis* spp. such as *Agrotis fucosa, Agrotis segetum, Agrotis ipsilon; Alabama argillacea, Anticarsia gemmatalis, Anticarsia* spp., *Argyresthia conjugella, Autographa gamma, Barathra brassicae, Bucculatrix thurberiella, Bupalus piniarius, Cacoecia murinana, Cacoecia podana, Capua reticulana, Carpocapsa pomonella, Cheimatobia brumata, Chilo* spp. such as *Chilo suppressalis; Choristoneura fumiferana, Choristoneura occidentalis, Cirphis unipuncta, Clysia ambiguella, Cnaphalocerus* spp., *Cydia pomonella, Dendrolimus pini, Diaphania nitidalis, Diatraea grandiosella, Earias insulana, Elasmopalpus lignosellus, Ephestia cautella, Ephestia kuehniella, Eupoecilia ambiguella, Euproctis chrysorrhoea, Euxoa* spp., *Evetria bouliana, Feltia* spp. such as *Feltia subterranean; Galleria mellonella, Grapholitha funebrana, Grapholitha molesta, Helicoverpa* spp. such as *Helicoverpa armigera, Helicoverpa zea, Heliothis* spp. such as Heliothis armigera, Heliothis virescens, Heliothis zea, Hellula undalis, Hibernia defoliaria, Hofmannophila pseudospretella, Homona magnanima, Hyphantria cunea, Hyponomeuta padella, Hyponomeuta malinellus, Keiferia lycopersicella, Lambdina fiscellaria, *Laphygma* spp. such as *Laphygma exigua, Leucoptera coffeella, Leucoptera scitella, Lithocolletis blancardella, Lithophane antennata, Lobesia botrana, Loxagrotis albicosta, Loxostege sticticalis, Lymantria* spp. such as *Lymantria dispar, Lymantria monacha, Lyonetia clerkela, Malacosoma neustria, Mamestra* spp. such as *Mamestra brassicae; Mocis repanda, Mythimna separata, Orgyia pseudotsugata, Oria* spp., *Ostrinia* spp. such as *Ostrinia nubilalis, Oulema oryzae, Panolis flammea, Pectinophora* spp. such as *Pectinophora gossypiella; Peridroma saucia, Phalera bucephala, Phthorimaea* spp. such as *Phthorimaea operculella; Phyllocnistis citrella, Pieris* spp. such as *Pieris brassicae, Pieris rapae, Plathypena scabra, Plutella maculipennis, Plutella xyostella, Prodenia* spp., *Pseudaletia* spp., *Pseudoplusia includens, Pyrausta nubilalis, Rhyacionia frustrana, Scrobipalpula absoluta, Sitotroga cerealella, Sparganothis pilleriana, Spodoptera* spp. such as *Spodoptera frugiperda, Spodoptera littoralis, Spodoptera litura, Thaumatopoea pityocampa, Thermesia gemmatalis, Tinea pellionella, Tineola bisselliella, Tortrix viridana, Trichoplusia* spp. such as *Trichoplusia ni; Tuta absoluta,* and *Zeiraphera canadensis;*

Beetles (Coleoptera), for example *Acanthoscehdes obtectus, Adoretus* spp., *Agelastica alni, Agrilus sinuatus, Agriotes* spp. such as *Agriotes fuscicollis, Agriotes lineatus, Agriotes obscurus, Amphimallus solstitialis, Anisandrus dispar, Anobium punctatum, Anomala rufocuprea, Anoplophora* spp. such as *Anoplophora glabripennis; Anthonomus* spp. such as *Anthonomus grandis, Anthonomus pomorum; Anthrenus* spp., *Aphthona euphoridae, Apogonia* spp., *Athous haemorrhoidalis, Atomaria* spp. such as *Atomaria linearis; Attagenus* spp., *Aulacophora femoralis, Blastophagus piniperda, Blitophaga undata, Bruchidius obtectus, Bruchus* spp. such as *Bruchus lentis, Bruchus pisorum, Bruchus rufimanus; Byctiscus betulae, Callosobruchus chinensis, Cassida nebulosa, Cerotoma trifurcata, Cetonia aurata, Ceuthorhynchus* spp. such as *Ceuthorrhynchus assimilis, Ceuthorrhynchus napi; Chaetocnema tibialis, Cleonus mendicus, Conoderus* spp. such as *Conoderus vespertinus; Cosmopolites* spp., *Costelytra zealandica, Crioceris asparagi, Cryptorhynchus lapathi, Ctenicera* ssp. such as *Ctenicera destructor; Curculio* spp., *Dectes texanus, Dermestes* spp., *Diabrotica* spp. such as *Diabrotica 12-punctata Diabrotica speciosa, Diabrotica longicornis, Diabrotica semipunctata, Diabrotica virgifera; Epilachna* spp. such as *Epilachna varivestis, Epilachna vigintioctomaculata; Epitrix* spp. such as *Epitrix hirtipennis, Eutinobothrus brasiliensis, Faustinus cubae, Gibbium psylloides, Heteronychus arator, Hylamorpha elegans, Hylobius abietis, Hylotrupes bajulus, Hypera brunneipennis, Hypera postica, Hypothenemus* spp., *Ips typographus, Lachnosterna consanguinea, Lema bilineata, Lema melanopus, Leptinotarsa* spp. such as *Leptinotarsa decemlineata; Limonius californmicus, Lissorhoptrus oryzophilus, Lissorhoptrus oryzophilus, Lixus* spp., *Lyctus* spp. such as *Lyctus bruneus; Melanotus communis, Meligethes* spp. such as *Meligethes aeneus; Melolontha hippocastani, Melolontha melolontha, Migdolus* spp., *Monochamus* spp. such as *Monochamus alternatus; Naupactus xanthographus, Niptus hololeucus, Oryctes rhinoceros, Oryzaephilus surinamensis, Otiorrhynchus sulcatus, Otiorrhynchus ovatus, Otiorrhynchus sulcatus, Oulema oryzae, Oxycetonia jucunda, Phaedon cochleariae, Phyllobius pyri, Phyllopertha horticola, Phyllophaga* spp., *Phyllotreta* spp. such as *Phyllotreta chrysocephala, Phyllotreta nemorum, Phyllotreta striolata; Phyllophaga* spp., *Phyllopertha horticola, Popillia japonica, Premnotrypes* spp., *Psylliodes chrysocephala, Ptinus* spp., *Rhizobius ventralis, Rhizopertha dominica, Sitona lineatus, Sitophilus* spp. such as *Sitophilus granaria, Sitophilus zeamais; Sphenophorus* spp. such as *Sphenophorus levis; Sternechus* spp. such as *Sternechus subsignatus; Symphyletes* spp., *Tenebrio molitor, Tribolium* spp. such as *Tribolium castaneum; Trogoderma* spp., *Tychius* spp., *Xylotrechus* spp., and *Zabrus* spp. such as *Zabrus tenebrioides;*

Flies, mosquitoes (Diptera), e.g. *Aedes* spp. such as *Aedes aegypti, Aedes albopictus, Aedes vexans; Anastrepha ludens, Anopheles* spp. such as *Anopheles albimanus, Anopheles crucians, Anopheles freeborni, Anopheles gambiae, Anopheles leucosphyrus, Anopheles maculipennis,*

*Anopheles minimus, Anopheles quadrimaculatus, Anopheles sinensis; Bibio hortulanus, Calliphora erythrocephala, Calliphora vicina, Cerafitis capitata, Ceratitis capitata, Chrysomyia* spp. such as *Chrysomya bezziana, Chrysomya hominivorax, Chrysomya macellaria, Chrysops atlanticus, Chrysops discalis, Chrysops silacea, Cochliomyia* spp. such as *Cochliomyia hominivorax, Contarinia* spp. such as *Contarinia sorghicola, Cordylobia anthropophaga, Culex* spp. such as *Culex nigripalpus, Culex pipens, Culex quinquefasciatus, Culex tarsalis, Culex tritaeniorhynchus, Cullcoides furens, Culiseta inornata, Culiseta melanura, Cuterebra* spp., *Dacus cucurbitae, Dacus oleae, Dasineura brassicae, Delia* spp. such as *Delia antique, Delia coarctata, Delia platura, Delia radicum; Dermatobia hominis, Drosophila* spp., *Fannia* spp. such as *Fannia canicularis, Gastraphilus* spp. such as *Gasterophilus intestinalis, Geomyza Tripunctata, Glossina fuscipes, Glossina morsitans, Glossina palpalis, Glossina tachinoides, Haematobia irritans, Haplodiplosis equestris, Hippelates* spp., *Hylemyia* spp. such as *Hylemyia platura; Hypoderma* spp. such as *Hypoderma lineata; Hyppobosca* spp., *Leptoconops torrens, Liriomyza* spp. such as *Liriomyza sativae, Liriomyza trifolii; Lucilia* spp. such as *Lucilia caprina, Lucilia cuprina, Lucilia sericata; Lycoria pectoralis, Mansonia titillanus, Mayetiola* spp. such as *Mayetiola destructor; Musca* spp. such as *Musca autumnalis, Musca domestica; Muscina stabulans, Oestrus* spp. such as *Oestrus ovis; Opomyza florum, Oscinella* spp. such as *Oscinella frit; Pegomya hysocyami, Phlebotomus argentipes, Phorbia* spp. such as *Phorbia antiqua, Phorbia brassicae, Phorbia coarctata; Prosimulium mixtum, Psila rosae, Psorophora columbiae, Psorophora discolor, Rhagoletis cerasi, Rhagoletis pomonella, Sarcophaga* spp. such as *Sarcophaga haemorrhoidaliis; Simulium vittatum, Stomoxys* spp. such as *Stomoxys calcitrans; Tabanus* spp. such as *Tabanus atratus, Tabanus bovinus, Tabanus lineola, Tabanus similis; Tannia* spp., *Tipula oleracea, Tipula paludosa,* and *Wohlfahrtia* spp.;

Thrips (Thysanoptera), e.g. *Baliothrips biformis, Dichromothrips corbetti, Dichromothrips* ssp., *Enneothrips flavens, Frankliniella* spp. such as *Frankliniella fusca, Frankliniella occidentalis, Frankliniella tritici; Heliothrips* spp., *Hercinothrips femoralis, Kakothrips* spp., *Rhipiphorothrips cruentatus, Scirtothrips* spp. such as *Scirtothrips citri; Taeniothrips cardamoni, Thrips* spp. such as *Thrips oryzae, Thrips palmi, Thrips palmer;*

Termites (Isoptera), e.g. *Calotermes flavicollis, Coptotermes formosanus, Heterotermes aureus, Heterotermes longiceps, Heterotermes tenuis, Leucotermes flavipes, Odontotermes* spp., *Reticulitermes* spp. such as *Reticulitermes speratus, Reticulitermes flavipes, Reticulitermes grasse Reticulitermes lucifugus, Reticulitermes santonensis, Reticulitermes virginicus; Termes natalensis;*

Cockroaches (*Blattaria*-Blattodea), e.g. *Acheta domesticus, Blatta orientalis, Blattella asahinae, Blattella germanica, Gryllotalpa* spp., *Leucophaea maderae, Locusta* spp., *Melanoplus* spp., *Periplaneta americana, Periplaneta australasiae, Periplaneta brunnea, Periplaneta fuligginosa, Periplaneta japonica;*

Bugs, aphids, leafhoppers, whiteflies, scale insects, cicadas (Hemiptera), e.g. *Acrosternum* spp. such as *Acrosternum hilare; Acyrthosipon* spp. such as *Acyrthosiphon onobrychis, Acyrthosiphon pisum; Adelges laricis, Aeneolamia* spp., *Agonoscena* spp., *Aleurodes* spp., *Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii Aphis* spp. such as *Aphis fabae, Aphis forbesi, Aphis gossypii, Aphis grossulariae, Aphis pomi, Aphis sambuci, Aphis schneideri, Aphis spiraecola; Arboridia apicalis, Arilus critatus, Aspidella* spp., *Aspidiotus* spp., *Atanus* spp., *Aulacorthum solani, Bemisia* spp. such as *Bemisia argentifolii, Bemisia tabaci; Blissus* spp. such as *Blissus leucopterus; Brachycaudus cardui, Brachycaudus helichrysi, Brachycaudus persicae, Brachycaudus prunicola, Brachycolus* spp., *Brevicoryne brassicae, Calligypona marginata, Calocoris* spp., *Campylomma livida, Capitophorus horni, Carneocephala fulgida, Cavelerius* spp., *Ceraplastes* spp., *Ceratovacuna lanigera, Cercopidae, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. such as *Cimex hemipterus, Cimex lectularius; Coccomytilus halli, Coccus* spp., *Creontiades dilutus, Cryptomyzus ribis, Cryptomyzus ribis, Cyrtopeltis notatus, Dalbulus* spp., *Dasynus piperis, Dialeurades* spp., *Diaphorina* spp., *Diaspis* spp., *Dichelops furcatus, Diconocoris hewetti, Doralis* spp., *Dreyfusia nordmannianae, Dreyfusia piceae, Drosicha* spp., *Dysaphis* spp. such as *Dysaphis plantaginea, Dysaphis pyri, Dysaphis radicola; Dysaulacorthum pseudosolani, Dysdercus* spp. such as *Dysdercus cingulatus, Dysdercus intermedius; Dysmicoccus* spp., *Empoasca* spp. such as *Empoasca fabae, Empoasca solana; Eriosoma* spp., *Erythroneura* spp., *Eurygaster* spp. such as *Eurygaster integriceps; Euscelis bilobatus, Euschistus* spp. such as *Euschistuos heros, Euschistus impictiventris, Euschistus servus; Geococcus coffeae, Halyomorpha* spp. such as *Halyomorpha halys; Heliopeltis* spp., *Homalodisca coagulata, Horcias nobilellus, Hyalopterus pruni, Hyperomyzus lactucae, Icerya* spp., *Idiocerus* spp., *Idioscopus* spp., *Laodelphax striatellus, Lecanium* spp., *Lepidosaphes* spp., *Leptocorisa* spp., *Leptoglossus phyllopus, Lipaphis erysimi, Lygus* spp. such as *Lygus hesperus, Lygus lineolaris, Lygus pratensis; Macropes excavatus, Macrosiphum* spp. such as *Macrosiphum rosae, Macrosiphum avenae, Macrosiphum euphorbiae; Mahanarva fimbriolata, Megacopta cribraria, Megoura viciae, Melanaphis pyrarius, Melanaphis sacchari, Metcafiella* spp., *Metopolophium dirhodum, Miridae* spp., *Monellia costalis, Monelliopsis pecanis, Myzus* spp. such as *Myzus ascalonicus, Myzus cerasi, Myzus persicae, Myzus varians; Nasonovia ribis-nigr, Nephotettix* spp. such as *Nephotettix malayanus, Nephotettix nigropictus, Nephotettix parvus, Nephotettix virescens; Nezara* spp. such as *Nezara viridula; Nilaparvata lugens, Oebalus* spp., *Oncometopia* spp., *Orthezia praelonga, Parabemisia myricae, Paratrioza* spp., *Parlatoria* spp., *Pemphigus* spp. such as *Pemphigus bursarius; Pentomidae, Peregrinus maidis, Perkinsiella saccharicida, Phenacoccus* spp., *Phloeomyzus passerinii, Phorodon humuli, Phylloxera* spp., *Piesma quadrata, Piezodorus* spp. such as *Piezodorus guildinii, Pinnaspis aspidistrae, Planococcus* spp., *Protopulvinaria pyriformis, Psallus seriatus, Pseudacysta persea, Pseudaulacaspis pentagona, Pseudococcus* spp. such as *Pseudococcus comstocki; Psylla* spp. such as *Psylla mali, Psylla piri; Pteromalus* spp., *Pyrilla* spp., *Quadraspidiotus* spp., *Quesada gigas, Rastrococcus* spp., *Reduvius senilis, Rhodnius* spp., *Rhopalomyzus ascalonicus, Rhopalosiphum* spp. such as *Rhopalosiphum pseudobrassicas, Rhopalosiphum insertum, Rhopalosiphum maidis, Rhopalosiphum padi; Sagatodes* spp., *Sahlbergella singularis, Saissetia* spp., *Sappaphis mala, Sappaphis mali, Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Stephanitis nashi, Stictocephala festina, Tenalaphara malayensis, Thyanta* spp. such as *Thyanta perditor; Tibraca* spp., *Tinocallis caryaefoliae,*

*Tomaspis* spp., *Toxoptera* spp. such as *Toxoptera aurantii; Trialeurodes* spp. such as *Trialeurodes vaporariorum; Triatoma* spp., *Trioza* spp., *Typhlocyba* spp., *Unaspis* spp. such as *Unaspis yanonensis*; and *Viteus vitifolii;*

Ants, bees, wasps, sawflies (Hymenoptera), e.g. *Athalia rosae, Atta capiguara, Atta cephalotes, Atta cephalotes, Atta laevigata, Atta robusta, Atta sexdens, Atta texana, Bombus* spp., *Camponotus floridanus, Crematogaster* spp., *Dasymutilla occidentalis, Diprion* spp., *Dolichovespula maculata, Hoplocampa* spp. such as *Hoplocampa minuta, Hoplocampa testudinea; Lasius* spp. such as *Lasius niger, Linepithema humile, Monomorium pharaonis, Paravespula germanica, Paravespula pennsylvanica, Paravespula vulgaris, Pheidole megacephala, Pogonomyrmex barbatus, Pogonomyrmex californicus, Polistes rubiginosa, Solenopsis geminata, Solenopsis invicta, Solenopsis richteri, Solenopsis xyloni, Vespa* spp. such as *Vespa crabro*, and *Vespula squamosal;*

Crickets, grasshoppers, locusts (Orthoptera), e.g. *Acheta domestica, Calliptamus italicus, Chortoicetes terminifera, Dociostaurus maroccanus, Gryllotalpa africana, Gryllotalpa gryllotalpa, Hieroglyphus daganensis, Kraussaria angulifera, Locusta migratoria, Locustana pardalina, Melanoplus bivittatus, Melanoplus femurrubrum, Melanoplus mexicanus, Melanoplus sanguinipes, Melanoplus spretus, Nomadacris septemfasciata, Oedaleus senegalensis, Schistocerca americana, Schistocerca gregaria, Tachycines asynamorus*, and *Zonozerus variegatus;*

Earwigs (Demaptera), e.g. *forficula auricularia,*

Lice (Phthiraptera), e.g. *Damalinia* spp., *Pediculus* spp. such as *Pediculus humanus capitis, Pediculus humanus corporis; Pthirus pubis, Haematopinus* spp. such as *Haematopinus eurysternus, Haematopinus suis, Linognathus* spp. such as *Linognathus vituli; Bovicola bovis, Menopon gallinae, Menacanthus stramineus* and *Solenopotes capillatus, Trichodectes* spp.;

Fleas (Siphonaptera), e.g. *Ceratophyllus* spp., *Ctenocephalides felis, Ctenocephalides canis, Xenopsylla cheopis, Pulex irritans, Tunga penetrans*, and *Nosopsyllus fasciatus.*

The compounds of the formula (I) are also suitable for efficiently combating arthropod pests different from insects such as, in particular the following pests:

arachnids (Arachnida), such as acari, e.g. of the families Argasidae, Ixodidae and Sarcoptidae, such as *Amblyomma* spp. (e.g. *Amblyomma americanum, Amblyomma variegatum, Amblyomma maculatum*), *Argas* spp. (e.g. *Argas persicus*), *Boophilus* spp. (e.g. *Boophilus annulatus, Boophilus decoloratus, Boophilus microplus*), *Dermacentor silvarum, Dermacentor andersoni, Dermacentor variabilis, Hyalomma* spp. (e.g. *Hyalomma truncatum*), *Ixodes* spp. (e.g. *Ixodes ricinus, Ixodes rubicundus, Ixodes scapularis, Ixodes holocyclus, Ixodes pacificus*), *Ornithodorus* spp. (e.g. *Ornithodorus moubata, Ornithodorus hermsi, Ornithodorus turicata*), *Ornithonyssus bacoti, Otobius megnini, Dermanyssus gallinae, Psoroptes* spp. (e.g. *Psoroptes ovis*), *Rhipicephalus* spp. (e.g. *Rhipicephalus sanguineus, Rhipicephalus appendiculatus, Rhipicephalus evertsi*), *Rhizoglyphus* spp., *Sarcoptes* spp. (e.g. *Sarcoptes scabiei*), and *Eriophyidae* spp. such as *Acaria sheldoni Aculops* spp. (e.g. *Aculops pelekassi*) *Aculus* spp. (e.g. *Aculus schlechtendali*), *Epitrimerus pyri, Phyllocoptruta oleivora* and *Eriophyes* spp. (e.g. *Eriophyes sheldoni*); *Tarsonemidae* spp. such as *Hemitarsonemus* spp., *Phytonemus pallidus* and *Polyphagotarsonemus latus, Stenotarsonemus* spp.; *Tenuipalpidae* spp. such as *Brevipalpus* spp. (e.g. *Brevipalpus phoenicis*); *Tetranychidae* spp. such as *Eotetranychus* spp., *Eutetranychus* spp., *Oligonychus* spp., *Tetranychus cinnabarinus, Tetranychus kanzawai, Tetranychus pacificus, Tetranychus telarius* and *Tetranychus urticae; Bryobia praetiosa, Panonychus* spp. (e.g. *Panonychus ulmi Panonychus citri*), *Metatetranychus* spp. and *Oligonychus* spp. (e.g. *Oligonychus pratensis*), *Vasates lycopersici, Araneida*, e.g. *Latrodectus mactans*, and *Loxosceles reclusa*. And *Acarus siro, Chorioptes* spp., *Scorpio maurus;*

Silverfish, firebrat (Thysanura), e.g. *Lepisma saccharina* and *Thermobia domestica;*

Centipedes (Chilopoda), e.g. *Geophilus* spp., *Scutigera* spp. such as *Scutigera coleoptrata;*

Millipedes (Diplopoda), e.g. *Blaniulus guttulatus, Narceus* spp.,

Springtails (Collembola), e.g. *Onychiurus* ssp. such as *Onychiurus armatus,*

They are also suitable for controlling nematodes: plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species such as *Aphelenchoides besseyi*; Sting nematodes, *Belonolaimus longicaudatus* and other *Belonolaimus* species; Pine nematodes, *Bursaphelenchus lignicolus Mamiya et Kiyohara, Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus brachyurus, Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species such as *Tylenchulus semipenetrans*, Dagger nematodes, *Xiphinema* species; and other plant parasitic nematode species.

Examples of further pest species which may be controlled by compounds of formula (I) include: from the class of the Bivalva, for example, *Dreissena* spp.; from the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoellium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenole-*

*pis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti*; from the order of the Isopoda, for example, *Armadillidium vulgare, Oniscus asellus, Porcellio scaber*; from the order of the Symphyla, for example, *Scutigerella immaculata*.

Further examples of pest species which may be controlled by compounds of formula (I) include: *Anisopllia austriaca, Apamea* spp., *Austroasca viridigrisea, Baliothrips biformis, Caenorhabditis elegans, Cephus* spp., *Ceutorhynchus napi, Chaetocnema aridula, Chilo auricilius, Chilo indicus, Chilo polychrysus, Chortiocetes terminifera, Cnaphalocroci medinalis, Cnaphalocrosis* spp., *Colias eurytheme, Collops* spp., *Cornitermes cumulans, Creontiades* spp., *Cyclocephala* spp., *Dalbulus maidis, Deraceras reticulatum, Diatrea saccharalis, Dichelops furcatus, Dicladispa armigera, Diloboderus* spp. such as *Diloboderus abderus; Edessa* spp., *Epinotia* spp., *Formicidae, Geocoris* spp., *Globitermes sulfureus, Gryllotalpidae, Halotydeus destructor, Hipnodes bicolor, Hydrellia philippina, Julus* spp., *Laodelphax* spp., *Leptocorsia acuta, Leptocorsia oratorius, Liogenys fuscus, Lucillia* spp., *Lyogenys fuscus, Mahanarva* spp., *Maladera matrida, Marasmia* spp., *Mastotermes* spp., *Mealybugs, Megascelis* ssp, *Metamasius hemipterus, Microtheca* spp., *Mocis latipes, Murgantia* spp., *Mythemina separata, Neocapritermes opacus, Neocapritermes parvus, Neomegalotomus* spp., *Neotermes* spp., *Nymphula depunctalis, Oebalus pugnax, Orseolia* spp. such as *Orseollia oryzae; Oxycaraenus hyalinipennis, Plusia* spp., *Pomacea canaliculata, Procornitermes* ssp, *Procornitermes triacifer, Psylloides* spp., *Rachiplusia* spp., *Rhodopholus* spp., *Scaptocoris castanea, Scaptocoris* spp., *Scirpophaga* spp. such as *Scirpophaga incertulas, Scirpophaga innotata; Scotinophara* spp. such as *Scotinophara coarctata; Sesamia* spp. such as *Sesamia inferens, Sogaella frucifera, Solenapsis geminata, Spissistilus* spp., *Stalk borer, Stenchaetothrips biformis, Steneotarsonemus spinki, Sylepta derogata, Telehin licus, Trichostrongylus* spp.

Compounds of the formula (I) are particularly useful for controlling insects of the orders Hemiptera and Thysanoptera.

For use in a method according to the present invention, the compounds of the formula (I) can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula (I) according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-metyhl-pyrrolidone (NMP),N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.

carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers, for example polyoxyethylene fatty alcohol ethers, alkylsulfonates and arylsulfonates.

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen und benzyl alcohol hemiformal Suitable thickeners are compounds which confer a pseudoplastic flow behavior to the formulation, i.e. high viscosity at rest and low viscosity in the agitated stage. Mention may be made, in this context, for example, of commercial thickeners based on polysaccharides, such as Xanthan Gum® (Kelzan® from Kelco), Rhodopol®23 (Rhone Poulenc) or Veegum® (from R. T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula (I) can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of formulations:
1. Products for dilution with water. For seed treatment purposes, such products may be applied to the seed diluted or undiluted.

A) Water-Soluble Concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained.

Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

In the method of this invention compounds of formula (I) may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathionmethyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alphacypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or the compounds M.4A.1: 1-[(6-chloro-3-pyridinyl)methyl]-2,3,5,6,7,8-hexahydro-9-nitro-(5S,8R)-5,8-Epoxy-1H-imidazo[1,2-a]azepine; or M.4A.2: 1-[(6-chloro-3-pyridyl)methyl]-2-nitro-1-[(E)-pentylideneamino]guanidine; or M4.A.3: 1-[(6-chloro-3-pyridyl)methyl]-7-methyl-8-nitro-5-propoxy-3,5,6,7-tetrahydro-2H-imidazo[1,2-a]pyridine;

or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example

M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *Bacillus thuringiensis* or *Bacillus sphaericus* and the insecticdal proteins they produce such as *Bacillus thuringiensis* subsp. *israelensis, Bacillus sphaericus, Bacillus thuringiensis* subsp. *aizawai Bacillus thuringiensis* subsp. *kurstaki* and *Bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or M.22B metaflumizone, or M.22C 1-[(E)-[2-(4-cyanophenyl)-1-[3-(trifluoromethyl)phenyl] ethylidene]amino]-3-[4-(difluoromethoxy)phenyl]urea;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide.

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5l):

M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;

M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;

M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

M.28.5i) N-[2-(5-amino-1,3,4-thiadiazol-2-yl)-4-chloro-6-methyl-phenyl]-5-bromo-2-(3-chloro-2-pyridyl)pyrazole-3-carboxamide;

M.28.5j) 5-chloro-2-(3-chloro-2-pyridyl)-N-[2,4-dichloro-6-[(1-cyano-1-methylethyl)carbamoyl]phenyl]pyrazole-3-carboxamide;

M.28.5k) 5-bromo-N-[2,4-dichloro-6-(methylcarbamoyl) phenyl]-2-(3,5-dichloro-2-pyridyl)pyrazole-3-carboxamide;

M.28.5l) N-[2-(tert-butylcarbamoyl)-4-chloro-6-methyl-phenyl]-2-(3-chloro-2-pyridyl)-5-(fluoromethoxy)pyrazole-3-carboxamide; or a compound selected from M.28.6 N2-(1-cyano-1-methyl-ethyl)-N1-(2,4-dimethyl-phenyl)-3-iodo-phthalamide; or M.28.7 3-chloro-N2-(1-cyano-1-methyl-ethyl)-N1-(2,4-dimethylphenyl)phthalamide;

M.UN.X insecticidal active compounds of unknown or uncertain mode of action, as for example afidopyropen, azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, pyflubumide or the compounds M.UN.X.1: 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide, or the compound M.UN.X.2: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide, or the compound M.UN.X.3: 11-(4-chloro-2,6-dimethylphenyl)-12-hydroxy-1,4-dioxa-9-azadispiro[4.2.4.2]-tetradec-11-en-10-one, or the compound M.UN.X.4: 3-(4'-fluoro-2,4-dimethylbiphenyl-3-yl)-4-hydroxy-8-oxa-1-azaspiro[4.5]dec-3-en-2-one, or the compound M.UN.X.5: 1-[2-fluoro-4-methyl-5-[(2,2,2-trifluoroethyl) sufinyl]phenyl]-3-(trifluoromethyl)-1H-1,2,4-triazole-5-amine, or actives on basis of *Bacillus firmus* (Votivo, I-1582); or M.UN.X.6; a compound selected from the group of M.UN.X.6a) (E/Z)—N-[1-[(6-chloro-3-pyridyl)methyl]-2-pyridylidene]-2,2,2-trifluoroacetamide;

M.UN.X.6b) (E/Z)—N-[1-[(6-chloro-5-fluoro-3-pyridyl) methyl]-2-pyridylidene]-2,2,2-trifluoroacetamide;

M.UN.X.6c) (E/Z)-2,2,2-trifluoro-N-[1-[(6-fluoro-3-pyridyl)methyl]-2-pyridylidene]acetamide M.UN.X.6d) (E/Z)—N-[1-[(6-bromo-3-pyridyl)methyl]-2-pyridylidene]-2,2,2-trifluoroacetamide;

M.UN.X.6e) (E/Z)—N-[1-[1-(6-chloro-3-pyridyl)ethyl]-2-pyridylidene]-2,2,2-trifluoroacetamide;

M.UN.X.6f) (E/Z)—N-[1-[(6-chloro-3-pyridyl)methyl]-2-pyridylidene]-2,2-difluoro-acetamide;

M.UN.X.6g) (E/Z)-2-chloro-N-[1-[(6-chloro-3-pyridyl) methyl]-2-pyridylidene]-2,2-difluoro-acetamide;

M.UN.X.6h) (E/Z)—N-[1-[(2-chloropyrimidin-5-yl) methyl]-2-pyridylidene]-2,2,2-trifluoroacetamide and M.UN.X.6i) (E/Z)—N-[1-[(6-chloro-3-pyridyl)methyl]-2-pyridylidene]-2,2,3,3,3-pentafluoropropanamide.); or of the compounds M.UN.X.7: 3-[3-chloro-5-(trifluoromethyl)phenyl]-4-oxo-1-(pyrimidin-5-ylmethyl)pyrido[1,2-a]pyrimidin-1-ium-2-olate; or M.UN.X.8: 8-chloro-N-[2-chloro-5-methoxyphenyl)sulfonyl]-6-trifluoromethyl)-imidazo[1,2-a]pyridine-2-carboxamide; or M.UN.X.9: 4-[5-(3,5-dichlorophenyl)-5-(trifluoromethyl)-4H-isoxazol-3-yl]-2-methyl-N-(1-oxothietan-3-yl) benzamide; or M.UN.X.10: 5-[3-[2,6-dichloro-4-(3,3-dichloroallyloxy) phenoxy]propoxy]-1H-pyrazole.

The commercially available compounds of the group M listed above may be found in The Pesticide Manual, 15th Edition, C. D. S. Tomlin, British Crop Protection Council (2011) among other publications.

The quinoline derivative flometoquin is shown in WO 2006/013896. The aminofuranone compounds flupyradifurone is known from WO 2007/115644. The sulfoximine compound sulfoxaflor is known from WO 2007/149134. The pyrethroid momfluorothrin is known from U.S. Pat. No. 6,908,945. The pyrazole acaricide pyflubumide is known from WO 2007/020986. The isoxazoline compounds have been described likewise M.UN.X.1 in WO 2005/085216, M.UN.X2. in WO 2009/002809 and in WO 2011/149749 and the isoxazoline M.UN.X.9 in WO 2013/050317. The pyripyropene derivative afidopyropen has been described in WO 2006/129714. The spiroketal-substituted cyclic ketoenol derivative M.UN.X.3 is known from WO 2006/089633 and the biphenyl-substituted spirocyclic ketoenol derivative M.UN.X.4 from WO 2008/067911. Finally triazoylphenylsulfide like M.UN.X.5 have been described in WO 2006/043635 and biological control agents on basis of *Bacillus firmus* in WO 2009/124707. The neonicotionids 4A.1 is known from WO 20120/069266 and WO 2011/06946, the M.4.A.2 from WO 2013/003977, the M4.A.3. from WO 2010/069266.

The Metaflumizone analogue M.22C is described in CN 10171577. The phthalamides M.28.1 and M.28.2 are both known from WO 2007/101540. The anthranilamide M.28.3 has been described in WO 2005/077934. The hydrazide compound M.28.4 has been described in WO 2007/043677. The anthranilamides M.28.5a) to M.28.5h) can be prepared as described in WO 2007/006670, WO 2013/024009 and WO 2013/024010, the anthranilamide M.28.5i) is described in WO 2011/085575, the M.28.5j) in WO 2008/134969, the M.28.5k) in US 2011/046186 and the M.28.5l) in WO 2012/034403. The diamide compounds M.28.6 and M.28.7 can be found in CN 102613183.

The compounds M.UN.X.6a) to M.UN.X.6i) listed in M.UN.X.6 have been described in WO 2012/029672. The mesoionic antagonist compound M.UN.X.7 was described in WO 2012/092115, the nematicide M.UN.X.8 in WO 2013/055584 and the Pyridalyl-type analogue M.UN.X.10 in WO 2010/060379.

In another embodiment of the invention, the compounds of formula (I), or their stereoisomers, salts, tautomers and N-oxides, may also be applied with fungicides as compound II.

The following list F of active substances, in conjunction with which the compounds according to the invention can be used, is intended to illustrate the possible combinations but does not limit them:

F.I) Respiration Inhibitors

F.I-1) Inhibitors of complex III at Qo site:
strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)-phenyl)-2-methoxy-imino-N methyl-acetamide;

oxazolidinediones and imidazolinones: famoxadone, fenamidone;

F.I-2) Inhibitors of complex II (e.g. carboxamides):
carboxanilides: benodanil, benzovindiflupyr, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide (fluxapyroxad), N-(4'-trifluoromethylthiobiphenyl-2-yl)-3 difluoromethyl-1-methyl-1H pyrazole-4-carboxamide, N-(2-(1,3,3-trimethyl-butyl)-phenyl)-1,3-dimethyl-5 fluoro-1H-pyrazole-4 carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl) pyrazole-4-carboxamide, 1,3-dimethyl-N-(1,1,3-trimethylindan-4-yl)pyrazole-4-carboxamide, 3-(trifluoromethyl)-1, 5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, 3-(difluoromethyl)-1-methyl-N-(1,1,3- trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

F.I-3) Inhibitors of complex III at Qi site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate, [(3S,6S,7R,8R)-8-benzyl-3-[(3-isobutoxycarbonyyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate, 3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

F.I-4) Other respiration inhibitors (complex I, uncouplers) diflumetorim; (5,8-difluoroquinazolin-4-yl)-{2-[2-fluoro-4-(4-trifluoromethylpyridin-2-yloxy)-phenyl]-ethyl}-amine; tecnazen; ametoctradin; silthiofam; nitrophenyl derivates: binapacryl, dinobuton, dinocap, fluazinam, ferimzone, nitrthal-isopropyl,
and including organometal compounds: fentin salts, such as fentin-acetate, fentin chloride or fentin hydroxide;

F.II) Sterol biosynthesis inhibitors (SBI fungicides)
F.II-1) C14 demethylase inhibitors (DMI fungicides, e.g. triazoles, imidazoles)

triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, 1-[rel-(2S3R)-3-(2-chlorophenyl)-2-(2,4-difluorophenyl)-oxiranylmethyl]-5-thiocyanato-1H-[1,2,4]triazole, 2-[rel(2S;3R)-3-(2-chlorophenyl)-2-(2,4-difluorophenyl)-oxiranylmethyl]-2H-[1,2,4]triazole-3-thiol;

imidazoles: imazalil, pefurazoate, oxpoconazole, prochloraz, triflumizole;

pyrimidines, pyridines and piperazines: fenarimol, nuarimol, pyrifenox, triforine, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol;

F.II-2) Delta 14-reductase initors (Amines, e.g. morpholines, piperidines)

morpholines: aldimorph, dodemorph, dodemorph-acetate, fenpropimorph, tridemorph;

piperidines: fenpropidin, piperalin; spiroketalamines: spiroxamine;

F.II-3) Inhibitors of 3-keto reductase: hydroxyanilides: fenhexamid;

F.III) Nucleic acid synthesis inhibitors
F.III-1) RNA, DNA synthesis phenylamides or acyl amino acid fungicides: benalaxyl, benalaxyl-M, kiralaxyl, metalaxyl, metalaxyl-M (mefenoxam), ofurace, oxadixyl;

isoxazoles and iosothiazolones: hymexazole, octhilinone;

F.III-2) DNA topisomerase inhibitors: oxolinic acid;
F.III-3) Nucleotide metabolism (e.g. adenosin-deaminase), hydroxy (2-amino)-pyrimidines: bupirimate;

F.IV) Inhibitors of cell division and or cytoskeleton
F.IV-1) Tubulin inhibitors: benzimidazoles and thiophanates: benomyl, carbendazim, fuberidazole, thiabendazole, thiophanate-methyl;

triazolopyrimidines: 5-chloro-7 (4-methylpiperidin-1-yl)-6-(2,4,6-trifluorophenyl)-[1,2,4]triazolo[1,5 a]pyrimidine;

F.IV-2) Other cell division inhibitors
benzamides and phenyl acetamides: diethofencarb, ethaboxam, pencycuron, fluopicolide, zoxamide;

F.IV-3) Actin inhibitors: benzophenones: metrafenone; pyriofenone;

F.V) Inhibitors of amino acid and protein synthesis
F.V-1) Methionine synthesis inhibitors (anilino-pyrimidines)

anilino-pyrimidines: cyprodinil, mepanipyrim, nitrapyrin, pyrimethanil;

F.V-2) Protein synthesis inhibitors (anilino-pyrimidines)
antibiotics: blasticidin-S, kasugamycin, kasugamycin hydrochloride-hydrate, mildiomycin, streptomycin, oxytetracyclin, polyoxine, validamycin A;

F.VI) Signal transduction inhibitors
F.VI-1) MAP/Histidine kinase inhibitors (e.g. anilinopyrimidines)

dicarboximides: fluoroimid, iprodione, procymidone, vinclozolin;

phenylpyrroles: fenpiclonil, fludioxonil;
F.VI-2) G protein inhibitors: quinolines: quinoxyfen;
F.VII) Lipid and membrane synthesis inhibitors
F.VII-1) Phospholipid biosynthesis inhibitors
organophosphorus compounds: edifenphos, iprobenfos, pyrazophos;

dithiolanes: isoprothiolane;
F.VII-2) Lipid peroxidation: aromatic hydrocarbons: dicloran, quintozene, tecnazene, tolclofos-methyl, biphenyl, chloroneb, etridiazole;

F.VII-3) Carboxyl acid amides (CAA fungicides)
cinnamic or mandelic acid amides: dimethomorph, flumorph, mandipropamid, pyrimorph;

valinamide carbamates: benthiavalicarb, iprovalicarb, pyribencarb, valifenalate and N-(1-(1-(4-cyano-phenyl)ethanesulfonyl)-but-2-yl) carbamic acid-(4-fluorophenyl) ester;

F.VII-4) Compounds affecting cell membrane permeability and fatty acids:
1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, carbamates: propamocarb, propamocarbhydrochlorid, F.VII-5) fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone;

F.VIII) Inhibitors with Multi Site Action
F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles):
anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitrophenyl)-N-ethyl-4-methyl-benzenesulfonamide;

F.VIII-4) Guanidines and other: guanidine, dodine, dodine free base, guazatine, guazatine-acetate, iminoctadine, iminoctadine-triacetate, iminoctadine-tris(albesilate), 2,6-dimethyl-1H,5H-[1,4]dithiino[2,3-c:5,6-c']dipyrrole-1,3,5,7(2H,6H)-tetraone;

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defence inducers

F.X-1) Salicylic acid pathway: acibenzolar-S-methyl;

F.X-2) Others: probenazole, isotianil, tiadinil, prohexadione-calcium;

phosphonates: fosetyl, fosetyl-aluminum, phosphorous acid and its salts;

F.XI) Unknown mode of action:bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)methyl)-2-phenyl acetamide, N'-(4-(4-chloro-3-trifluoromethyl-phenoxy)-2,5-dimethyl-phenyl)-N-ethyl-N-methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tertbutyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl) cyclopropanecarboxylic acid amide, 5-chloro-1 (4,6-dimethoxypyrimidin-2-yl)-2-methyl-1H-benzoimidazole, 2-(4-chloro-phenyl)-N-[4-(3,4-dimethoxy-phenyl)isoxazol-5-yl]-2-prop-2-ynyloxyacetamide;

F.XI) Growth regulators: abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6-benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XII) Biological control agents

*Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea f. catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. Endothia parasitica from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and *TRICHODERMA* 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO—CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ).

The commercially available compounds II of the group F listed above may be found in The Pesticide Manual, 15th Edition, C. D. S. Tomlin, British Crop Protection Council (2011) among other publications. Their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EP A 141 317; EP-A 152 031; EP A 226 917; EP A 243 970; EP A 256 503; EP-A 428 941; EP-A 532 022; EP-A 1 028 125; EP-A 1 035 122; EP A 1 201 648; EP A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657).

The invertebrate pest, e.g. the insects, arachnids and nematodes, the plant, soil or water in which the plant is growing can be contacted with the present compounds of formula (I), including their stereoisomers and tautomers, as well the salts thereof, or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula (I), including their stereoisomers and tautomers, as well the salts thereof, or the pesticidal compositions comprising them may be used to protect growing plants and crops from attack or infestation by animal pests, especially insects, acaridae or arachnids by contacting the plant/crop with a pesticidally effective amount of compounds of formula (I). The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of at least one active compound of the formula (I), a stereoisomers, a tautomere or a salt thereof.

Moreover, animal pests may be controlled by contacting the target pest, its food supply, habitat, breeding ground or its locus with a pesticidally effective amount of compounds of formula (I), a stereoisomer, a tautomere or a salt thereof. As such, the application may be carried out before or after the infection of the locus, growing crops, or harvested crops by the pest.

The compounds of the invention can also be applied preventively to places at which occurrence of the pests is expected.

The compounds of formula (I), including their stereoisomers and their tautomers, as well as their salts may be also used to protect growing plants from attack or infestation by pests. The use includes contacting the plant with a pesticidally effective amount of compounds of formula (I), a stereoisomer, a tautomere or a salt thereof. As such, "contacting" includes both direct contact, i.e. applying the compounds/compositions directly on the pest and/or plant—typically to the foliage, stem or roots of the plant, and indirect contact, i.e. applying the compounds/compositions to the locus of the pest and/or plant.

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat Protoc. 2007; 2(5):1225-35., Curr Opin Chem Biol. 2006 October; 10(5):487-91. Epub 2006 Aug. 28., Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246)

or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e. g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are, e.g. by the use of recombinant DNA techniques, capable of synthesizing one or more proteins in order to increase the resistance or tolerance of those plants to bacterial, viral or fungal pathogens. Examples of such proteins are the so-called "pathogenesis-related proteins", also termed PR proteins—see, for example EP-A 0 392 225—, or plant disease resistance genes—for example potato cultivars, which express resistance genes acting against *Phytophthora infestans* derived from the mexican wild potato *Solanum bulbocastanum*—or T4-lysozym—e. g. potato cultivars capable of synthesizing these proteins with increased resistance against bacteria such as *Erwinia amylvora*. The methods for producing such genetically modified plants are generally known to the person skilled in the art and are described, for example, in the publications mentioned above.

The term "cultivated plants" is to be understood also including plants that are, e.g. by the use of recombinant DNA techniques, capable of synthesizing one or more proteins to increase the productivity, e. g. bio mass production, grain yield, starch content, oil content or protein content, or to improve tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for ex-ample oil crops that produce health-promoting long-chain omega-3 fatty acids or unsaturated omega-9 fatty acids (e. g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e. g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula (I), including the tautomers and stereoisomers, as well as their salts, are effective through both contact, e.g. via soil, glass, wall, bed net, carpet, plant parts or animal parts, and ingestion, e.g. via ingestion of bait or plant part.

The compounds of the invention may also be applied against non-crop insect pests, such as ants, termites, wasps, flies, mosquitos, crickets, or cockroaches. For use against said non-crop pests, compounds of formula (I), including the tautomers and stereoisomers, as well as their salts, are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitos, crickets etc. or cockroaches to eat it.

The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula (I), including the tautomers and stereoisomers, as well as their salts, as aerosols, e.g in spray cans, oil sprays or pump sprays are highly suitable for the non-professional user for controlling pests such as flies, fleas, ticks, mosquitos or cockroaches. Aerosol recipes are preferably composed of the active compound, solvents such as lower alcohols, e.g. methanol, ethanol, propanol or butanol, ketones, e.g. acetone, methyl ethyl ketone, paraffin hydrocarbons, e.g. kerosenes or mineral oils, having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula (I), including the tautomers and stereoisomers, as well as their salts, and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects, such as malaria, dengue and yellow fever, lymphatic filariasis, and leishmaniasis, with compounds of formula (I) or the stereoisomers, tautomers or salts thereof, and with their respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula (I), including the tautomers and stereoisomers, as well as their salts, and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being, e.g. when the pests invade into houses and public facilities. The compounds of formula (I), their stereoisomers, their tautomers or their salts are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formula (I), including the tautomers and stereoisomers, as well as their salts, are also suitable for the treatment of seeds in order to protect the seed from insect pest, in particular from soil-living insect pests and the resulting plant's roots and shoots against soil pests and foliar insects.

The compounds of formula (I), including the tautomers and stereoisomers, as well as their salts, are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedling's roots and shoots from insects, in particular from soil and foliar insects, said method comprising contacting the seeds before sowing and/or after pregermination with a compound of the general formula (I), a tautomer, a stereosiomer or a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed includes seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment includes all suitable seed treatment techniques known in the art, such as seed dressing, seed coating, seed dusting, seed soaking and seed pelleting.

The present invention also relates to seeds coated with or containing the active compound of the present invention, i.e. containing a compound of formula (I), a stereoisomer, a tautomer or a salt thereof.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maizeisweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the compounds of formula (I), including the tautomers and stereoisomers, as well as their salts, may also be used for the treatment seeds from plants, which tolerate the action of herbicides or fungicides or insecticides owing to breeding, including genetic engineering methods.

For example, the compounds of formula (I), including the tautomers and stereoisomers, as well as their salts, can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the compounds of formula (I), including the tautomers and stereoisomers, as well as their salts, can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/l Surfactant, 0 to 200 g/l anti-freezing agent, 0 to 400 g/l of binder, 0 to 200 g/l of a pigment and up to 1 liter of a solvent, preferably water.

Especially preferred FS formulations of a compound of formula (I), a stereoisomer, a tautomer or a salt, for seed treatment usually comprise from 0.1 to 80% by weight (1 to 800 g/l) of the the compound of formula (I), including its tautomers and stereoisomers, or a salt thereof, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a Gelling Agent is Carrageen (Satiagel®)

In the treatment of seed, the application rates of the compounds of formula (I) are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula (I), a tautomer, a stereoisomer or an agriculturally useful salt thereof, as defined herein. The amount of the compound of the formula (I) or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds of formula (I), including their stereoisomers and their tautomers, and the veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of a compound of formula (I) or a stereoisomer or a tautomer or a veterinarily acceptable salt thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula (I) or a stereoisomer or a tautomer or a veterinarily acceptable salt thereof or a composition comprising it.

The invention also provides a process for the preparation of a composition for treating, controlling, preventing or protecting animals against infestation or infection by parasites which comprises a parasiticidally effective amount of a compound of formula (I) or a stereoisomer or a tautomer or a veterinarily acceptable salt thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula (I), including their stereoisomers and tautomers, and the salts thereof, are suitable for combating endo- and ectoparasites in and on animals.

Compounds of formula (I), including their stereoisomers and their tautomers, and the veterinarily acceptable salts thereof, and compositions comprising them are preferably used for controlling and preventing infestations and infections animals including warm-blooded animals, including humans, and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula (I), including their stereoisomers and their tautomers, and the veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula (I), including their stereoisomers and their tautomers, and the veterinarily acceptable salts thereof and compositions comprising them are suitable for systemic and/or non-systemic control of ecto- and/or endoparasites. They are active against all or some stages of development.

The compounds of formula (I) including their stereoisomers and their tautomers, and the veterinarily acceptable salts thereof are especially useful for combating ectoparasites.

The compounds of formula (I), including their stereoisomers and their tautomers, and the veterinarily acceptable salts thereof are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (*Blattaria*-Blattodea), e.g. *Battella germanica, Battella asahinae, Periplaneta americana, Periplaneta japonica, Periplaneta brunnea, Periplaneta fuligginosa, Periplaneta australasiae*, and *Blatta orientalis;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discallis, Chrysops sillacea, Chrysops atlanticus, Cochliomyia hominivorax, Cordylobia anthropophaga, Cullcoides furens, Culex pipiens, Culex nigripalpus, Culex quinque-fasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucila caprina, Lucila cuprina, Lucila sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis;* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus;* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae;*

Actinedida (Prostigmata) und Acaridida (Astigmata) e.g. *Acarapis* spp., *Cheyetiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp;

Bugs (Heteropterida): *Cimex lectularius, Cimex hemipterus, Reduvius senilis, Triatoma* spp., *Rhodnius* ssp., *Panstrongylus* ssp. and *Arilus critatus;*

Anoplurida, e.g. *Haematopinus* spp., *Linognathus* spp., *Pediculus* spp., *Phtirus* spp., and *Solenopotes* spp.;

Mallophagida (suborders Amblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp;

Roundworms Nematoda:

Wipeworms and Trichinosis (Trichosyringida), e.g. Trichinellidae (*Trichinella* spp.), (Trichuridae) *Trichuris* spp., *Capillaria* spp.;

Rhabditida, e.g. *Rhabditis* spp, *Strongyloides* spp., *Helicephalobus* spp;

Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus* dentatus, *Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi;*

Camallanida, e.g. *Dracunculus medinensis* (guinea worm);

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp.;

Thorny headed worms (Acanthocephala), e.g. *Acanthocephalus* spp., *Macracanthorhynchus hirudinaceus* and *Oncicola* spp;

Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp;

Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula (I), including their stereoisomers and their tautomers, and the salts thereof and compositions containing them are particularly useful for the control of pests from the orders Diptera, Siphonaptera and Ixodida.

Moreover, the use of the compounds of formula (I), including their stereoisomers and their tautomers, and the salts thereof and compositions containing them for combating mosquitoes is especially preferred.

The use of the compounds of formula (I), including their stereoisomers and their tautomers, and the salts thereof and compositions containing them for combating flies is a further preferred embodiment of the present invention.

Furthermore, the use of the compounds of formula (I), including their stereoisomers and their tautomers, and the salts thereof and compositions containing them for combating fleas is especially preferred.

The use of the compounds of formula (I), including their stereoisomers and their tautomers, and the salts thereof and compositions containing them for combating ticks is a further preferred embodiment of the present invention.

The compounds of formula (I), including their stereoisomers and their tautomers, and the salts thereof also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the compounds of the present invention may be formulated as animal feeds, animal feed premixes, animal feed concentrates, pills, solutions, pastes, suspensions, drenches, gels, tablets, boluses and capsules. In addition, the compounds of the present invention may be administered to the animals in their drinking water. For oral administration, the dosage form chosen should provide the animal with 0.01 mg/kg to 100 mg/kg of animal body weight per day of the formula (I) compound, preferably with 0.5 mg/kg to 100 mg/kg of animal body weight per day.

Alternatively, the compounds of the present invention may be administered to animals parenterally, for example, by intraruminal, intramuscular, intravenous or subcutaneous injection. The compounds of the present invention may be dispersed or dissolved in a physiologically acceptable carrier for subcutaneous injection. Alternatively, the compounds of the present invention may be formulated into an implant for subcutaneous administration. In addition the compounds of the present invention may be transdermally administered to animals. For parenteral administration, the dosage form chosen should provide the animal with 0.01 mg/kg to 100 mg/kg of animal body weight per day of a compound of the present invention.

The compounds of the present invention may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compounds of the present invention. In addition, the compounds of the present invention may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The compounds of the present invention can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents are, for example, water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are, for example, sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are, for example: liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are, for example, water, alcohols such as propylene glycol, glycerol, sorbitol and mixtures thereof.

Suitable emulsifiers are, for example,
non-ionic surfactants, e.g. polyethoxylated castor oil, polyethoxylated sorbitan monooleate, sorbitan monostearate, glycerol monostearate, polyoxyethyl stearate, alkylphenol polyglycol ether;
ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries, which may be mentioned, are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of a compound of formula (I), a stereoisomer, a tautomer or a salt thereof.

Generally it is favorable to apply the compounds of the present invention in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations for controlling endoparasites comprise a compound of the present invention usually in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the a compound of the present invention are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of the present invention. A detailed list of plastics and elastomers as well as preparation procedures for the shaped articles is given e.g. in WO 03/086075.

The present invention is now illustrated in further details by the following examples, without imposing any limitation thereto.

The following abbreviations are used:
TFA: trifluoroacetic acid
EtOAc: ethyl acetate
HPLC: High Performance Liquid Chromatography
MS: Mass spectrometry
MeOH: Methanol The Compound examples were characterized by coupled High Performance Liquid Chromatography with mass spectrometry (HPLC/MS) or by their melting point.

Method A: Analytical HPLC column 1: RP-18 column Chromolith Speed ROD (from Merck KgaA, Germany). Elution: acetonitrile/water in a ratio of from 5:95 to 95:5 in 5 minutes at 40° C.

Method B:
Analytical UPLC column: Phenomenex Kinetex 1.7 μm XB-C18 100A; 50×2.1 mm; mobile phase: A: water; B:

acetonitrile; gradient: 5-100% B in 1.50 minutes; 100% B 0.20 min; flow: 0.8-1.0 mL/min in 1.50 minutes at 60° C. MS-method: ESI positive.

A. PREPARATION EXAMPLES

Example 1: (Compound Example E1.2; Compound of Formula I, Wherein Het is 6-chloropyridin-3-yl, -$W^1$-$W^2$-$W^3$-$W^4$- Represent —CH=CH—CH=CH—, X is O, $R^3$ is H, $R^5$ is H and m is 0)

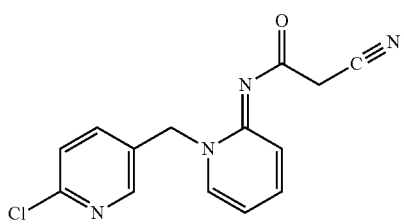
(E1.2)

1.1 Synthesis of Amine Salt E1.1

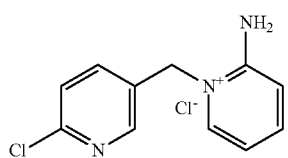
(E1.1)

A solution of 2-chloro-5-chloromethylpyridine (16.20 g, 100 mmol) and 2-amino-pyridine (9.60 g, 102 mmol) in ethanol (100 mL) was refluxed for 24 hours. The reaction was then cooled to room temperature, and concentrated in vacuo. Then 100 mL of toluene were added to the residue, and the mixture was concentrated in vacuo. Then, 75 mL of $CH_2Cl_2$ were added to the residue and the mixture was rapidly stirred for 15 minutes, during which time a precipitate forms. The precipitate was then filtered, and washed with $CH_2Cl_2$ (50 mL), diethyl ether (50 mL), and dried under vacuum to afford the title product as a pale yellow solid (14.0 g, 55% yield).

LC-MS: mass calculated for $C_{11}H_{11}ClN_3$ $[M]^+$ 220.1, found 220.1; $t_R$=0.529 min ($t_R$: retention time).

1.2 Synthesis of Compound E1.2

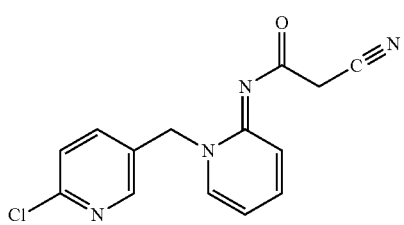
(E1.2)

To a suspension of amine salt E1.1 (1.50 g, 5.85 mmol), cyanoacetic acid (0.600 g, 7.05 mmol), and triethylamine (1.48 g, 14.65 mmol) in dichloromethane (30 mL) at room temperature was added a solution of propyl phosphoric anhydride (2.23 g, 7.05 mmol, 50% by weight solution in ethyl acetate). The reaction was then heated in the microwave at 100 C for 3 hrs. The reaction was diluted with ethyl acetate (100 mL), washed with saturated aqueous NaHCO$_3$ (100 mL) and water (100 mL). The layers were separated, the organic layer dried over Na$_2$SO$_4$ and then concentrated in vacuo to afford a residue, which was purified using column chromatography over silica gel (0→30% MeOH/EtOAc) to afford the title product as a beige solid (0.520 g, 31% yield).

LC-MS: mass calculated for $C_{14}H_{12}N_4OCl$ $[M+H]^+$ 287.1, found 287.1; $t_R$=0.607 min.

Example 2: (Compound Example E1.3; Compound of Formula I, Wherein Het is 6-chloropyridin-3-yl, -$W^1$-$W^2$-$W^3$-$W^4$- Represent —CH=CH—CH=CH—, X is O, $R^3$ and $R^5$ Together Form with the Carbon Atom to which they are Attached Form a Cyclopropyl Ring and m is 0)

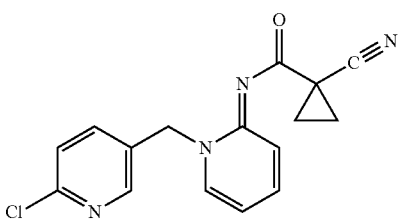
(E1.3)

To a suspension of amine salt E1.1 (6.00 g, 23.43 mmol), 1-cyanocyclopropanecarboxylic acid (3.12 g, 28.10 mmol), and triethylamine (5.93 g, 58.71 mmol) in CH$_2$Cl$_2$ (80 mL) at room temperature was added a solution of propyl phosphoric anhydride (8.95 g, 28.10 mmol, 50% by weight solution in ethyl acetate). The reaction was then heated in the microwave at 100 C for 3 hrs. The reaction was then diluted with ethyl acetate (200 mL), washed with saturated aqueous NaHCO$_3$ (200 mL) and water (200 mL). The layers were separated, and the organic layer dried over Na$_2$SO$_4$ and concentrated in vacuo to afford a residue, which was purified using column chromatography over silica gel (0→30% MeOH/EtOAc), followed by preparative HPLC using 5%-95% CH$_3$CN/H$_2$O to afford the title product as a beige solid (0.130 g, 2% yield).

LC-MS: mass calculated for $C_{16}H_{14}N_4OCl$ $[M+H]^+$ 313.1, found 313.1; $t_R$=0.788 min.

By the method described above for example 1 and 2, the compounds of formula (I.A) summarized in table A.1 can be prepared.

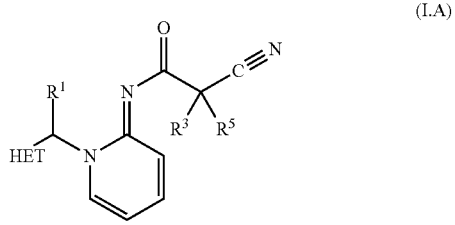
(I.A)

TABLE A.1

| # | HET | R¹ | R³ | R⁵ | method | RT [min] | m/z [M + H]+ |
|---|---|---|---|---|---|---|---|
| I.A-1 | 6-chloro-3-pyridyl | H | H | H | B | 0.607 | 287.1 |
| I.A-2 | 6-chloro-3-pyridyl | CH₃ | H | H |  | NMR* |  |
| I.A-3 | 6-chloro-3-pyridyl | CH₃ | F | F |  | NMR* |  |
| I.A-4 | 2-chlorothiazol-5-yl | H | H | H | B | 0.713 | 292.7 |
| I.A-5 | tetrahydrofuran-3-yl | H | H | H | B | 0.348 | 245.8 |
| I.A-6 | 6-chloro-3-pyridyl | H | CH₂CH₂CH₂CH₃ | H | B | 0.937 | 343.7 |
| I.A-7 | 6-chloro-3-pyridyl | H | CH₃ | CH₃ | B | 0.845 | 315.5 |
| I.A-8 | 6-chloro-3-pyridyl | H | CH₂CH₂CH₂ | | B | 0.848 | 326.8 |
| I.A-9 | 6-chloro-3-pyridyl | H | CH₂CH₂CH₂CH₂ | | B | 0.930 | 341.5 |
| I.A-10 | 6-chloro-3-pyridyl | H | C₆H₅ | H | B | 0.927 | 362.7 |
| I.A-11 | pyrimidin-5-yl | H | H | H | B | 0.517 | 253.8 |
| I.A-12 | 6-chloro-3-pyridyl | H | allyl | H | B | 0.922 | 326.4 |
| I.A-13 | 6-chloro-3-pyridyl | H | allyl | allyl | B | 1.121 | 366.4 |
| I.A-14 | 6-chloro-3-pyridyl | H | 2-methylallyl | 2-methylallyl | B | 1.227 | 394.9 |
| I.A-15 | 6-chloro-3-pyridyl | H | CH₂CH=CHCH₂ | | B | 1.008 | 338.4 |
| I.A-16 | 6-chloro-3-pyridyl | H | 3-methylbut-2-enyl | H | B | 0.960 | 354.8 |
| I.A-17 | 6-chloro-3-pyridyl | H | 3-methylbut-2-enyl | 3-methylbut-2-enyl | B | 1.216 | 422.9 |
| I.A-18 | 6-chloro-3-pyridyl | H | CH₂OCH₂ | |  | NMR* |  |
| I.A-19 | 2-chlorothiazol-5-yl | H | CH₂OCH₂ | |  | NMR* |  |
| I.A-20 | 6-chloro-3-pyridyl | CH₃ | CH₂OCH₂ | |  | NMR* |  |
| I.A-21 | 2-chlorothiazol-5-yl | CH₃ | CH₂OCH₂ | |  | NMR* |  |

NMR* Spectra:

I.A-2

Characterization by ¹H-NMR (400 MHz, CDCl₃): δ[delta]=1.86 (d, 3H), 3.49 (s, 2H), 6.74 (m, 1H), 7.30 (m, 1H), 7.57 (d. 1H), 7.65 (m, 1H), 7.69-7.72 (m, 2H), 8.37 (d, 1H), 8.45 (d, 1H) ppm.

I.A-3

Characterization by ¹H-NMR (400 MHz, CDCl₃): δ[delta]=1.92 (d, 3H), 6.95 (dd, 1H), 7.15 (m, 1H), 7.38 (d. 1H), 7.66-7.73 (m, 2H), 7.83 (m, 1H), 8.44 (d, 1H), 8.61 (d, 1H) ppm.

I.A-18

Characterization by ¹H-NMR (400 MHz, CDCl₃): δ[delta]=4.97 (d, 2H), 5.04 (d, 2H), 5.55 (s, 2H), 6.81 (dd, 1H), 7.34 (d, 1H), 7.73-7.77 (m, 2H), 7.83 (m, 1H), 8.41 (d, 1H), 8.54 (d, 1H) ppm.

I.A-19

Characterization by ¹H-NMR (400 MHz, CDCl₃): δ[delta]=5.05 (d, 2H), 5.17 (d, 2H), 5.60 (s, 2H), 6.82 (dd, 1H), 7.65 (s, 1H), 7.74-7.77 (m, 2H), 8.57 (d, 1H) ppm.

I.A-20

Characterization by ¹H-NMR (400 MHz, CDCl₃): δ[delta]=1.87 (d, 3H), 4.98 (m, 2H), 5.08 (d, 2H), 6.79 (dd, 1H), 7.10 (m, 1H), 7.35 (d, 1H), 7.61 (d, 1H), 7.65-7.71 (m, 2H), 8.42 (d, 1H), 8.53 (d, 1H) ppm.

I.A-21

Characterization by ¹H-NMR (400 MHz, CDCl₃): δ[delta]=1.91 (d, 3H), 5.01 (m, 2H), 5.14 (d, 2H), 6.80 (dd, 1H), 7.22 (m, 1H), 7.65-7.73 (m, 3H), 8.52 (d, 1H) ppm.

By the method described above for example 1 and 2, the compounds of formula (I.B) summarized in table B.1 can be prepared.

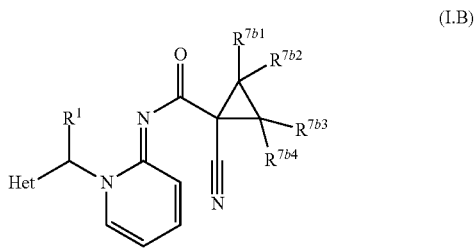

(I.B)

TABLE B.1

| # | Het | R¹ | R⁷ᵇ¹ | R⁷ᵇ² | R⁷ᵇ³ | R⁷ᵇ⁴ | method | RT [min] | m/z [M + H]+ |
|---|---|---|---|---|---|---|---|---|---|
| I.B-1 | 6-chloro-3-pyridyl | H | H | H | H | H | B | 0.788 | 313.1 |
| I.B-2 | 6-chloro-3-pyridyl | CH₃ | H | H | H | H | | NMR* | |
| I.B-3 | 6-chloro-3-pyridyl | H | CH₃ | CH₃ | CH₃ | CH₃ | B | 0.981 | 369.6 |
| I.B-4 | pyrimidin-5-yl | H | H | H | H | H | B | 0.620 | 279.8 |
| I.B-5 | 6-chloro-3-pyridyl | H | H | CH(CH₃)₂ | H | H | B | 1.042 | 354.8 |
| I.B-6 | 6-chloro-3-pyridyl | H | H | CH₂CH₂CH₂CH₃ | H | H | B | 1.102 | 368.9 |
| I.B-7 | 6-chloro-3-pyridyl | H | H | CH₂CH₂CH₃ | H | H | B | 1.030 | 354.8 |
| I.B-8 | 6-chloro-3-pyridyl | H | H | cC₃H₅ | H | H | B | 0.962 | 352.8 |
| I.B-9 | 6-chloro-3-pyridyl | H | H | CH₂CH₃ | H | H | B | 0.954 | 341.3 |
| I.B-10 | 6-chloro-3-pyridyl | H | H | cC₅H₉ | H | H | B | 1.105 | 380.9 |
| I.B-11 | 6-chloro-3-pyridyl | H | H | 2-methyl-sulfanylpropyl | H | H | B | 1.039 | 400.9 |
| I.B-12 | 6-chloro-3-pyridyl | H | H | 2,2-dimethyl-propyl | H | H | B | 1.134 | 382.9 |
| I.B-13 | 6-chloro-3-pyridyl | H | H | CH₃ | H | H | B | 0.875 | 326.8 |
| I.B-14 | 6-chloro-3-pyridyl | H | H | 1-methylbutyl | H | H | B | 1.150 | 382.9 |
| I.B-15 | 6-chloro-3-pyridyl | H | H | CH₂CH(CH₃)₂ | H | H | B | 1.086 | 368.9 |
| I.B-16[1)] | 6-chloro-3-pyridyl | H | H | C₆H₅ | H | H | B | 1.017 | 389.4 |
| I.B-17[2)] | 6-chloro-3-pyridyl | H | H | C₆H₅ | H | H | B | 1.057 | 389.4 |
| I.B-18 | 6-chloro-3-pyridyl | H | H | phenethyl | H | H | B | 1.150 | 417.4 |
| I.B-19 | 6-chloro-3-pyridyl | H | H | 1,2-dimethyl-butyl | H | H | B | 1.221 | 397.4 |
| I.B-20 | 6-chloro-3-pyridyl | H | H | Tetrahydro-pyran-4-yl | H | H | B | 0.892 | 397.4 |
| I.B-21 | 6-chloro-3-pyridyl | H | H | pentyl | H | H | B | 1.188 | 383.4 |
| I.B-22 | 6-chloro-3-pyridyl | H | H | cycloheptyl | H | H | B | 1.238 | 409.4 |
| I.B-23 | 6-chloro-3-pyridyl | H | H | non-3-enyl | H | H | B | 1.376 | 437.5 |
| I.B-24 | 6-chloro-3-pyridyl | H | H | 1-ethylpentyl | H | H | B | 1.297 | 411.4 |
| I.B-25 | 6-chloro-3-pyridyl | H | H | 1,1-dimethyl-2-(3-pyridyl)ethyl | H | H | B | 0.790 | 446.4 |
| I.B-26 | 6-chloro-3-pyridyl | H | H | C(CH₃)₃ | H | H | B | 1.090 | 369.4 |
| I.B-27 | 6-chloro-3-pyridyl | H | H | c-C₆H₁₁ | H | H | B | 1.184 | 395.5 |
| I.B-28 | 6-chloro-3-pyridyl | H | H | 6,6-dimethyl-norpinan-2-yl | H | H | B | 1.305 | 435.4 |
| I.B-29 | 6-chloro-3-pyridyl | H | H | tetrahydrothiopyran-3-yl | H | H | B | 1.064 | 413.4 |
| I.B-30 | 6-chloro-3-pyridyl | H | H | 3,3-dimethyl-butyl | H | H | B | 1.229 | 397.5 |
| I.B-31 | 6-chloro-3-pyridyl | H | H | CF₃ | H | H | B | 1.028 | 381.3 |
| I.B-32 | 6-chloro-3-pyridyl | H | H | 1-acetoxyethyl | H | H | B | 0.932 | 399.4 |
| I.B-33 | 6-chloro-3-pyridyl | H | H | 1-isopropoxy-ethyl | H | H | B | 1.047 | 399.4 |
| I.B-34 | 6-chloro-3-pyridyl | H | H | 2-propoxyethyl | H | H | B | 1.050 | 399.4 |
| I.B-35 | 6-chloro-3-pyridyl | H | H | 1-methyl-2-methylsulfanyl-ethyl | H | H | B | 1.061 | 401.3 |
| I.B-36 | 6-chloro-3-pyridyl | H | H | 2-methyl-cyclohex-3-en-1-yl | H | H | B | 1.181 | 407.4 |
| I.B-37 | 6-chloro-3-pyridyl | H | H | 4-methyl-cyclohexyl | H | H | B | 1.251 | 409.3 |

TABLE B.1-continued

| # | Het | $R^1$ | $R^{7b1}$ | $R^{7b2}$ | $R^{7b3}$ | $R^{7b4}$ | method | RT [min] | m/z [M + H]+ |
|---|---|---|---|---|---|---|---|---|---|
| I.B-38 | 6-chloro-3-pyridyl | H | H | 5,5-dimethyl-tetrahydrofuran-2-yl | H | H | B | 1.011 | 410.9 |
| I.B-39 | 6-chloro-3-pyridyl | H | H | tetrahydropyran-4-ylmethyl | H | H | B | 0.950 | 410.8 |
| I.B-40 | 6-chloro-3-pyridyl | H | H | 2-isobutoxyethyl | H | H | B | 1.116 | 412.9 |
| I.B-41 | 6-chloro-3-pyridyl | H | H | 1-(2-methoxy-ethoxy)ethyl | H | H | B | 0.918 | 414.8 |
| I.B-42 | 6-chloro-3-pyridyl | H | H | cyclooctyl | H | H | B | 1.263 | 422.9 |
| I.B-43 | 6-chloro-3-pyridyl | H | H | 2-ethoxy-carbonylcyclopropyl | H | H | B | 0.997 | 424.9 |
| I.B-44 | 6-chloro-3-pyridyl | H | H | 1-methoxyethyl | H | H | B | 0.911 | 371.4 |
| I.B-45 | 6-chloro-3-pyridyl | H | H | 1,2-dimethyl-propyl | H | H | B | 1.155 | 383.4 |
| I.B-46 | 6-chloro-3-pyridyl | H | H | tetrahydropyran-3-yl | H | H | B | 0.918 | 397.4 |
| I.B-47 | 6-chloro-3-pyridyl | H | H | 4-methylthiazol-5-yl | H | H | B | 0.866 | 409.8 |
| I.B-48 | 6-chloro-3-pyridyl | H | H | tetrahydrothiopyran-4-ylmethyl | H | H | B | 1.085 | 426.9 |
| I.B-49[1)] | 6-chloro-3-pyridyl | H | H | 1-phenoxyethyl | H | H | B | 1.127 | 432.9 |
| I.B-50 | 6-chloro-3-pyridyl | H | H | 1-(cyclohexoxy)ethyl | H | H | B | 1.198 | 438.9 |
| I.B-51 | 6-chloro-3-pyridyl | H | H | 6-methoxy-3-methyl-tetra-hydropyran-2-yl | H | H | B | 1.048 | 440.9 |
| I.B-52 | 6-chloro-3-pyridyl | H | H | (4-isopropyl-cyclohexyl)methyl | H | H | B | 1.400 | 451.0 |
| I.B-53 | 6-chloro-3-pyridyl | H | H | 6-acetoxyhexyl | H | H | B | 1.096 | 455.0 |
| I.B-54 | 6-chloro-3-pyridyl | H | H | 3-(trifluoro-methyl)phenyl | H | H | B | 1.167 | 457.4 |
| I.B-55 | 6-chloro-3-pyridyl | H | H | 2-pyridyl | H | H | B | 0.743 | 390.4 |
| I.B-56[1)] | 6-chloro-3-pyridyl | H | H | 3-nitrophenyl | H | H | B | 1.023 | 433.9 |
| I.B-57[2)] | 6-chloro-3-pyridyl | H | H | 3-nitrophenyl | H | H | B | 1.040 | 433.8 |
| I.B-58[1)] | 6-chloro-3-pyridyl | H | H | 4-(trifluoro-methyl)phenyl | H | H | B | 1.130 | 456.9 |
| I.B-59[2)] | 6-chloro-3-pyridyl | H | H | 4-(trifluoro-methyl)phenyl | H | H | B | 1.149 | 456.9 |
| I.B-60 | 6-chloro-3-pyridyl | H | $CH_3$ | methoxycarbonyl | H | H | B | 0.899 | 385.4 |
| I.B-61 | 6-chloro-3-pyridyl | H | H | benzyl | H | H | B | 1.096 | 403.4 |
| I.B-62 | 6-chloro-3-pyridyl | H | H | $CH_2CF_3$ | H | H | B | 1.011 | 395.1 |
| I.B-63 | 6-chloro-3-pyridyl | H | H | tetrahydrofuran-3-yl | H | H | B | 0.849 | 383.4 |

If not otherwise indicated, the compounds of table B.1 are mixtures of cis-trans isomers.

1) Isomer 1
2) Isomer 2

NMR* Spectra:

I.B-2

Characterization by $^1$H-NMR (400 MHz, CD$_3$OD): δ[delta]=1.48-1.56 (m, 4H), 1.93 (d, 3H), 6.93 (m, 1H), 7.01 (m, 1H), 7.46 (d, 1H), 7.80 (m, 1H), 7.88 (m, 1H), 8.14-8.17 (m, 2H), 8.51 (d, 1H) ppm.

By the method described above for example 1 and 2, the compounds of formula (I.C) summarized in table C.1 can be prepared.

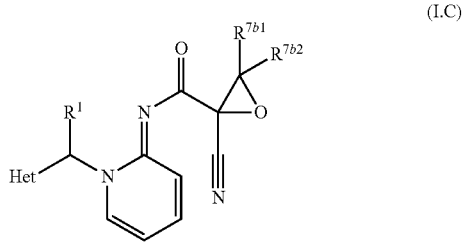

(I.C)

TABLE C.1

| # | HET | R¹ | R⁷ᵇ¹ | R⁷ᵇ² | RT [min] | m/z [M + H]+ | method |
|---|---|---|---|---|---|---|---|
| I.C-1 | 6-chloro-3-pyridyl | H | H | H | B | 0.823 | 315.3 |

B. BIOLOGICAL EXAMPLES

The biological activity of the compounds of formula I of the present invention may be evaluated in biological tests as described in the following.

General conditions: If not otherwise specified, most test solutions are to be prepared as follows: The active compound is to be dissolved at the desired concentration in a mixture of 1:1 (vol:vol) distilled water:acteon. Further, the test solutions are to be prepared at the day of use (and, if not otherwised specified, in general at concentrations wt/vol).

B.1 Green Peach Aphid (*Myzus persicae*)

For evaluating control of green peach aphid (*Myzus persicae*) through systemic means, the test unit consists of 96-well-microtiter plates containing liquid artificial diet under an artificial membrane.

The compounds are formulated using a solution containing 75% v/v water and 25% v/v DMSO. Different concentrations of formulated compounds are pipetted into the aphid diet, using a custom built pipetter, at two replications.

After application, 5-8 adult aphids are placed on the artificial membrane inside the microtiter plate wells. The aphids are then allowed to suck on the treated aphid diet and incubated at about 23+1° C. and about 50+5% relative humidity for 3 days. Aphid mortality and fecundity is then visually assessed.

In this test, compounds I.A-1, I.A-10, I.A-12, I.A-13, I.A-15, I.A-16, I.A-17, I.A-18, I.A-19, I.A-2, I.A-20, I.A-21, I.A-3, I.A-4, I.A-5, I.A-6, I.A-7, I.A-8, I.A-9, I.B-1, I.B-10, I.B-11, I.B-12, I.B-13, I.B-14, I.B-15, I.B-16, I.B-17, I.B-18, I.B-19, I.B-2, I.B-20, I.B-21, I.B-23, I.B-25, I.B-26, I.B-27, I.B-29, I.B-3, I.B-32, I.B-33, I.B-34, I.B-35, I.B-36, I.B-37, I.B-38, I.B-39, I.B-4, I.B-41, I.B-43, I.B-44, I.B-45, I.B-46, I.B-47, I.B-48, I.B-49, I.B-5, I.B-51, I.B-52, I.B-54, I.B-55, I.B-56, I.B-57, I.B-6, I.B-60, I.B-61, I.B-62, I.B-63, I.B-7, I.B-8, I.B-9, I.C-1 at 2500 ppm showed at least 75% mortality in comparison with untreated controls.

B.2 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids were placed on the leaf disks inside the microtiter plate wells. The aphids were then allowed to suck on the treated leaf disks and were incubated at about 23±1° C. and about 50±5% relative humidity for 5 days. Aphid mortality and fecundity was then visually assessed.

In this test, compounds I.A-1, I.A-10, I.A-12, I.A-13, I.A-14, I.A-15, I.A-16, I.A-18, I.A-19, I.A-2, I.A-20, I.A-21, I.A-3, I.A-4, I.A-6, I.A-7, I.A-8, I.A-9, I.B-1, I.B-10, I.B-11, I.B-12, I.B-13, I.B-14, I.B-15, I.B-16, I.B-17, I.B-19, I.B-2, I.B-20, I.B-21, I.B-25, I.B-26, I.B-29, I.B-3, I.B-32, I.B-33, I.B-34, I.B-35, I.B-36, I.B-37, I.B-38, I.B-39, I.B-4, I.B-41, I.B-43, I.B-44, I.B-45, I.B-46, I.B-47, I.B-48, I.B-49, I.B-5, I.B-50, I.B-53, I.B-54, I.B-55, I.B-56, I.B-6, I.B-60, I.B-61, I.B-62, I.B-63, I.B-7, I.B-8, I.B-9, I.C-1 at 2500 ppm showed at least 75% mortality in comparison with untreated controls.

B.3 Cotton Aphid (*Aphis gossypii*)

The active compound is dissolved at the desired concentration in a mixture of 1:1 (vol:vol) distilled water:acetone. Surfactant (Alkamuls® EL 620) is added at a rate of 0.1% (vol/vol). The test solution is prepared at the day of use.

Potted cowpea plants were colonized with approximately 50-100 aphids of various stages by manually transferring a leaf tissue cut from infested plant 24 hours before application. Plants were sprayed after the pest population has been recorded. Treated plants are maintained on light carts at about 28° C. Percent mortality was assessed after 72 hours.

In this test, compounds I.A-1, I.A-15, I.A-18, I.A-19, I.A-20, I.A-21, I.B-13 at 500 ppm showed over 75% mortality in comparison with untreated controls.

B.4 Cowpea Aphid (*Aphis craccivora*)

The active compound is dissolved at the desired concentration in a mixture of 1:1 (vol:vol) distilled water:acetone. Surfactant (Alkamuls® EL 620) is added at a rate of 0.1% (vol/vol). The test solution is prepared at the day of use.

Potted cowpea plants are colonized with approximately 50-100 aphids of various stages by manually transferring a leaf tissue cut from infested plant 24 hours before application. Plants are sprayed after the pest population has been recorded. Treated plants are maintained on light carts at about 28° C. Percent mortality is assessed after 72 hours.

In this test, compounds I.A-1, I.A-10, I.A-12, I.A-13, I.A-15, I.A-16, I.A-18, I.A-19, I.A-2, I.A-20, I.A-21, I.A-5, I.A-6, I.A-7, I.A-8, I.B-1, I.B-13, I.B-2, I.B-4, I.B-7, I.B-8, I.B-9, I.C-1 at 500 ppm showed at least 75% mortality in comparison with untreated controls.

B.5 Silverleaf Whitefly (*Bemisia Argentifoli*)

The active compounds are formulated in cyclohexanone as a 10,000 ppm solution supplied in tubes. The tubes are inserted into an automated electrostatic sprayer equipped with an atomizing nozzle and they serve as stock solutions for which lower dilutions are made in 50% acetone:50% water (v/v). A nonionic surfactant (Kinetic®) is included in the solution at a volume of 0.01% (v/v).

Cotton plants at the cotyledon stage (one plant per pot) are sprayed by an automated electrostatic plant sprayer equipped with an atomizing spray nozzle. The plants are dried in the sprayer fume hood and then removed from the sprayer. Each pot is placed into a plastic cup and about 10 to 12 whitefly adults (approximately 3-5 days old) are introduced. The insects are collected using an aspirator and a nontoxic Tygon® tubing connected to a barrier pipette tip. The tip, containing the collected insects, is then gently inserted into the soil containing the treated plant, allowing insects to crawl out of the tip to reach the foliage for feeding. Cups are covered with a reusable screened lid. Test plants are maintained in a growth room at about 25° C. and about 20-40% relative humidity for 3 days, avoiding direct exposure to fluorescent light (24 hour photoperiod) to prevent trapping of heat inside the cup. Mortality is assessed 3 days after treatment, compared to untreated control plants.

In this test, compounds I.A-1, I.A-18, I.A-20, I.A-21, I.A-7, I.A-9, I.B-4 at 500 ppm showed at least 75% mortality in comparison with untreated controls.

B.6 Orchid Thrips (*Dichromothrips Corbetti*)

*Dichromothrips corbetti* adults used for bioassay are obtained from a colony maintained continuously under laboratory conditions. For testing purposes, the test compound is diluted in a 1:1 mixture of acetone:water (vol:vol), plus 0.01% vol/vol Alkamuls® EL 620 surfactant.

*Thrips* potency of each compound is evaluated by using a floral-immersion technique. Plastic petri dishes are used as test arenas. All petals of individual, intact orchid flowers are dipped into treatment solution and allowed to dry. Treated flowers are placed into individual petri dishes along with about 20 adult *thrips*. The petri dishes are then covered with lids. All test arenas are held under continuous light and a temperature of about 28° C. for duration of the assay. After 3 days, the numbers of live *thrips* are counted on each flower, and along inner walls of each petri dish. The percent mortality is recorded 72 hours after treatment.

In this test, compounds I.A-1, I.A-18, I.A-19, I.A-2, I.A-20, I.A-21, I.A-3, I.A-4, I.A-6, I.A-7, I.B-1, I.B-11, I.B-13, I.B-2, I.B-3, I.B-5, I.B-9, I.C-1 at 500 ppm showed at least 75% mortality in comparison with untreated controls.

B.7 Rice Green Leafhopper (*Nephotettix virescens*)

Rice seedlings are cleaned and washed 24 hours before spraying. The active compounds are formulated in 50:50 acetone:water (vol:vol), and 0.1% vol/vol surfactant (EL 620) is added. Potted rice seedlings are sprayed with 5 ml test solution, air dried, placed in cages and inoculated with 10 adults. Treated rice plants are kept at about 28-29° C. and relative humidity of about 50-60%. Percent mortality is recorded after 72 hours.

In this test, compounds I.A-1, I.A-10, I.A-12, I.A-18, I.A-19, I.A-2, I.A-20, I.A-21, I.A-3, I.A-4, I.A-6, I.A-7, I.A-8, I.A-9, I.B-1, I.B-10, I.B-11, I.B-13, I.B-15, I.B-2, I.B-4, I.B-5, I.B-7, I.B-8, I.B-9 at 500 ppm showed at least 75% mortality in comparison with untreated controls.

B.8 Rice Brown Plant Hopper (*Nilaparvata lugens*)

Rice seedlings are cleaned and washed 24 hours before spraying. The active compounds is formulated in 50:50 acetone:water (vol:vol) and 0.1% vol/vol surfactant (EL 620) was added. Potted rice seedlings are sprayed with 5 ml test solution, air dried, placed in cages and inoculated with 10 adults. Treated rice plants are kept at about 28-29° C. and relative humidity of about 50-60%. Percent mortality is recorded after 72 hours.

In this test, compounds I.A-1, I.A-18, I.A-2, I.A-20, I.A-3, I.A-4, I.A-6, I.A-7, I.A-8, I.B-1, I.B-13, I.B-2, I.B-4, I.B-8, I.B-9 at 500 ppm showed at least 75% mortality in comparison with untreated controls.

B.9 Diamond Back Moth (*Plutella Xylostella*)

The active compound is dissolved at the desired concentration in a mixture of 1:1 (vol:vol) distilled water:aceteone. Surfactant (Alkamuls® EL 620) is added at a rate of 0.1% (vol/vol). The test solution is prepared at the day of use.

Leaves of cabbage were dipped in test solution and air-dried. Treated leaves were placed in petri dish eslined with moist filter paper and inoculated with ten 3$^{rd}$ instar larvae. Mortality was recorded 72 hours after treatment. Feeding damages were also recorded using a scale of 0-100%.

In this test, compounds I.A-18, I.A-2, I.A-7, I.B-1, I.B-9 at 500 ppm showed over 75% mortality in comparison with untreated controls.

B.10 Green Soldier Stink Bug (*Nezara viridula*)

The active compound is dissolved at the desired concentration in a mixture of 1:1 (vol:vol) distilled water:aceteone. Surfactant (Kinetic HV) is added at a rate of 0.01% (vol/vol). The test solution is prepared at the day of use.

Soybean pods were placed in microwavable plastic cups lined with moist filter paper and inoculated with ten 3rd instar *N. viridula*. Using a hand atomizer, approximately 2 ml solution is sprayed into each cup. Treated cups were kept at about 28-29° C. and relative humidity of about 50-60%. Percent mortality was recorded after 5 days.

In this test, compounds I.A-1, I.A-18, I.A-21 at 500 ppm showed over 75% mortality in comparison with untreated controls.

The invention claimed is:

1. An N-acylimino compound of formula (I):

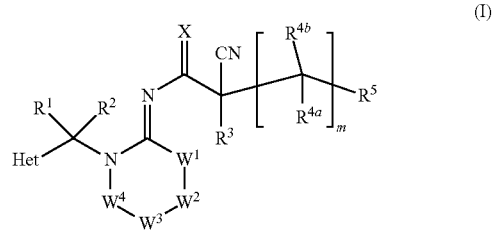

wherein
m is an integer selected from 0, 1, 2, 3, 4, 5 or 6;
X is O or S;
Het is

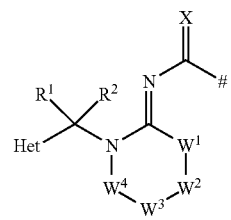

wherein the moiety of the formula

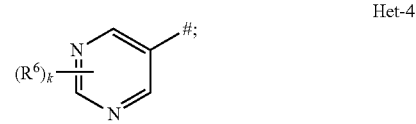

represents a radical A selected from the group consisting of W.Het-1, W.Het-2, W.Het-3, W.Het-4:

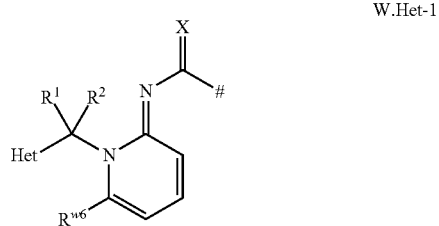

-continued

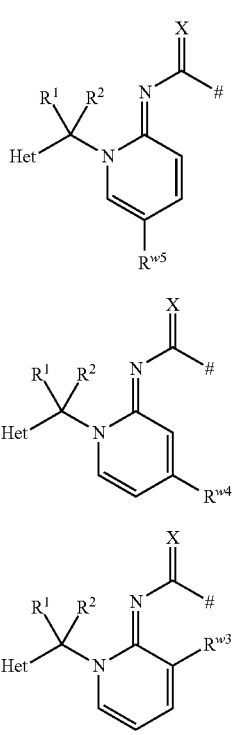

W.Het-2

W.Het-3

W.Het-4 wherein # denotes the bond to the remainder of the molecule, wherein each $R^{w3}$, $R^{w4}$, $R^{w5}$, $R^{w6}$ independently from each other, is selected from the group consisting hydrogen, halogen, cyano, azido, nitro, SCN, SF$_5$, C$_1$-C$_{10}$-alkyl, C$_3$-C$_8$-cycloalkyl, C$_2$-C$_{10}$-alkenyl, C$_2$-C$_{10}$-alkynyl, and wherein the carbon atoms of the aforementioned aliphatic and cycloaliphatic radicals may be unsubstituted or may be partly or fully halogenated and/or may optionally be substituted with 1, 2 or 3 identical or different radicals $R^7$, $OR^8$, $NR^{9a}R^{9b}$, $S(O)_nR^8$, $S(O)_nNR^{9a}R^{9b}$, $C(=O)R^{7a}$, $C(=O)NR^{9a}R^{9b}$, $C(=O)OR^8$, $C(=S)R^{7a}$, $C(=S)NR^{9a}R^{9b}$, $C(=S)OR^8$, $C(=S)SR^8$, $C(=NR^{17})R^{7a}$, $C(=NR^{17})NR^{9a}R^{9b}$ and $Si(R^{11})_2R^{12}$;

$R^1$, $R^2$ are independently from each other selected from the group consisting of hydrogen, halogen, CN, SCN, nitro, C$_1$-C$_6$-alkyl, C$_3$-C$_6$-cycloalkyl, wherein each of the two aforementioned radicals are unsubstituted, partly or completely halogenated or may carry any combination of 1, 2 or 3 radicals $R^7$, $Si(R^{11})_2R^{12}$, $OR^8$, $OSO_2R^8$, $S(O)_nR^8$, $S(O)_nNR^{9a}R^{9b}$, $NR^{9a}R^{9b}$, $C(=O)NR^{9a}R^{9b}$, $C(=S)NR^{9a}R^{9b}$, $C(=O)OR^8$, $C(=O)R^{7a}$, $C(=S)R^{7a}$, phenyl, benzyl, where the phenyl ring in the last two radicals is unsubstituted or optionally substituted with 1, 2, 3, 4 or 5 identical or different substituents $R^{10}$, $R^1$ and $R^2$ may together be =O, =CR$^{13}$R$^{14}$, =S, =NR$^{17}$, =NOR$^{16}$ or =NNR$^{9a}$R$^{9b}$;

$R^3$ is selected from the group consisting of hydrogen, halogen, CN, C$_1$-C$_6$-alkyl, mentioned radicals are unsubstituted, partly or completely halogenated or carries 1 or 2 radicals $R^7$, it being also possible for cycloalkyl to carry 1, 2, 3, 4, 5 or 6 C$_1$-C$_4$-alkyl groups, $S(O)_nR^{9a}R^{9b}$, $NR^{9a}R^{9b}$, $C(=O)OR$, $C(=O)NR^{9a}R^{9b}$, $C(=S)NR^{9a}R^{9b}$, $C(=O)R^{7a}$, $C(=S)R^{7a}$, $NR^{9a}-C(=O)R^{7a}$, $NR^{9a}-C(=S)R^{7a}$, $NR^{9a}-S(O)_nR^{8a}$, phenyl, benzyl, where the phenyl ring in the last two mentioned radicals is unsubstituted or may be substituted with one or more, e.g. 1, 2, 3, 4 or 5 identical or different substituents $R^{10}$;

$R^{4a}$, $R^{4b}$ are selected each independently from one another and independently from the integer of m from the group consisting of hydrogen, halogen, CN, C$_1$-C$_6$-alkyl, C$_1$-C$_6$-alkoxy, C$_1$-C$_6$-alkylthio, and C$_3$-C$_8$-cycloalkyl, wherein each of the four last mentioned radicals are unsubstituted, partly or completely halogenated, or $R^{4a}$ and $R^{4b}$ may form together with the carbon atom they are bound to, a 3, 4, 5 or 6 membered aliphatic ring, wherein each of the carbon atoms of the ring may be unsubstituted or may be partly or fully halogenated, and/or may carry 1, 2, 3, 4, 5 or 6 radicals selected from C$_1$-C$_4$-alkyl, C$_1$-C$_4$-haloalkyl, C$_1$-C$_4$-alkoxy and C$_1$-C$_4$-haloalkoxy;

or $R^{4a}$ and $R^{4b}$ may together form =O, =CR$^{13}$R$^{14}$, =S, =NR$^{17}$, =NOR$^{16}$, =NNR$^{9a}$R$^{9b}$, $R^5$ is selected from the group consisting of hydrogen, halogen, C$_1$-C$_6$-alkyl, C$_2$-C$_6$-alkenyl, C$_2$-C$_6$-alkynyl, C$_3$-C$_8$-cycloalkyl, wherein each of the four last mentioned radicals are unsubstituted, partly or completely halogenated or carries 1 or 2 radicals $R^7$, it being also possible for cycloalkyl radicals to carry 1, 2, 3, 4, 5 or 6 C$_1$-C$_4$-alkyl groups, $S(O)_nNR^{9a}R^{9b}$, $NR^{9a}R^{9b}$, $C(=O)OR^8$, $C(=O)NR^{9a}R^{9b}$, $C(=S)NR^{9a}R^{9b}$, $C(=O)R^{7a}$, $C(=S)R^{7a}$, $NR^{9a}$-C(=O)R$^{7a}$, $NR^{9a}$-C(=S)R$^{7a}$, $NR^{9a}$-S(O)$_n$R$^{8a}$, a moiety Q-phenyl, where the phenyl ring is optionally substituted with one or more, e.g. 1, 2, 3, 4 or 5 identical or different substituents $R^{10}$, and a moiety Q-Het$^\#$, where Het$^\#$ represents a 3-, 4-, 5-, 6- or 7-membered saturated, partly saturated or unsaturated aromatic heterocyclic ring comprising 1, 2 or 3 heteroatoms as ring members, which are selected from oxygen, nitrogen and/or sulfur, where the heterocyclic ring is optionally substituted with 1, 2, 3 or 4 identical or different substituents $R^{10}$, and wherein the nitrogen and/or the sulfur atom(s) of the heterocyclic ring may optionally be oxidized, and Q irrespectively of its occurrence, is a single bond, $NR^{9a}$, $NR^{9a}$-C$_1$-C$_4$-alkylene, -O-C(=O)-, -NR$^{9a}$-C(=O)-, -O-S(=O)$_2$-, -NR$^{9a}$-S(=O)$_2$-, -O-C(=O)-C$_1$-C$_4$-alkylene or -NR$^{9a}$-C(=O)-C$_1$-C$_4$-alkylene, where the heteroatom in the last 6 moieties is bound to the carbon atom of C(CN)R$^3$ or CR$^{4a}$R$^{4a}$, respectively;

or, if m=0, $R^3$ and $R^5$ together may also form with the carbon atom they are bound to, a 3, 4, 5 or 6 membered saturated partially unsaturated carbocycle or heterocycle, wherein the carbocycle or heterocycle may be unsubstituted or may carry 1, 2, 3, 4, 5 or 6 radicals $R^{7b}$, and where the heterocycle has 1 or 2 non-adjacent identical or different heteroatoms or heteroatom moieties as ring members, which are selected from O, S, N and N—$R^{17c}$, or $R^3$ and $R^5$ may together form =O or =S;

where, independently of their occurrence, n is 0, 1 or 2;

$R^6$ is selected from the group consisting of halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, and wherein the carbon atoms of the aforementioned aliphatic and cyclo-aliphatic radicals may optionally be further substituted independently from one another with 1, 2 or 3 radicals $R^7$, $OR^8$, $NR^{17a}R^{17b}$, $S(O)_nR^8$, $S(O)_nNR^{17a}R^{17b}$, $C(=O)R^{7a}$, $C(=O)NR^{17a}R^{17b}$, $C(=O)OR^8$, $C(=S)R^{7a}$, $C(=S)NR^{17a}R^{17b}$, $C(=S)OR^8$, $C(=S)SR^8$, $C(=NR17)R^{7a}$, $C(=NR^{17})NR^{17a}R^{17b}$, $Si(R^{11})_2R^{12}$;

phenyl, optionally substituted with 1, 2, 3, 4 or 5 identical or different substituents $R^{10}$, or two of $R^6$ present on one ring carbon may together form =O, =$CR^{13}R^{14}$, =S, =$NR^{17}$, =$NOR^{16}$, =$NNR^{9a}R^{9b}$, or two $R^6$ together form a linear $C_2$-$C_7$ alkylene chain, thus forming, together with the ring atom(s) to which they are bound, a 3-, 4-, 5-, 6-, 7- or 8-membered ring, where 1 or 2 $CH_2$ moieties of the alkylene chain may be replaced by 1 or 2 heteroatom moieties selected from O, S and $NR^{17c}$ and/or 1 or 2 of the $CH_2$ groups of the alkylene chain may be replaced by a group C=O, C=S and/or C=$NR^{17}$; and where the alkylene chain is unsubstituted or may be substituted with 1, 2, 3, 4, 5 or 6 radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted with 1, 2, 3, 4 or 5 radicals $R^{10}$;

$R^7$ independently of its occurrence, is selected from the group consisting of cyano, azido, nitro, —SCN, $SF_5$, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $Si(R^{11})_2R^{12}$, $OR^8$, $OSO_2R^8$, $S(O)_nR^8$, $S(O)_nNR^{17a}R^{17b}$, $NR^{17a}R^{17b}$, $C(=O)NR^{17a}R^{17b}$, $C(=S)NR^{17a}R^{17b}$, $C(=O)OR^8$, $C(=O)R^{15}$, $C(=S)R^{15}$, $C(=NR^{17})R^{15}$, phenyl, phenyl-$C_1$-$C_4$-alkyl, where the phenyl ring in the last two groups is optionally substituted with 1, 2, 3, 4 or 5 identical or different substituents $R^{10}$, or two $R^7$ present on one carbon atom may together form =O, =$CR^{13}R^{14}$, =S, =$NR^{17}$, =$NOR^{16}$, =$NNR^{9a}R^{9b}$, or two $R^7$ may form a 3-, 4-, 5-, 6-, 7- or 8-membered saturated or partly unsaturated carbocyclic or heterocyclic ring together with the carbon atoms to which the two $R^7$ are bonded, where the heterocyclic ring comprises 1, 2 or 3 heteroatoms as ring members, which are identical or different and selected from oxygen, nitrogen and sulfur, where the heterocyclic ring is optionally substituted with 1, 2, 3 or 4 identical or different substituents $R^{10}$;

$R^{7a}$ independently of its occurrence, is selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, phenyl, optionally substituted with 1, 2, 3, 4 or 5 identical or different substituents $R^{10}$;

$R^{7b}$ is selected from the group consisting of halogen, cyano, $C_1$-$C_{10}$-alkyl, $C_3$-$C_8$-cycloalkyl, $C_2$-$C_{10}$-alkenyl, $C_2$-$C_{10}$-alkynyl, $C_3$-$C_8$-cycloalkenyl, and wherein the carbon atoms of the aforementioned aliphatic and cycloaliphatic radicals may be partly or completely halogenated, and/or be substituted with 1, 2,3 or 4, in particular 1, 2 or 3, identical or different radicals $R^7$, $OR^8$, $NR^{17a}R^{17b}$, $S(O)_nR^8$, $S(O)_nNR^{17a}R^{17b}$, $C(=O)R^{7a}$, $C(=O)NR^{17a}R^{17b}$, $C(=O)OR^8$, $C(=S)R^{7a}$, $C(=S)NR^{17a}R^{17b}$, $C(=S)OR^8$, $C(=NR^{17})R^{7a}$, $C(=NR^{17})NR^{17a}R^{17b}$, $Si(R^{11})_2R^{12}$;

phenyl, optionally substituted with 1, 2, 3, 4 or 5 identical or different substituents $R^{10}$, or two of $R^{7b}$ present on one ring carbon may together form =O, =S or =$CR^{13}R^{14}$, or two $R^{7b}$ together form a linear $C_2$-$C_7$ alkylene chain, thus forming, together with the ring atom(s) to which they are bound, a 3-, 4-, 5-, 6-, 7- or 8-membered ring, where 1 or 2 $CH_2$ moieties of the alkylene chain may be replaced by 1 or 2 heteroatom moieties selected from O, S and $NR^{17c}$ and/or 1 or 2 of the $CH_2$ groups of the alkylene chain may be replaced by a group C=O, C=S and/or C=$NR^{17}$; and where the alkylene chain is unsubstituted or may be substituted with 1, 2, 3, 4, 5 or 6 radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted with 1, 2, 3, 4 or 5 radicals $R^{10}$;

$R^8$ independently of its occurrence, is selected from the group consisting of hydrogen, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $C_1$-$C_6$-alkoxy-$C_1$-$C_6$-alkyl, $C(=O)R^{15}$, $C(=O)NR^{17a}R^{17b}$, $C(=S)NR^{17a}R^{17b}$, $C(=O)OR^{16}$, phenyl, phenyl-$C_1$-$C$-4-alkyl, where the phenyl ring in the last two mentioned radicals is unsubstituted or substituted with 1, 2, 3, 4 or 5 identical or different substituents $R^{10}$, $R^{8a}$ independently of its occurrence, is selected from the group consisting of $C_1$-$C_6$-alkyl, $C_3$-$C_8$-cycloalkyl, $C_3$-$C_8$-cycloalkyl-$C_1$-$C_4$-alkyl, $C_2$-$C_6$-alkenyl, $C_2$-$C_6$-alkynyl, wherein each of the five last mentioned radicals are unsubstituted, partly or completely halogenated, phenyl, benzyl, where the phenyl ring in the last two mentioned radicals is unsubstituted or may be substituted with one or more, e.g. 1, 2, 3, 4 or 5 identical or different substituents $R^{10}$, $R^{9a}$, $R^{9b}$ are each independently from one another selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$ haloalkynyl, $S(O)_nR^{16}$, —$S(O)_nNR^{17a}R^{17b}$, $C(=O)R^{15}$, $C(=O)OR^{16}$, $C(=O)NR^{17a}R^{17b}$, $C(=S)R^{15}$, $C(=S)SR^{16}$, $C(=S)NR^{17a}R^{17b}$, $C(=NR^{17})R^{15}$;

phenyl, benzyl, 1-phenethyl or 2-phenethyl, where the phenyl ring in the last four mentioned radicals is unsubstituted or may be substituted with 1, 2, 3, 4 or 5 identical or different substituents $R^{10}$;

or, $R^{9a}$ and $R^{9b}$ are together a $C_2$-$C_7$ alkylene chain and form a 3-, 4-, 5-, 6-, 7- or 8-membered saturated, partly saturated or unsaturated aromatic ring together with the nitrogen atom they are bonded to, wherein the alkylene chain may contain one or two heteroatoms, which are, independently of each other, selected from oxygen, sulfur or nitrogen, and where the alkylene chain may optionally be substituted with 1, 2, 3 or 4 radicals selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, phenyl, optionally substituted with 1, 2, 3, 4 or 5 identical or different substituents $R^{10}$, or $R^{9a}$ and $R^{9b}$ together may form $=CR^{13}R^{14}$, $=NR^{17}$, $=NOR^{16}$, $=NNR^{17a}R^{17b}$ moiety;

$R^{9c}$, $R^{9d}$ are each independently from one another selected from the group consisting of hydrogen, $C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $S(O)_nR^{16}$, $—S(O)_nNR^{17a}R^{17b}$, $C(=O)R^5$, $C(=O)OR^{16}$, $C(=O)NR^{17a}R^{17b}$, $C(=S)R^{15}$, $C(=S)SR^{16}$, $C(=S)NR^{17a}R^{17b}$, $C(=NR^{17})R^{15}$;

phenyl, benzyl, where the phenyl ring in the last two mentioned radicals is unsubstituted or may be substituted with 1, 2, 3, 4 or 5 identical or different substituents $R^{10}$;

$R^{10}$ independently of its occurrence, is selected from the group consisting of halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cycloaliphatic radicals may optionally be substituted with 1, 2, 3, 4 or 5 identical or different radicals $R^{10a}$, $Si(R^{11})_2R^{12}$, $OR^{16}$, $OS(O)_nR^{16}$, $—S(O)_nR^{16}$, $S(O)_nNR^{17a}R^{17b}$, $NR^{17a}R^{17b}$, $C(=O)R^{15}$, $C(=S)R^{15}$, $C(=O)OR^{16}$, $—C(=NR^{17})R^{15}$, $C(=O)NR^{17a}R^{17b}$, $C(=S)NR^{17a}R^{17b}$, phenyl, optionally substituted with 1, 2, 3, 4 or 5 identical or different radicals selected from OH, halogen, cyano, nitro, $C_1$-$C_6$-alkyl, $C_1$-$C_6$-haloalkyl, $C_1$-$C_6$-alkoxy and $C_1$-$C_6$-haloalkoxy;

or two $R^{10}$ present together on one carbon ring atom of a saturated or partly unsaturated heterocyclic radical may form $=O$, $=CR^{13}R^{14}$, $=S$, $=NR^{17}$, $=NOR^{16}$, $=NNR^{17a}R^{17b}$;

or, two $R^{10}$ on adjacent carbon ring atoms may also be a bivalent radical selected from $CH_2CH_2CH_2CH_2$, $CH=CH—CH=CH$, $N=CH—CH=CH$, $CH=N—CH=CH$, $N=CH—N=CH$, $OCH_2CH_2CH_2$, $OCH=CHCH_2$, $CH_2OCH_2CH_2$, $OCH_2CH_2O$, $OCH_2OCH_2$, $CH_2CH_2CH_2$, $CH=CHCH_2$, $CH_2CH_2O$, $CH=CHO$, $CH_2OCH_2$, $CH_2C(=O)O$, $C(=O)OCH_2$, $O(CH_2)O$, $SCH_2CH_2CH_2$, $SCH=CHCH_2$, $CH_2SCH_2CH_2$, $SCH_2CH_2S$, $SCH_2SCH_2$, $CH_2CH_2S$, $CH=CHS$, $CH_2SCH_2$, $CH_2C(=S)S$, $C(=S)SCH_2$, $S(CH_2)S$, $CH_2CH_2NR^{17}$, $CH_2CH=N$, $CH=CH-NR^{17}$, $OCH=N$, $SCH=N$ and form together with the carbon atoms to which the two $R^{10}$ are bonded to a 5-membered or 6-membered partly saturated or unsaturated, aromatic carbocyclic or heterocyclic ring, wherein the ring may optionally be substituted with one or two substituents selected from $=O$, OH, $CH_3$, $OCH_3$, halogen, cyano, halomethyl and halomethoxy;

$R^{10a}$ independently of its occurrence, is selected from the group consisting of halogen, cyano, $NO_2$, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, $Si(R^{11})_2R^{12}$, $OR^{16}$, $OS(O)_nR^{16}$, $—S(O)_nR^{16}$, $S(O)_nNR^{17a}R^{17b}$, $NR^{17a}R^{17b}$, $C(=O)R^{15}$, $C(=S)R^{15}$, $C(=O)OR^{16}$, $—C(=NR^{17})R^{15}$, $C(=O)NR^{17a}R^{17b}$, $C(=S)NR^{17a}R^{17b}$, phenyl, optionally substituted with 1, 2, 3, 4 or 5 identical or different radicals selected from OH, halogen, cyano, nitro, $C_1$-$C_6$-alkyl, $C_1$-$C_6$-haloalkyl, $C_1$-$C_6$-alkoxy and $C_1$-$C_6$-haloalkoxy;

$R^{11}$, $R^{12}$ independently of their occurrence, are selected from the group consisting of $C_1$-$C_6$-alkyl, $C_1$-$C_6$-haloalkyl, $C_1$-$C_6$-alkoxy, $C_1$-$C_6$-alkoxy-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_3$-$C_8$-cycloalkyl-$C_1$-$C_4$-alkyl, $C_3$-$C_8$-halocycloalkyl-$C_1$-$C_4$-alkyl, $C_1$-$C_6$-haloalkoxy-$C_1$-$C_4$-alkyl, phenyl and benzyl, where the phenyl ring in last two radicals are unsubstituted or substituted with 1, 2, 3, 4 or 5 identical or different radicals selected from halogen, OH, cyano, $NO_2$, $C_1$-$C_6$-alkyl, $C_1$-$C_6$-haloalkyl, $C_1$-$C_6$-alkoxy and $C_1$-$C_6$-haloalkoxy;

$R^{13}$, $R^{14}$ independently of their occurrence, are selected from the group consisting of hydrogen, halogen, CN, $C_1$-$C_6$-alkyl, $C_3$-$C_6$-cycloalkyl, $C_1$-$C_4$-alkoxy-$C_1$-$C_4$-alkyl, phenyl and benzyl;

$R^{15}$ independently of its occurrence, is selected from the group consisting of hydrogen, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cycloaliphatic radicals may be unsubstituted, partially or fully halogenated and/or oxygenated and/or may carry 1 or 2 radicals selected from $C_1$-$C_4$ alkoxy;

phenyl, benzyl and pyridyl, wherein the last three radicals may be unsubstituted, partially or fully halogenated and/or to carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino or di-($C_1$-$C_6$-alkyl)amino;

$R^{16}$ independently of its occurrence, is selected from the group consisting of hydrogen, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, wherein the five last mentioned aliphatic and cycloaliphatic radicals may be unsubstituted, partially or fully halogenated and/or oxygenated and/or may carry 1 or 2 radicals selected from $C_1$-$C_4$ alkoxy, phenyl, benzyl and pyridyl, wherein the last three radicals may be unsubstituted, partially or fully halogenated and/or to carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino or di-($C_1$-$C_6$-alkyl)amino;

$R^{17}$ independently of its occurrence, is selected from the group consisting of hydrogen, $C_1$-$C_6$-alkoxy, $C_1$-$C_6$-haloalkoxy, $C_1$-$C_6$-alkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cycloaliphatic radicals may be unsubstituted, partially or fully halogenated and/or oxygenated and/or may carry 1 or 2 radicals selected from $C_1$-$C_4$-alkoxy, phenyl, benzyl, pyridyl, phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, $R^{17a}$, $R^{17b}$ are each independently from one another selected from the group consisting of hydrogen, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy, phenyl, benzyl, pyridyl, phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl, or, $R^{17a}$ and $R^{17b}$ may together be a $C_2$-$C_6$ alkylene chain forming a 3- to 7-membered saturated, partly saturated or unsaturated ring together with the nitrogen atom $R^{17a}$ and $R^{17b}$ are bonded to, wherein the alkylene chain may contain 1 or 2 heteroatoms selected, independently of each other, from oxygen, sulfur or nitrogen, and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

or $R^{17a}$ and $R^{17b}$ together may form =$CR^{13}R^{14}$, =$NR^{17}$ or =$NOR^{16}$ moiety;

$R^{17c}$ independently of its occurrence, is selected from the group consisting of hydrogen, CN, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkyl-$C_1$-$C_4$-alkyl, wherein the five last mentioned aliphatic and cycloaliphatic radicals may be unsubstituted, partially or fully halogenated and/or oxygenated and/or may carry 1 or 2 radicals selected from $C_1$-$C_4$ alkoxy, phenyl, benzyl and pyridyl, wherein the last three radicals may be unsubstituted, partially or fully halogenated and/or to carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino or di-($C_1$-$C_6$-alkyl)amino;

the stereoisomers, tautomers and the salts thereof.

2. The compound of claim 1, wherein
$R^1$, $R^2$ are independently from each other selected from the group consisting of hydrogen, halogen, CN, $C_1$-$C_6$-alkyl, $C_3$-$C_6$-cycloalkyl, $C_1$-$C_6$-haloalkyl, $C_3$-$C_6$-halocycloalkyl;
or
$R^1$ and $R^2$ may together be =$CR^{13}R^{14}$;
or
$R^1$ and $R^2$ form, together with the carbon atom, which they attached to, a 3- to 5-membered saturated carbocyclic ring.

3. The compound of claim 2, wherein both $R^1$ and $R^2$ are hydrogen.

4. The compound of claim 1, wherein
$R^3$ is selected from the group consisting of hydrogen, halogen, CN, $C_1$-$C_6$-alkyl, $C_1$-$C_6$-haloalkyl, $C_3$-$C_6$-cycloalkyl, $C_3$-$C_6$-halocycloalkyl, $NR^{9a}R^{9b}$ and $NR^{9a}$-C(=O)$R^{7a}$.

5. The compound of claim 4, wherein
$R^3$ is selected from the group consisting of hydrogen, fluorine, chlorine, $C_1$-$C_4$-alkyl, NHC(=O)—$C_1$-$C_4$-alkyl and CN.

6. The compound of claim 1, wherein m is 0 or 1.

7. The compound of claim 1, wherein
m is 1, and
$R^{4a}$, $R^{4b}$ are selected independently from one another from hydrogen, methyl and halogen or $R^{4a}$ and $R^{4b}$ together are =O.

8. The compound of claim 1, wherein
$R^5$ is hydrogen, halogen, CN, $NR^{9a}R^{9b}$, $C_1$-$C_6$-alkyl, $C_1$-$C_6$-haloalkyl, $C_3$-$C_6$-cycloalkyl, $C_3$-$C_6$-halocycloalkyl, C(=O)$OR^8$, C(=O)$NR^{9a}R^{9b}$, C(=S)$NR^{9a}R^{9b}$, C(=O)$R^{7a}$, C(=S)$R^{7a}$, Q-phenyl, where phenyl is unsubstituted or substituted with 1, 2, 3, 4 or 5 identical or different substituents $R^{10}$, or Q-Het$^\#$, where Het$^\#$ is unsubstituted or substituted with 1, 2, 3, 4 or 5 identical or different substituents $R^{10}$, and where Q, irrespectively of its occurrence, is a bond, $NR^{9a}$, $NR^{9a}$-C(=O), OC(=O), $NR^{9a}CH_2$, OC(=O)$CH_2$, or $NR^{9a}$C(=O)$CH_2$.

9. The compound of claim 1, wherein
$R^5$ is hydrogen, halogen, CN, $C_1$-$C_6$-alkyl, $C_1$-$C_6$-haloalkyl, $C_3$-$C_6$-cycloalkyl, $C_3$-$C_6$-halocycloalkyl and phenyl, which is unsubstituted or carries 1, 2, 3, 4 or 5 identical or different substituents $R^{10}$.

10. The compound of claim 1, wherein
m is 0, and
$R^3$ and $R^5$ together with the carbon atom, to which they are bound, form a 3, 4, 5 or 6 membered saturated carbocycle, wherein the carbocycle may be unsubstituted or may carry 1, 2, 3, 4, 5 or 6 radicals $R^{7b}$, or
$R^3$ and $R^5$ together with the carbon atom, to which they are bound, form a 3, 4, 5 or 6 membered saturated heterocycle having 1 or 2 non adjacent heteroatoms as ring members which are selected from O and S, wherein the heterocycle may be unsubstituted or may carry 1, 2, 3, 4, 5 or 6 radicals $R^{7b}$,
wherein
$R^{7b}$ is selected from the group consisting of halogen, $C_1$-$C_6$-alkyl, $C_1$-$C_6$-alkoxy, and $C_2$-$C_6$-alkynyl, and wherein the carbon atoms of the aforementioned aliphatic radicals may optionally be partly or completely halogenated, and wherein one or two radicals $R^{7b}$ may also be
$C_3$-$C_6$-cycloalkyl, which is unsubstituted or carries 1, 2, 3, 4 or 5 radicals selected from fluorine, chlorine or methyl,
phenyl, optionally substituted with 1, 2, 3, 4 or 5 identical or different substituents $R^{10a}$,
or two of $R^{7b}$ present on one ring carbon may together form =O or =S,
or two $R^{7b}$ together form a linear $C_2$-$C_7$ alkylene chain, thus forming, together with the carbon atom to which they are bound, a 3-, 4-, 5- or 6-membered ring, where 1 or 2 $CH_2$ moieties of the alkylene chain may be replaced by 1 or 2 heteroatom moieties selected from O and S, and where the alkylene chain is unsubstituted or may be substituted with 1, 2, 3, 4, 5 or 6 radicals selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^{10a}$ is selected from the group consisting of halogen, $C_1$-$C_4$-alkyl, $C_1$-$C_4$-haloalkyl, $C_1$-$C_4$-alkoxy and $C_1$-$C_4$-haloalkoxy;

or $R^3$ and $R^5$ together form =O.

11. The compound of claim 10, wherein $R^3$ and $R^5$ together with the carbon atom, to which they are bound, form a 3 or 4 membered saturated carbocycle, wherein the carbocycle may be unsubstituted or may carry 1, 2, 3, 4, 5 or 6 radicals $R^{7b}$, or $R^3$ and $R^5$ together with the carbon atom, to which they are bound, form a 3, 4, 5 or 6 membered saturated heterocycle having 1 or 2 non adjacent heteroatoms as ring members which are selected from O and S, wherein the heterocycle may be unsubstituted or may carry 1, 2, 3, 4, 5 or 6 radicals $R^{7b}$, wherein $R^{7b}$ is selected from the group consisting of halogen, $C_1$-$C_4$-alkyl, and wherein one radical $R^{7b}$ may also be phenyl, optionally substituted with 1, 2, 3, 4 or 5 identical or different substituents $R^{10a}$, where $R^{10a}$ is selected from the group consisting of halogen, CN, $C_1$-$C_4$-alkyl, $C_1$-$C_4$-haloalkyl, $C_1$-$C_4$-alkoxy and $C_1$-$C_4$-haloalkoxy.

12. The compound of claim 1, wherein $R^{w3}$, $R^{w4}$, $R^{w5}$ and $R^{w6}$ are, independently of each other, selected from hydrogen, halogen, $C_1$-$C_4$-alkoxy, $C_1$-$C_4$-haloalkoxy, $C_1$-$C_4$-alkyl and $C_1$-$C_4$-haloalkyl.

13. The compound of claim 12, wherein the radical A is W.Het-2.

14. The compound of claim 13, wherein $R^{w5}$ is hydrogen.

15. The compound of claim 12, wherein m is 0 or 1;

$R^1$, $R^2$ are independently from each other selected from the group consisting of hydrogen, halogen, CN, $C_1$-$C_6$-alkyl, $C_3$-$C_6$-cycloalkyl, $C_1$-$C_6$-haloalkyl, $C_2$-$C_6$-halocycloalkyl;

or $R^1$ and $R^2$ may together be =$CR^{13}R^{14}$;

or $R^1$ and $R^2$ form, together with the carbon atom, which they attached to, a 3- to 5-membered saturated carbocyclic ring;

$R^3$ is selected from the group consisting of hydrogen, halogen, CN, $C_1$-$C_6$-alkyl, $C_1$-$C_6$-haloalkyl, $C_3$-$C_6$-cycloalkyl, $C_3$-$C_6$-halocycloalkyl, $NR^{9a}R^{9b}$ and $NR^{9a}$—C(=O)$R^{7a}$;

$R^5$ is hydrogen, halogen, CN, $NR^{9a}R^{9b}$, $C_1$-$C_6$-alkyl, $C_1$-$C_6$-haloalkyl, $C_3$-$C_6$-cycloalkyl, $C_3$-$C_6$-halocycloalkyl, C(=O)$OR^8$, C(=O)$NR^{9a}R^{9b}$, C(=S) $NR^{9a}R^{9b}$, C(=O)$R^{7a}$, C(=S)$R^{7a}$, Q-phenyl, where phenyl is unsubstituted or substituted with 1, 2, 3, 4 or 5 identical or different substituents $R^{10}$, or Q-Het$^\#$, where Het$^\#$ is unsubstituted or substituted with 1, 2, 3, 4 or 5 identical or different substituents $R^{10}$, and where Q, irrespectively of its occurrence, is a bond, $NR^{9a}$, $NR^{9a}$-C(=O), OC(=O), $NR^{9a}CH_2$, OC(=O)$CH_2$, or $NR^{9a}$C(=O)$CH_2$, if m is 1, $R^{4a}$, $R^{4b}$ are selected independently from one another from hydrogen, methyl and halogen or $R^{4a}$ and $R^{4b}$ together are =O, or if m is 0, $R^3$ and $R^5$ together with the carbon atom, to which they are bound, form a 3, 4, 5 or 6 membered saturated carbocycle, wherein the carbocycle may be unsubstituted or may carry 1, 2, 3, 4, 5 or 6 radicals $R^{7b}$, or $R^3$ and $R^5$ together with the carbon atom, to which they are bound, form a 3, 4, 5 or 6 membered saturated heterocycle having 1 or 2 non adjacent heteroatoms as ring members which are selected from O and S, wherein the heterocycle may be unsubstituted or may carry 1, 2, 3, 4, 5 or 6 radicals $R^{7b}$, wherein $R^{7b}$ is selected from the group consisting of halogen, $C_1$-$C_6$-alkyl, $C_1$-$C_6$-alkoxy, and $C_2$-$C_6$-alkynyl, and wherein the carbon atoms of the aforementioned aliphatic radicals may optionally be partly or completely halogenated, and wherein one or two radicals $R^{7b}$ may also be $C_3$-$C_6$-cycloalkyl, which is unsubstituted or carries 1, 2, 3, 4 or 5 radicals selected from fluorine, chlorine or methyl, phenyl, optionally substituted with 1, 2, 3, 4 or 5 identical or different substituents $R^{10a}$, or two of $R^{7b}$ present on one ring carbon may together form =O or =S, or two $R^{7b}$ together form a linear $C_2$-$C_7$ alkylene chain, thus forming, together with the carbon atom to which they are bound, a 3-, 4-, 5- or 6-membered ring, where 1 or 2 $CH_2$ moieties of the alkylene chain may be replaced by 1 or 2 heteroatom moieties selected from O and S, and where the alkylene chain is unsubstituted or may be substituted with 1, 2, 3, 4, 5 or 6 radicals selected from the group consisting of halogen, $C_1$-$C_4$-alkyl, $C_1$-$C_4$-haloalkyl, $C_1$-$C_4$-alkoxy and $C_1$-$C_4$-haloalkoxy, $R^{10a}$ is selected from the group consisting of halogen, $C_1$-$C_4$-alkyl, $C_1$-$C_4$-haloalkyl, $C_1$-$C_4$-alkoxy and $C_1$-$C_4$-haloalkoxy;

or $R^3$ and $R^5$ together form =O.

16. The compound of claim 12, wherein both $R^1$ and $R^2$ are hydrogen;

$R^3$ is selected from the group consisting of hydrogen, fluorine, chlorine, $C_1$-$C_4$-alkyl, NHC(=O)—$C_1$-$C_4$-alkyl and CN;

$R^5$ is hydrogen, halogen, CN, $C_1$-$C_6$-alkyl, $C_1$-$C_6$-haloalkyl, $C_3$-$C_6$-cycloalkyl, $C_3$-$C_6$-halocycloalkyl and phenyl, which is unsubstituted or carries 1, 2, 3, 4 or 5 identical or different substituents $R^{10}$;

if m is 1, $R^{4a}$, $R^{4b}$ are each hydrogen or $R^{4a}$ and $R^{4b}$ together are =O, or if m is 0, $R^3$ and $R^5$ together with the carbon atom, to which they are bound, form a 3 or 4 membered saturated carbocycle, wherein the carbocycle may be unsubstituted or may carry 1, 2, 3, 4, 5 or 6 radicals $R^{7b}$, wherein or $R^3$ and $R^5$ together with the carbon atom, to which they are bound, form a 3, 4, 5 or 6 membered saturated heterocycle having 1 or 2 non adjacent heteroatoms as ring members which are selected from O and S, wherein the heterocycle may be unsubstituted or may carry 1, 2, 3, 4, 5 or 6 radicals $R^{7b}$, $R^{7b}$ is selected from the group consisting of halogen, $C_1$-$C_4$-alkyl, and wherein one radical $R^{7b}$ may also be phenyl, optionally substituted with 1, 2, 3, 4 or 5 identical or different substituents $R^{10a}$, where
$R^{10a}$ is selected from the group consisting of halogen, CN, $C_1$-$C_4$-alkyl, $C_1$-$C_4$-haloalkyl, $C_1$-$C_4$-alkoxy and $C_1$-$C_4$-haloalkoxy.

17. The compound of claim 1, wherein
X is O.

18. An agricultural or veterinary composition for combating animal pests comprising at least one compound of claim 1, and at least one inert liquid and/or solid acceptable carrier and optionally, if desired, at least one surfactant.

19. A method for combating or controlling invertebrate pests, comprising contacting said pest or its food supply, habitat or breeding grounds with a pesticidally effective amount of at least one compound of claim 1.

20. A method for protecting growing plants from attack or infestation by invertebrate pests, comprising contacting a plant, or soil or water in which the plant is growing, with a pesticidally effective amount of at least one compound of claim 1.

21. A method for the protection of plant propagation material from soil insects and of the seedlings roots and shoots from soil and foliar insects comprising contacting the plant propagation material before sowing and/or after pregermination with at least one compound of claim 1.

22. A method for treating animals infested or infected by parasites or preventing animals of getting infected or infested by parasites or protecting animals against infestation or infection by parasites comprising administering or applying to the animals a parasiticidally effective amount of the compound of claim 1.

* * * * *